(12) United States Patent
Langley et al.

(10) Patent No.: US 11,439,758 B2
(45) Date of Patent: Sep. 13, 2022

(54) DEVICES AND METHODS FOR PRECISION DOSE DELIVERY

(71) Applicant: Regeneron Pharmaceuticals, Inc., Tarrytown, NY (US)

(72) Inventors: Trevor Langley, Rensselaer, NY (US); Justin Bechstein, Philadelphia, PA (US); Jeremy Odegard, Hudson, WI (US); Sibgat Ulla, Rensselaer, NY (US); Daniel Halbig, Rensselaer, NY (US); Bryan Grygus, Clifton Park, NY (US); Prithvi Singh, Rensselaer, NY (US); Andrew Dumont, Rensselaer, NY (US); David Nett, Rensselaer, NY (US); Tasha Gillum, Rensselaer, NY (US); Ryan Ainsworth, Rensselaer, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 17/354,850

(22) Filed: Jun. 22, 2021

(65) Prior Publication Data

US 2021/0330887 A1 Oct. 28, 2021

Related U.S. Application Data

(63) Continuation of application No. PCT/US2020/036200, filed on Jun. 4, 2020.
(Continued)

(51) Int. Cl.
*A61M 5/31* (2006.01)
*A61M 5/315* (2006.01)

(52) U.S. Cl.
CPC ...... *A61M 5/31505* (2013.01); *A61M 5/3135* (2013.01); *A61M 5/3146* (2013.01);
(Continued)

(58) Field of Classification Search
CPC ........ A61M 2005/3139; A61M 5/3135; A61M 5/3137; A61M 5/31501
See application file for complete search history.

(56) References Cited

U.S. PATENT DOCUMENTS

| 4,391,272 A | 7/1983 | Staempfli |
|---|---|---|
| 4,654,035 A | 3/1987 | Ando |

(Continued)

FOREIGN PATENT DOCUMENTS

| AU | 2010320885 B2 | 3/2013 |
|---|---|---|
| CA | 2773015 A1 | 4/2011 |

(Continued)

OTHER PUBLICATIONS

Accura Xtreme White, Xtreme Class, 3D Systems, Manufacturing the future, 2015, 1 page.
(Continued)

*Primary Examiner* — Deanna K Hall
(74) *Attorney, Agent, or Firm* — Bookoff McAndrews, PLLC

(57) ABSTRACT

Disclosed herein are devices and methods for delivering a predetermined volume of a drug substance or other product including a fluid. An exemplary device may include a body configured to receive a drug substance therein, and a plunger rod disposed at least partially inside the body to distally move a stopper in the body. The device may include a component configured to regulate distal movement of the plunger rod in a priming step and in a subsequent delivery
(Continued)

step, so that the device may be accurately primed and may accurately dispense a predetermined volume of a drug substance.

20 Claims, 84 Drawing Sheets

Related U.S. Application Data

(60) Provisional application No. 62/860,481, filed on Jun. 12, 2019, provisional application No. 62/857,678, filed on Jun. 5, 2019.

(52) U.S. Cl.
CPC .............. *A61M 2005/3139* (2013.01); *A61M 2005/31508* (2013.01)

(56) References Cited

U.S. PATENT DOCUMENTS

| | | |
|---|---|---|
| 4,840,616 A | 6/1989 | Banks |
| 4,852,768 A | 8/1989 | Bartsch |
| 4,915,695 A | 4/1990 | Koobs |
| 5,009,645 A | 4/1991 | Silver et al. |
| RE33,821 E | 2/1992 | Banks |
| 5,092,842 A | 3/1992 | Bechtold et al. |
| 5,318,544 A | 6/1994 | Drypen et al. |
| 5,358,497 A | 10/1994 | Dorsey et al. |
| 5,370,620 A | 12/1994 | Shonfeld |
| 5,439,643 A | 8/1995 | Liebert |
| 5,533,970 A | 7/1996 | Berger et al. |
| 5,554,122 A | 9/1996 | Emanuel |
| 5,593,391 A | 1/1997 | Stanners |
| 5,688,251 A | 11/1997 | Chanoch |
| 5,700,247 A | 12/1997 | Grimard et al. |
| 5,807,343 A | 9/1998 | Tucker et al. |
| 5,807,345 A | 9/1998 | Grabenkort |
| 5,820,603 A | 10/1998 | Tucker et al. |
| 5,833,669 A | 11/1998 | Wyrick |
| 5,961,495 A | 10/1999 | Walters et al. |
| 5,976,113 A | 11/1999 | Morigi et al. |
| 6,096,010 A | 8/2000 | Walters et al. |
| 6,126,640 A | 10/2000 | Tucker et al. |
| 6,142,977 A | 11/2000 | Kolberg et al. |
| 6,164,044 A | 12/2000 | Porfano et al. |
| 6,189,195 B1 | 2/2001 | Reilly et al. |
| 6,189,292 B1 | 2/2001 | Odell et al. |
| 6,263,641 B1 | 7/2001 | Odell et al. |
| 6,319,235 B1 | 11/2001 | Yoshino et al. |
| 6,398,762 B1 | 6/2002 | Vetter et al. |
| 6,450,993 B1 | 9/2002 | Lin |
| 6,511,457 B2 | 1/2003 | Thompson |
| 6,530,906 B2 | 3/2003 | Hu |
| 6,562,006 B1 | 5/2003 | Hjertman et al. |
| 6,792,743 B2 | 9/2004 | Odell et al. |
| 6,807,797 B2 | 10/2004 | Forsberg et al. |
| 7,169,133 B2 | 1/2007 | Broennimann et al. |
| 7,396,347 B2 | 7/2008 | Hjertman et al. |
| 7,407,494 B2 | 8/2008 | Bostrom et al. |
| 7,564,983 B2 | 7/2009 | Ibuka et al. |
| 7,704,237 B2 | 4/2010 | Fisher et al. |
| 7,704,426 B2 | 4/2010 | Earhart et al. |
| 7,727,195 B2 | 6/2010 | Norton |
| 7,727,201 B2 | 6/2010 | Kirchhofer |
| 7,749,200 B2 | 7/2010 | Graf et al. |
| 7,811,263 B2 | 10/2010 | Burren et al. |
| 7,954,672 B2 | 6/2011 | Keller |
| 8,075,533 B2 | 12/2011 | Lee |
| 8,075,547 B2 | 12/2011 | Lee |
| 8,118,788 B2 | 2/2012 | Frezza |
| 8,196,741 B2 | 6/2012 | Finke et al. |
| 8,246,577 B2 | 8/2012 | Schrul et al. |
| 8,276,583 B2 | 10/2012 | Farieta et al. |
| 8,348,905 B2 | 1/2013 | Radmer et al. |
| 8,366,680 B2 | 2/2013 | Raab |
| 8,394,068 B2 | 3/2013 | Kosinski et al. |
| 8,628,501 B2 | 1/2014 | Hadden |
| 8,663,555 B2 | 3/2014 | Shiosawa |
| 8,721,601 B2 | 5/2014 | Burren et al. |
| 8,945,048 B2 | 2/2015 | Thorley et al. |
| 8,979,807 B2 | 3/2015 | Grunhut et al. |
| 8,992,484 B2 | 3/2015 | Radmer et al. |
| 9,033,934 B2 | 5/2015 | Karlsson et al. |
| 9,044,548 B2 | 6/2015 | Miller et al. |
| 9,114,212 B2 | 8/2015 | Enggaard et al. |
| 9,220,631 B2 | 12/2015 | Sigg et al. |
| 9,238,106 B2 | 1/2016 | Jones |
| 9,352,104 B2 | 5/2016 | Thorley et al. |
| 9,408,965 B2 | 8/2016 | Christensen |
| 9,480,763 B2 | 11/2016 | Dufresne et al. |
| 9,533,100 B2 | 1/2017 | Jones |
| 9,539,391 B2 | 1/2017 | Lee et al. |
| 9,572,932 B2 | 2/2017 | Eggert et al. |
| 9,572,940 B2 | 2/2017 | Horlock |
| 9,604,015 B2 | 3/2017 | Gramage Pina |
| D790,691 S | 6/2017 | Davis et al. |
| 9,669,988 B2 | 6/2017 | Kojima et al. |
| D794,185 S | 8/2017 | Dolk et al. |
| 9,717,854 B2 | 8/2017 | Evans et al. |
| 9,750,887 B2 | 9/2017 | Hirschel et al. |
| 9,750,888 B2 | 9/2017 | Raab et al. |
| D800,900 S | 10/2017 | Darras et al. |
| 9,849,244 B2 | 12/2017 | Plumptre et al. |
| 9,867,948 B2 | 1/2018 | Selz et al. |
| D810,282 S | 2/2018 | Ratjen |
| D812,223 S | 3/2018 | Evans et al. |
| D814,026 S | 3/2018 | Darras et al. |
| 9,907,913 B2 | 3/2018 | Kosinski et al. |
| 9,925,340 B2 | 3/2018 | Glocker |
| D815,279 S | 4/2018 | Darras et al. |
| 9,950,116 B2 | 4/2018 | Plumptre et al. |
| 9,962,493 B2 | 5/2018 | Guthart |
| 9,968,743 B2 | 5/2018 | Kuwahara et al. |
| 10,064,997 B2 | 9/2018 | Evans et al. |
| 10,092,708 B2 | 10/2018 | Thorley et al. |
| 10,137,249 B2 | 11/2018 | Oakley et al. |
| 10,179,206 B2 | 1/2019 | Bendek et al. |
| 10,195,348 B2 | 2/2019 | Komann |
| 10,213,557 B2 | 2/2019 | Eggert et al. |
| 10,213,558 B2 | 2/2019 | Raghuveer et al. |
| 10,232,119 B2 | 3/2019 | Raab et al. |
| D845,476 S | 4/2019 | Evans et al. |
| 10,391,259 B2 | 8/2019 | Tran et al. |
| 2003/0032928 A1 | 2/2003 | Sudo et al. |
| 2004/0064105 A1 | 4/2004 | Capes et al. |
| 2004/0097883 A1 | 5/2004 | Roe |
| 2004/0199113 A1 | 10/2004 | Capes et al. |
| 2004/0236285 A1 | 11/2004 | Fisher et al. |
| 2005/0182370 A1 | 8/2005 | Hato |
| 2005/0215957 A1 | 9/2005 | Hynes |
| 2006/0153693 A1 | 7/2006 | Fiechter et al. |
| 2006/0264815 A1 | 11/2006 | Hommann et al. |
| 2006/0270984 A1 | 11/2006 | Hommann |
| 2006/0270985 A1 | 11/2006 | Hommann et al. |
| 2007/0233009 A1 | 10/2007 | Kirchhofer |
| 2008/0202961 A1 | 8/2008 | Sharp |
| 2008/0208123 A1 | 8/2008 | Hommann |
| 2009/0005735 A1 | 1/2009 | Wikner et al. |
| 2010/0292672 A1 | 11/2010 | Lee |
| 2010/0318063 A1 | 12/2010 | Soll |
| 2011/0009829 A1 | 1/2011 | Kosinski et al. |
| 2011/0190709 A1 | 8/2011 | Mitsuno et al. |
| 2012/0114524 A1 | 5/2012 | Sigg |
| 2012/0203184 A1 | 8/2012 | Selz et al. |
| 2012/0226240 A1 | 9/2012 | Bedford et al. |
| 2012/0232492 A1 | 9/2012 | Hato |
| 2012/0283654 A1 | 11/2012 | MacDonald et al. |
| 2013/0004384 A1 | 1/2013 | Yoo |
| 2013/0085452 A1 | 4/2013 | Schiff et al. |
| 2013/0218130 A1 | 8/2013 | Plumptre et al. |
| 2014/0180217 A1 | 6/2014 | Kuczek et al. |
| 2014/0223862 A1 | 8/2014 | Nicoletti et al. |
| 2015/0078961 A1 | 3/2015 | Opie |

(56) References Cited

U.S. PATENT DOCUMENTS

| | | | |
|---|---|---|---|
| 2015/0190566 A1 | 7/2015 | Okihara | |
| 2015/0335826 A1 | 11/2015 | Huet | |
| 2016/0144122 A1 | 5/2016 | Locati et al. | |
| 2017/0080159 A1 | 3/2017 | Wei | |
| 2017/0281872 A1 | 10/2017 | Guthart | |
| 2017/0290987 A1 | 10/2017 | Mandaroux et al. | |
| 2018/0036488 A1 | 2/2018 | Wei | |
| 2018/0126085 A1 | 5/2018 | Bowman et al. | |
| 2018/0126086 A1 | 5/2018 | Kosinski et al. | |
| 2018/0177948 A1 | 6/2018 | Raab et al. | |
| 2018/0177949 A1 | 6/2018 | De Waal Malefijt et al. | |
| 2018/0221584 A1 | 8/2018 | Grimoldby et al. | |
| 2018/0250474 A1* | 9/2018 | Wei .................. | A61M 5/31505 |
| 2018/0280622 A1 | 10/2018 | Li et al. | |
| 2018/0326126 A1 | 11/2018 | Fiedler | |
| 2018/0361080 A1 | 12/2018 | Diaz et al. | |
| 2019/0001065 A1 | 1/2019 | Daniel | |
| 2019/0030253 A1 | 1/2019 | Barbour | |
| 2019/0076603 A1 | 3/2019 | Thorley et al. | |
| 2019/0111212 A1 | 4/2019 | Schiff et al. | |
| 2020/0188589 A1 | 6/2020 | Hawson et al. | |
| 2020/0188590 A1 | 6/2020 | Hamlin | |

FOREIGN PATENT DOCUMENTS

| | | |
|---|---|---|
| CA | 2781483 A1 | 5/2011 |
| CN | 1649638 A | 8/2005 |
| CN | 100540077 C | 9/2009 |
| CN | 102481418 A | 5/2012 |
| CN | 204972542 U | 1/2016 |
| CN | 110913926 A | 3/2020 |
| DE | 19856167 C1 | 5/2000 |
| EP | 0846072 B1 | 5/2001 |
| EP | 1061975 B1 | 2/2004 |
| EP | 0971749 B1 | 7/2004 |
| EP | 0937477 B1 | 11/2004 |
| EP | 1409046 B1 | 3/2005 |
| EP | 0976415 B1 | 5/2005 |
| EP | 1675632 B1 | 9/2007 |
| EP | 1829577 A2 | 9/2007 |
| EP | 1525015 B1 | 10/2007 |
| EP | 1071487 B1 | 3/2008 |
| EP | 1818069 B1 | 9/2008 |
| EP | 1704887 B1 | 10/2008 |
| EP | 1488818 B1 | 3/2010 |
| EP | 1735014 B1 | 8/2010 |
| EP | 2253548 A1 | 11/2010 |
| EP | 2253549 A1 | 11/2010 |
| EP | 2482890 B1 | 12/2014 |
| EP | 2253549 B1 | 3/2015 |
| EP | 2862587 A1 | 4/2015 |
| EP | 1940476 B1 | 5/2015 |
| EP | 2436407 B1 | 6/2015 |
| EP | 2436408 B1 | 6/2015 |
| EP | 1433705 B1 | 7/2015 |
| EP | 2939649 A1 | 11/2015 |
| EP | 1019120 B1 | 8/2016 |
| EP | 1973592 B1 | 6/2017 |
| EP | 2550043 B1 | 10/2017 |
| EP | 2869813 B1 | 11/2018 |
| EP | 2451511 B1 | 1/2019 |
| EP | 3057633 B1 | 5/2020 |
| GB | 1230522 A | 5/1971 |
| GN | 304679488 | 6/2018 |
| JP | 2008307237 A | 12/2008 |
| JP | 2009011481 A | 1/2009 |
| JP | D1531421 S | 8/2015 |
| JP | 5801314 B2 | 10/2015 |
| JP | 5907874 B2 | 4/2016 |
| JP | D1552403 S | 6/2016 |
| JP | 5978742 B2 | 8/2016 |
| JP | D1646523 S | 11/2019 |
| JP | 2020522351 A | 7/2020 |
| KR | 20050004800 A | 1/2005 |
| RU | 2012125349 A | 12/2013 |
| TW | M261222 U | 4/2005 |
| TW | D187080 S | 12/2017 |
| WO | WO-9512418 A1 | 5/1995 |
| WO | WO-9708054 A1 | 3/1997 |
| WO | WO-9744068 A1 | 11/1997 |
| WO | WO-9819715 A1 | 5/1998 |
| WO | WO-9856438 A1 | 12/1998 |
| WO | WO-9856439 A1 | 12/1998 |
| WO | WO-9915215 A1 | 4/1999 |
| WO | WO-9927971 A2 | 6/1999 |
| WO | WO-9945984 A1 | 9/1999 |
| WO | WO-9945985 A1 | 9/1999 |
| WO | WO-0178812 A1 | 10/2001 |
| WO | WO-02072157 A1 | 9/2002 |
| WO | WO-03004080 A1 | 1/2003 |
| WO | WO-03077976 A1 | 9/2003 |
| WO | WO-03080160 A1 | 10/2003 |
| WO | WO-2004035113 A2 | 4/2004 |
| WO | WO-2005032627 A1 | 4/2005 |
| WO | WO-2005067984 A1 | 7/2005 |
| WO | WO-2006047325 A1 | 5/2006 |
| WO | WO-2007024957 A1 | 3/2007 |
| WO | WO-2007035621 A1 | 3/2007 |
| WO | WO-2007083034 A2 | 7/2007 |
| WO | 2008/058666 A1 | 5/2008 |
| WO | 2008/058668 A1 | 5/2008 |
| WO | WO-2008051561 A2 | 5/2008 |
| WO | WO-2008110890 A1 | 9/2008 |
| WO | WO-2009092430 A1 | 7/2009 |
| WO | 2010/127449 A1 | 11/2010 |
| WO | WO-2011006877 A1 | 1/2011 |
| WO | WO-2011038487 A1 | 4/2011 |
| WO | WO-2011039211 A1 | 4/2011 |
| WO | WO-2011061313 A1 | 5/2011 |
| WO | WO-2011073174 A1 | 6/2011 |
| WO | WO-2011115428 A2 | 9/2011 |
| WO | WO-2011117878 A1 | 9/2011 |
| WO | WO-2011125133 A1 | 10/2011 |
| WO | WO-2012007056 A1 | 1/2012 |
| WO | WO-2012148717 A1 | 11/2012 |
| WO | WO-2013028537 A2 | 2/2013 |
| WO | WO-2013048310 A1 | 4/2013 |
| WO | WO-2013178771 A1 | 12/2013 |
| WO | WO-2013184270 A1 | 12/2013 |
| WO | WO-2014005728 A1 | 1/2014 |
| WO | WO-2014049712 A1 | 4/2014 |
| WO | WO-2014049714 A1 | 4/2014 |
| WO | WO-2014102987 A1 | 7/2014 |
| WO | WO-2014162551 A1 | 10/2014 |
| WO | WO-2014187779 A1 | 11/2014 |
| WO | WO-2015007811 A1 | 1/2015 |
| WO | WO-2015033280 A1 | 3/2015 |
| WO | 2015045180 A1 | 4/2015 |
| WO | WO-2015055608 A1 | 4/2015 |
| WO | WO-2016033701 A1 | 3/2016 |
| WO | WO-2016052037 A1 | 4/2016 |
| WO | WO-2016068333 A1 | 5/2016 |
| WO | WO-2016094387 A2 | 6/2016 |
| WO | WO-2016191535 A2 | 12/2016 |
| WO | 2017062304 A1 | 4/2017 |
| WO | WO-2017180480 A1 | 10/2017 |
| WO | WO-2017191306 A1 | 11/2017 |
| WO | WO-2017204787 A1 | 11/2017 |
| WO | WO-2018085759 A1 | 5/2018 |
| WO | WO-2018085768 A2 | 5/2018 |
| WO | WO-2018141634 A1 | 8/2018 |
| WO | WO-2018204140 A1 | 11/2018 |
| WO | WO-2018224640 A1 | 12/2018 |
| WO | WO-2018224644 A1 | 12/2018 |
| WO | WO-2018232408 A1 | 12/2018 |
| WO | WO-2019197361 A1 | 10/2019 |

OTHER PUBLICATIONS

U.S. Appl. No. 62/467,065, filed Mar. 3, 2017.
Dilution Table 3Dose Unit Dose Injector, Instructions for Use, www.tsklab.com, 1 page.

(56) References Cited

OTHER PUBLICATIONS

Gattex (teduglutide) for Injection, Instructions for Use, 2019, 2 pages.
International Search Report and Written Opinion for Application No. PCT/US2018/065192, dated Jun. 4, 2019, 22 pages.
Lucentis Dosage, Generic name: Ranibizumab 10mg in 1mL, Dosage form: injection, solution, Lucentis Dosage Guide—Drugs.com , [retrieved on May 28, 2020], Retrieved from the Internet: (URL: https://www.drugs.com/dosage/lucentis.html), 7 pages.
Lucentis Ranibizumab Injection, Prefilled Syringe Administration Preparation, Genentech, 2018, 30 pages.
New, Novel Prefillable Microfilter Injection Device for Intraocular Therapeutics, Congruence Medical Solutions Inc, Gautam Shetty, phD , 2018, 19 Pages.
Proven and innovative injection systems delivering your product's potential, Vetter—Packaging systems and technologies for pharmaceutical products, Retrieved from Internet: (https://www.vetter-pharma.com/en/clinical-manufacturing/packaging/systems), 7 pages.
International Search Report and Written Opinion dated Oct. 26, 2020, in counterpart International Patent Application No. PCT/US2020/036200 (19 pages, in English).
Krader, Cheryl Guttman. "Pearls for Selecting a Syringe for Intravitreal Injection," Ophthamology Times, Jan. 2021, pp. 1 & 25, 52 pages.
International Preliminary Report on Patentability dated May 6, 2021, in counterpart International Patent Application No. PCT/US2020/036200 (12 pages, in English).
Taiwanese Search Report dated Sep. 8, 2021, in counterpart Taiwanese Patent Application No. 109306859 (1 page, in English).
Japanese Notice of Allowance dated Oct. 25, 2021, in counterpart Japanese Patent Application No. 2020-026268 (4 pages, in Japanese with partial English translation).
Chilean Office Action dated Jan. 26, 2022, in counterpart Chilean Patent Application No. 01590-2020 (16 pages, in Spanish).
Chinese Office Action dated Nov. 26, 2021, in counterpart Chinese Patent Application No. 201880080564.7 (8 pages, in Chinese).

* cited by examiner

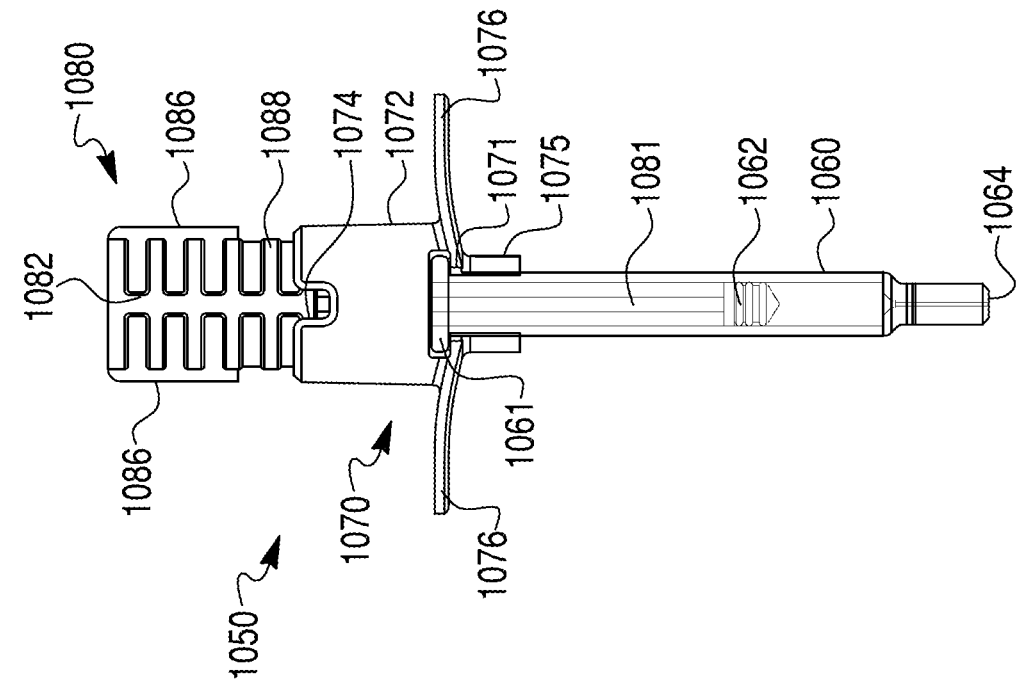
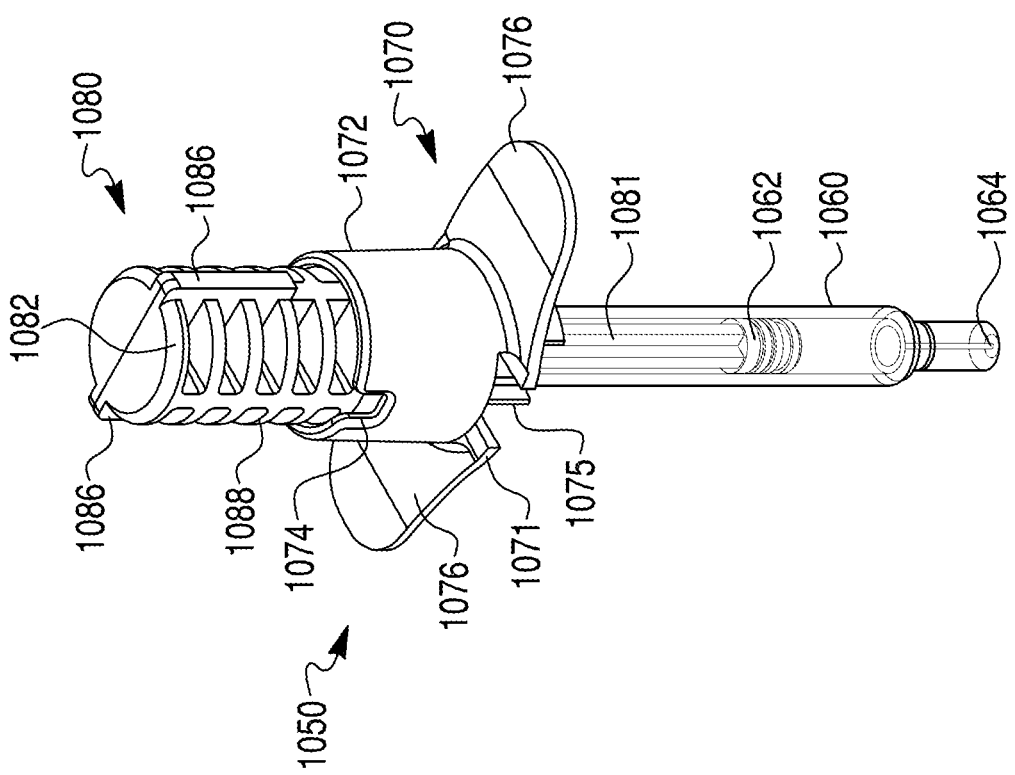

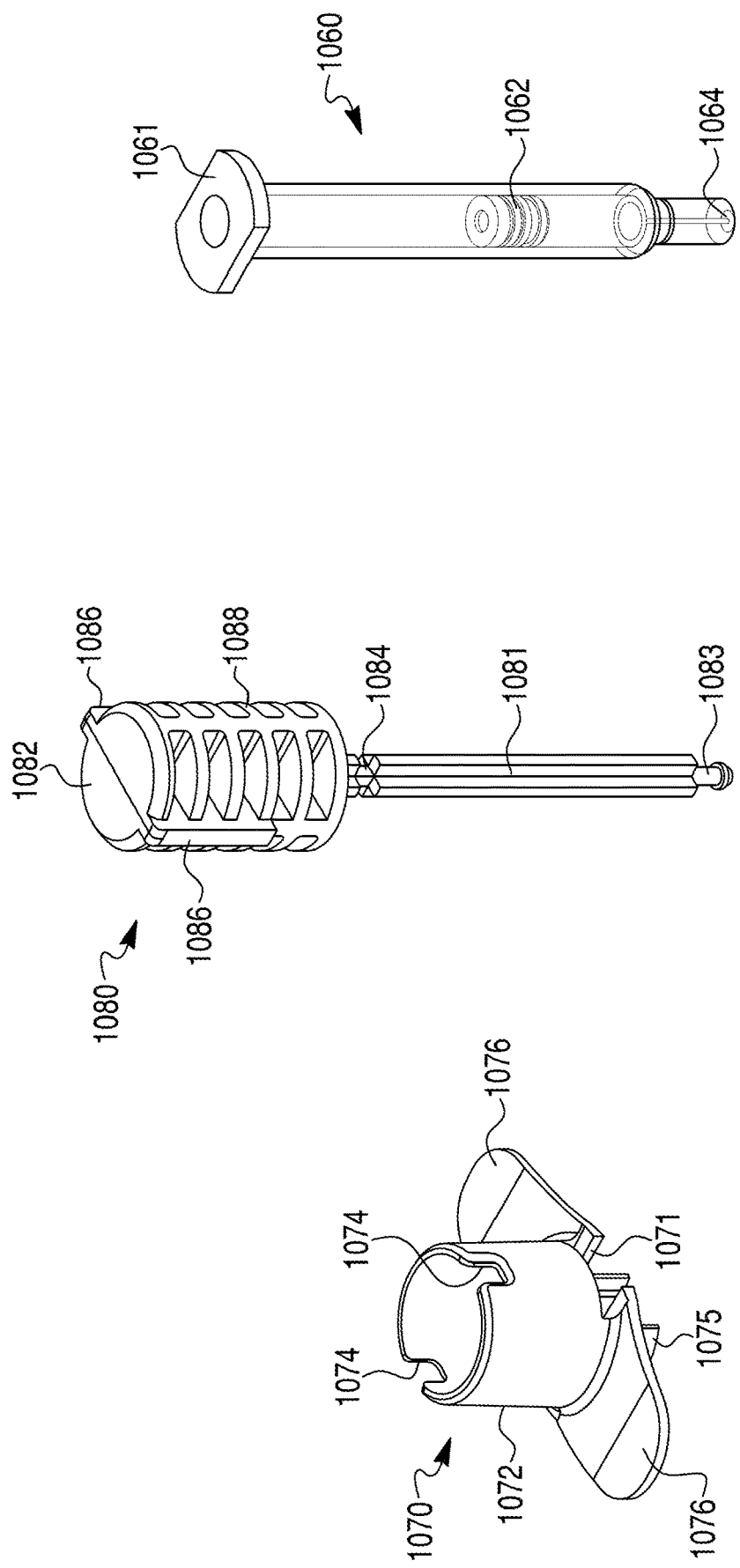

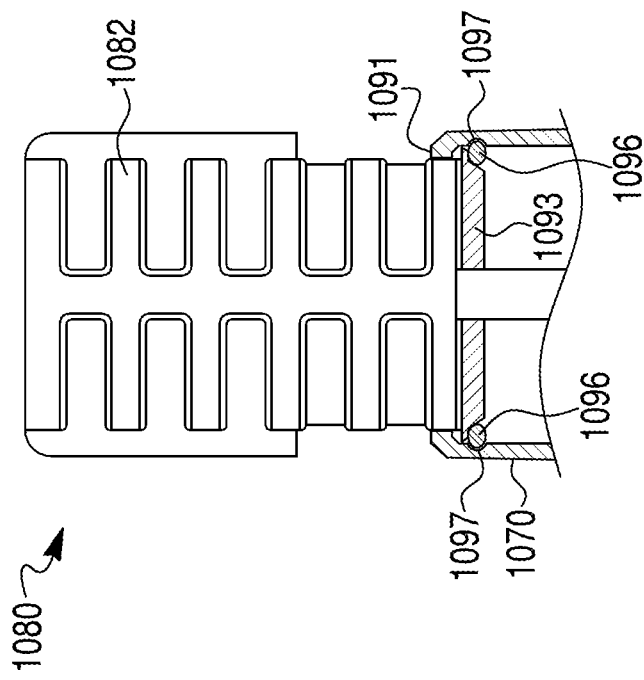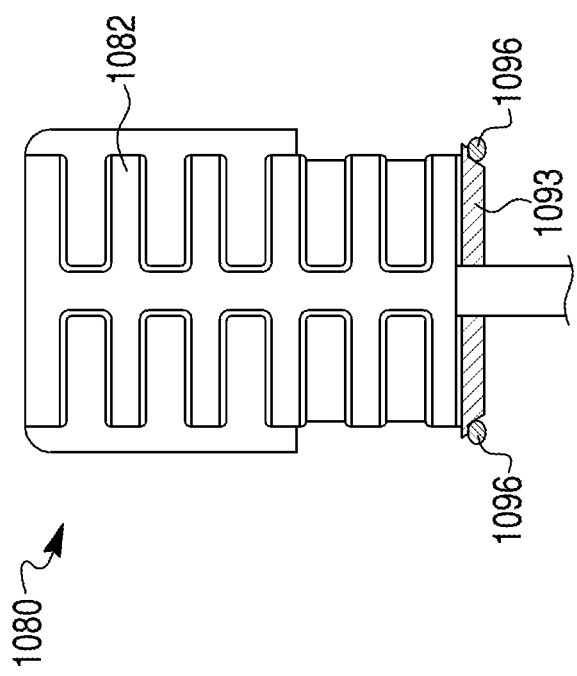

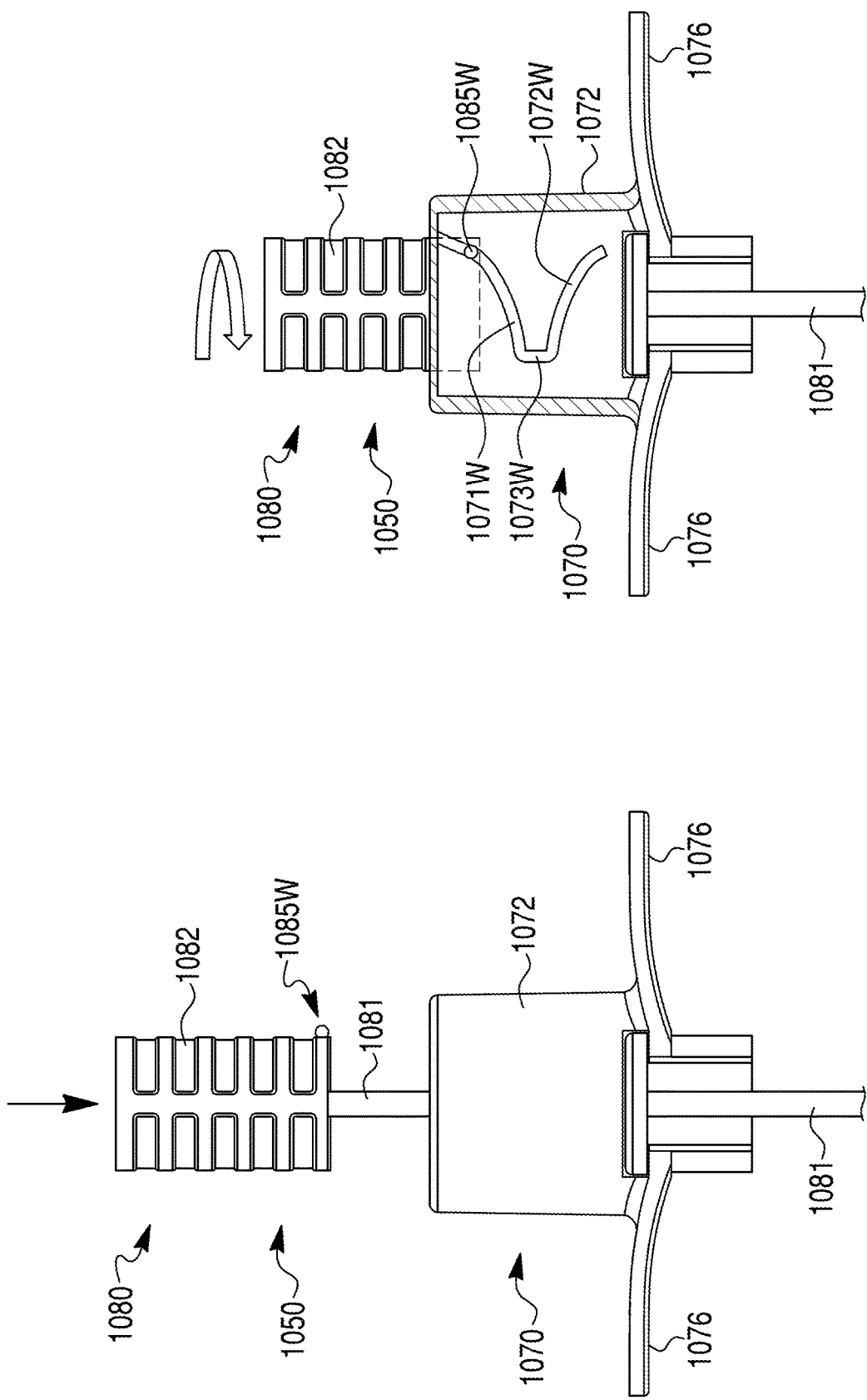

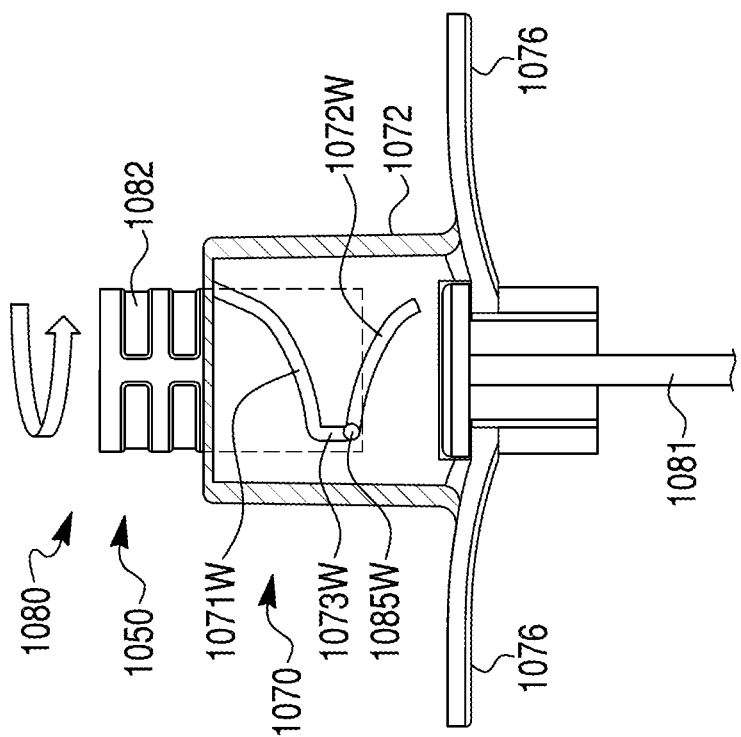
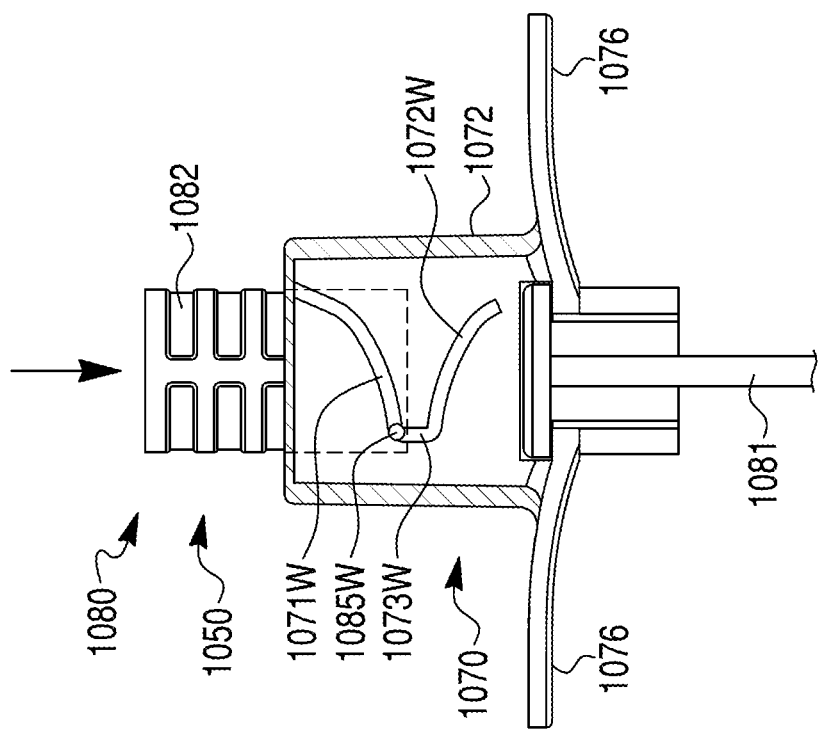

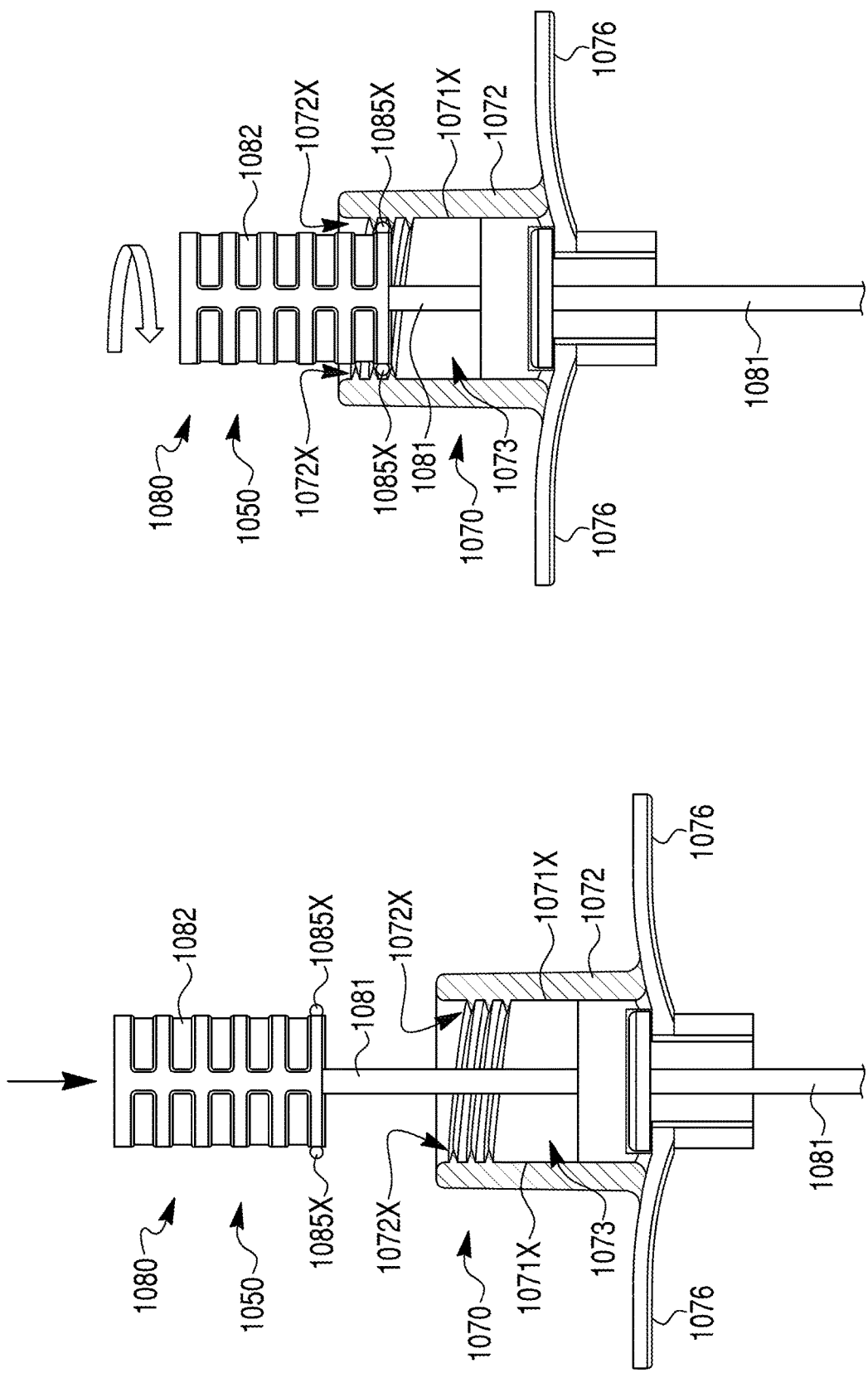

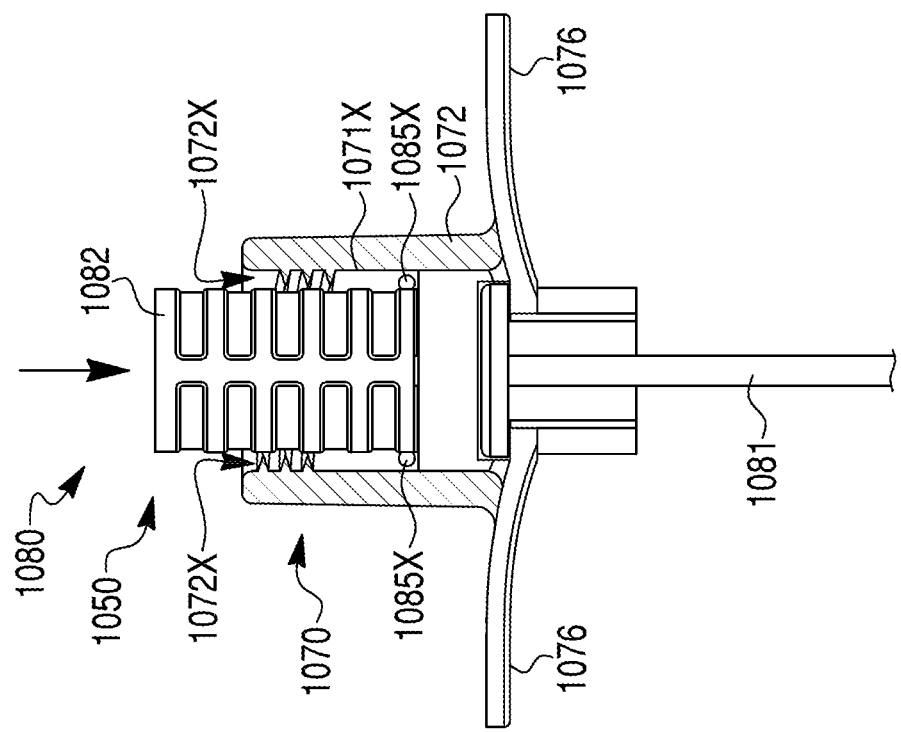
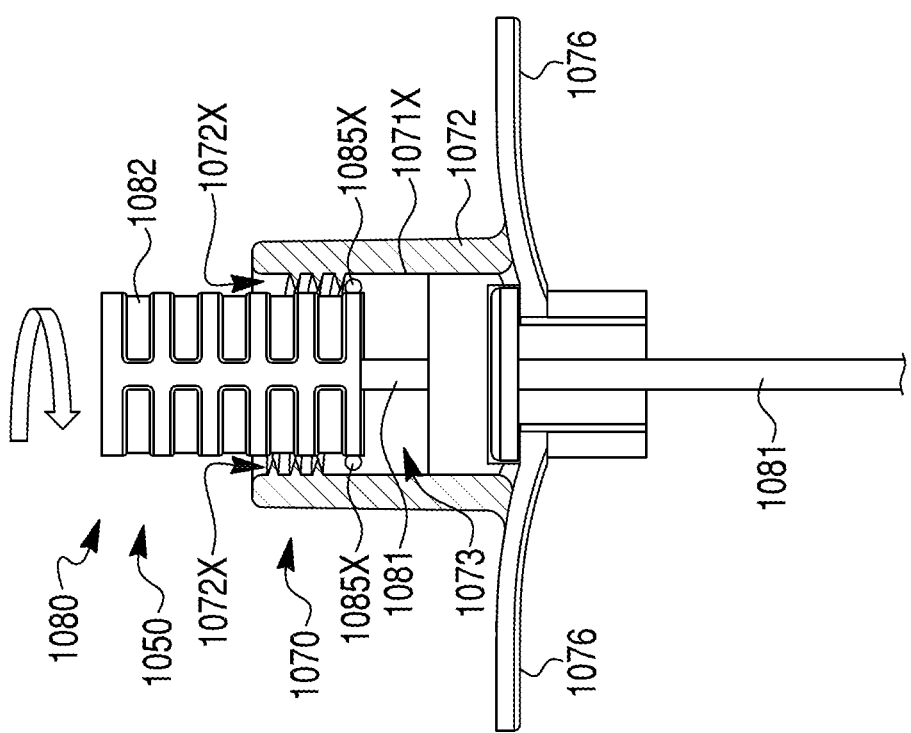

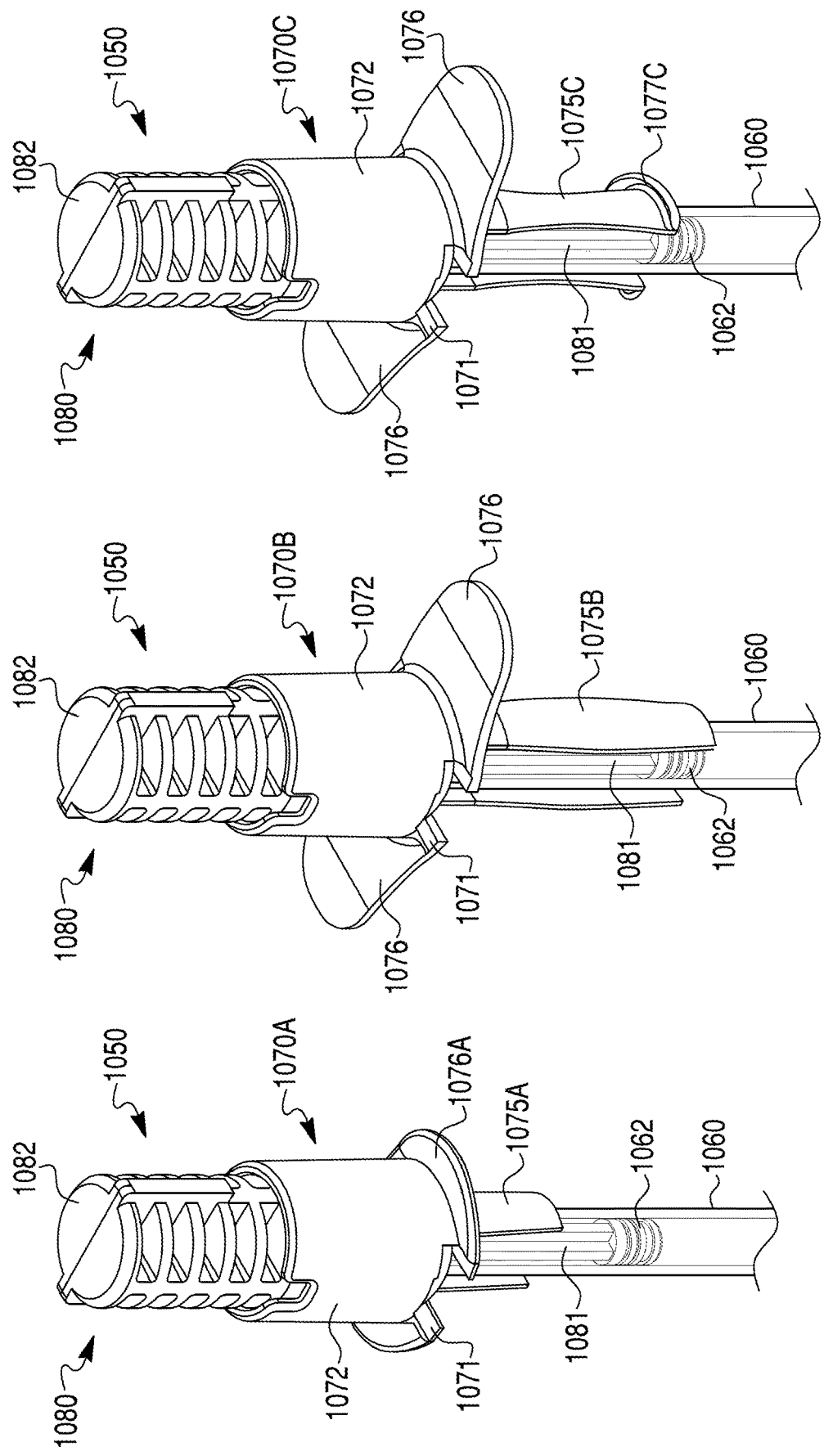

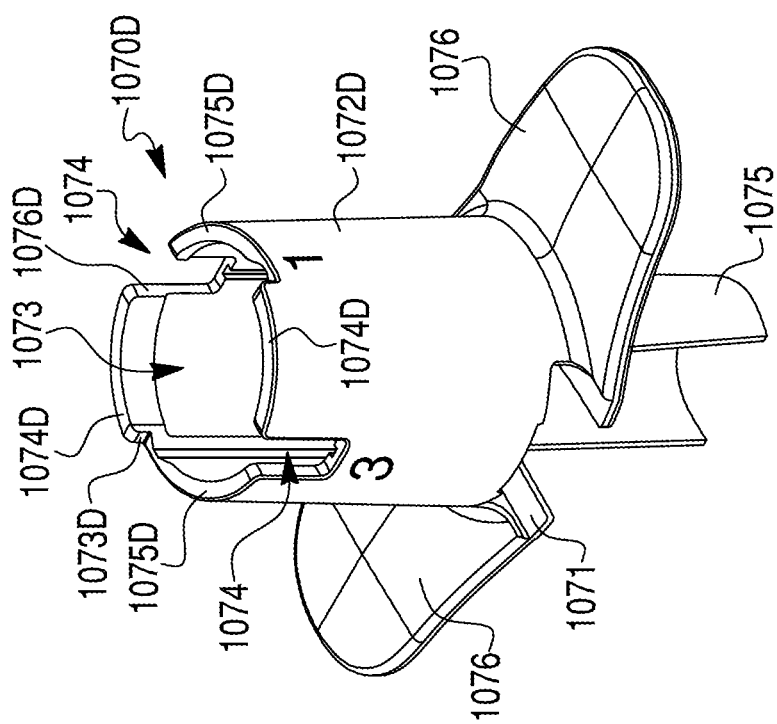
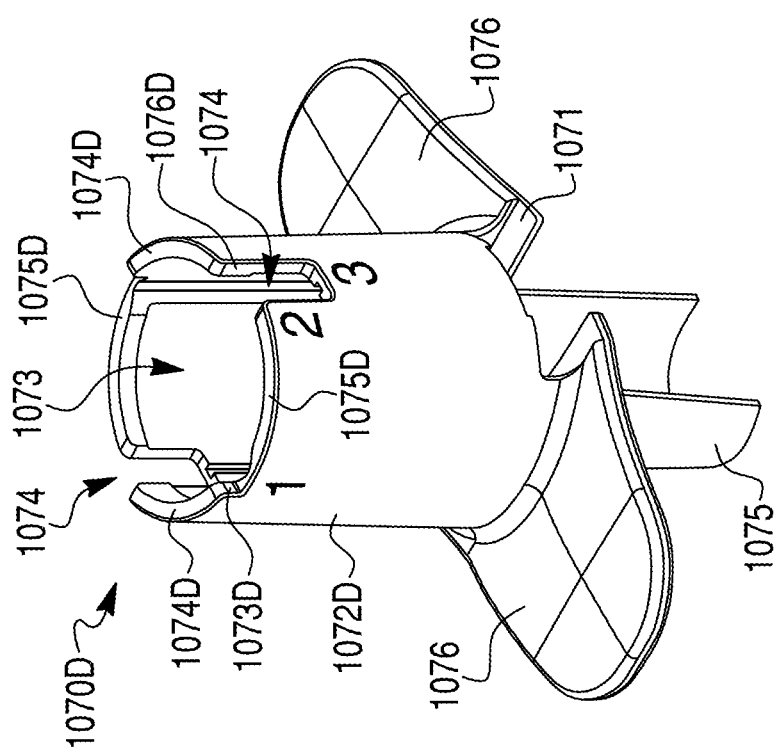
FIG. 2T
FIG. 2S

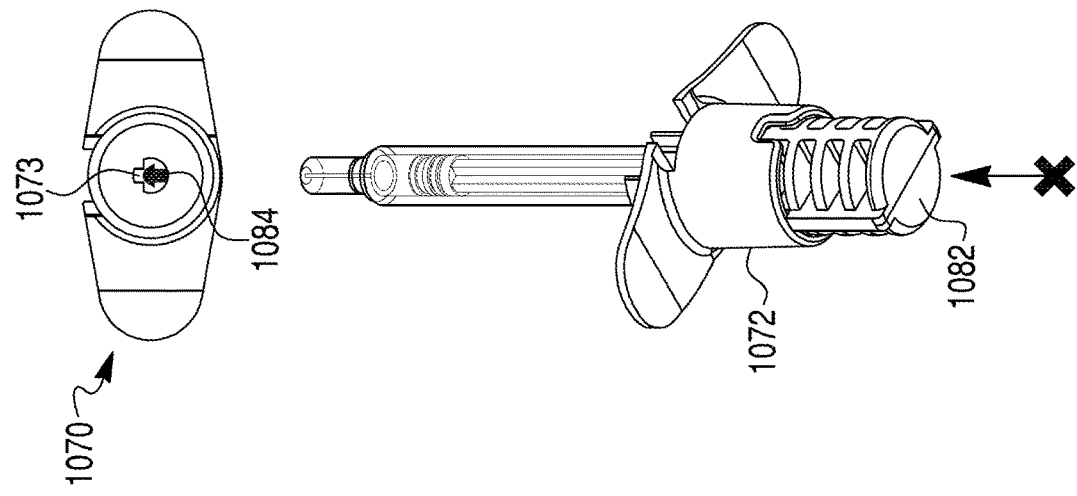
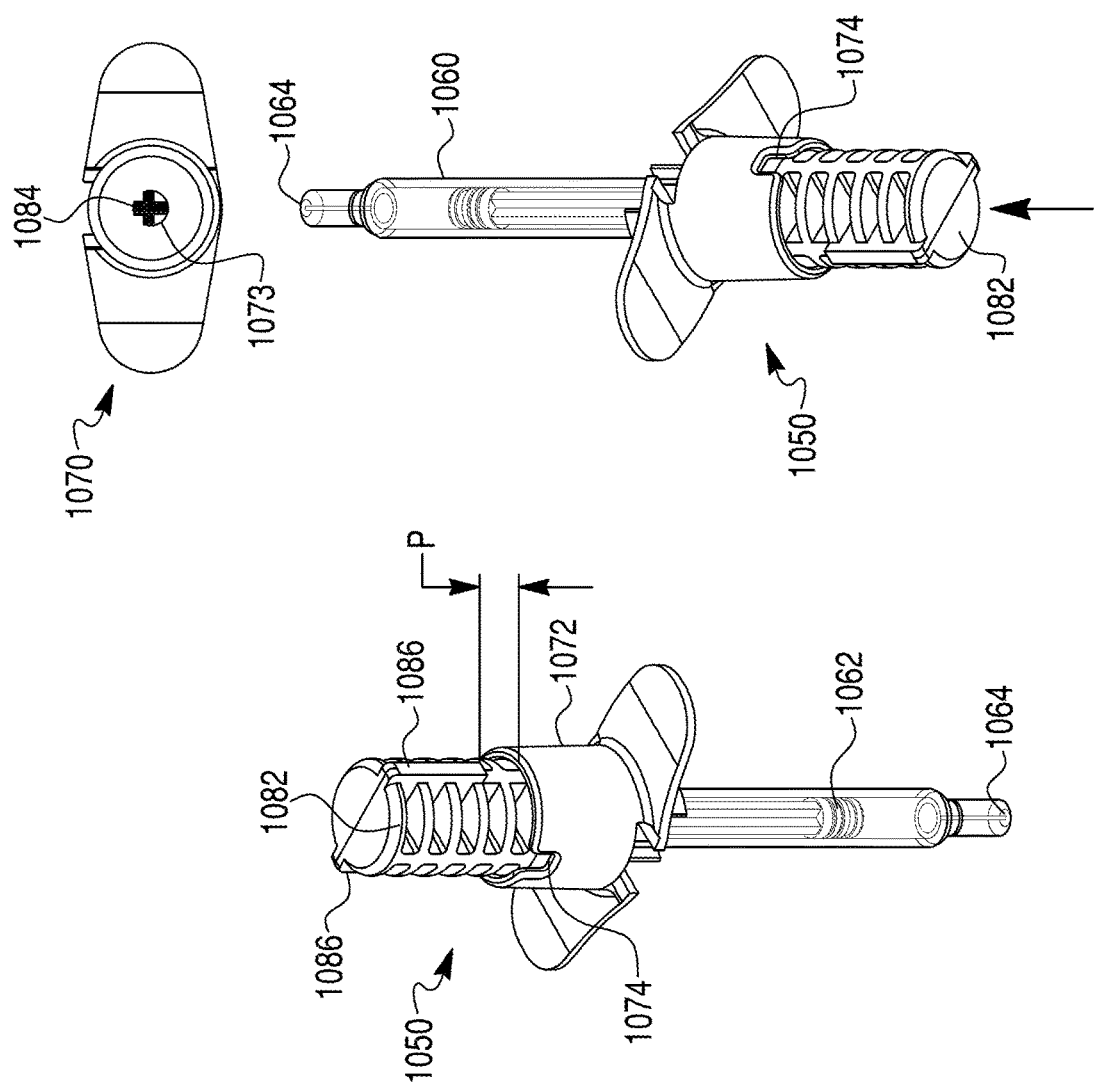

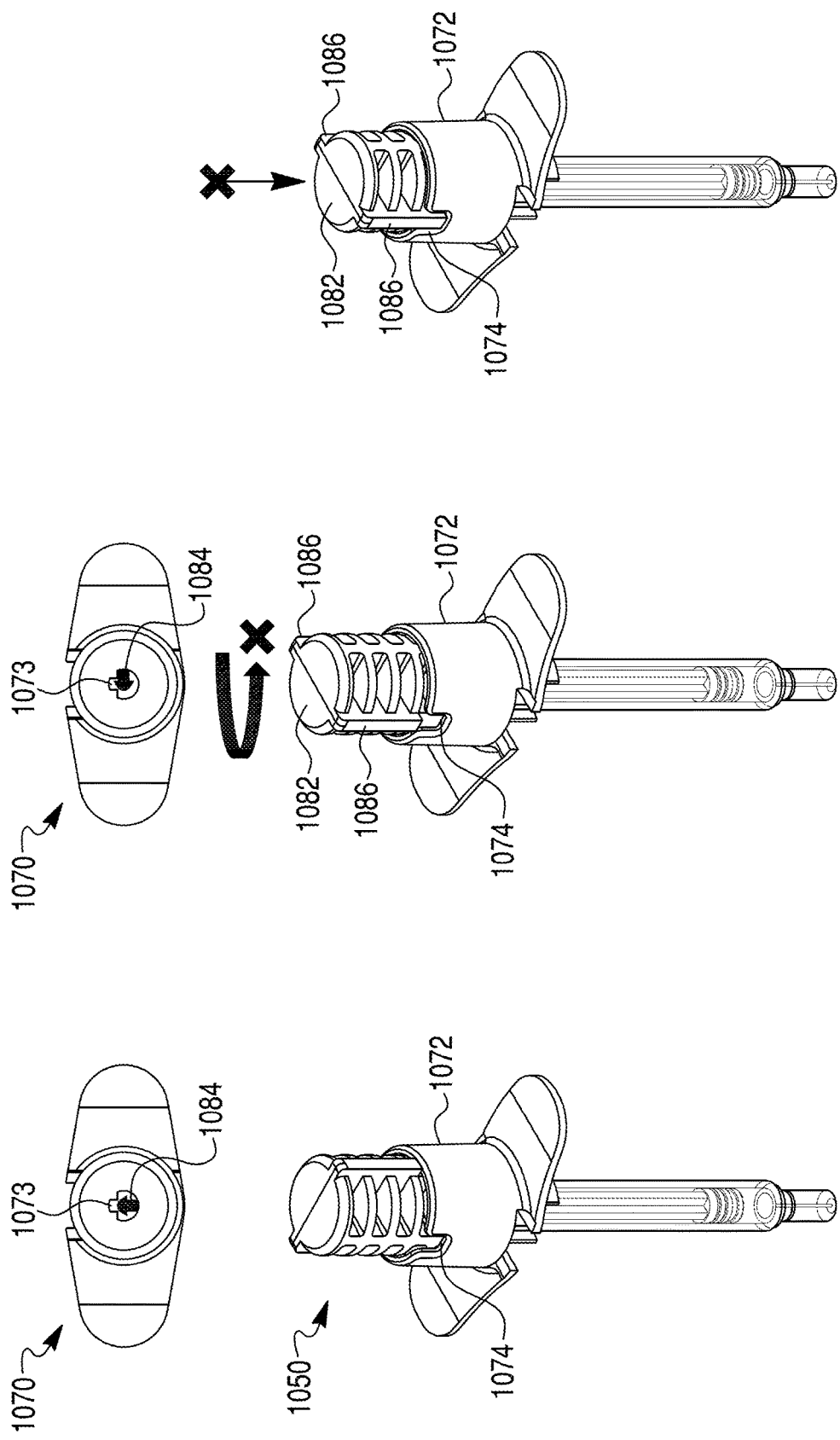

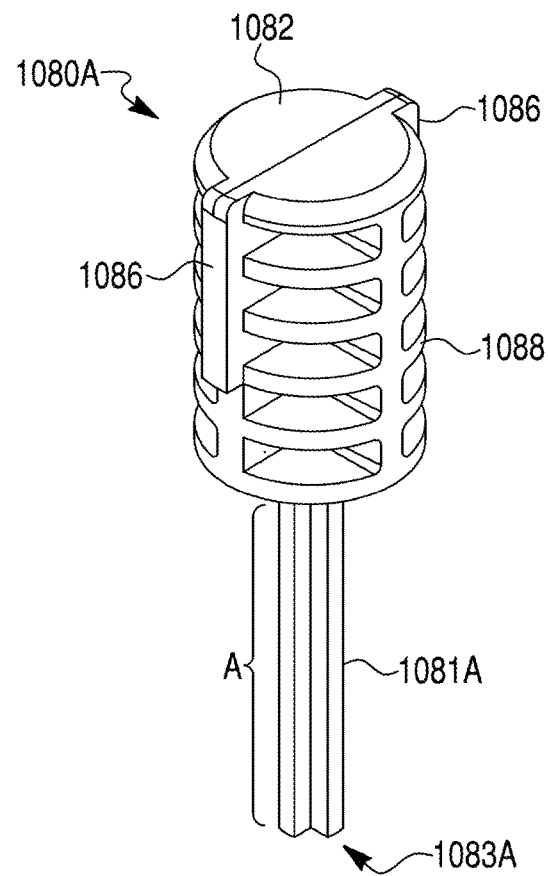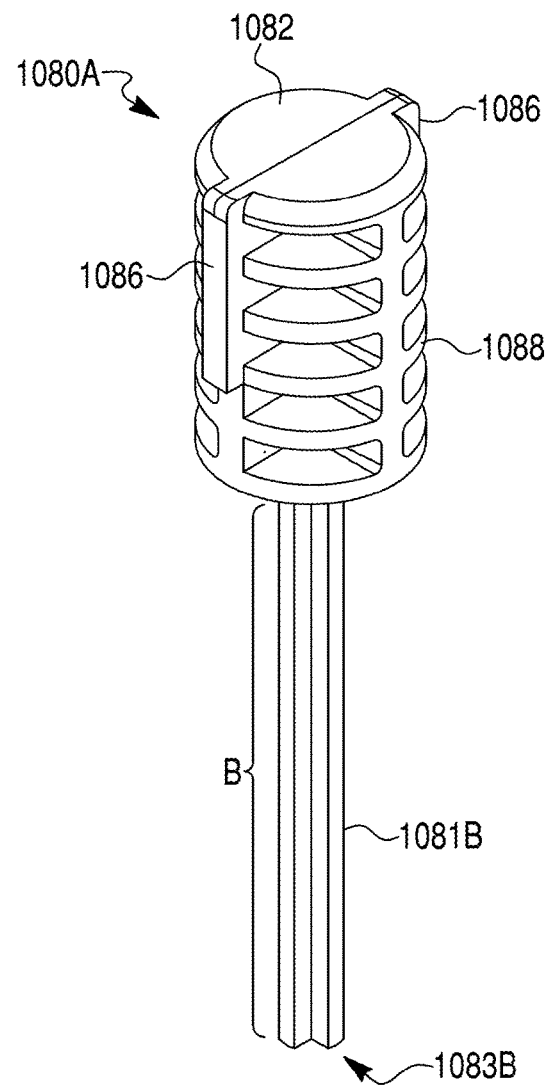
FIG. 4Y
FIG. 4Z

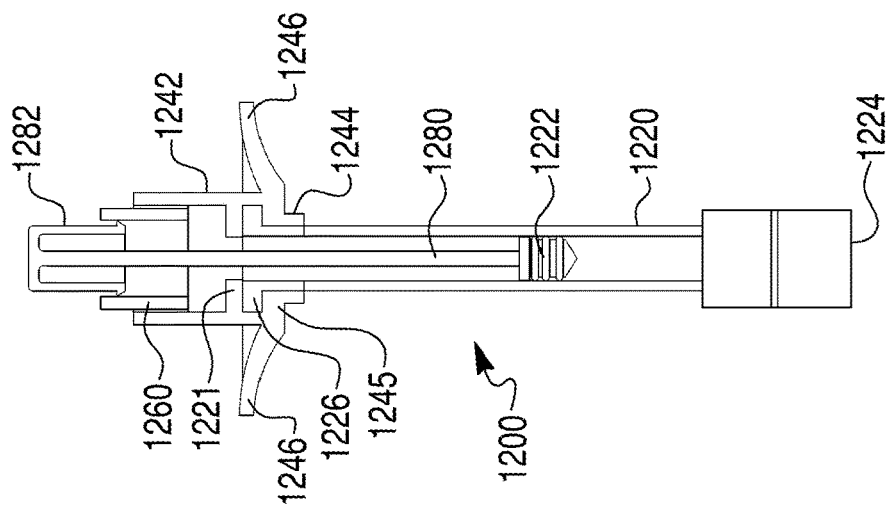
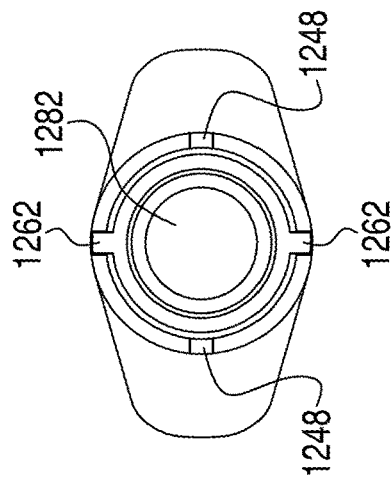
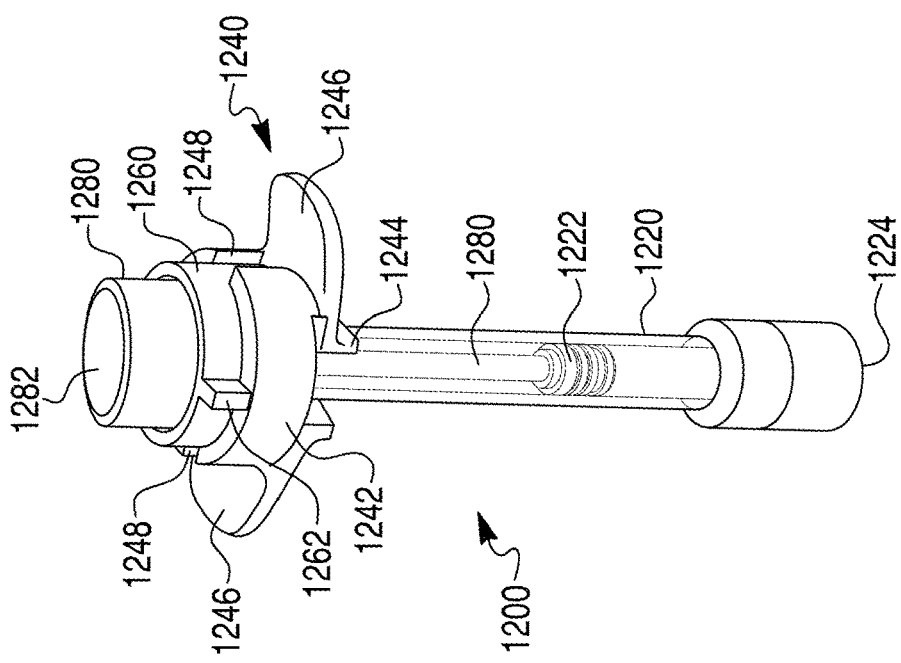

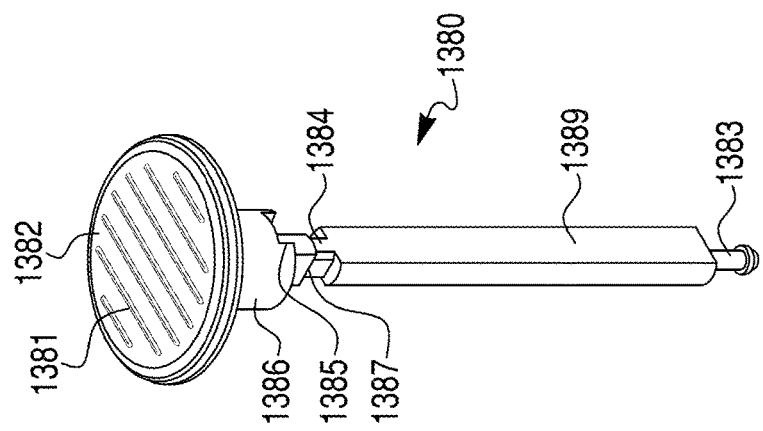
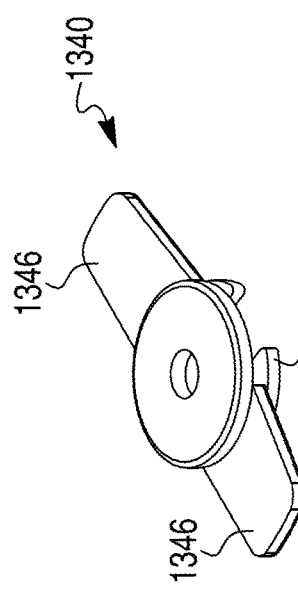
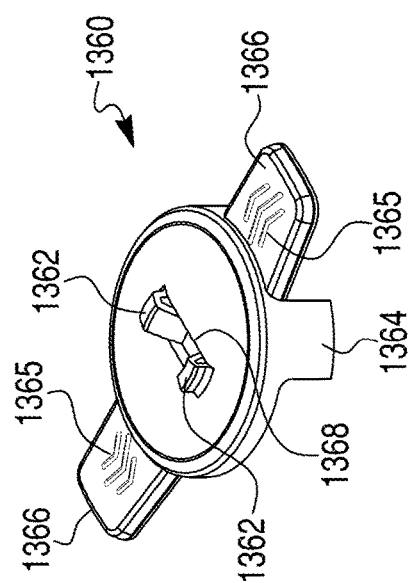
FIG. 6C
FIG. 6A
FIG. 6B

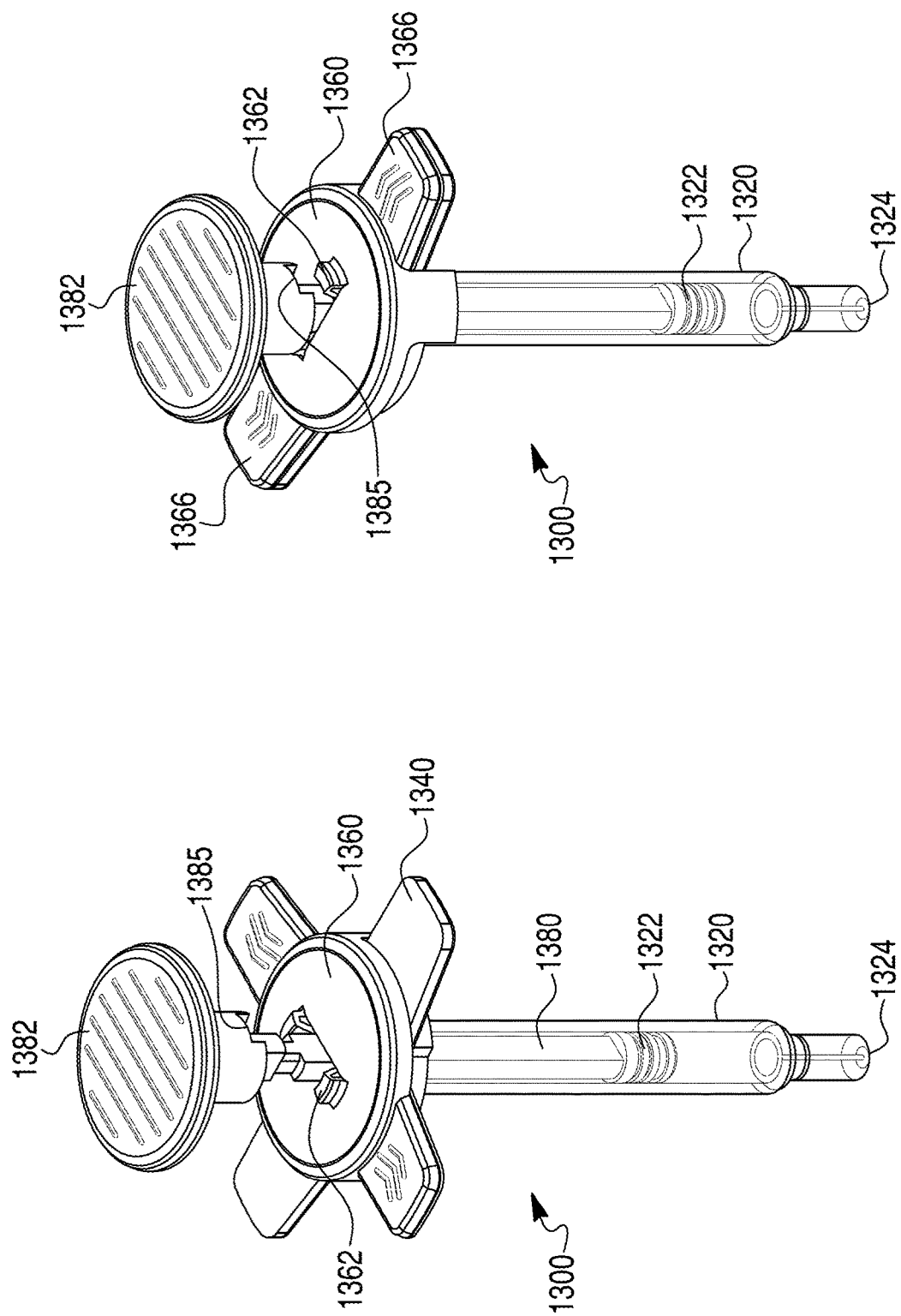

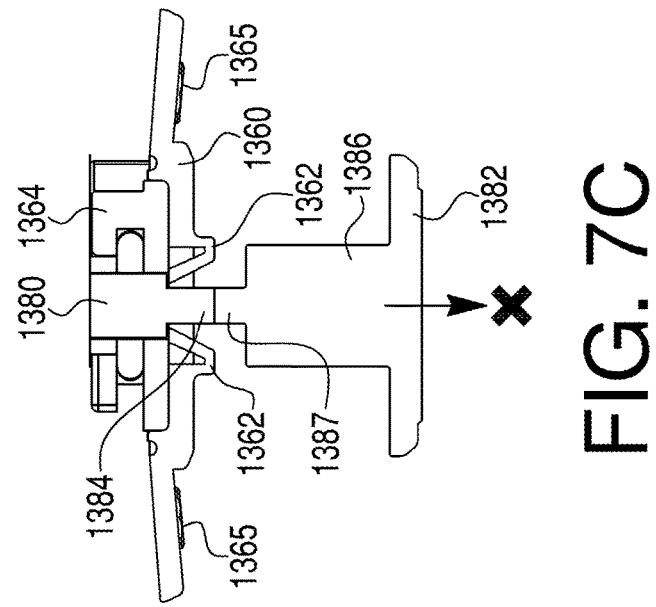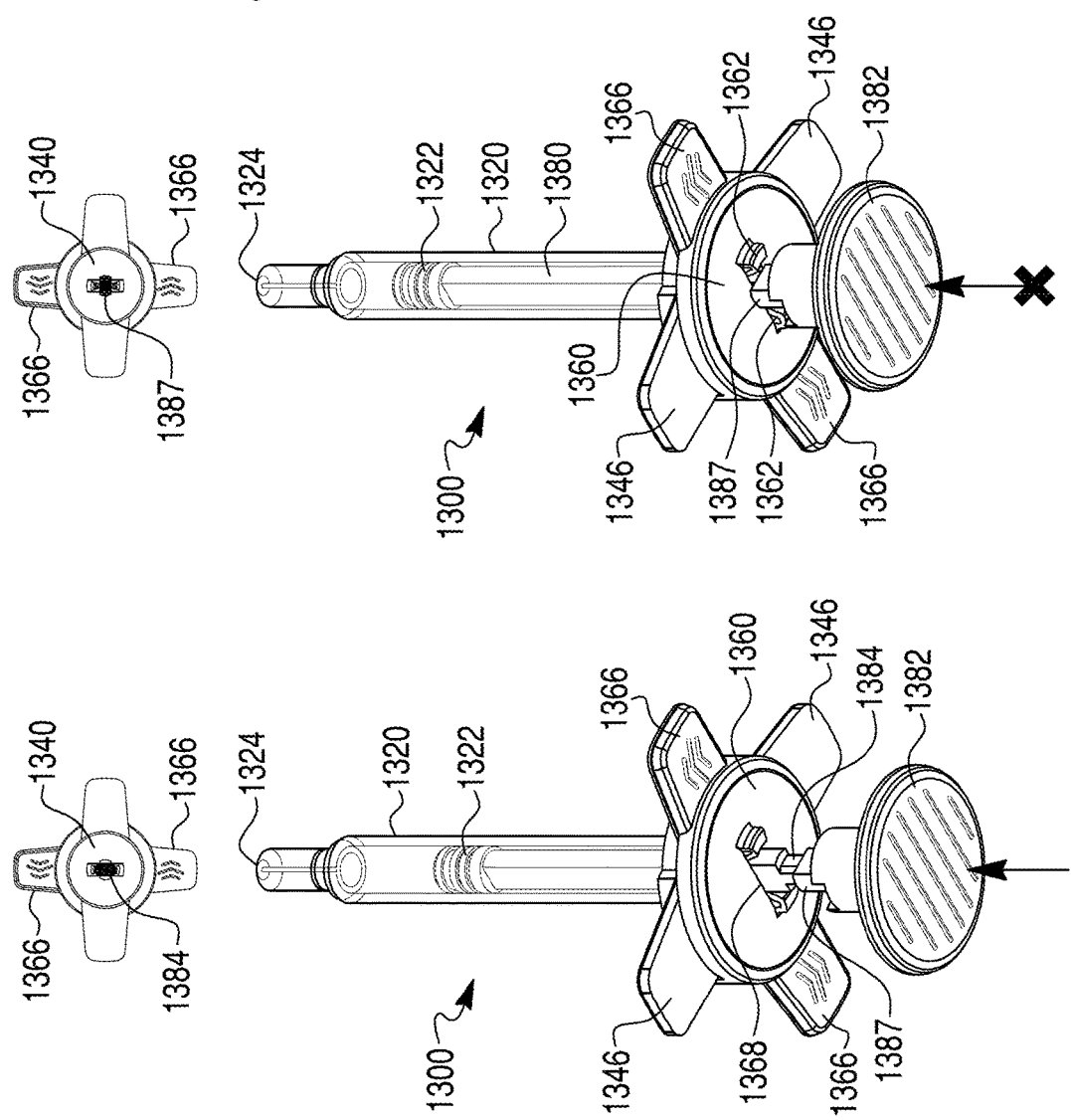

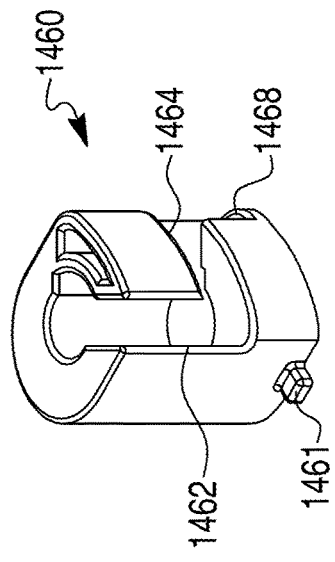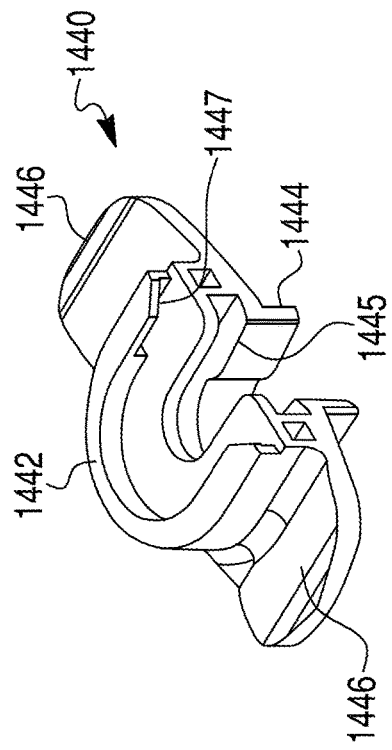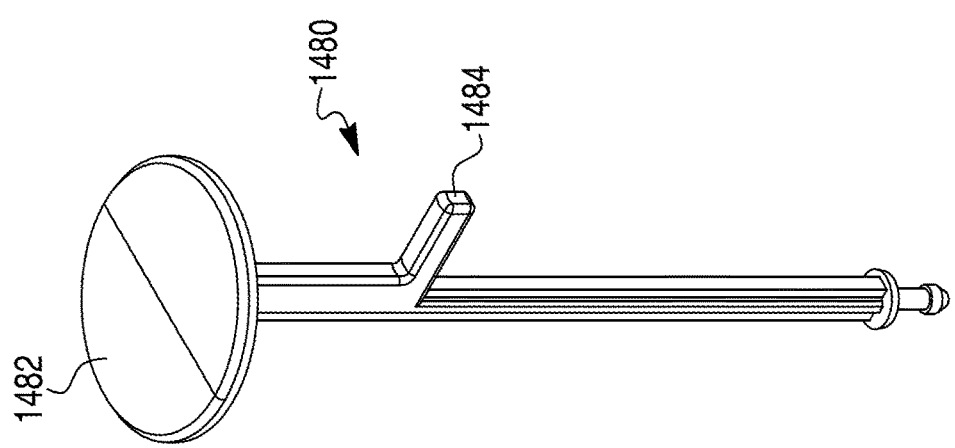

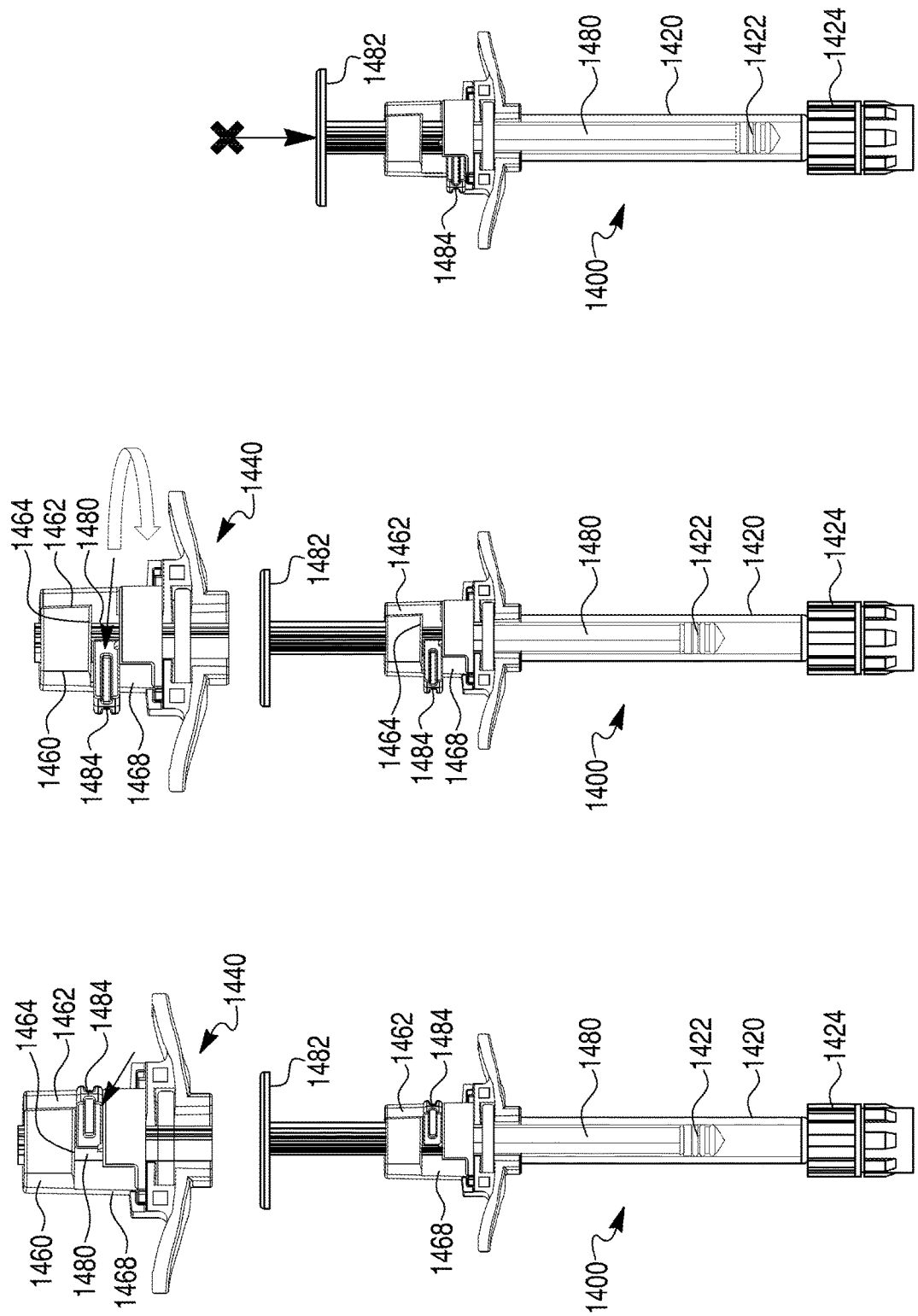

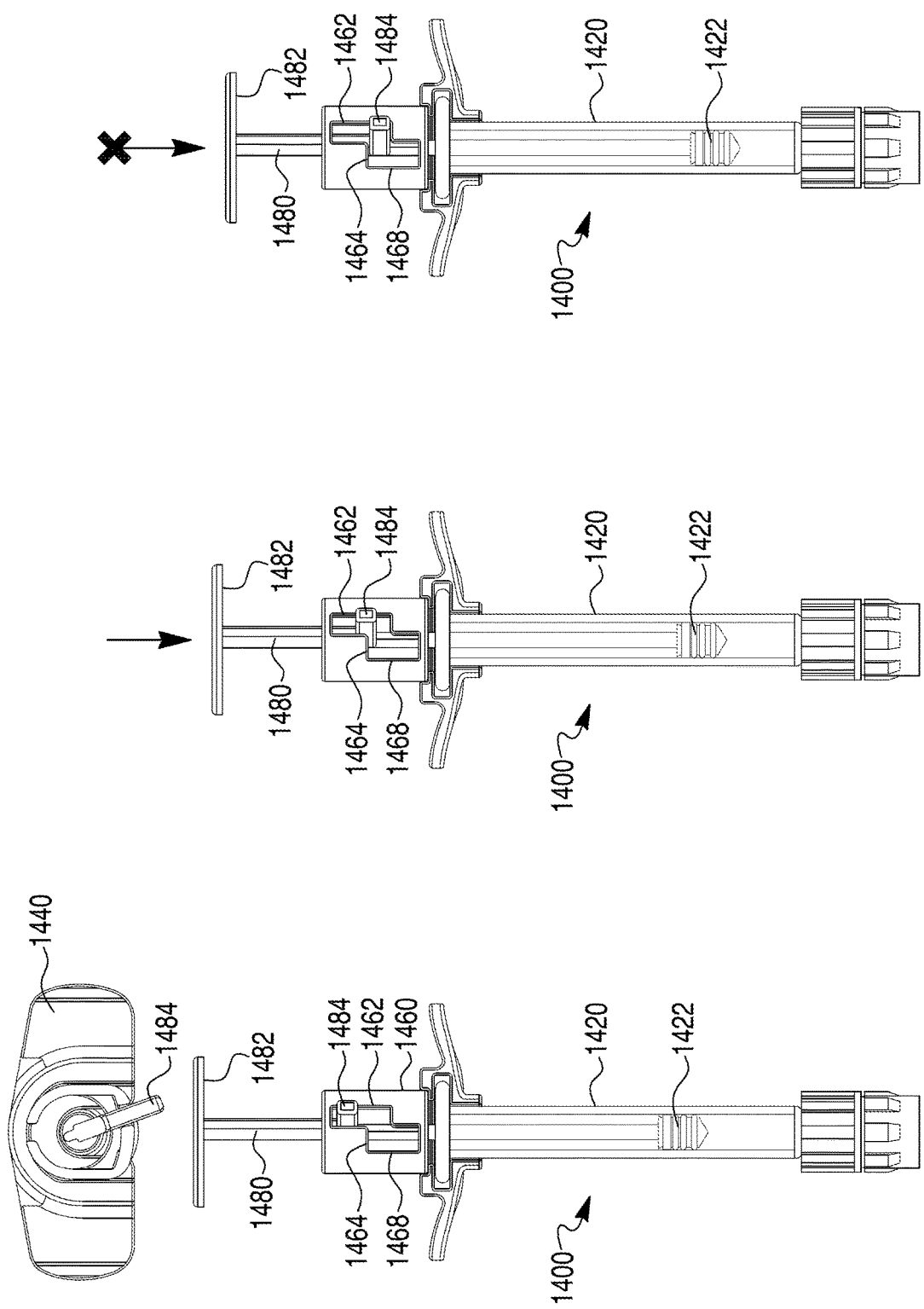

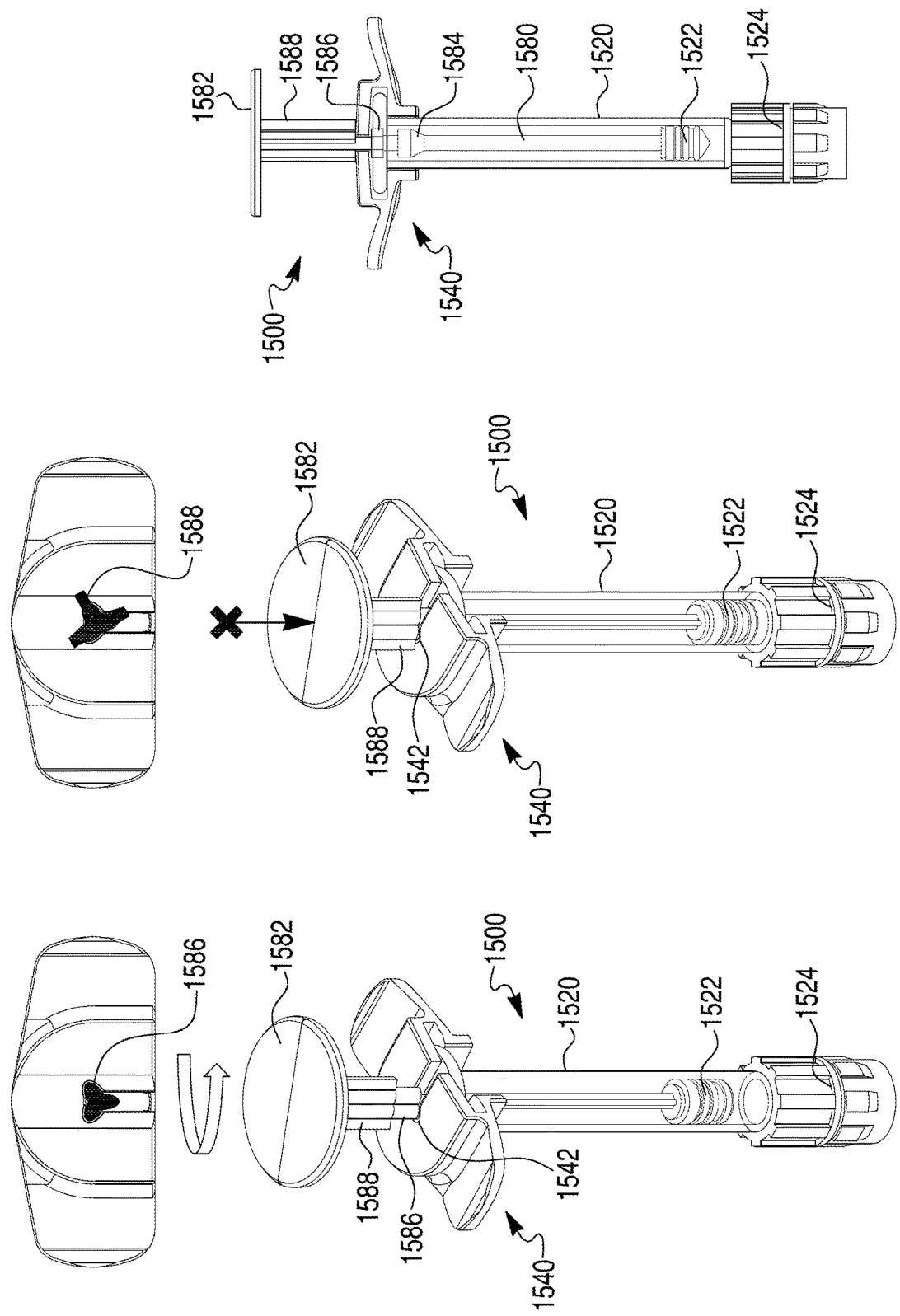

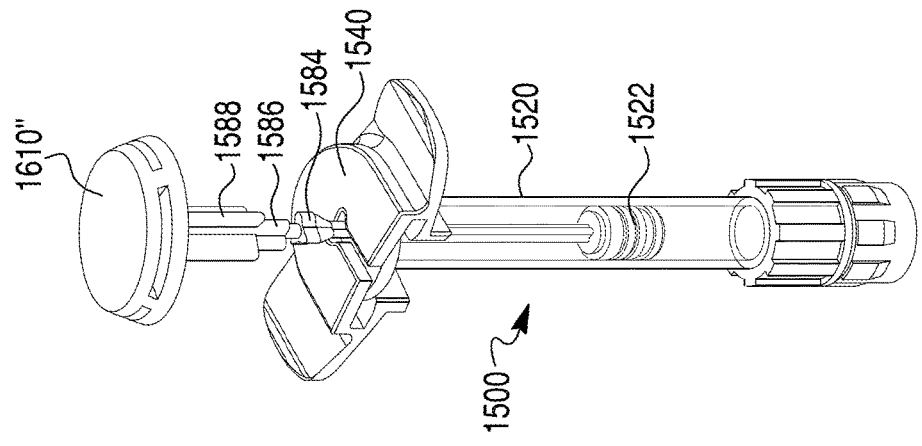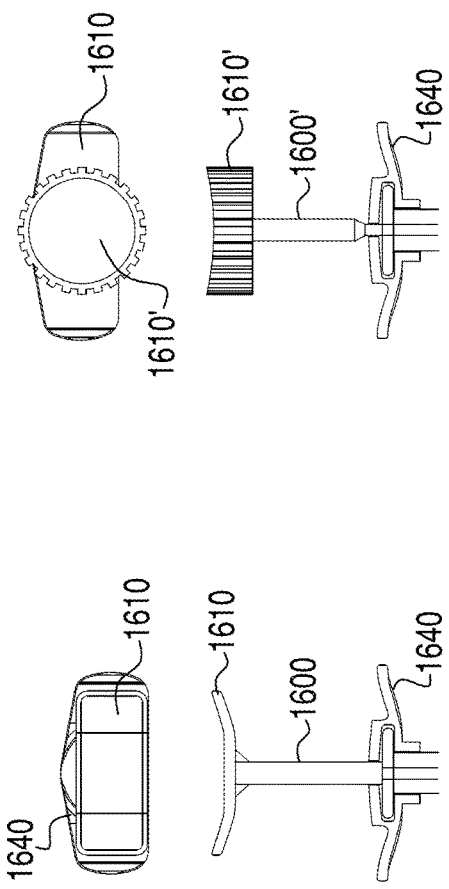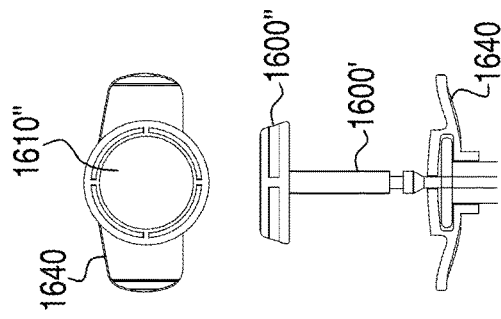

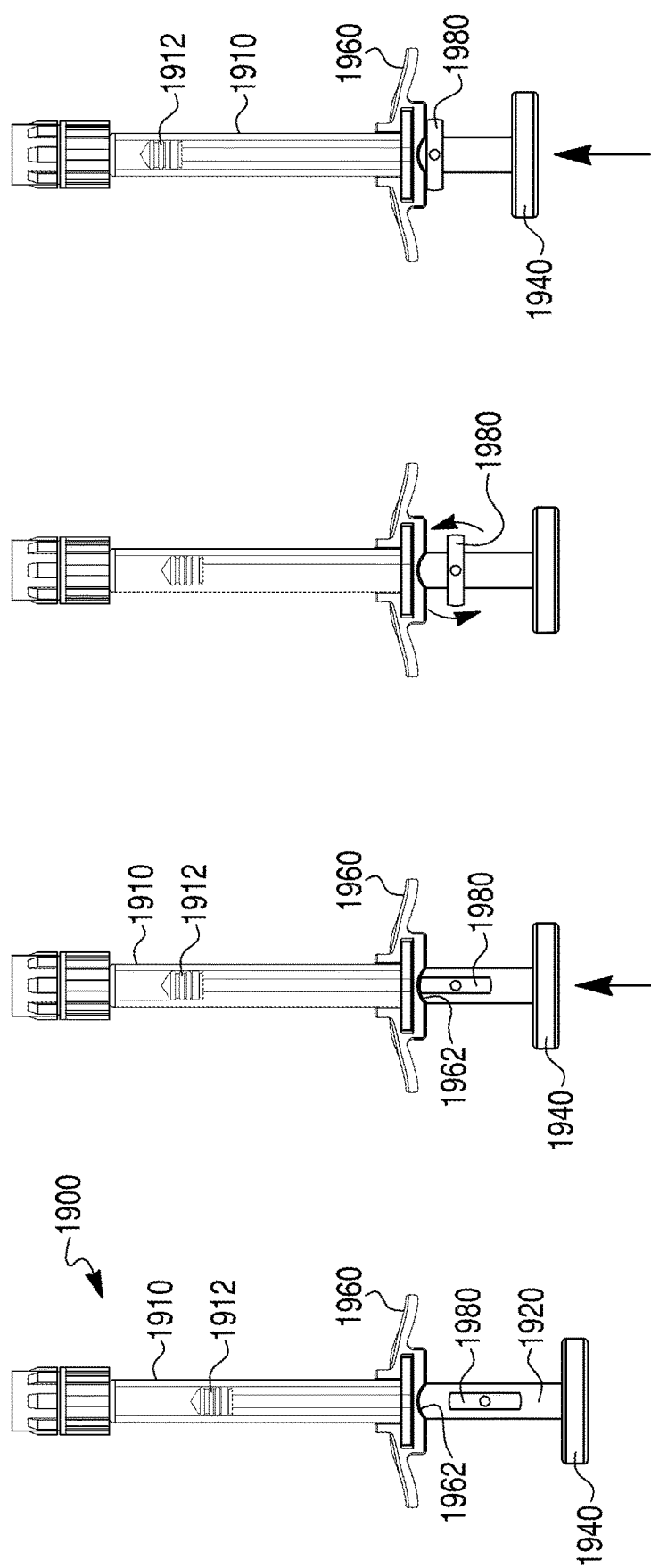

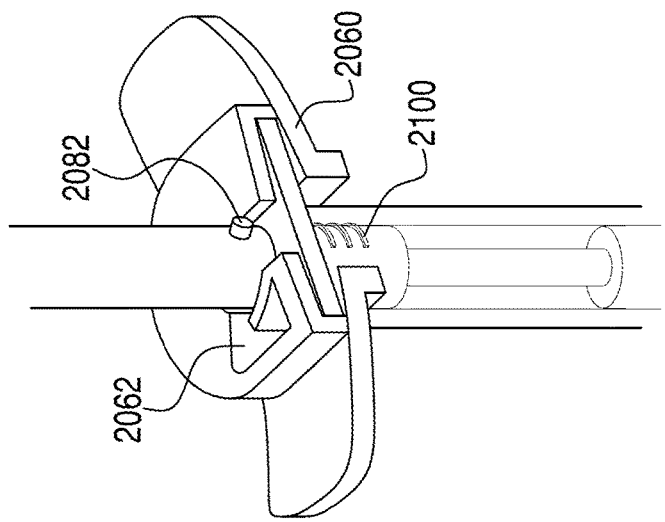
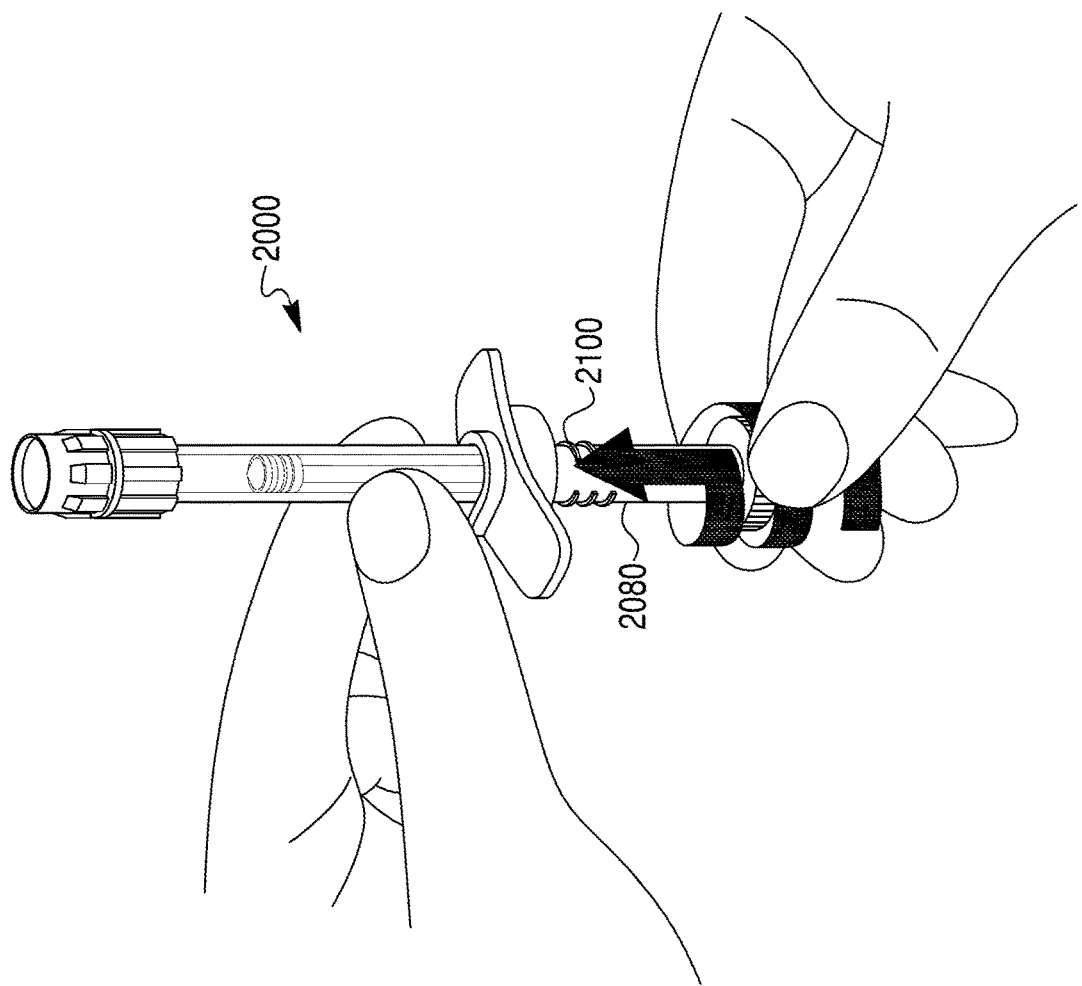
FIG. 25B
FIG. 25A

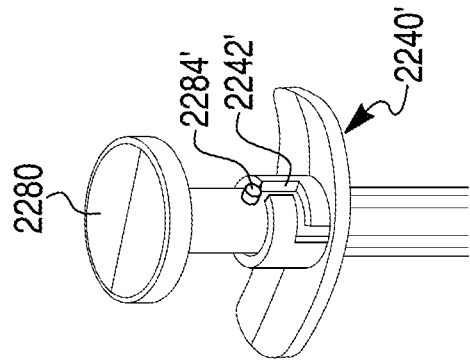
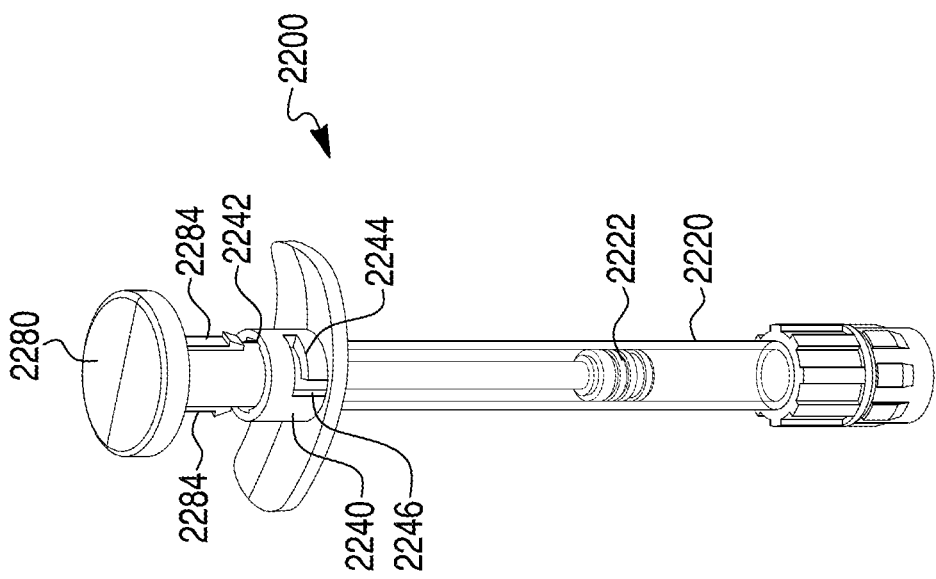

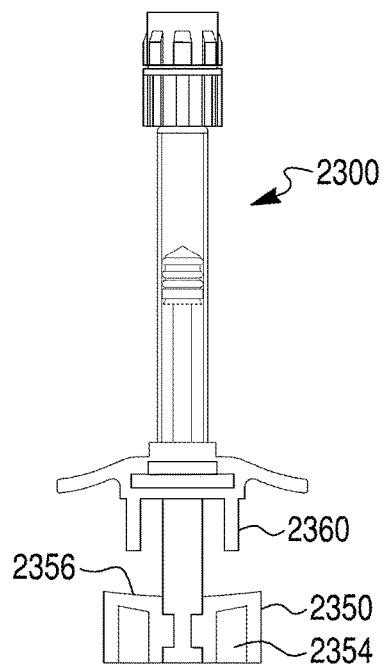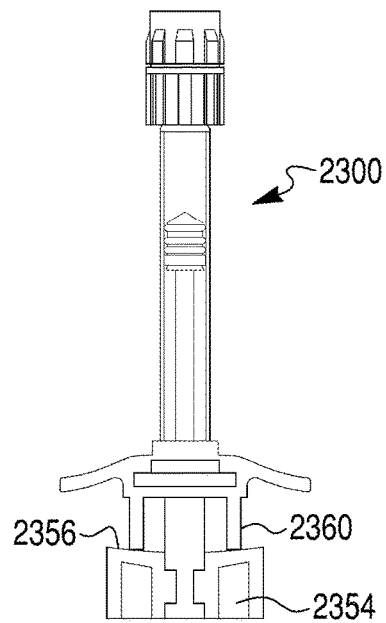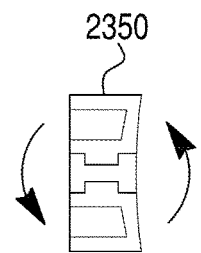
FIG. 27D    FIG. 27E    FIG. 27F
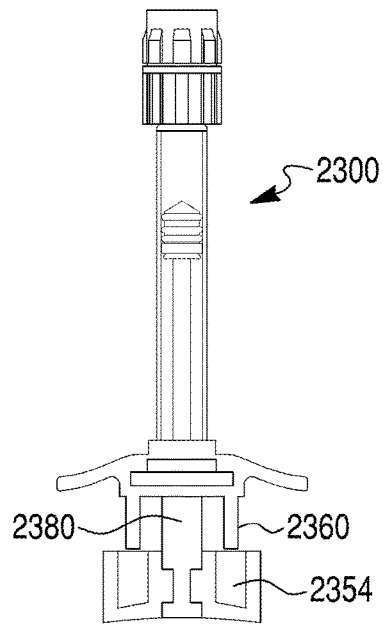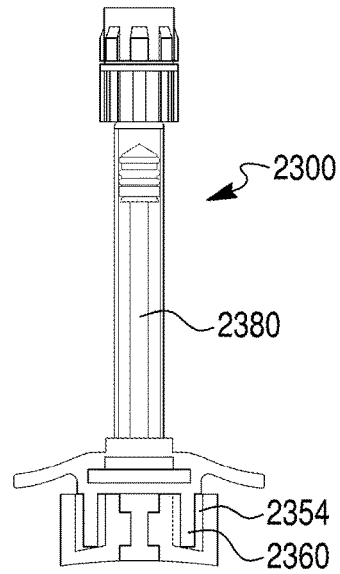
FIG. 27G    FIG. 27H

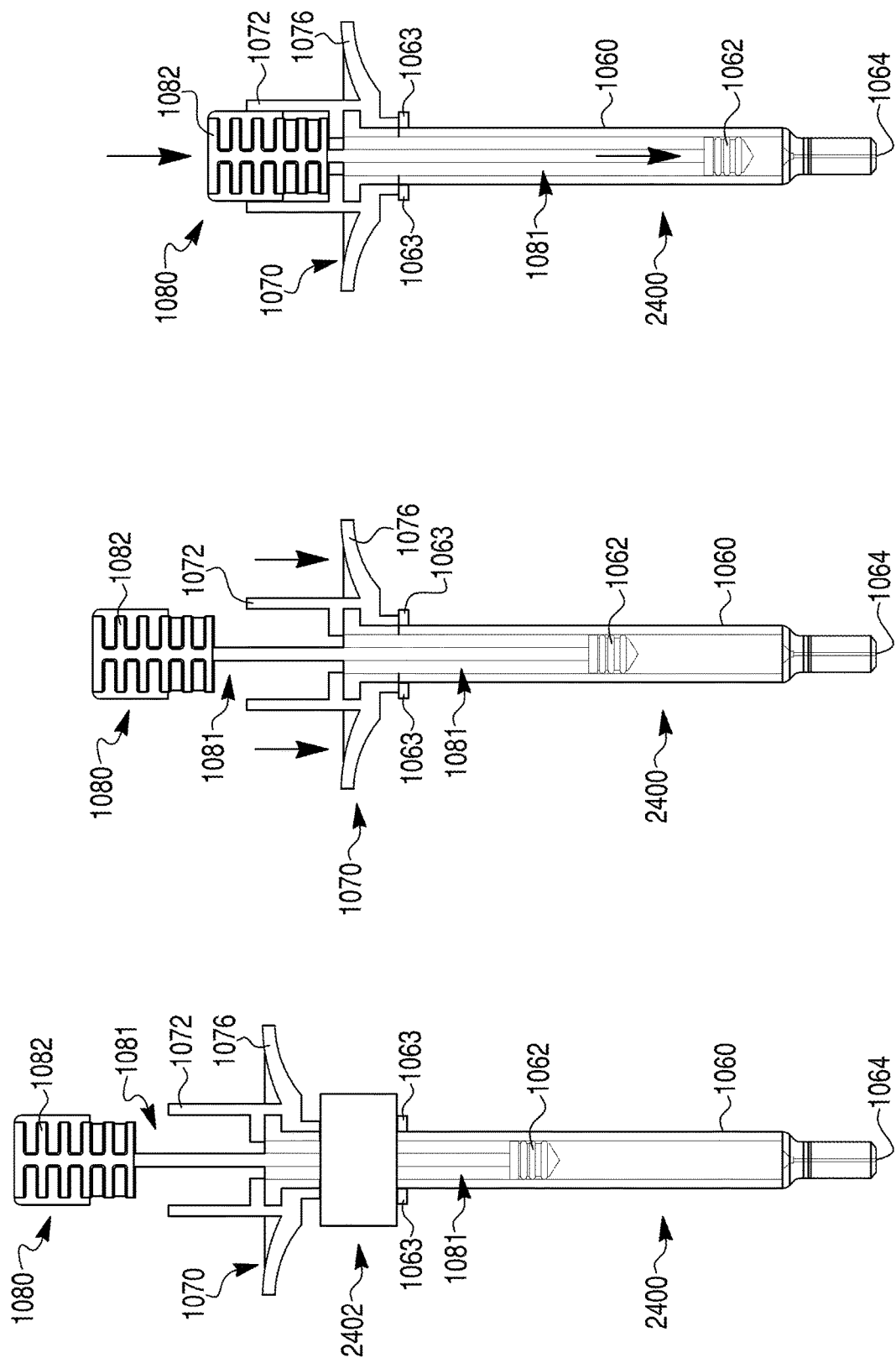

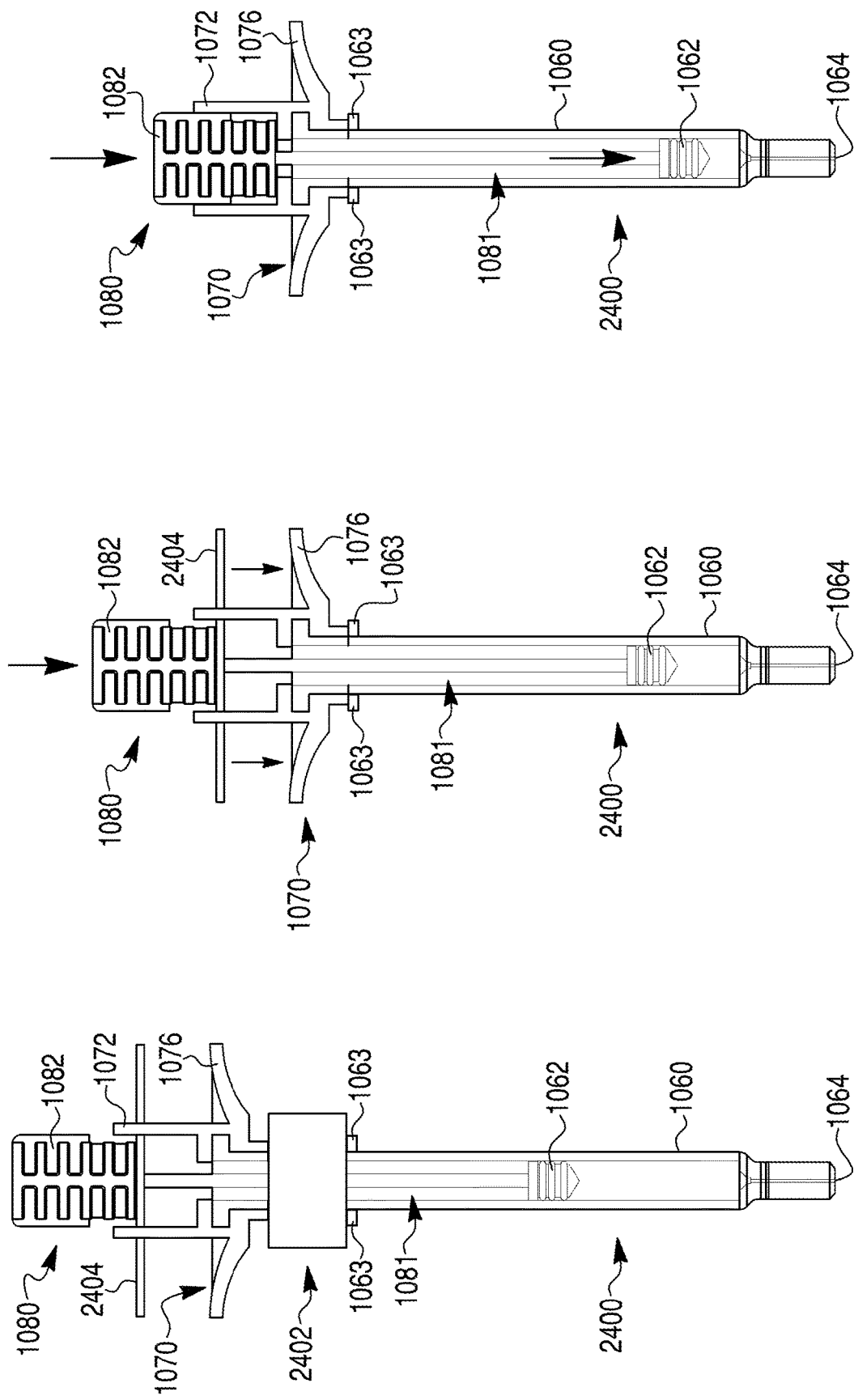

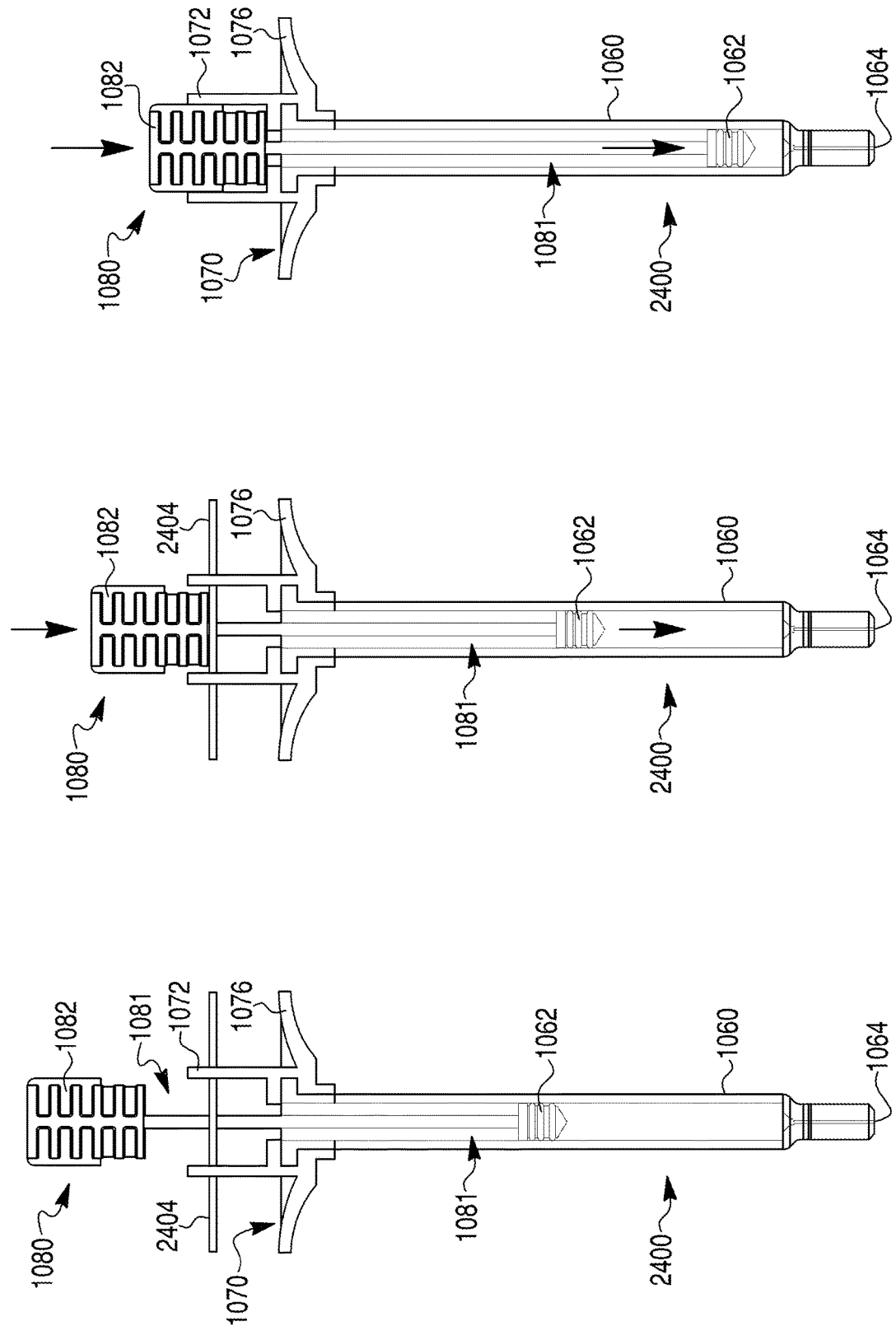

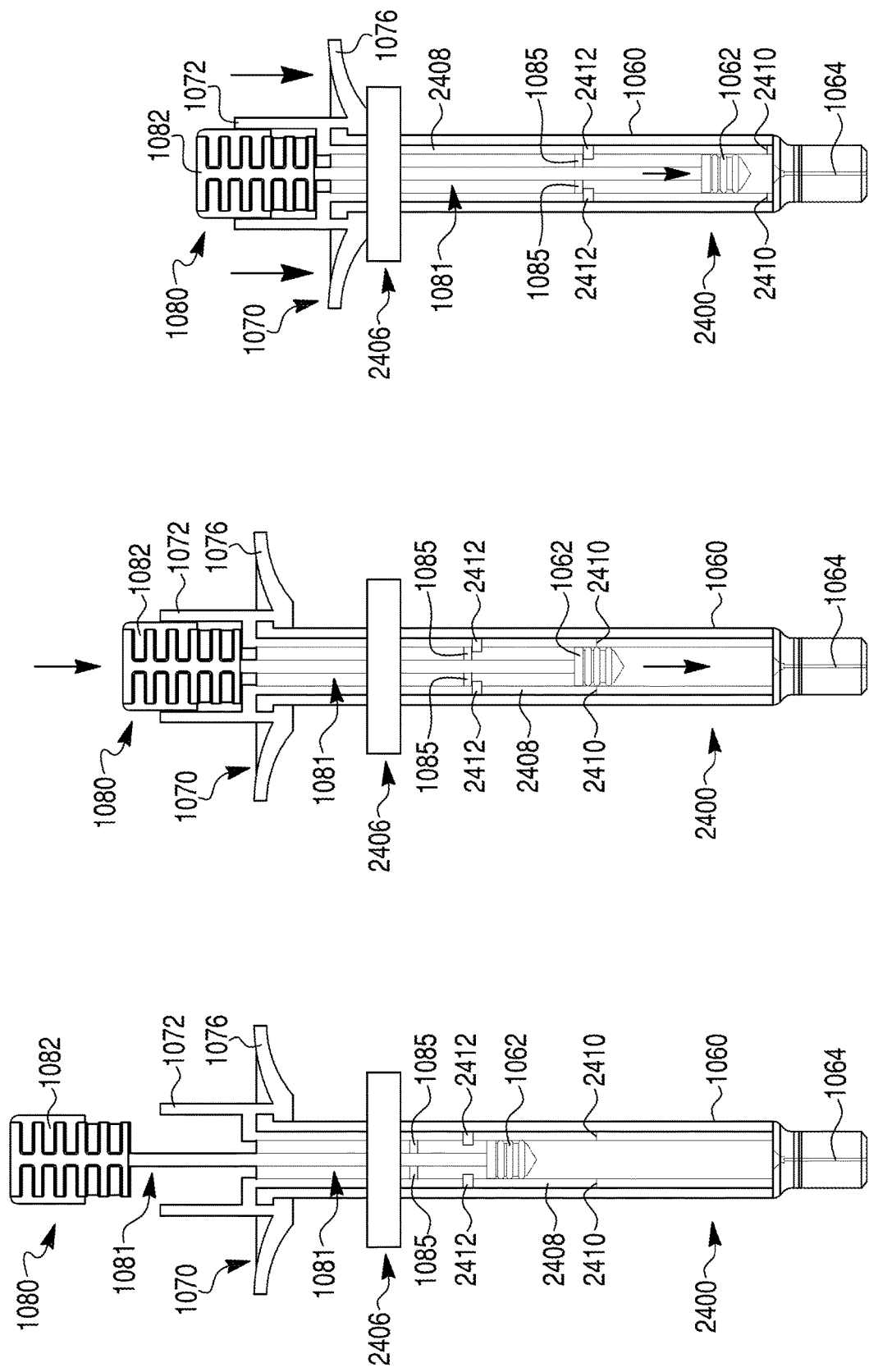

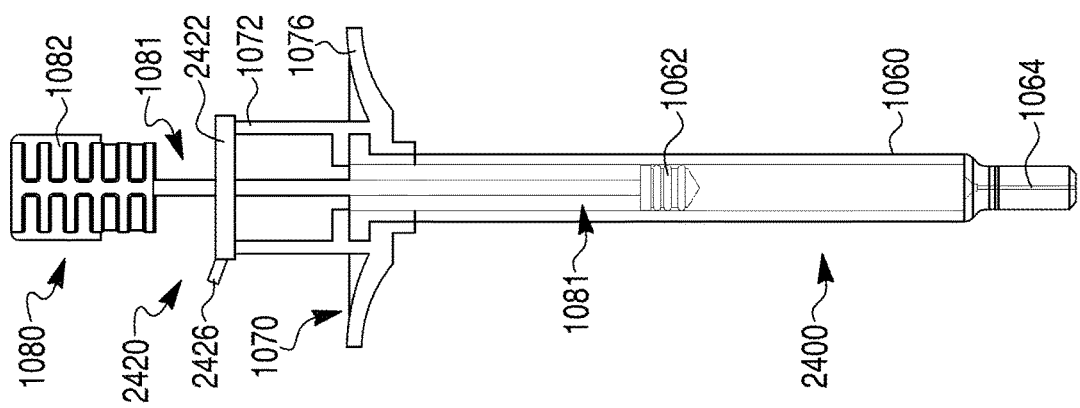
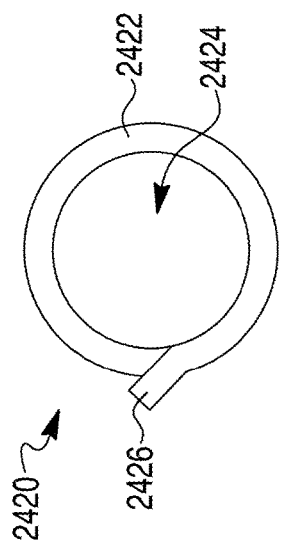
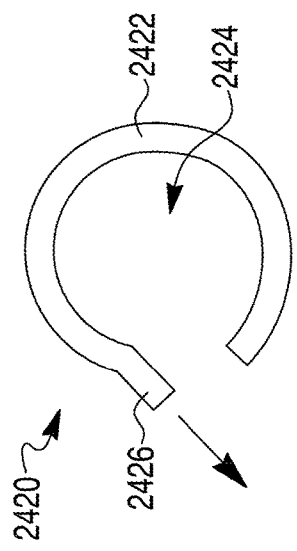

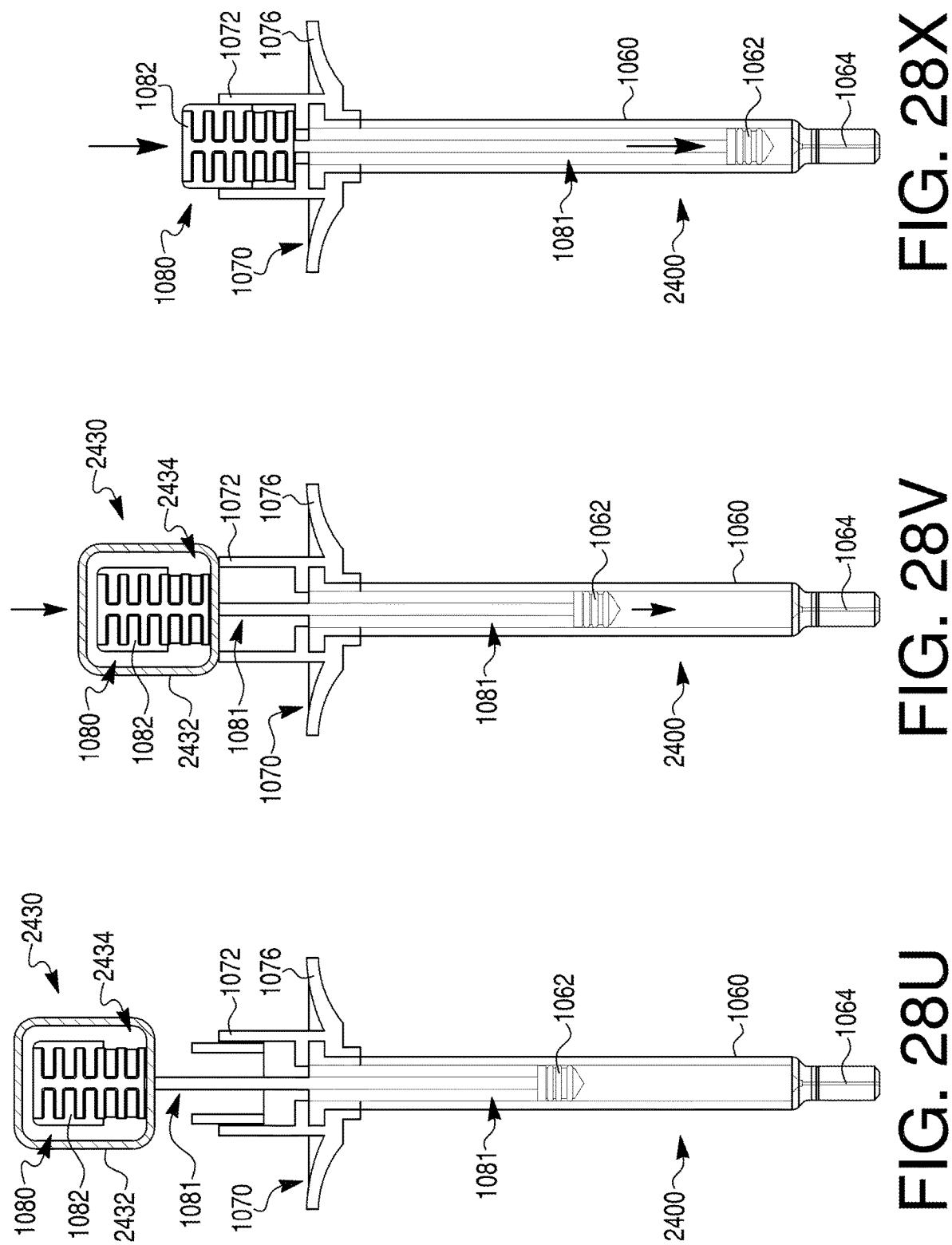

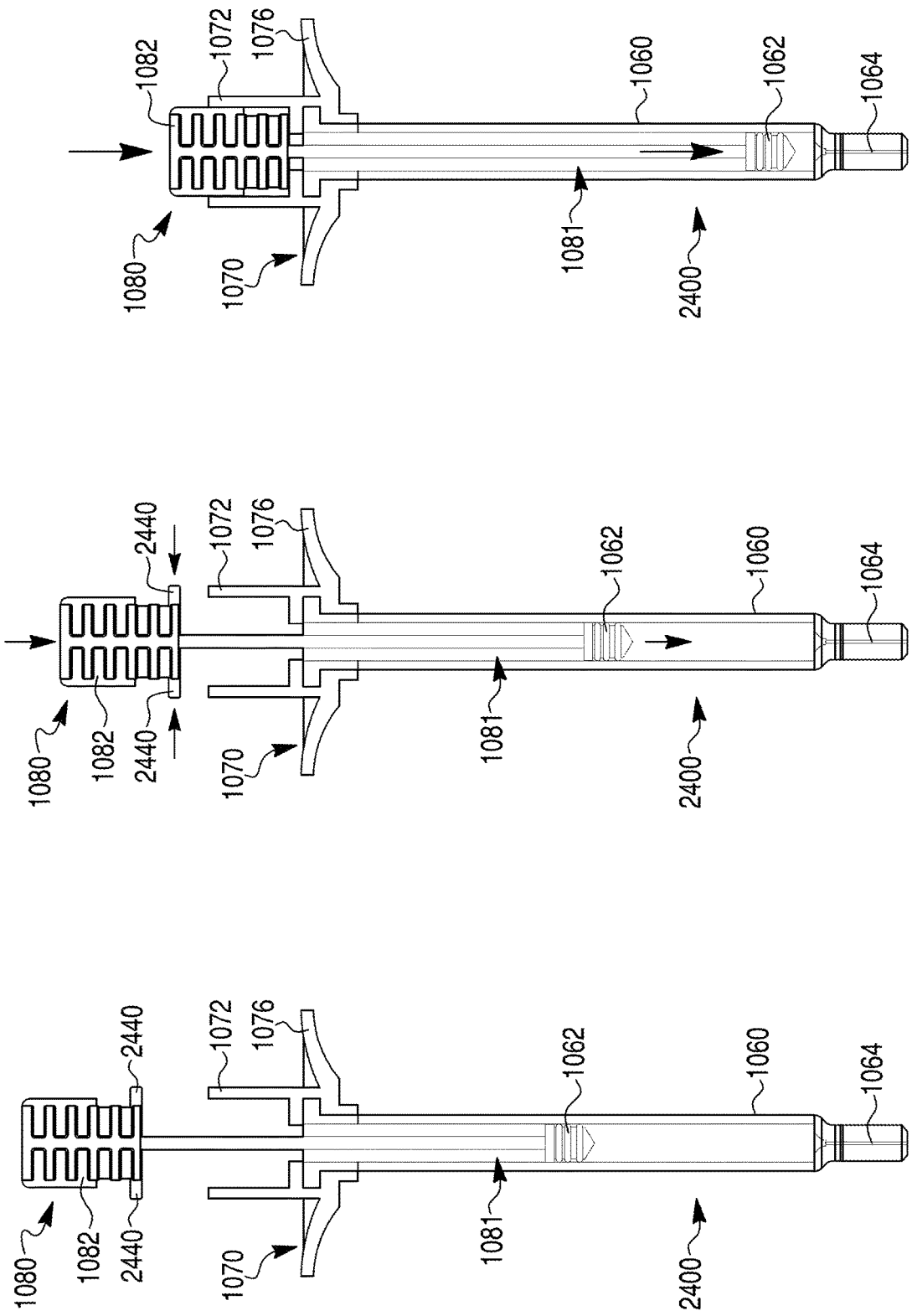

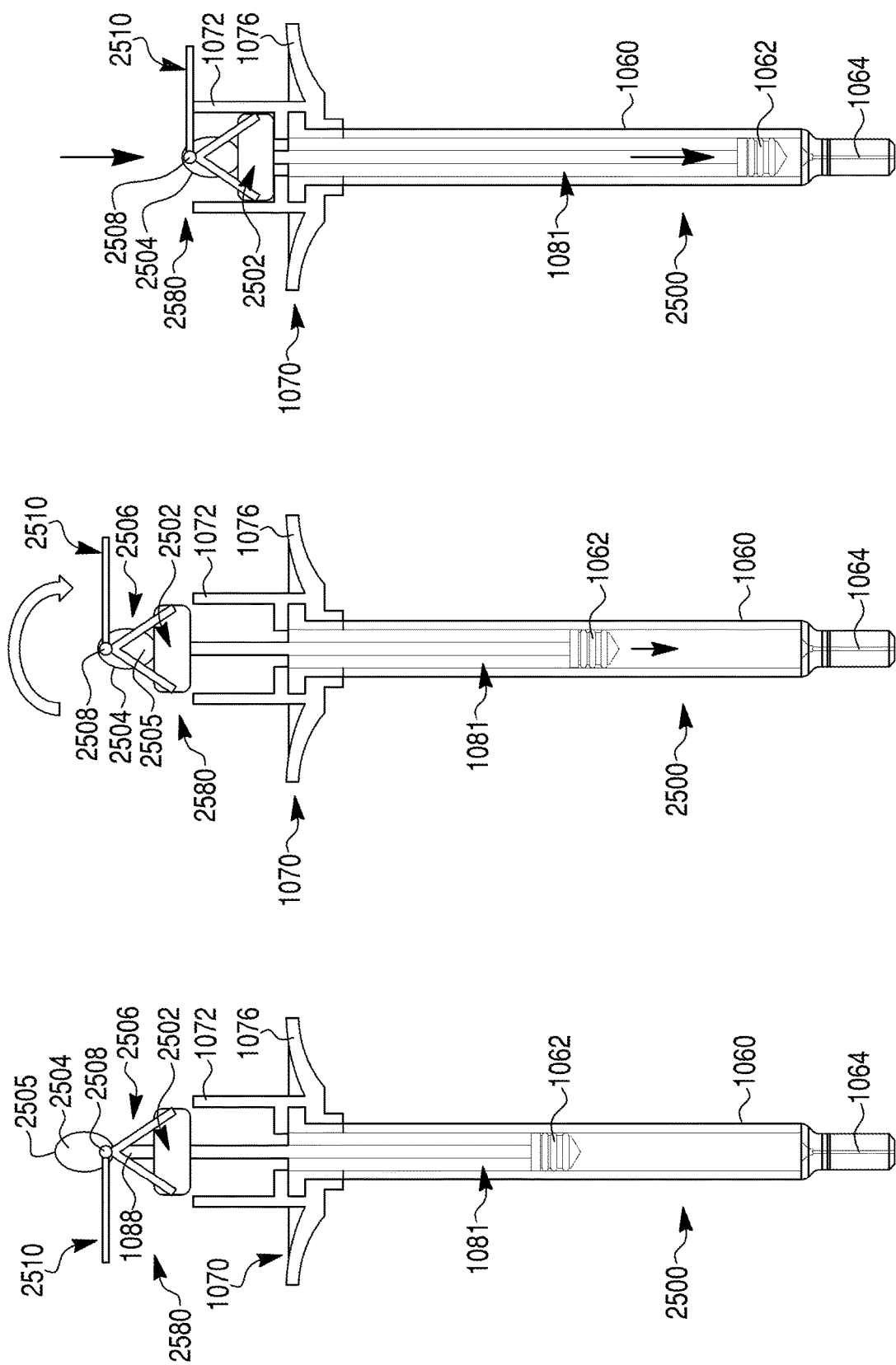

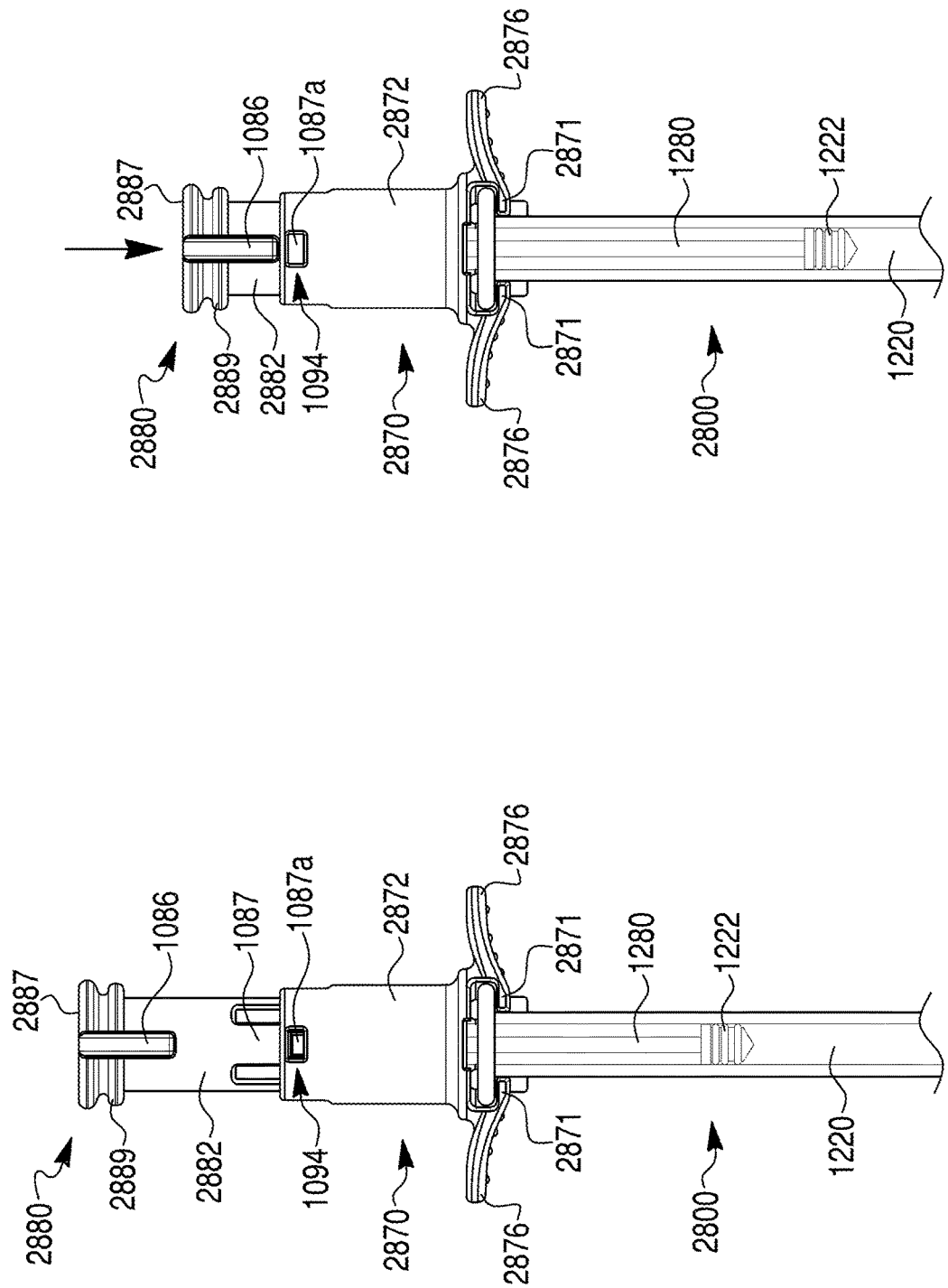

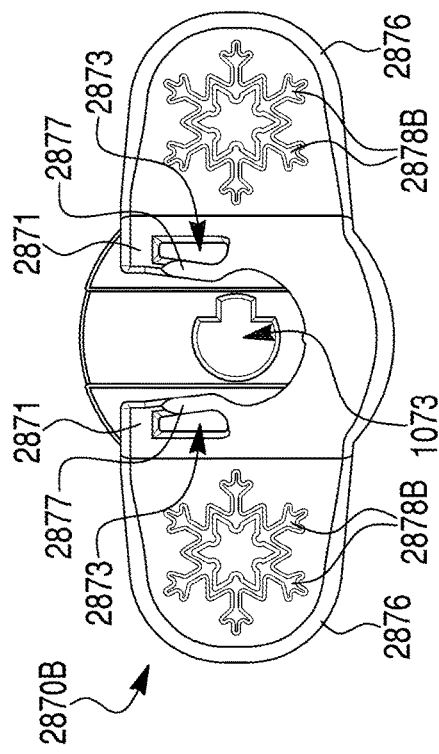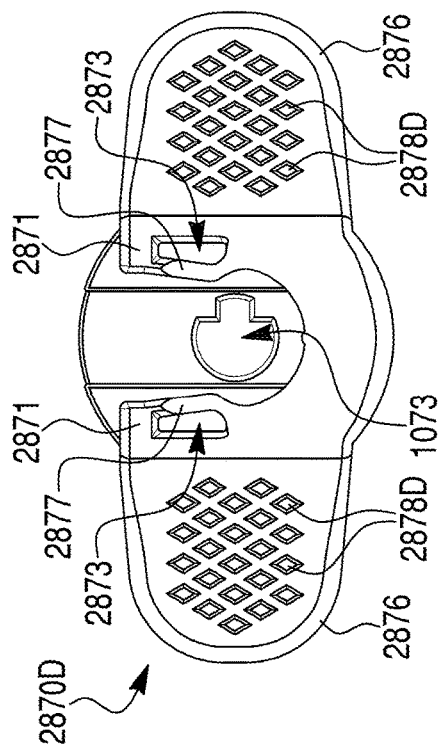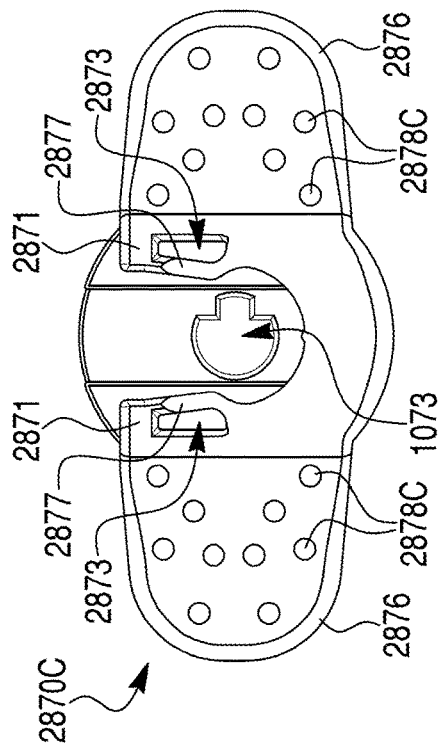

DEVICES AND METHODS FOR PRECISION DOSE DELIVERY

CROSS-REFERENCE TO RELATED APPLICATIONS

This application is a continuation application under 35 U.S.C. § 111(a) of pending International Application No. PCT/US2020/036200, filed Jun. 4, 2020, which claims priority to U.S. Provisional Application No. 62/857,678, filed on Jun. 5, 2019; and U.S. Provisional Application No. 62/860,481, filed on Jun. 12, 2019.

FIELD OF DISCLOSURE

Aspects of the present disclosure relate to devices and methods for priming or otherwise configuring a dose delivery device, e.g., a syringe, to promote precision dose delivery. More specifically, embodiments of the present disclosure relate to devices and methods for loading, storing, transporting, and/or delivering precise doses of a drug substance or other fluid substance.

INTRODUCTION

Drug products including fluid drug substances may be deliverable to patients in a variety of ways, including via injection. In many cases, the precision and accuracy of a liquid drug product's volume is crucial. For example, medical professionals may have an interest in ensuring that an approved or prescribed volume of a drug substance is consistently delivered to each patient requiring the drug. Additionally, over- or under-dosing a patient with a drug substance, even slightly, may have an undesired (or even negative) clinical impact on the patient. Moreover, some drug products are prescribed at low volumes (e.g., under 100 μL). At low volumes, human error in preparing and delivering an accurate dose of a drug substance for injection may impact the drug's efficacy in a patient and the subsequent clinical effect on the patient.

Additional aspects of fluid drug delivery can complicate the goal of accurate dose delivery via injection. For example, for a correct dose of a drug substance to be dispensed from a device (e.g., a syringe), a corresponding accurate volume of the substance must be loaded into the device. Furthermore, handling, storage, packaging, and/or transportation of loaded devices must not result in inadvertent expulsion of drug substance from the devices. Additionally, prior to administration of a drug substance from a device, the device may need to be primed, e.g., to remove air bubbles and excess drug substance from within the device's needle and barrel. Incorrectly priming a device may result in expulsion of too much or too little drug substance from the device, which likewise may result in a decreased dose being delivered to a patient, or air bubbles being injected from the device into the patient.

The present disclosure also addresses needs unmet by prior publications WO2018/232408, published on Dec. 20, 2018; WO2018/224640, published on Dec. 13, 2018; and WO2018/224644, published on Dec. 13, 2018. Further, at least some embodiments of the present disclosure include features that are different than those features disclosed in publication WO2019/118588, published on Jun. 20, 2019. Some features include, for example, a plunger rod including one or more extensions extending distally from an actuation portion of the plunger rod and having hook or clip shaped parts for receipt with side openings of a flange piece. The plunger rod may include a neck having three or more sections, each having a different cross-sectional profile and/or shape relative to one another. Further features may include, for example, a flange piece including a collar having one or more internal grooves for receiving the hook or clip shaped parts of the one or more extensions, thereby allowing the extensions to flex radially-outward from a compressed configuration to an expanded configuration. The flange piece may include an opening configured to receive each of the three or more sections of the neck based on, for example, a rotational arrangement of the plunger rod relative to the flange piece.

A flange piece of the present disclosure may further include one or more movable ribs and/or one or more movable tabs for engaging a syringe body to couple the flange piece to the syringe body. For example, one or more movable ribs may be positioned proximal to a lip and lateral opening of the flange piece for receiving a top flange of the syringe body. The movable ribs may move, deflect, and/or deform in response to receiving the top flange through the lateral opening, and may be configured to apply a distally-directed force onto the top flange to secure the syringe body to the flange piece. By way of further example, the one or more movable tabs may be positioned distal to the lip and lateral opening. The movable tabs may move, deflect, and/or deform in response to the flange piece receiving the syringe body, and may be configured to apply a radially-directed force onto the syringe body to secure the syringe body to the flange piece. It should be appreciated that embodiments of the present disclosure include various other features shown and described herein that are different than those features disclosed in publication WO2019/118588.

SUMMARY

Disclosed herein are drug delivery devices. In one embodiment of the present disclosure, a drug delivery device includes a body, a plunger rod disposed partially inside the body, a protrusion extending from the plunger rod, and a blocking component on the body. When the protrusion is in a first position relative to the blocking component, the blocking component restricts distal movement of the plunger rod to a first stopping point, and when the protrusion is in a second position relative to the blocking component, the blocking component restricts distal movement of the plunger rod to a second stopping point.

In some aspects of the present disclosure, the drug delivery device further includes a stopper disposed in the body. Distal movement of the plunger rod distally moves the stopper, and a drug substance disposed in the body in between the stopper and a distal end of the body. Distal movement of the plunger rod to the first stopping point primes the drug delivery device, and distal movement of the plunger rod to the second stopping point dispenses a predetermined volume of the drug substance from a distal end of the device.

In some aspects of the present disclosure, moving the protrusion from the first position to the second position includes twisting the plunger rod relative to the blocking component. In some aspects of the present disclosure, the drug delivery device further includes a cavity in a proximal side of the blocking component, the cavity sized and configured to receive a portion of the protrusion. When the protrusion is in the second position relative to the blocking component, the protrusion is positioned proximally from the cavity, such that distal movement of the plunger rod moves the protrusion into the cavity.

In some aspects of the present disclosure, the cavity is a first cavity, and the drug delivery device further includes a second cavity in a proximal side of the blocking component, the second cavity sized and configured to receive a portion of the protrusion. The first and second cavity are located on opposite sides of a central longitudinal axis of the drug delivery device. In some aspects of the present disclosure, the blocking component includes a flange and is coupled to a proximal end portion of the body, and the plunger rod passes through an opening in the blocking component. In some aspects of the present disclosure, the drug delivery device further includes an actuation portion at a proximal end portion of the plunger rod, and the protrusion extends from the actuation portion.

In some aspects of the present disclosure, the actuation portion includes a generally cylindrical shape having a diameter greater than a width of the remainder of the plunger rod. The protrusion extends from a side of the generally cylindrical shape, and the actuation portion further includes a thumb pad on a proximal end of the actuation portion, and a ring on an exterior surface on the side of the generally cylindrical shape. In some aspects of the present disclosure, the drug delivery device further includes a proximal collar on the blocking component, and the actuation portion partially fits inside the proximal collar.

In some aspects of the present disclosure, the plunger rod further includes a pair of extensions protruding distally from the actuation portion and the blocking component includes a pair of openings. A portion of each extension is configured to be received by one of the pair of openings in the first stopping point. In some aspects of the present disclosure, the blocking component includes one or more indents formed along a bottom wall of the blocking component. A portion of each extension is configured to be received by the one or more indents upon distal movement of the plunger rod relative to the blocking component to allow distal movement of the plunger rod to the second stopping point.

In some aspects of the present disclosure, the blocking component includes a pair of internal grooves formed along a sidewall of the blocking component. A portion of each extension is configured to be received by at least one of the pair of internal grooves upon rotation of the plunger rod relative to the blocking component to expand the extensions radially-outward from a compressed state to a relaxed state. In some aspects of the present disclosure, the protrusion is a first protrusion, and the drug delivery device further includes a second protrusion extending from the plunger rod in a direction opposite to the first protrusion. In some aspects of the present disclosure, the blocking component is slidably coupled to the body and includes a pair of internal ribs that are configured to engage a top flange of the body when the body is slidably coupled to the blocking component. The pair of internal ribs are configured to apply a distally-directed force onto the top flange.

In some aspects of the present disclosure, the blocking component is slidably coupled to the body and includes a pair of movable tabs that are configured to engage a sleeve of the body when the body is slidably coupled to the blocking component. The pair of movable tabs are laterally deflectable upon receiving the sleeve in the blocking component and are configured to apply a radially-directed force onto the sleeve. In some aspects of the present disclosure, the blocking component further includes a pair of finger flanges. Each of the finger flanges includes a textured surface having a predefined pattern that increases a grip of the blocking component.

According to another embodiment of the present disclosure, a drug delivery device includes a body, a plunger rod having a distal end coupled to a stopper inside the body, and a proximal end including an actuation portion with a thumb pad, a plurality of protrusions extending from the actuation portion, and a blocking component disposed on the body, the blocking component including a proximal collar. When the protrusions and the blocking component are in a first configuration, the blocking component restricts distal movement of the plunger rod to a first stopping point, and when the protrusions and the blocking component are in a second configuration, the blocking component restricts distal movement of the plunger rod to a second stopping point. The proximal collar is configured to receive the protrusions upon distal movement of the plunger rod when the protrusions are in the second configuration.

In some aspects of the present disclosure, the protrusions and the blocking component are movable from the first configuration to the second configuration by rotation of the actuation portion about a longitudinal axis in relation to the blocking component. In some aspects of the present disclosure, a difference between the first stopping point and the second stopping point is equivalent to a distance that the stopper must travel to expel a predetermined volume of a drug product from a distal end of the body. In some aspects of the present disclosure, the plurality of protrusions includes two protrusions disposed symmetrically about the actuation portion. In some aspects of the present disclosure, the blocking component further includes a pair of finger flanges. In some aspects of the present disclosure, the drug delivery device is a pre-filled syringe.

In some aspects of the present disclosure, the drug delivery device is changeable: (a) from a pre-use state to a primed state, by longitudinally moving the plunger rod until the plunger rod reaches the first stopping point; (b) from the primed state to a delivery state by rotating the plunger rod in relation to the blocking component until the protrusions and the blocking component are in the second configuration; and (c) from a delivery state to a used state by longitudinally moving the plunger rod until the plunger reaches the second stopping point. In some aspects of the present disclosure, the plunger rod includes a neck disposed distally from the actuation portion, and the neck interfaces with an opening in the blocking component to prevent proximal movement of the plunger rod. In some aspects of the present disclosure, the neck further interfaces with the opening in the blocking component to prevent movement of the drug delivery device from the delivery state to the primed state.

In a further embodiment of the present disclosure, a drug delivery device includes a body, a plunger rod, including: a distal portion coupled to a stopper inside the body; a proximal end including a generally cylindrical actuation portion disposed outside of the body; and two protrusions extending from opposite sides of the actuation portion in a symmetrical configuration. The drug delivery device further includes a blocking component coupled to the body, the blocking component including a collar configured to accept a distal part of the actuation portion and two cavities in the collar having proximally-facing openings. Each cavity is configured to accept a distal portion of one of the two protrusions. The plunger rod is longitudinally movable and rotatable about a longitudinal axis relative to the blocking component. When the drug delivery device is in a pre-use state, the protrusions and the cavity openings are not longitudinally aligned, and when the drug delivery device is in a delivery state, the protrusions and the cavity openings are longitudinally aligned. In some aspects of the present disclosure, the blocking component further includes a finger flange, and the drug delivery device further comprises a ribbed surface on a side of the actuation portion.

In a further embodiment of the present disclosure, a method of dispensing a substance from a drug delivery device having a plunger rod and a body is disclosed. The method includes advancing the plunger rod by a predetermined distance into the body until advancement of the plunger rod is resisted by a stop, rotating the plunger rod about a longitudinal axis, and actuating the plunger rod to dispense a predetermined volume of the substance.

In some aspects of the present disclosure, advancing the plunger rod and actuating the plunger rod include pressing an actuation portion of the plunger rod. In some aspects of the present disclosure, the plunger rod includes a protrusion, the stop includes a blocking component coupled to the body, and the blocking component abuts against the protrusion to resist advancement of the plunger rod.

In some aspects of the present disclosure, rotating the plunger rod includes twisting an actuation portion of the plunger rod relative to a blocking component of the plunger rod, until a protrusion on the plunger rod becomes longitudinally aligned with a cavity in the blocking component. In some aspects of the present disclosure, actuating the plunger rod includes pressing the actuation portion of the plunger rod to advance the protrusion into the cavity.

In some aspects of the present disclosure, the method further includes advancing the protrusion into the cavity until the protrusion abuts a distal side of the cavity, and the predetermined volume of the substance is dispensed when the protrusion abuts the distal side of the cavity.

In a further embodiment of the present disclosure, a drug delivery device includes a body, a stopper disposed inside the body, and a sleeve having a proximal end and a distal end. The distal end being disposed inside the body, proximally from the stopper. The device includes a plunger rod disposed at least partially inside the sleeve. When the stopper is in a ready position, distal advancement of one of (a) only the sleeve, (b) only the plunger rod, or (c) both the sleeve and the plunger rod together, relative to the body advances the stopper to a primed position. When the stopper is in the primed position, distal advancement of another of (a) only the sleeve, (b) only the plunger rod, or (c) both the sleeve and the plunger rod together, relative to the body advances the stopper to a dose completion position.

In some aspects of the present disclosure, the drug delivery device further includes a removable blocking component disposed between a proximal portion of the sleeve and a proximal end of the body. The blocking component obstructing distal advancement of the sleeve relative to the body. Distal advancement of the sleeve relative to the body after removal of the blocking component advances the stopper to the primed position. The blocking component is a clip removably secured around at least a portion of the sleeve.

In some aspects of the present disclosure, the drug delivery device further includes a removable locking component that couples the plunger rod to the sleeve. Distal advancement of both the sleeve and the plunger rod together relative to the body advances the stopper to the primed position. Distal advancement of only the plunger rod relative to the body after removal of the locking component advances the stopper to the dose completion position. In the dose completion position, a proximal end of the plunger rod abuts against a distal end of the sleeve, such that the plunger rod is prevented from advancing distally any further relative to the body. The removable locking component includes one of a pin, a tab, or a bar.

In some aspects of the present disclosure, the drug delivery device further includes a protrusion disposed on the plunger rod and an inner protrusion disposed on an interior wall of the sleeve distally to the protrusion of the plunger rod. Distal advancement of only the plunger rod relative to the body advances the stopper to the primed position and causes the protrusion of the plunger rod to contact the inner protrusion of the sleeve. Distal advancement of both the plunger rod and the sleeve relative to the body, after the protrusion of the plunger rod has contacted the inner protrusion of the sleeve, advances the stopper to the dose completion position.

In some aspects of the present disclosure, a compressible protrusion on the plunger rod and an opening disposed on an interior wall of the sleeve, proximally from the protrusion on the plunger rod. Distal advancement of only the plunger rod relative to the body advances the stopper to the primed position. Proximal withdrawal of the plunger rod until the compressible protrusion of the plunger rod enters the opening of the sleeve couples the sleeve to the plunger rod. Distal advancement of both the plunger rod and sleeve coupled together relative to the body advances the stopper to the dose completion position. In some aspects of the present disclosure, when the sleeve is coupled to the plunger rod, a total length of the combined sleeve and plunger rod along a proximal-distal axis is greater than a length of the plunger rod alone.

In some aspects of the present disclosure, the sleeve includes a finger flange. In some aspects of the present disclosure, the drug delivery device further includes a stop disposed at a proximal end of the body. The stop sized to block distal advancement of the sleeve or the plunger rod once the stopper is in the completion position.

In further embodiments of the present disclosure, a drug delivery device includes a body and a plunger rod having a distal portion disposed inside the body and a proximal portion disposed outside a proximal end of the body. The proximal portion having a width greater than a width of the distal portion. The device further includes an obstruction that, in an obstructing position relative to the plunger rod, prevents distal advancement of the plunger rod from a primed position to a dose completion position. Displacement of the obstruction from the obstructing position permits distal advancement of the plunger rod to the dose completion position.

In some aspects of the present disclosure, the drug delivery device further includes a collar affixed to a proximal end portion of the body. The collar surrounding the proximal portion of the plunger rod. The drug delivery device further includes a collar projection extending radially inward from the collar. The proximal portion of the plunger rod includes a channel into which the collar projection protrudes, the channel including a circumferential path and an axial dose completion path. The obstruction comprises the collar projection, which, when disposed in the circumferential path of the channel, prevents distal advancement of the plunger rod to the dose completion position. Displacement of the obstruction from the obstructing position comprises twisting the plunger rod about a longitudinal axis to align the collar projection with the axial dose completion path.

In some aspects of the present disclosure, the channel further includes an axial priming path offset from the axial dose completion path, and connected to the axial dose completion path by the circumferential path. Distal movement of the plunger rod such that the collar projection travels on the axial priming path advances the plunger rod to the primed position. In some aspects of the present disclosure, the collar further comprises a finger flange.

In some aspects of the present disclosure, the proximal portion of the plunger rod includes a projection extending radially outward. The drug delivery device further includes a rotatable alignment component disposed in between the proximal portion of the plunger rod and the body. The alignment component including a channel, the channel sized and configured to accommodate the plunger rod projection. The obstruction comprises a wall of the channel that blocks a distal axial path of the plunger rod projection when the plunger rod is in the primed position. Displacement of the obstruction from the obstructing position comprises rotating the alignment component to remove the wall of the channel from the distal axial path of the plunger rod projection.

In some aspects of the present disclosure, the drug delivery device further includes a finger flange coupled to a proximal end portion of the body. The rotatable alignment component is disposed between the finger flange and the proximal portion of the plunger rod. In some aspects of the present disclosure, the drug delivery device further includes a flange piece disposed at the proximal end of the body. The obstruction includes a removable cap that, when in the obstructing position relative to the plunger rod, is disposed partially in between the proximal portion of the plunger rod and the flange piece. In some aspects of the present disclosure, removal of the cap allows the proximal portion of the plunger rod to advance to a dose completion position. In the dose completion position, the proximal portion of the plunger rod contacts the flange piece. In some aspects of the present disclosure, the removable cap covers the proximal portion of the plunger rod when in the obstructing position.

In some aspects of the present disclosure, drug delivery device further includes a collar disposed between the proximal end of the body and the proximal portion of the plunger rod. The collar defining an opening sized to accommodate the proximal portion of the plunger rod upon distal advancement of the plunger rod beyond a primed position. The obstruction comprises a tab protruding radially outward from the proximal portion of the plunger rod, the tab preventing the proximal portion of the plunger rod from fitting into the opening of the collar. A depth of the collar opening coincides with a distance the plunger rod must travel to advance distally to the dose completion position.

In some aspects of the present disclosure, displacement of the obstruction from the obstructing position comprises either removing the tab or compressing the tab into a side of the proximal portion of the plunger rod. In some aspects of the present disclosure, the tab is a first tab, and wherein the obstruction further comprises a second tab protruding radially outward from the proximal portion of the plunger rod in a direction opposite the protruding direction of the first tab. In some aspects of the present disclosure, the obstruction comprises a tab that, when in the obstructing position, is disposed between the body and the proximal portion of the plunger rod. The plunger rod includes a geometry disposed proximally from the tab, and the geometry cannot advance distally past the tab when the tab is in the obstructing position.

In some aspects of the present disclosure, displacement of the obstruction comprises removing the tab from the drug delivery device by pulling the tab. In some aspects of the present disclosure, the drug delivery device further includes a flange piece, wherein a portion of the tab is disposed inside a cavity of the flange piece. In some aspects of the present disclosure, displacement of the obstruction comprises removing the tab from the drug delivery device by breaking the tab.

In some aspects of the present disclosure, the obstruction includes a flange piece that, in the obstructing position, is disposed proximally from the proximal end of the body, between the proximal portion of the plunger rod and the body, and is spaced from the proximal end of the body by a removable blocking component. Displacement of the obstruction from the obstructing position includes removing the blocking component and shifting the flange piece distally towards the proximal end of the body.

In some aspects of the present disclosure, the plunger rod includes a projection extending radially outward. The obstruction includes a lever having an end that, in the obstructing position, is located distally from the projection and blocks distal movement of the projection and thereby distal movement of the plunger rod. Displacement of the obstruction from the obstructing position comprises actuating the lever to remove the end of the lever from its location distal from the projection. In some aspects of the present disclosure, distal advancement of the plunger rod beyond the dose completion position is prevented by contact between the proximal portion of the plunger rod and a portion of a flange piece coupled to the body.

In further embodiments of the present disclosure, a drug delivery device includes a body and a sleeve affixed to the body. The sleeve including a proximal end, a distal end, and an opening disposed in a circumferential wall of the sleeve. The drug delivery device further includes a plunger rod passing through the sleeve, the plunger rod including a distal end portion disposed inside the body, and a radially-extending protrusion. The plunger rod may be distally advanced into the body from a ready position to a primed position. In the primed position, the protrusion of the plunger rod is disposed inside the opening, and further distal advancement of the plunger rod is resisted by contact between the protrusion and a wall of the opening. Pressure may be exerted on the protrusion to overcome the resistance to further distal advancement of the plunger rod.

In some aspects of the present disclosure, the opening in the sleeve is a second opening, and the sleeve further includes a first opening disposed in the circumferential wall of the sleeve proximally from the second opening, and a third opening disposed in the circumferential wall of the sleeve distally from the second opening. In the ready position, the protrusion of the plunger rod is disposed in the first opening, and further distal advancement of the plunger rod is resisted by contact between the protrusion and a wall of the first opening. After further distal advancement of the plunger rod past the primed position, the protrusion of the plunger rod is disposed in the third opening, and further distal advancement of the plunger rod is prevented.

In some aspects of the present disclosure, the radially-extending protrusion is a first protrusion, and the plunger rod further includes a second radially-extending protrusion opposite the first protrusion. Squeezing the first and second protrusions towards one another while applying axial pressure in the distal direction on the plunger rod overcomes the resistance to further distal advancement of the plunger rod. In some aspects of the present disclosure, a proximal end of the sleeve includes a flared opening. Distally advancing the plunger rod from the ready position to the primed position includes advancing the protrusion into the flared opening and through the sleeve, whereby the protrusion is compressed between an interior of the sleeve and the plunger rod, until the protrusion extends into the opening disposed in the circumferential wall of the sleeve. In some aspects of the present disclosure, the protrusion includes a distally-tapering profile to aid in distal advancement of the plunger rod.

In further embodiments of the present disclosure, a drug delivery device includes a body, a plunger rod including a distal end portion disposed inside the body and a rotatable element, and a sleeve affixed to the body, the sleeve including a proximal opening into which the plunger rod may be advanced. Rotating the rotatable element causes distal advancement of the plunger rod to a primed position. Once the plunger rod is in the primed position, further rotation of the rotatable element is resisted.

In some aspects of the present disclosure, the rotatable element includes a cam lever. Once the plunger rod is in the primed position, the plunger rod may be depressed into the body to distally advance the plunger rod to a dose completion position. In some aspects of the present disclosure, the drug delivery device further includes a collar disposed at a proximal end of the body, an interior of the collar including a proximal threaded portion forming a proximal helical path. The rotatable element comprises a proximal portion of the plunger rod including a protrusion. The proximal portion of the plunger rod may be rotated about a longitudinal axis to cause the protrusion to travel distally along the proximal helical path. Once the protrusion reaches the end of the proximal threaded portion of the collar, the plunger rod is in the primed position.

In some aspects of the present disclosure, once the plunger rod is in the primed position, the plunger rod may be depressed axially into the body to distally advance the plunger rod to a dose completion position. In some aspects of the present disclosure, the interior of the collar further includes a distal threaded portion. Threads of the distal threaded portion form a distal helical path offset from, and opposite to, the proximal helical path. Alignment of the protrusion with the distal helical path places the plunger rod in the primed position. Rotation of the proximal portion of the plunger rod to cause the protrusion to travel distally along the distal helical path causes distal advancement of the plunger rod to a dose completion position.

In further embodiments of the present disclosure, a drug delivery device includes a body, a stopper disposed inside the body, and a first plunger rod having a first proximal end portion and a first distal end portion narrower than the first proximal end portion. The first distal end portion having a first length. The drug delivery device further includes a second plunger rod having a second proximal end portion and a second distal end portion narrower than the proximal end portion. The second distal end portion having a second length. The drug delivery device further includes a finger flange affixed to a proximal end portion of the body. The finger flange having a through hole aligned with a proximal opening of the body. The through hole sized to accommodate each of the first and second distal end portions without accommodating either of the first or second proximal end portions. Advancement of the first distal end portion through the through hole until the first proximal end portion abuts against the finger flange pushes the stopper distally to a primed position. Advancement of the second distal end portion through the through hole until the second proximal end portion abuts against the finger flange pushes the stopper distally to a dose completion position.

In further embodiments of the present disclosure, a method of assembling a drug delivery device includes coupling a body to a blocking component, wherein the blocking component is a flange piece, and coupling a plunger rod to the blocking component such that the plunger rod is disposed partially inside the body in a preassembled state and inhibited from proximal movement relative to the blocking component. In the preassembled state, the plunger rod is configured to move distally relative to the blocking component to a first stopping point with a protrusion of the plunger rod engaging the blocking component, thereby causing a priming dose of a medicament to be expelled from the body. When the protrusion is engaged to the blocking component, the blocking component is configured to restrict distal movement of the plunger rod to a first stopping point. The plunger rod is further configured to, while the plunger rod is at the first stopping point, rotate relative to the blocking component to disengage the protrusion from the blocking component, and move distally relative to the blocking component to a second stopping point with the protrusion engaging the blocking component, thereby causing a delivery dose of a medicament to be expelled from the body.

In some aspects of the present disclosure, the method further includes inserting a top flange of the body into an opening of the blocking component causing a tab of the blocking component to deflect radially-outward and a rib of the blocking component to deflect proximally. The tab applies a radially-inward directed force onto the body and the rib applies a distal force onto the top flange to secure the body to the blocking component. The method further includes inserting an extension of the plunger rod into a side opening of the blocking component to attach the plunger rod to the blocking component in the preassembled state. The plunger rod is configured to deflect the extension radially-inward in response to moving the plunger rod distally relative to the blocking component to the first stopping point, such that the extension is removed from the side opening. The extension is configured to move against an interior of the blocking component when the plunger rod rotates relative to the blocking component to align the protrusion with a slot of the blocking component. The extension flexes radially-outward within the blocking component when the protrusion is aligned with the slot. The extension is configured to extend into an indent along the interior of the blocking component when the plunger rod moves distally to the second stopping point.

BRIEF DESCRIPTION OF THE DRAWINGS

The accompanying drawings, which are incorporated into and constitute a part of this specification, illustrate various exemplary embodiments and, together with the description, serve to explain principles of the disclosed embodiments. The drawings show different aspects of the present disclosure and, where appropriate, reference numerals illustrating like structures, components, materials, and/or elements in different figures are labeled similarly. It is understood that various combinations of the structures, components, and/or elements in various embodiments, other than those specifically shown, are contemplated and are within the scope of the present disclosure.

There are many embodiments described and illustrated herein. The described devices and methods are neither limited to any single aspect nor embodiment thereof, nor to any combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein.

FIGS. 4A-4F depict an exemplary method of using the delivery device depicted in FIGS. 1A-1E, according to aspects of the present disclosure.

FIGS. 4Y-4Z depict exemplary aspects of plunger rods for use in embodiments of the delivery device depicted in FIGS. 1A-1E.

FIGS. 5A-5C depict another exemplary delivery device according to additional embodiments of the present disclosure.

FIGS. 6A-6E depict a further exemplary delivery device according to additional embodiments of the present disclosure.

FIGS. 7A-7F depict an exemplary method of using the delivery device depicted in FIGS. 6A-6E, according to aspects of the present disclosure.

FIGS. 8A-8E depict a further exemplary delivery device according to embodiments of the present disclosure.

FIGS. 9A-9E depict an exemplary method of using the delivery device depicted in FIGS. 8A-8E, according to aspects of the present disclosure.

FIGS. 11A-11E depict an exemplary method of using the delivery device depicted in FIGS. 10D-10G according to aspects of the present disclosure.

FIG. 14A-14F depict a method of using the delivery device depicted in FIGS. 12A and 12B.

FIGS. 15A-15B, and 16A-16B depict exemplary plunger rod dials according to further embodiments of the present disclosure.

FIGS. 24A-24E depict a further exemplary delivery device and method of using said delivery device, according to aspects of the present disclosure.

FIGS. 25A-25E depict a further exemplary delivery device and method of using said delivery device, according to aspects of the present disclosure.

FIGS. 26A-26G depict further exemplary delivery devices and a method of using one such delivery device, according to aspects of the present disclosure.

FIGS. 27A-27H depict a further exemplary delivery device and method of using said delivery device, according to aspects of the present disclosure.

FIGS. 29A-29C depict a further exemplary delivery device and method of using said delivery device, according to aspects of the present disclosure.

FIGS. 41A-41D depict exemplary flange pieces according to further embodiments of the present disclosure.

Figure 1H:
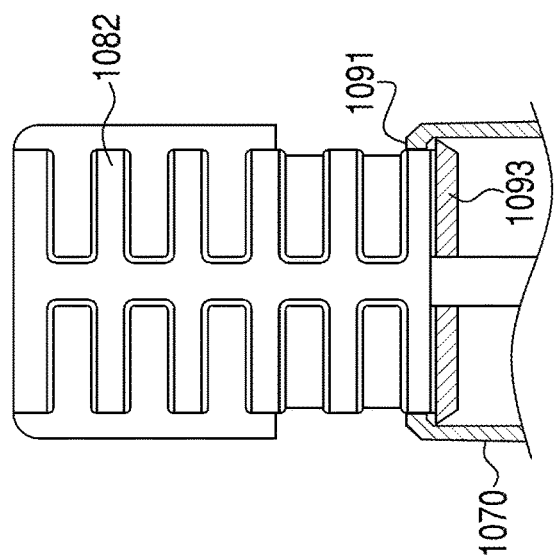
FIGS. 1A-1E depict an exemplary delivery device and components thereof, according to some embodiments of the present disclosure.
FIGS. 1F-2T depict additional aspects and embodiments of the exemplary delivery device of FIGS. 1A-1E.

There are many embodiments described and illustrated herein. The present disclosure is neither limited to any single aspect nor embodiment thereof, nor to any combinations and/or permutations of such aspects and/or embodiments. Each of the aspects of the present disclosure, and/or embodiments thereof, may be employed alone or in combination with one or more of the other aspects of the present disclosure and/or embodiments thereof. For the sake of brevity, many of those combinations and permutations are not discussed separately herein.

DETAILED DESCRIPTION

Embodiments of the present disclosure may be used in addition to and/or in combination with aspects of International Application No. PCT/US2018/065192, filed Dec. 12, 2018, which in incorporated by reference in its entirety herein.

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Notably, an embodiment or implementation described herein as an "example" or "exemplary" is not to be construed as preferred or advantageous, for example, over other embodiments or implementations; rather, it is intended reflect or indicate the embodiment(s) is/are one "example," rather than "ideal." In addition, the terms "first," "second," and the like, herein do not denote any order, quantity, or importance, but rather are used to distinguish an element, a structure, a step or a process from another. Moreover, the terms "a" and "an" herein do not denote a limitation of quantity, but rather denote the presence of one or more of the referenced items. Additionally, the terms "about," "approximately," "substantially," and the like, when used in describing a numerical value, denote a variation of +/−10% of that value, unless specified otherwise.

Embodiments of the present disclosure may be used with any type of fluid-containing products, such as liquid drug substances, liquid placebos, or other liquids that may be dispensed in a dose form. As used herein, the term "drug substance" may refer to a formulated substance including an active ingredient or ingredients, such as, e.g., small or large molecules, such as pain medications, steroids, or biologics. As used herein, the term "biologic" may refer to a large molecule (e.g., having a size greater than 15 kDa, greater than 30 kDa, greater than 50 kDa, greater than 75 kDa, or greater than 100 kDa) created in a living system such as a cell. Biologics may include proteins (e.g., antibodies), nucleic acids, large sugars, etc. Unlike small molecules that may have well-defined chemical structures, biologics may have highly complex structures that cannot be easily quantified by laboratory methods. As used herein, the term "drug product" may refer to a volume of a drug substance apportioned into a primary packaging component for packaging, transportation, delivery, and/or administration to a patient.

The term "primary packaging component" refers to a packaging component for a drug product, such as a drug container, that is designed and manufactured to be in direct physical contact with the formulated drug substance. (See, for example, Guidance for Industry on Container Closure Systems for Packaging Human Drugs and Biologics, U.S. Department of Health and Human Services, Food and Drug Administration, Center for Drug Evaluation and Research, and Center for Biologics Evaluation and Research (May 1999), which is incorporated by reference herein.) Examples of primary packaging components include pre-fillable syringes, Luer syringes, cartridges, and vials made of glass, plastic, other polymers or co-polymers, and/or other materials.

As used herein, the terms "distal" and "distally" refer to a location (or portion of a device) relatively closer to, or in the direction of, a patient delivery site, and the terms "proximal" and "proximally" refer to a location (or portion of a device) relatively closer to, or in the direction of, a user end opposite a distal location/portion of a device.

As used herein, the term "body," when used in reference to a part of a device, may refer to a component of the device suitable for containing a volume of a drug substance. A body may include, e.g., a barrel (such as a syringe barrel), tube, cylinder, or other containing portion of a device. In some embodiments, a body may also include a distal end portion having a nozzle, needle, needle attachment site, and/or distal cap.

Embodiments of the present disclosure may be used with products typically having small dose volumes, such as, e.g., ophthalmic drug products. In some embodiments, devices of the present disclosure may be used with drug products including a large molecule, e.g., a molecular weight of 30 kDA or greater. In some embodiments, devices of the present disclosure may be used with drug products including a fragment of a large molecule. For example, in some embodiments, devices of the present disclosure may be used with drug products including an antigen-binding molecule. In some aspects, the antigen-binding molecule may be an antibody or antigen-binding fragment. In some embodiments, devices of the present disclosure may be suitable for use with drug products including ingredients such as, e.g., aflibercept, alirocumab, abicipar pegol, bevacizumab, brolucizumab, conbercept, dupilumab, evolocumab, tocilizumab, certolizumab, abatacept, rituximab, infliximab, ranibizumab, sarilumab, adalimumab, anakinra, trastuzumab, pegfilgrastim, interferon beta-1a, insulin glargine [rDNA origin], epoetin alpha, darbepoetin, filigrastim, golimumab, etanercept, antigen-binding fragments of any of the above, or combinations of such binding domains, such as a bispecific antibody to VEGF or angiopoietin-2, among others.

In some embodiments, devices and aspects of the present disclosure can be used with any therapies for ophthalmic diseases, including for the treatment of patients with Diabetic Eye Disease, post-injection noninfectious Endophthalmitis, Neovascular (Wet) Age-related Macular Degeneration (AMD), Macular Edema following Retinal Vein Occlusion (RVO), Diabetic Macular Edema (DME), and Diabetic Retinopathy (DR). In particular, large molecule and small molecule antagonists of VEGF and/or ANG-2, such as aflibercept, ranibizumab, bevacizumab, conbercept, OPT-302, RTH258 (brolocizumab), abicipar pegol (a pegylated designed ankyrin repeating protein (DARPin)), RG7716, or fragments thereof and in any concentration. Intravitreal (IVT) administration of therapeutic agents may be an effective treatment for such eye disorders (e.g., macular degeneration, retinal vein occlusion, macular edema, retinopathy, etc.), however, IVT administration includes various challenges such as drug product development, administration procedure and adverse events. For example, providing accurate and precise delivery of small volumes (10-100 μL) requires precise design of container components. Accordingly, inaccuracies in a dosage delivery (e.g., over or under-dosing) may provide undesired adverse events or lack of efficacy resulting in unpredictable and variable clinical responses.

In some embodiments, devices and aspects of the present disclosure may provide accurate dose delivery while also providing a container closure system for maintaining the agent in a sterile, stable, and safe condition to increase an intended shelf-life and efficacy of the agent. IVT drug products are primarily presented in glass vials, however, pre-filled syringes offer a more convenient administration by reducing the number of steps required for dose preparation. Preassembling the agent in the devices of the present disclosure may minimize the steps necessary for preparing a dose for delivery to a patient. Product development studies may focus on primary container component characterization, material compatibility with the formulation, formulation stability, fill volume determination, extractable/leachable and terminal sterilization.

Additionally, careful selection of ancillary components such as disposable syringes and needles, and a detailed administration procedure that includes dosing instructions can ensure successful administration of the product. Despite significant efforts in improving the drug product and administration procedures, ocular safety concerns such as endophthalmitis, increased intraocular pressure and presence of silicone floaters have been reported. Devices and aspects of the present disclosure may provide detailed administration procedures (e.g., priming instructions, dosing instructions, etc.) to ensure successful administration of the agent to a patient to minimize such ocular safety concerns. In some embodiments, devices and aspects of the present disclosure can also be used for cosmetic applications or medical dermatology, such as treatment or diagnosis of allergic responses.

In some embodiments, devices and aspects of the present disclosure can be used to perform various eye injection procedures, such as, for example, intraocular treatments and surgeries involving an intravitreal injection of a drug product. Devices and aspects of the present disclosure may be used to dispense drug products of varying protein concentration and/or viscosity, including, for example, drug products having a viscosity ranging from about 1 centipoise to about 10 centipoise, from about 2 centipose to about 9 centipose, from about 3 centipose to about 8 centipose, from about 4 centipose to about 7 centipose, or from about 5 centipose to about 6 centipose. Drug products having still other viscosities also are contemplated. Providing a precise dose with a device of the present disclosure may be important given a possible variability in protein concentration or viscosity of a drug product being delivered to a patient. Devices and aspects of the present disclosure may be further used to dispense varying volumes and/or quantities of a drug product, such as, for example, volumes ranging from about 1 µL to about 200 µL, from about 10 µL to about 190 µL, from about 50 µL to about 150 µL, from about 75 µL to about 125 µL, from about 90 µL to about 110 µL, or about 100 µL. Devices of the present disclosure may be configured and operable to require application of a minimum force exceeding a threshold for performing one or more procedures, such as, for example, priming a device, delivering a dosage, and the like. By requiring application of the minimum force, devices of the present disclosure may promote control in administering a consistent dose of a drug product, and promote safety by minimizing inadvertent movement of the device's components, thereby potentially reducing pain, discomfort, and injury to a patient.

For some products in particular, e.g., ophthalmic or other drug products, dose accuracy may be particularly important. However, it is also contemplated that embodiments of the present disclosure may be applicable to any other liquid products or any other context for which precise methods for setting and administering a reliably accurate dose or delivery volume are beneficial.

In some embodiments, devices according to the present disclosure may be manufactured, packaged, filled, and/or otherwise prepared according to processes relevant to the products (e.g., drug products) of which they may be a part. For example, in some embodiments, devices according to the present disclosure may be sterilized, either before or after being filled and/or packaged. For example, in some embodiments, devices according to the present disclosure may be filled and packaged in, e.g., blister packaging, and/or may be terminally sterilized using any suitable method in the art. For example, devices according to the present disclosure may be terminally sterilized using a chemical sterilization method, such as a method including ethylene oxide or hydrogen peroxide (e.g., vaporized hydrogen peroxide). In some embodiments, devices according to the present disclosure may be terminally sterilized using methods described in, e.g., International Application No. PCT/US2018/021013, filed Mar. 6, 2018, which is incorporated by reference herein in its entirety.

Dose delivery devices available on the market, such as pre-filled syringes or syringes for use with vials, may not necessarily assist with accurately loading a desired volume of a substance, priming the devices, expelling an excessive volume of drug substance from the devices, and/or removing air bubbles from the devices. In dose delivery devices containing a small volume of a drug substance in particular (e.g., about 500 µL or less, about 300 µL or less, about 250 µL or less, about 200 µL or less, about 150 µL or less, about 100 µL or less, about 50 µL or less, or about 25 µL or less, such as between about 25 µL and about 50 µL, between about 50 µL and about 100 µL, between about 25 µL and about 100 µL, between about 50 µL and about 150 µL, between about 100 µL and about 250 µL, between about 100 µL and about 150 µL, between about 150 µL and about 250 µL, between about 200 µL and about 250 µL, between about 200 µL and about 500 µL, or between about 250 µL and about 500 µL), it may also be difficult to confirm the presence of the correct dose of a drug substance in the device with the naked eye. Currently in the dose delivery device market, and specifically in the syringe market, there is a need for mechanisms that allow a user to set precisely for delivery a small volume of a product in a syringe (e.g., a pre-filled or fillable/refillable syringe), prime the syringe, remove air bubbles from the syringe, and/or confirm or be assured that the dose volume in the syringe is correct. Embodiments of the present disclosure may assist manufacturers, drug product providers, medical professionals, and/or patients with accurately making, filling, or otherwise preparing a dose administration device, priming the device, removing bubbles from the device, confirming the dose, and/or administering a dose from the device to a patient. Moreover, embodiments of the present disclosure may assist in preventing or mitigating errors or variation in device manufacture or use, such as errors or variation in placement of dose lines on devices, variation in device geometry (e.g., variation in syringe neck geometry), variations in component manufacturing tolerance, and/or variation or errors in setting a dose line prior to delivery of a product.

In some instances, embodiments of the present disclosure may be of particular assistance to individuals who may have difficulty setting doses with precision and accuracy. For example, embodiments of the present disclosure may assist elderly individuals, young children, or persons with physical or mental disabilities in setting accurate doses.

Described herein are various embodiments of dose delivery devices, and in particular, for syringes. In some instances, embodiments or aspects of embodiments disclosed herein may be used in conjunction with existing syringe body parts to modify off-the-shelf products, which may reduce the development and manufacturing time for the dose delivery devices. In other instances, embodiments or aspects of embodiments disclosed herein may be included in devices during their manufacture. The syringes described herein may be pre-filled or may be fillable/refillable.

Embodiments of the present disclosure may include syringes having rotating parts, threaded parts, springs, gears, detents, channels, grooves, and the like, that may allow a user to precisely control the movement of priming and dosage delivery elements such as, e.g., plungers and/or stoppers. Such parts may be intended to reduce human error and/or increase accuracy.

In some embodiments, visualization devices, such as magnifiers, may be provided with, attached to, or otherwise disposed on, delivery devices, in order to help enhance visibility of dose measurement markers on the devices. It is contemplated that aspects of one embodiment (such as sleeves, channels, blocking components, protrusions, detents, threaded parts, grips, visual, tactile, or auditory indicators, etc.) may be combined with aspects of one or more other embodiments, to create various combinations and permutations of features in a single device.

In some embodiments, devices according to the present disclosure may be depicted as including one type of plunger rod and plunger, or as including a general schematic representation of a plunger rod and plunger. For example, some devices according to the present disclosure may be depicted or described as including, e.g., a plunger rod having a ball-tipped end, which engages with a stopper such that the plunger rod and the stopper may be attached together. It is contemplated that multiple and/or different configurations of plunger rods and stoppers may be appropriate for each of the embodiments disclosed herein. For example, in some cases, the aforementioned ball-tipped plunger rod may be used with embodiments disclosed herein. In some embodiments, a plunger rod may not be affixed to a stopper, and instead may be disposed near, next to, or flush against a stopper such that pressure from the plunger rod towards the stopper may push the stopper, but withdrawal, twisting, or other movement of the plunger rod may not cause the stopper to likewise be withdrawn, twisted, or otherwise moved. As another example, in some embodiments, a plunger rod may be affixed to a stopper by threads, a clip, or an adhesive, or may be of a single piece with a stopper (e.g., may have been manufactured in a single mold with a stopper).

In some embodiments, devices according to the present disclosure may include various cosmetic features relevant to intended users of the devices. For example, devices according to the present disclosure may be manufactured and sold for use with pediatric, elderly, or differently-abled patients. In such cases, devices according to the present disclosure may include child-friendly coloring, cartoon images, or other cosmetic features to appeal to children, or high-contrast coloring, textured surfaces, or other features to enhance ease of identification and/or use. In some cases, devices according to the present disclosure may include lettering, labeling, or other features designed to be easily recognized by the intended users. For example, lettering on a pediatric device or a device for use by a disabled or differently-abled person or an elderly person may have larger, more accessible labeling so that it may be more easily recognized and read by the user(s) of the device. In some embodiments, lettering or labeling may be raised, molded, or embossed.

Referring now to FIGS. 1A-1E, views of a delivery device 1050 and component parts are depicted. Device 1050 includes a body 1060, and a blocking component in the form of a flange piece 1070 with a proximal collar 1072 surrounding an opening 1073 (shown in, e.g., FIGS. 4B-4E), through which a plunger rod 1080 may pass into body 1060. Plunger rod 1080 includes an actuation portion 1082 which may be actuated (e.g., pushed or twisted) to rotate plunger rod 1080, or to move plunger rod 1080 longitudinally into body 1060. Actuation portion 1082 may be sized and configured to fit (e.g., nest or otherwise fit) inside proximal collar 1072.

Device 1050 may be, for example, an injection device, such as a syringe, for dispensing a predetermined volume of a formulated drug substance. In some embodiments, device 1050 may be a pre-filled syringe. For example, a user may receive an assembled and packaged device 1050 ready for use, with a volume of formulated drug substance already disposed between a stopper 1062 in body 1060 and an expulsion end 1064 of body 1060. In some embodiments, an air bubble (not shown) may also be disposed between stopper 1062 and expulsion end 1064. In further embodiments, device 1050 may be a fillable syringe.

Body 1060 may be any suitable body configured for holding and expelling a predetermined volume of a formulated drug substance. In some embodiments, body 1060 may have, e.g., a hollow cylindrical portion. Body 1060 may be configured to hold any suitable volume of a formulated drug substance for delivering to, e.g., a patient, and (together with other components of device 1050) to expel a predetermined amount of the held volume through, e.g., expulsion end 1064 in a priming step and/or delivery step. In some embodiments, body 1060 may be configured to hold and (together with other components of device 1050) expel a relatively small volume of formulated drug substance (e.g., less than about 100 µl, such as less than about 80 µl, less than about 60 µl, less than about 40 µl, less than about 20 µl, less than about 10 µl, about 95 µl, about 90 µl, about 85 µl, about 80 µl, about 75 µl, about 70 µl, about 65 µl, about 60 µl, about 55 µl, about 50 µl, about 45 µl, about 40 µl, about 35 µl, about 30 µl, about 25 µl, about 20 µl, about 15 µl, about 10 µl, or about 5 µl). Device 1050, together with its other components, may be further configured to minimize a residual volume of the formulated drug substance remaining in body 1060 after delivering the predetermined small volume to the patient. In some embodiments, body 1060 may be pre-filled (e.g., prior to completed assembly, packaging, sterilization and/or shipment of device 1050 to users). In some embodiments, stopper 1062 may be configured to hold a predetermined volume of a formulated drug substance inside a cavity of body 1060.

Flange piece 1070 may be of any suitable size and/or shape to serve as a blocking component in delivery device 1050, to close, partially close, cover, or partially cover an end of body 1060 opposite expulsion end 1064, and/or to support and hold plunger rod 1080 in place inside body 1060. In some embodiments, flange piece 1070 may include a distal collar 1075 configured to engage with body 1060 and hold flange piece 1070 in place in relation to body 1060. For example, distal collar 1075 may include a lip 1071 that may slide under or otherwise in relation to a body flange 1061, to hold flange piece 1070 in place (e.g., to slidably couple flange piece 1070 to body 1060). In alternative embodiments, lip 1071 of distal collar 1075 may be made of a flexible or semi-flexible material, so that it may snap in place over body flange 1061. In further embodiments, distal collar 1075 or another portion of flange piece 1070 may be adhered to, molded to, or otherwise affixed to, body 1060, or may engage with body 1060 via a friction fit.

Flange piece 1070 may be or include a blocking component; i.e., part or all of flange piece 1070 may be sized and configured to control movement of plunger rod 1080 by blocking movement of plunger rod 1080 when plunger rod 1080 is in certain configurations relative to flange piece 1070. For example, flange piece 1070 may be configured to control rotational and longitudinal movement of plunger rod 1080, e.g., via opening 1073 (see, e.g., FIGS. 4B-4E) that complements the size and shape of parts of plunger rod 1080 (e.g., neck 1084 and actuation portion 1082, and/or other portions of plunger rod 1080 as shown in FIGS. 4K-4O). As described in further detail herein, flange piece 1070 may be formed of various materials having a minimum strength and/or rigidity which may provide further control of a rotational or longitudinal movement of plunger rod 1080. For example, flange piece 1070 may be configured to resist proximal movement (or "pull back") of plunger rod 1080 (e.g., to inhibit disassembly of device 1050 by retracting plunger rod 1080) up to a predetermined force based at least in part on a material composition of flange piece 1070. It should be appreciated that flange piece 1070 may be configured such that applying a force exceeding the predetermined force may cause one or more of flange piece 1070 and plunger rod 1080 to break, thereby rendering device 1050 inoperable.

By way of further example, flange piece 1070 may be configured to resist rotational movement of plunger rod 1080 (e.g., to inhibit inadvertent rotation) up to a predetermined force based at least in part on a material composition of flange piece 1070. Additionally and/or alternatively, flange piece 1070 may be configured to resist distal movement of plunger rod 1080 to control a rate of dosage delivery (e.g., to inhibit inadvertent delivery) based at least in part on a material composition of flange piece 1070. Various other components of device 1050 other than flange piece 1070 may include a material composition providing a frictional interference to inhibit disassembly of device 1050, inadvertent rotation of plunger rod 1080, and/or inadvertent dosage delivery.

Proximal collar 1072 of flange piece 1070 may be sized and configured to accept part of actuation portion 1082 of plunger rod 1080, while blocking protrusions 1086 of plunger rod 1080 from moving distally past a predetermined point until plunger rod 1080 is rotated to a particular position. As shown in FIGS. 1A and 1B, collar 1072 may be cylindrical; in alternate embodiments, collar 1072 may have any suitable size or shape compatible with actuation portion 1082. Collar 1072 may also include cavities, e.g., slots 1074 into which protrusions 1086 of plunger rod 1080 may be received. Slots 1074 may have proximally-facing openings and may have a depth dimension parallel to a longitudinal axis of device 1050. A number and configuration of slots 1074 may correspond to a number and configuration of protrusions 1086 on plunger rod 1080. In some embodiments, slots 1074 may be disposed about a perimeter of collar 1072 in a radially symmetrical configuration. In further embodiments, collar 1072 may include only one slot 1074. The depth of slots 1074 may correspond to a distance plunger rod 1080 must move in order to push stopper 1062 towards expulsion end 1064, and dispense a predetermined volume of formulated drug substance from body 1060 through expulsion end 1064. Advantageously, the predetermined volume of formulated drug substance that is to be dispensed from body 1060 may be controlled during manufacturing, by, e.g., selecting a particular depth of slots 1074. In some embodiments, device 1050 may be configured such that normal variations in manufacturing of other parts of device 1050 (e.g., body 1060 or plunger rod 1080) may not cause variations in the volume of formulated drug substance that is to be dispensed from body 1060. As such, the predetermined volume may be controlled by simply varying manufacture of flange piece 1070.

In some embodiments, flange piece 1070 may include one or more flanges 1076, which may be sized and configured to aid a user in holding device 1050 and/or expelling a formulated drug substance from device 1050. In some embodiments, as depicted in FIGS. 1A-1E, flange piece 1070 may include two flanges 1076 opposite to one another and extending perpendicularly from a longitudinal dimension of device 1050. In some embodiments, flange piece 1070 may include other arrangements of a flange or flanges, such as four flanges, or one circumferential flange extending radially outward from a central longitudinal axis of device 1050. In some embodiments, flange piece 1070 may extend radially outward from a central longitudinal axis of device 1050 farther than a circumference of body 1060. In such embodiments, flange piece 1070 may support device 1050 if device 1050 is placed on a surface, may prevent device 1050 from rolling on a flat surface, and/or may allow device 1050 to be picked up more easily. In still further embodiments, blocking component aspects of flange piece 1070 (e.g., collar 1072) may be separate from flange piece 1070, such that delivery device 1050 includes a separate flange piece and blocking component.

Plunger rod 1080 in general may be rotatable about a central longitudinal axis (e.g., in one direction or in both directions). In some embodiments, rotation of plunger rod 1080 may be accomplished by grasping and/or twisting actuation portion 1082 relative to flange piece 1070 and/or body 1060. In some embodiments, protrusions 1086 may assist a user in grasping and/or twisting actuation portion 1082 relative to flange piece 1070 and/or body 1060, by providing additional surface area that a user may grasp and/or push against to twist actuation portion 1082. In some embodiments, only a part or parts of plunger rod 1080 (e.g., actuation portion 1082 and/or a neck 1084) may be rotatable relative to flange piece 1070 and/or body 1060. In some embodiments, plunger rod 1080 may be configured to rotate relative to flange piece 1070 in response to applying a predetermined twisting force onto actuation portion 1082. A material composition of flange piece 1070 may be determinative of the predetermined twisting force required to rotate plunger rod 1080 relative to flange piece 1070. For example, flange piece 1070 may be formed of various materials having a predetermined rigidity that may generate frictional resistance against plunger rod 1080 to control rotational movement of plunger rod 1080 up to the predetermined force (e.g., to inhibit inadvertent rotation/accidental twisting of plunger rod 1080). Further, a material composition of flange piece 1070 may provide a frictional tolerance to control a distal translation of plunger rod 1080 up to a predetermined force (e.g., to inhibit inadvertent dosage delivery by device 1050).

A stem 1081 of plunger rod 1080 may have any thickness and cross-sectional shape suitable for fitting into body 1060, while maintaining sturdiness. For example, in some embodiments, stem 1081 may have as great a thickness, along at least one dimension, as can fit and slide into body 1060. Advantageously, such a thickness may help in preventing unwanted wobbling of plunger rod 1080 relative to the other components of device 1050. In further embodiments, stem 1081 may have a smaller thickness while still maintaining sturdiness (e.g., not bending, breaking, or warping during assembly and/or use of device 1050). In some embodiments, portions of stem 1081 may be configured to allow for plunger rod 1080 to rotate relative to flange piece 1070, whereas other portions of stem 1081 may not (see, e.g., FIGS. 4K-4S).

Plunger rod 1080 may also include a distal tip 1083 (see, e.g., FIG. 1D) sized and configured to push, attach to, or otherwise interface with stopper 1062. Tip 1083 may have any size or shape suitable to achieve this purpose. In some embodiments, for example, tip 1083 may be sized and configured to clip to stopper 1062 via an opening in stopper 1062. In further embodiments, tip 1083 may have a ball-shape configured to fit into an opening in stopper 1062. In yet further embodiments, tip 1083 may present a flat surface parallel to a proximal surface of stopper 1062, and may be configured to push stopper 1062 distally without attaching to stopper 1062. In further embodiments, tip 1083 may have any shaped surface suitable for pushing stopper 1062 distally.

In some embodiments, neck 1084 of plunger rod 1080 and opening 1073 of flange piece 1070 may have complementary geometries that restrict the extent and direction that plunger rod 1080 (or a part thereof) may rotate, depending on the specific longitudinal and/or rotational position of plunger rod 1080 relative to flange piece 1070. In some embodiments, actuation portion 1082 of plunger rod 1080 and collar 1072 may also include complementary geometries that control the extent and direction that plunger rod 1080 may move relative to flange piece 1070. For example, rotation and/or longitudinal movement of plunger rod 1080 may be restricted based on priming, preparing, and/or drug delivery steps of a method of using device 1050 (see, e.g., the method described with respect to FIGS. 4A-4F and the additional/alternative method described with respect to FIGS. 4G-4H and 4I-4J), and the corresponding position of plunger rod 1080 with respect to each step in such methods. For example, plunger rod 1080 may be restricted from being moved out of flange piece 1070 in a proximal direction (e.g., falling out or being pulled out) once device 1050 is assembled. Moreover, plunger rod 1080 may be restricted from rotation about a longitudinal axis before device 1050 is in a "primed" state, and/or after device 1050 is in a "delivery" state. Additionally, longitudinal movement of plunger rod 1080 in the proximal direction (e.g., to "back out" plunger rod 1080), may be restricted after device 1050 is in a "primed" and/or "delivery" state by complementary geometries of neck 1084 of plunger rod 1080 and opening 1073 of flange piece 1070 and/or of actuation portion 1082 of plunger rod 1080 and collar 1072 of flange piece 1070. Advantageously, this may prevent unwanted plunger rod back out in cases where plunger rod 1080 is not held inside body 1060 by, e.g., being affixed to stopper 1062. For example, in some embodiments, plunger rod 1080 may be configured to simply contact or rest against stopper 1062, such that proximal movement of plunger rod 1080 does not move stopper 1062 proximally. In such cases, proximal movement of plunger rod 1080 may be prevented by interaction between complementary geometries of plunger rod 1080 and flange piece 1070. Moreover, interaction between actuation portion 1082 of plunger rod 1080 and collar 1072 of flange piece 1070 may restrict longitudinal movement of plunger rod 1080 in a distal direction. As an example, plunger rod 1080 may be restricted from moving distally after the "primed" state but before the "delivery" state.

Upon being moved to the "delivery" state, protrusions 1086 on actuation portion 1082 may be longitudinally aligned with slots 1074 of collar 1072, allowing for distal movement of plunger rod 1080 to dispense a desired volume of a drug substance from body 1060. As such, plunger rod 1080 may include a number and configuration of protrusions 1086 such that each protrusion 1086 may move distally into a slot 1074 when plunger rod 1080 is in a particular position (e.g., a "delivery" state). In some embodiments, one, two, three, or more protrusions 1086 may extend from actuation portion 1082, corresponding to one, two, three, or more slots 1074, respectively. For example, as depicted, two protrusions 1086 may extend from the sides of actuation portion 1082 in a radially symmetrical configuration (corresponding to two slots 1074 in collar 1072). In some embodiments, radial symmetry of multiple protrusions 1086 (and slots 1074) may advantageously allow for protrusions 1086 to fit into slots 1074 in multiple configurations (e.g., depending on whether actuation portion 1082 is twisted in one direction or another). In such embodiments, actuation portion 1082 may be twisted in either direction based on, e.g., user preference, right-handedness or left-handedness, or other factors. In some embodiments, plunger rod 1080 may not be pulled proximally or backed out of body 1060 (e.g., towards actuation portion 1082) after plunger rod 1080 is in a "primed" state and/or after a desired volume of formulated drug substance has been delivered from device 1050 by depression of plunger rod 1080 into body 1060 (e.g., due to a geometry of neck 1084 and/or opening 1073).

In some embodiments, device 1050 may be configured for ease of use, and may include one or more features that aid a user by providing tactile or visual feedback. For example, one, two, or more components of device 1050 may have contrasting colors or textures. In some embodiments, for example, flange piece 1070 may have a different coloring than plunger rod 1080. As a further example, a single component of device 1050 may have two or more colors or textures. In some embodiments, for example, actuation portion 1082 may include a first color on a distal part of actuation portion 1082, that becomes covered by collar 1072 when device 1050 is primed, and a second color on a second portion of actuation portion 1082, that moves adjacent to collar 1072 when device 1050 is primed, to help indicate to a user that device 1050 has been properly primed. As a further example, in some embodiments, flange piece 1070 may have a different tactile feel than plunger rod 1080 and/or body 1060. For example, flange piece 1070 may be relatively rougher or smoother than plunger rod 1080 and/or body 1060. As yet another example, one or more components of device 1050 may have textures that aid in holding, gripping, identifying, or using device 1050. For example, flange piece 1070 may have a slightly rough or raised texture to aid a user in gripping flanges 1076, and/or to prevent a user's fingers from slipping off of the flanges 1076 during use. In some embodiments, some or all of flange piece 1070 may have a smooth-feeling surface. As another example, actuation portion 1082 of plunger rod 1080 may include a rough or raised texture to aid in gripping and rotating plunger rod 1080. For example, as depicted in FIGS. 1A-1I, 3A-3C, 3E, and 4A-4I, actuation portion 1082 may include circumferential ribbing on its side(s). Actuation portion 1082 may have any suitable number of ribs on its side(s) to provide texture. In further embodiments, actuation portion 1082 may have no ribbing on its side(s).

In some embodiments, device 1050 or one or more of its components may include colors, labels or markers, which may indicate contents or a status of device 1050, and/or which may direct or provide instructions to a user of device 1050. Examples include one or more labels to indicate a priming position versus a dosage delivery position of the plunger rod, one or more labels to indicate directions in which to rotate or otherwise move plunger rod 1080, and/or one or more labels to indicate an amount of formulated drug substance included in device 1050 (e.g., linear markings on body 1060). Labels may be, e.g., adhered or printed on components of device 1050, or may be embossed on, or molded as a part of, components of device 1050. In some embodiments, one or more textured labels (e.g., embossed or molded on device 1050) may also serve as a textured, rough, or raised surface to aid a user in gripping or using device 1050. One or more exemplary labels may include words, numerals, indicators, and/or symbols (e.g., lines, padlocks, arrows, diagrams, etc.).

In some embodiments, device 1050 may be configured to make one or more sounds during its use. For example, device 1050 may make a "clicking" noise upon completion of a priming step, or upon rotation of the plunger rod to a position suitable for dispensing a predetermined volume of a formulated drug substance. A "clicking" noise may be produced by, e.g., friction between two or more components (e.g., plunger rod 1080 and flange piece 1070), or a portion of one component contacting another portion (e.g., neck 1084 of plunger rod 1080 contacting opening 1073 of flange piece 1070). In some embodiments, device 1050 may include one or more detents or protrusions on adjacent surfaces of, e.g., plunger rod 1080 and flange piece 1070, which may produce a clicking sound when contacting one another (e.g., wings 1089 on neck 1084 contacting detents 1078 surrounding opening 1073, as shown in FIGS. 4T-4X). Such sounds may serve as auditory feedback to indicate that a user has reached a particular step in the use of device 1050.

In some embodiments, device 1050 may include additional features or components to control movement of plunger rod 1080 relative to body 1060. For example, as shown in FIG. 1F, flange piece 1070 may include an opening 1079 through which a pin 1077 may be disposed. Pin 1077 may be sized and configured to interface with actuation portion 1082 of plunger rod 1080 (e.g., to slide into an opening (not shown) in actuation portion 1082), such that when pin 1077 is inserted so as to engage actuation portion 1082, plunger rod 1080 may not be moved proximally or distally relative to body 1060 and flange piece 1070. In some embodiments, pin 1077 may also prevent rotational movement of plunger rod 1080 relative to flange piece 1070. Pin 1077 may be inserted upon filling and assembly of a device (e.g., device 1050 shown in FIGS. 1A and 1B), to prevent unwanted movement of plunger rod 1080 prior to its use. In some embodiments, pin 1077 may remain inserted during packaging, transportation, and delivery of device 1050. Before use of device 1050, pin 1077 may be removed or otherwise positioned so that it does not engage actuation portion 1082.

Figure 1G:
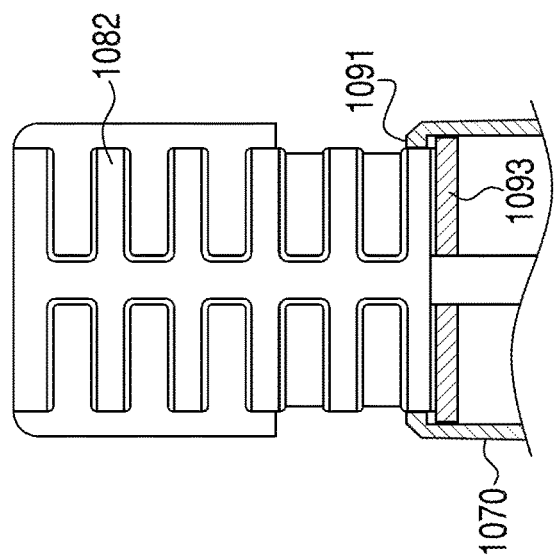
Figure 1F:
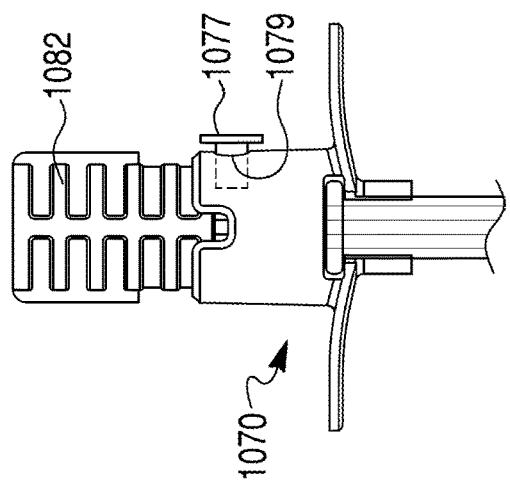

As shown in FIGS. 1G and 1H, in some embodiments, a protrusion 1093 may be disposed at a distal portion of actuation portion 1082, which may be located inside flange piece 1070 upon assembly of device 1050. An inward lip 1091 of flange piece 1070 may overhang protrusion 1093, such that actuation portion 1082 may not be pulled proximally out of flange piece 1070. In some embodiments, either protrusion 1093, lip 1091, or both may be disposed circumferentially about actuation portion 1082, such that lip 1091 blocks protrusion 1093 regardless of a rotational position of actuation portion 1082 relative to flange piece 1070. Protrusion 1093 and lip 1091 may have squared-off cross-sectional profiles, as shown in FIG. 1G, angled cross-sectional profiles, as shown in FIG. 1H, or any other suitable cross-sectional profiles. In some embodiments, a cross-sectional profile of protrusion 1093, lip 1091, or both may be selected to improve ease of manufacturing (e.g., machining or molding the shape of protrusion 1093 or lip 1091), or may be selected to improve assembly (e.g., insertion of plunger rod 1080 into and partially through flange piece 1070).

As shown in FIG. 1I, in some embodiments, actuation portion 1082 may include one or more projections 1096 extending radially outward from an exterior perimeter of protrusion 1093. For example, protrusion 1093 may include a pair of projections 1096 disposed about protrusion 1093 at opposite locations relative to one another. Projections 1096 may include various suitable sizes, shapes, and/or cross-sectional profiles. In some embodiments, projections 1096 may have a circular shape with a rounded exterior profile to facilitate movement of protrusion 1093 within flange piece 1070.

In the present example, projections 1096 may be positioned along a side of protrusion 1093 that longitudinally aligned with a corresponding side of actuation portion 1082 including protrusions 1086. In other examples, projections 1096 may be positioned along a side of protrusion 1093 that is offset (e.g., not in longitudinal alignment) with the side of actuation portion 1093 including protrusions 1086. Projections 1096 may be formed of various flexible materials, including, for example, a polymer such as plastic, rubber, etc. It should be appreciated that plunger rod 1080 may include additional and/or fewer projections 1096 on protrusion 1093, or other portions of actuation portion 1082, than those shown and described herein without departing from a scope of this disclosure.

FIG. 1J depicts a distal end portion of flange piece 1070 including one or more recesses 1097 along an interior surface. Recesses 1097 may be sized and shaped to receive projections 1096 when protrusion 1093 is received within flange piece 1070 and positioned adjacent and/or in contact with lip 1091. It should be appreciated that lip 1091 may be configured to require application of a hydrodynamic force onto plunger rod 1080 to receive projections 1096 and protrusion 1093 distally of lip 1091 and into flange piece 1070, thereby priming device 1050 and inhibiting retraction (e.g., proximal movement) of plunger rod 1080 relative to flange piece 1070. It should be appreciated that by inhibiting removal of plunger rod 1080 after an initial assembly into flange piece 1070, device 1050 may be configured to prevent reuse of device 1050 after an initial use, and/or to prevent inadvertent air intake forming bubbles within device 1050. In the present example, flange piece 1070 may include a plurality of recesses 1097 disposed about the distal end portion in an annular array relative to one another. The plurality of recesses 1097 may be spaced apart from one another about a circumference of flange piece 1070. In some embodiments, flange piece 1070 may include recesses 1097 having varying sizes and/or shapes relative to one another.

As described in further detail below, a subset of the plurality of recesses 1097 may be sized and shaped to receive and allow passage of projections 1096 therethrough upon movement of protrusion 1093 relative to flange piece 1070. A second subset of the plurality of recesses 1097 may be sized and shaped to receive and inhibit passage of projections 1096 therethrough such that protrusion 1093 is restricted from further movement relative to flange piece 1070, as explained in further detail below.

Figure 1K:
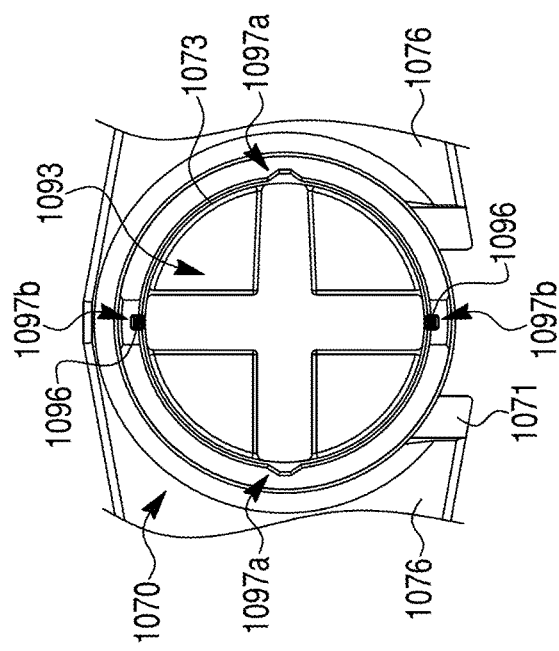

For example, as shown in FIG. 1K, flange piece 1070 includes a pair of widened recesses 1097a positioned about opening 1073 (with plunger rod 1080 received therethrough) at opposite locations relative to one another (e.g., spaced about 180 degrees apart from one another). Flange piece 1070 further includes a pair of narrowed recesses 1097b positioned about opening 1073 at opposite locations relative to one another (e.g., about 180 degrees from one another). A recess 1097a may be positioned about 90 degrees apart from an adjacent recess 1097b, along the circumference of flange piece 1070. Widened recesses 1097a may include a center wall transverse (e.g., perpendicular) to a longitudinal length of flanges 1076 and sidewalls that are angled relative to the center wall. Narrowed recesses 1097b may include a center wall parallel to the longitudinal length of flanges 1076 and sidewalls that are perpendicular to the center wall. It should be appreciated that widened recesses 1097a may form a larger opening for receiving projections 1096 relative to narrowed recesses 1097b. It should further be understood that sidewalls of recesses 1097a, 1097b may have a height that is parallel to a longitudinal length of device 1050.

In a first configuration seen in FIG. 1K, plunger rod 1080 is received through flange piece 1070 and protrusion 1093 is oriented relative to opening 1073 such that projections 1096 are received within widened recesses 1097a. The angled sidewalls of widened recesses 1097a may provide clearance to facilitate movement of projections 1096 out of widened recesses 1097a in response to a rotation of plunger rod 1080 relative to flange piece 1070. In this instance, projections 1096 may move along the angled sidewalls of widened recesses 1097a as protrusion 1093 rotates relative to opening 1073.

Figure 1L:
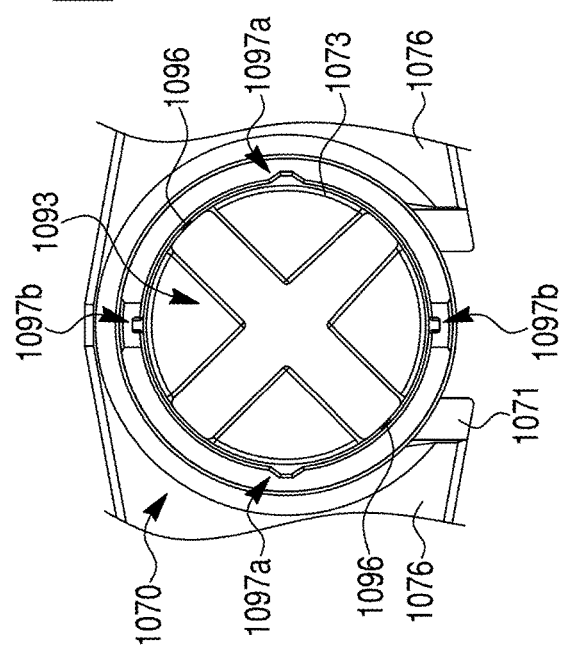
Figure 1M:
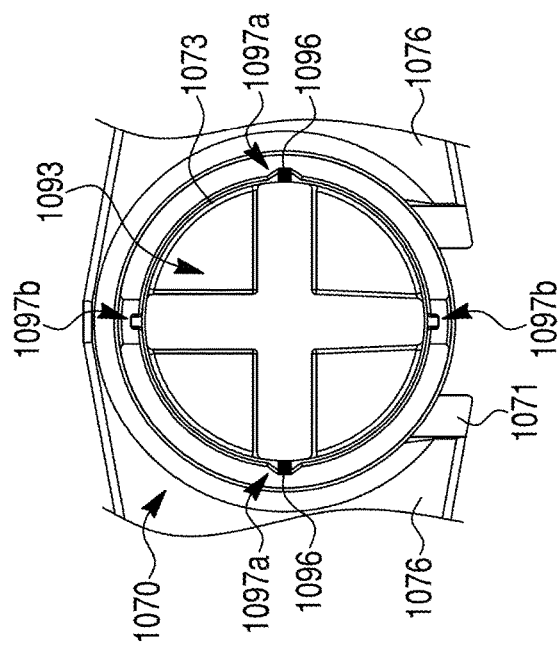

As seen in FIG. 1L, projections 1096 may abut against the interior surface of flange piece 1070 defining opening 1073 as protrusion 1093 rotates. Projections 1096 may generate a frictional interference against flange piece 1070 while moving between adjacent recesses 1097. FIG. 1M shows protrusion 1093 positioned relative to opening 1073 with projections 1096 aligned with and received in narrowed recesses 1097b. In this instance, plunger rod 1080 may be configured to generate an audible and/or tactile feedback in response to narrowed recesses 1097b receiving projections 1096. For example, a "click" or "snap" noise may be generated in response to a release of pressure applied to projections 1096 by the interior surface of flange piece 1070 when projections 1096 are received in narrowed recesses 1097b. Additionally and/or alternatively, an audible feedback may be produced in response to projections 1096 expanding and striking one or more walls defining narrowed recesses 1097b when received therein.

It should be appreciated that a frictional interference between projections 1096 and flange piece 1070 may be removed upon receipt of projections 1096 within narrowed recesses 1097b. The sidewalls of narrowed recesses 1097b may provide a physical restriction that inhibits further movement of projections 1096. In this instance, plunger rod 1080 may be fixed relative to flange piece 1070 such that protrusion 1093 is inhibited from further rotation relative to opening 1073 when projections 1096 are received within narrowed recesses 1097b.

Figure 1N:
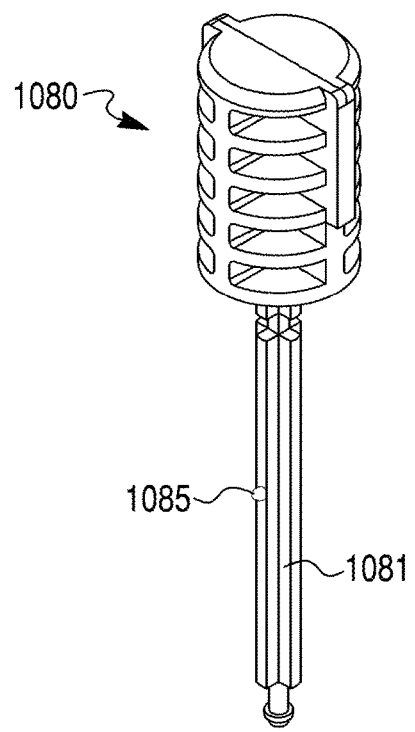
Figure 1O:
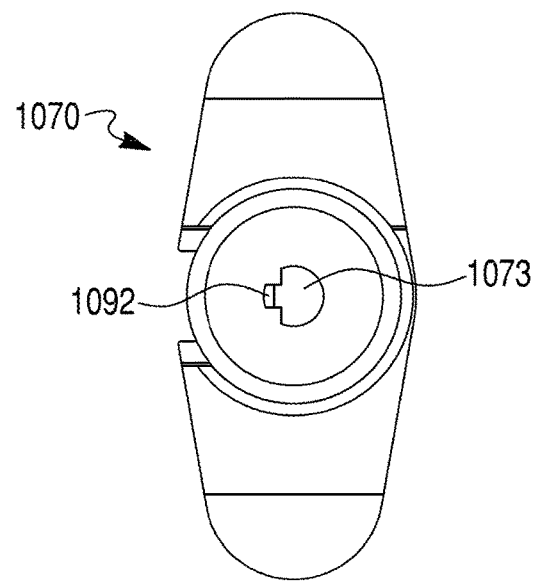
Figure 1P:
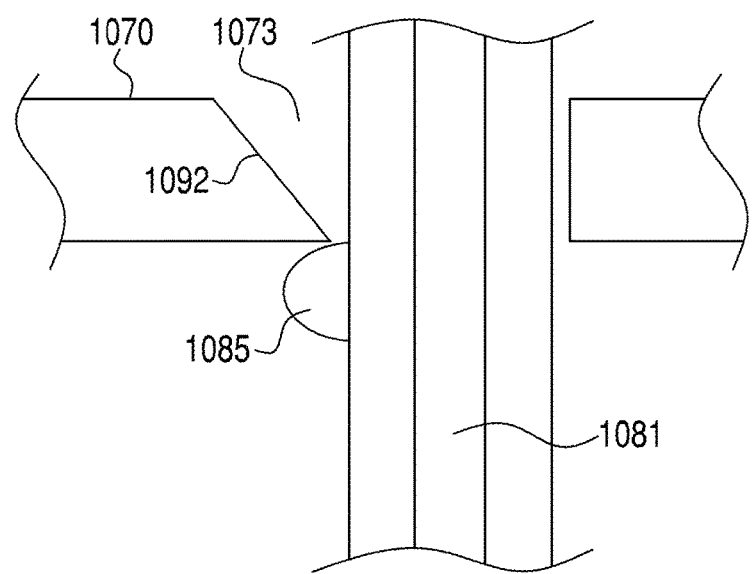

As shown in FIGS. 1N-1P, in some embodiments, plunger rod 1080 may additionally or alternatively include a protrusion 1085 on stem 1081, which may be configured to interact with opening 1073 of flange piece 1070, such that protrusion 1085 may only move distally through opening 1073. A side 1092 of opening 1073 may be angled to allow for distal passage of protrusion 1085, and to block proximal passage of protrusion 1085, as stem 1081 moves through opening 1073. Protrusion 1085 and/or side 1092 may have any suitable shape or configuration to achieve this purpose. In some embodiments, a shape or configuration of protrusion 1085 and/or side 1092 may be selected to improve ease of manufacturing (e.g., machining or molding the shape of protrusion 1085 and/or flange piece 1070).

Figure 1R:
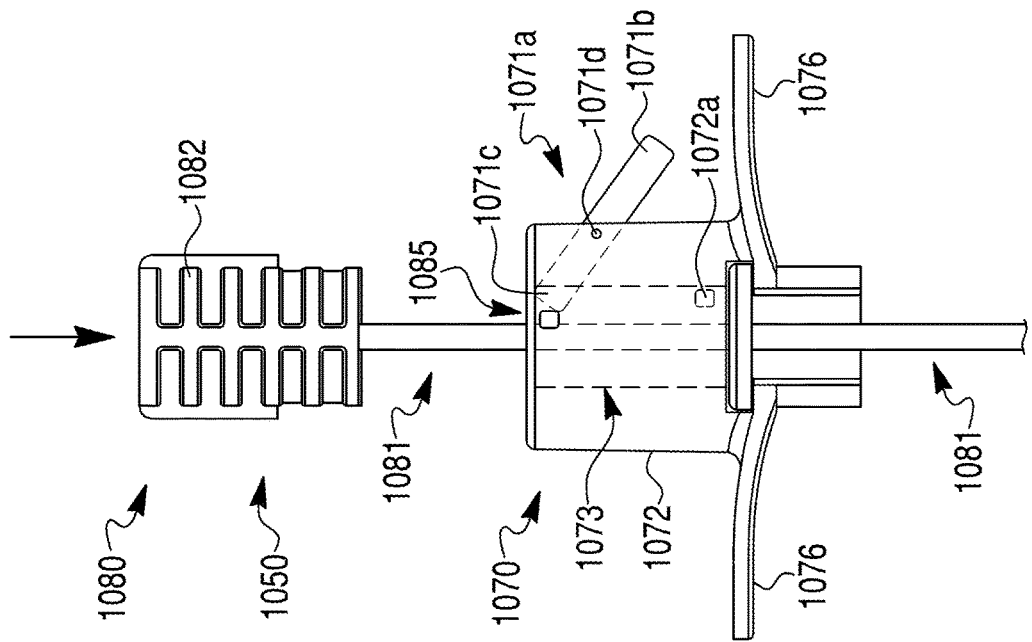
Figure 1Q:
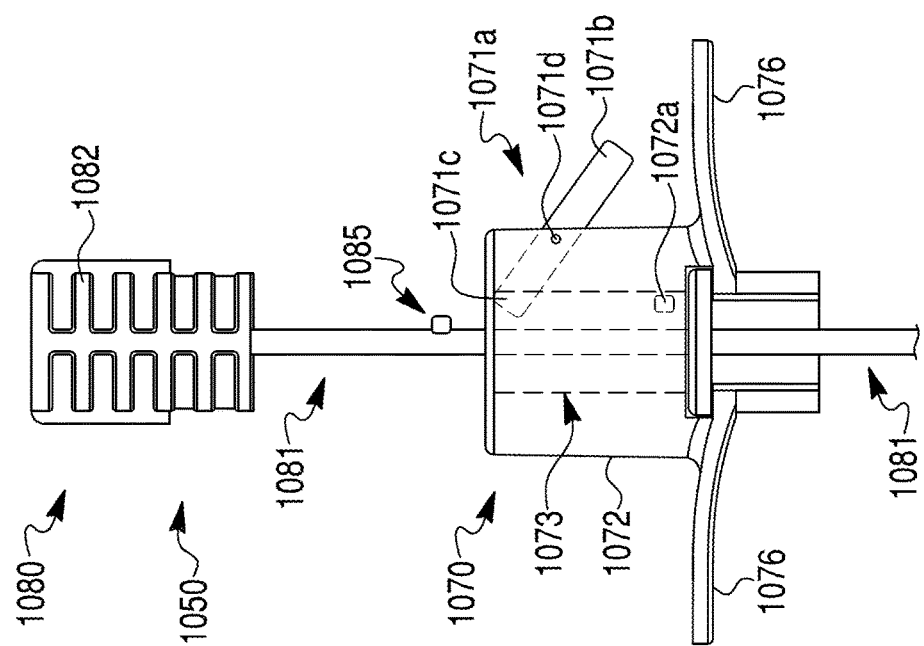

In other embodiments, flange piece 1070 may include a movable lever 1071a as seen in FIGS. 1Q-1T. Movable lever 1071a may include a first end 1071b extending outwardly from collar 1072 and a second end 1071c disposed within collar 1072. Movable lever 1071a may be movable (e.g., pivotable) about a rotation pin 1071d. Second end 1071c may be positioned within opening 1073 such that movable lever 1071a is configured to interact with protrusion 1085 upon receipt of plunger rod 1080 in flange piece 1070. Referring initially to FIG. 1Q, plunger rod 1080 may be configured to prime device 1050 by translating stem 1081 distally through flange piece 1070 until encountering movable lever 1071a.

As seen in FIG. 1R, second end 1071c may abut against protrusion 1085 when movable lever 1071a is in an obstructing position. Second end 1071c may be configured to inhibit translation of plunger rod 1080 relative to flange piece 1070 when plunger rod 1080 is in a primed position. It should be appreciated that a distance between second end 1071c and protrusion 1085 may define a priming distance for moving plunger rod 1080 to prime device 1050. Movable lever 1071a may be configured to move (e.g., pivot) relative to collar 1072 and about rotation pin 1071d to displace second end 1071c from the obstruction position. The pivoting axis, along which rotation pin 1071d extends, may be substantially perpendicular to the longitudinal axis along which plunger rod 1080 extends.

Figure 1T:
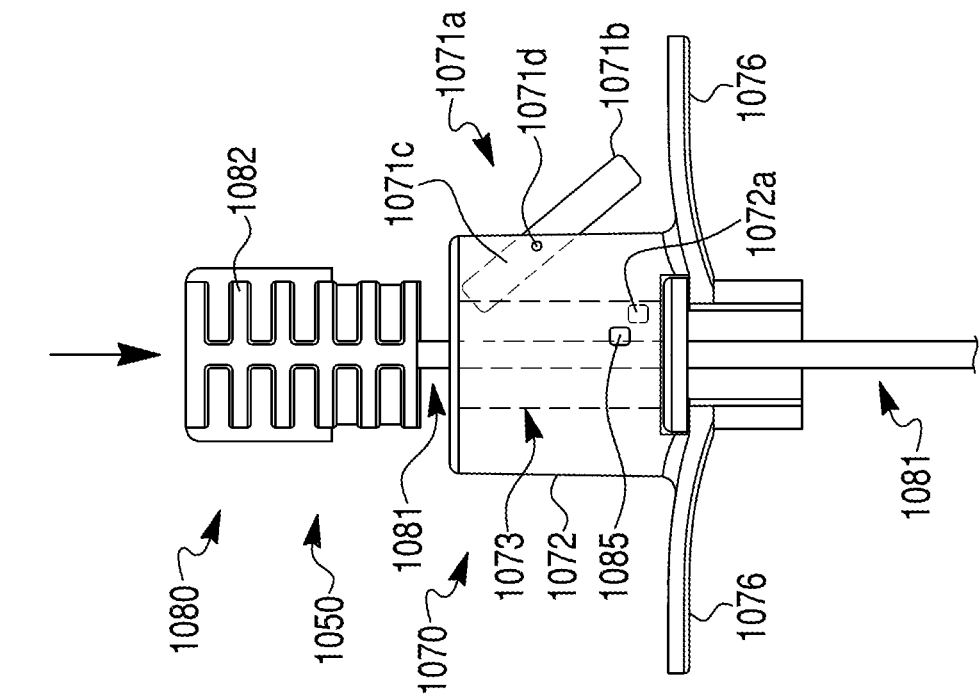
Figure 1S:
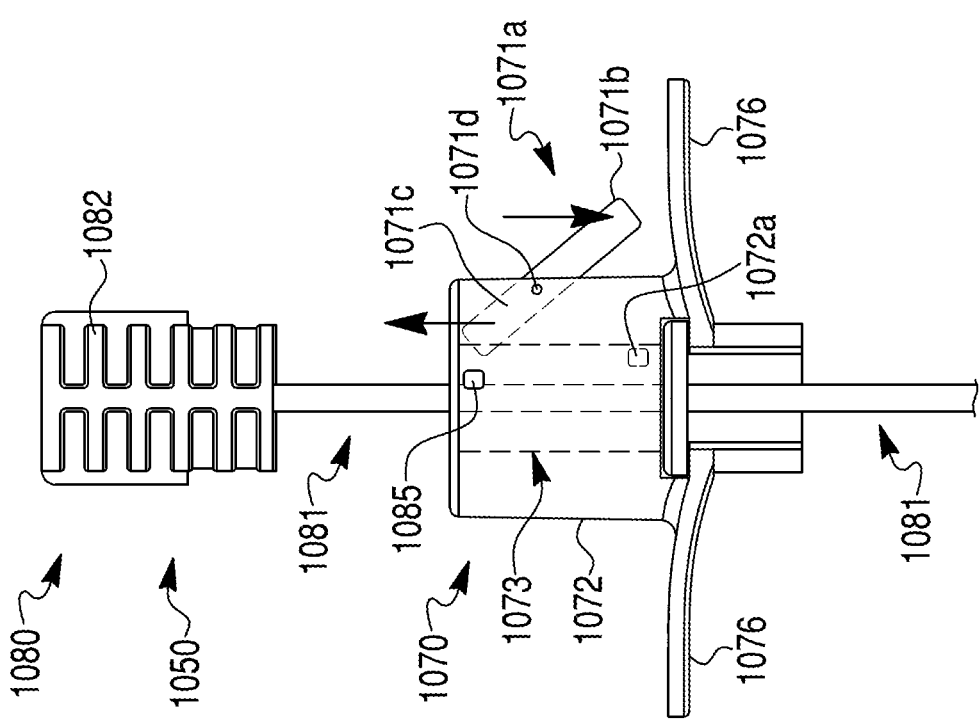

For example, as seen in FIG. 1S, movable lever 1071a may be actuated in response to moving first end 1071b distally toward flange 1076 and about rotation pin 1071d. In some embodiments, first end 1071b may be actuated in response to receiving a distally-directed force applied thereto by, for example, a user of device 1050. Second end 1071c may be moved in a proximal direction away from flange 1076 and relative to rotation pin 1071d in response to first end 1071b moving distally, thereby causing second end 1071c to disengage protrusion 1085.

Accordingly, as shown in FIG. 1T, movable lever 1071a may allow plunger rod 1080 to translate relative to flange piece 1070 until protrusion 1085 encounters an abutment 1072a positioned at a distal end of opening 1073. Abutment 1072a may cause plunger rod 1080 to settle into a dose completion position of plunger rod 1080 when protrusion 1085 is engaged thereto. It should be appreciated that a distance between second end 1071c and abutment 1072a may define a dosage delivery distance for moving plunger rod 1080 to dispense a controlled volume of substance from device 1050.

Figure 1V:
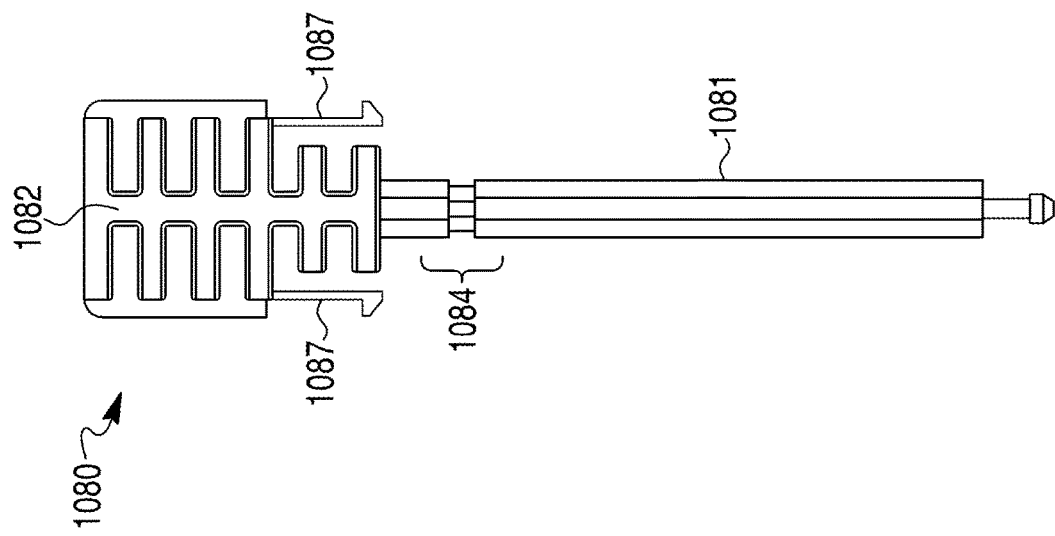
Figure 1U:
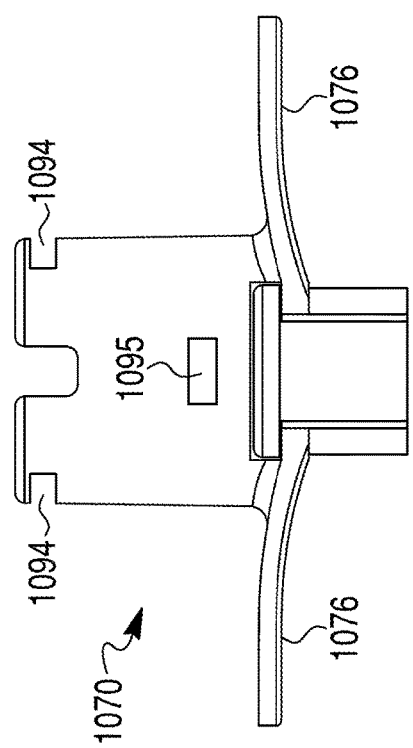

As shown in FIGS. 1U and 1V, in some embodiments, actuation portion 1082 of plunger rod 1080 may additionally or alternatively include one or more extensions 1087 configured to interface with side openings 1094, 1095 in collar 1072 of flange piece 1070. Extensions 1087 may extend distally from actuation portion 1082, and may have an angled or rounded distal portion sized and configured to be pushed inward toward a central axis of plunger rod 1080 when actuation portion 1082 is pushed distally into collar 1072. The angled or rounded distal portion of each extension 1087 may include a hook or clip shaped part 1087a. Extensions 1087 may additionally be made of a flexible material, allowing them to be pushed inward into collar 1072 and spring back outwards when no longer being restricted by a side of collar 1072. Side openings 1094, 1095 in collar 1072 may be sized and configured to receive hook or clip shaped part 1087a of an extension 1087, such that once an extension 1087 reaches a side opening 1094 or 1095, a hook or clip shaped part 1087a may spring outward into the side opening 1094 or 1095 and thereafter prevent proximal movement of plunger rod 1080. A number of extensions 1087 may coincide with a number of each of side openings 1094 and side openings 1095, such that each extension 1087 may be received in a corresponding side opening 1094 or 1095 simultaneously as plunger rod 1080 moves distally relative to flange piece 1070.

Specifically, first side openings 1094 may be configured to receive hook or clip shaped parts 1087a of extensions 1087 upon assembly of device 1050, to prevent proximal movement of plunger rod 1080 once plunger rod 1080 is inserted to a ready-to-use position. As hook or clip shaped part 1087a of each extension 1087 is received in first side openings 1094, it may make a "clicking" sound as it interfaces with collar 1072, thereby providing auditory and/or tactile feedback, indicating that the device is in a ready-to-use position. In some embodiments, first side openings 1094 may each extend around a partial circumference of collar 1072, such that the hook or clip shaped parts 1087a of extensions 1087 may be received in side openings 1094 in a range of rotational positions of plunger rod 1080 relative to flange piece 1070. Second side openings 1095 may be configured to receive hook or clip shaped parts 1087a of extensions 1087 once device 1050 is in a "delivery" configuration (e.g., after priming and additional rotation of actuation portion 1082 to align protrusions 1086 with slots 1074). In the embodiment depicted in FIGS. 1U and 1V, extensions 1087 are longitudinally aligned with protrusions 1086, and, as depicted in FIGS. 3C-3F, side openings 1095 are likewise longitudinally aligned with slots 1074, to allow for distal movement of actuation portion 1082 further into collar 1072 when device is in the "delivery" configuration. It should be appreciated that device may be transitioned to the "delivery" configuration in response to applying a distally-directed force onto actuation portion 1082, to overcome an engagement of side openings 1094 with extensions 1087, and a rotative force to overcome a frictional force between an interior of collar 1072 and extensions 1087. However, in other embodiments, it is contemplated that extensions 1087 and side openings 1094, 1095 may be in any suitable complementary configuration to assist in controlling proximal movement of plunger rod 1080.

Figure 1W:
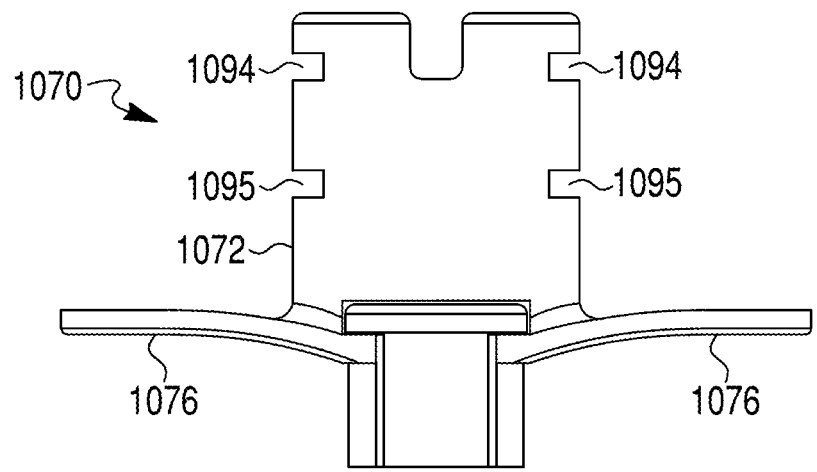

In other embodiments, as shown in FIG. 1W, side openings 1094 may be positioned along collar 1072 in longitudinal alignment with side openings 1095. Device 1050 may be primed upon receiving hook or clip shaped parts 1087a of extensions 1087, initially positioned proximally of side openings 1094, within side openings 1094. In some instances, a feedback (e.g., tactile, auditory, etc.) may be generated in response to extensions 1087 being received within side openings 1094. It should be understood that a proximal end of collar 1072 may resist distal advancement of plunger rod 1080 relative to flange piece 1070 in response to hook or clip shaped parts 1087a being engaged to collar 1072 at side openings 1094. Applying a distally-directed force onto plunger rod 1080 may cause extensions 1087 to be released from side openings 1094 and translated distally through collar 1072 until received within side openings 1095.

It should be appreciated that the distally-directed force required to deflect extensions 1087 inwardly and to release hook or clip shaped parts 1087a from side openings 1094 may correspond to a minimum priming and hydrodynamic force. Accordingly, plunger rod 1080 may be maintained in a constant radial orientation during a priming step and delivery step of device 1050. In other embodiments, additional and/or fewer side openings may be included along a circumferential wall of collar 1072 in longitudinal alignment and/or offset (e.g., not longitudinally aligned) with side openings 1094, 1095.

Figure 1X:
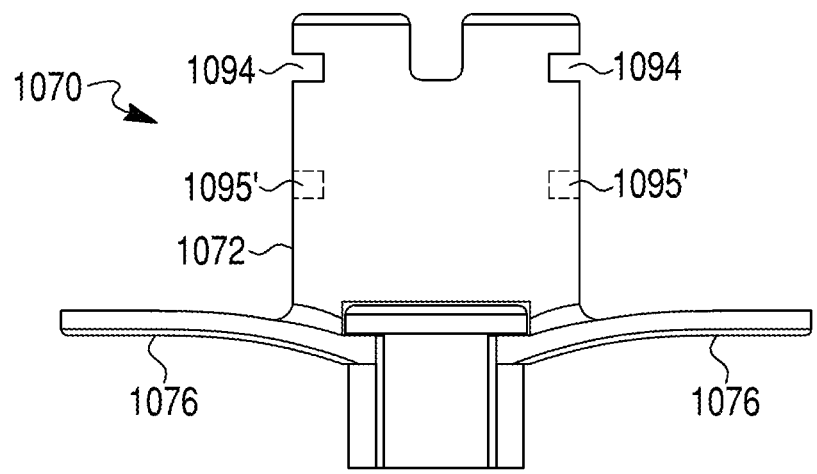

As seen in FIG. 1X, flange piece 1070 may alternatively include one or more inner projections 1095' in lieu of side openings 1095 shown and described above. In this instance, plunger rod 1080 may be preassembled into flange piece 1070 with extensions 1087 (FIG. 1V) squeezed into collar 1072 and positioned relatively proximal to side openings 1094. Device 1050 may be primed by pushing plunger rod 1080 distally through flange piece 1070 until extensions 1087 are received within side openings 1094. In some instances, a feedback (e.g., tactile, auditory, etc.) may be generated in response to extensions 1087 being received within side openings 1095. In further embodiments, side openings 1094 may be flared and/or extensions 1087 may have a distally-tapering profile to facilitate further distal advancement of plunger rod 1080 from a primed position to a dose completion position.

Further translation of plunger rod 1080 relative to flange piece 1070 may cause extensions 1087 to bend radially-inward toward one another, thereby allowing plunger rod 1080 to translate distally to deliver a dose from device 1050. Plunger rod 1080 may continue to translate distally relative to collar 1072 until hook or clip shaped parts 1087a (FIG. 1V) encounter inner projections 1095'. Inner projections 1095' may be configured to contact extensions 1087 and fix plunger rod 1080 to the dose completion position, and/or prevent further distal movement of plunger rod 1080 relative to flange piece 1070. Accordingly, further movement (e.g., proximal and/or distal) of plunger rod 1080 relative to flange piece 1070 may be inhibited by inner projections 1095' engaging hook or clip shaped parts 1087a within collar 1072. Inner projections 1095' may include complimentary hooks or clip-shaped parts that are sized and/or shaped to interact with hook or clip shaped parts 1087a or extensions 1087. It should be appreciated that a distance between side openings 1094 and inner projections 1095' may define a dosage delivery distance to dispense a controlled volume of substance from device 1050.

Figure 2A:
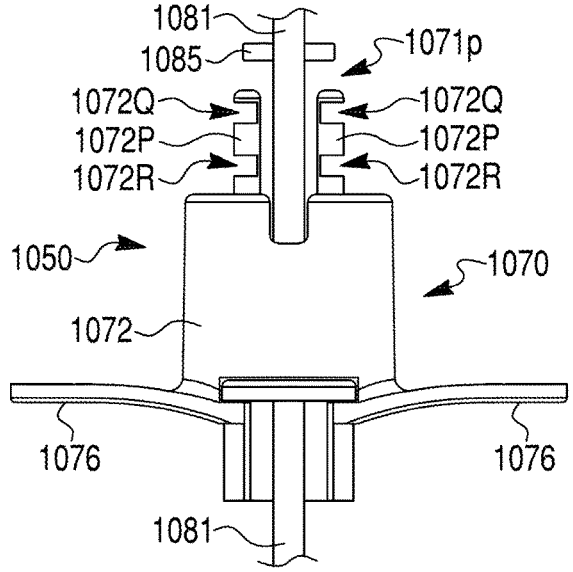
Figure 2B:
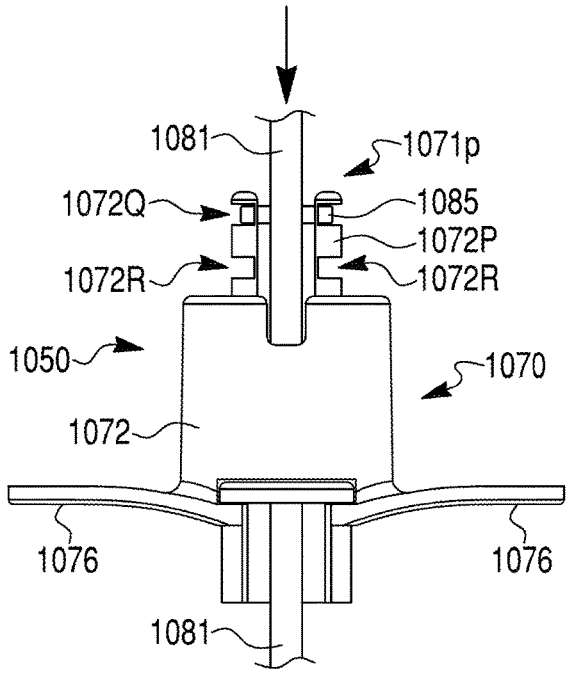
Figure 2C:
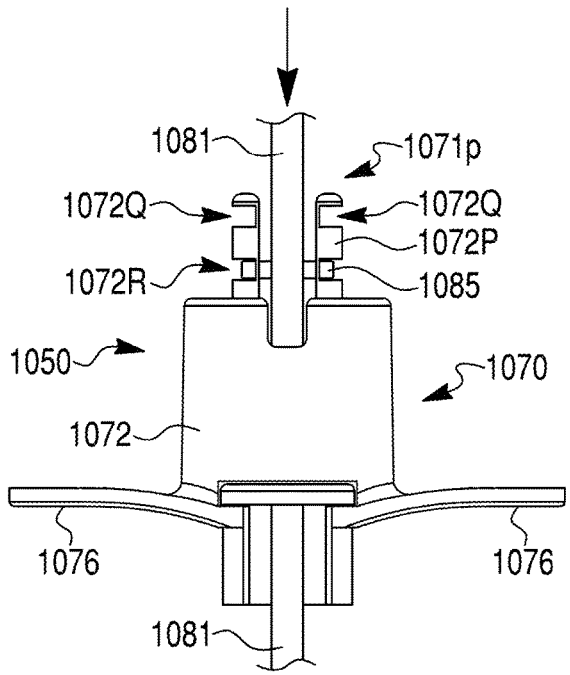

In other embodiments, as shown in FIGS. 2A-2C, flange piece 1070 may include a fixed sleeve 1072P extending proximally from collar 1072. Fixed sleeve 1072P may have a circular cross-section defining an inner channel with an opening at each terminal end of the fixed sleeve 1072P. The inner channel of fixed sleeve 1072P may extend through a longitudinal length of fixed sleeve 1072P and may be longitudinally aligned with opening 1073 (FIG. 1O) such that a respective longitudinal axis of the inner channel and opening 1073 are coaxial with one another. Fixed sleeve 1072P may be sized, shaped, and configured to receive stem 1081. In some embodiments, fixed sleeve 1072P may be integral with collar 1072, while in other embodiments fixed sleeve 1072P may be a separate component assembled onto flange piece 1070.

Fixed sleeve 1072P may include a plurality of openings that are sized and shaped to receive protrusion 1085. For example, fixed sleeve 1072P may include a pair of proximal openings 1072Q and a pair of distal openings 1072R longitudinally spaced apart from one another by an offset distance. Further, the pair of proximal openings 1072Q are located at the same longitudinal position as one another, and the pair of distal openings 1072R are located at the same longitudinal position as one another. As described in further detail below, the longitudinal offset between proximal openings 1072Q and distal openings 1072R may define a dosage delivery distance for moving plunger rod 1080 to dispense a controlled volume of substance from device 1050. Alternatively, the longitudinal offset between openings 1072Q, 1072R may define a priming distance of device 1050 such that protrusion 1085 may be initially received within proximal openings 1072Q during an assembly of device 1050 to inhibit proximal retraction of plunger rod 1080. In this instance, a dosage delivery distance may correspond to a longitudinal offset between a distal end of actuation portion 1082 and a bottom surface of collar 1072 when protrusion 1085 is received within distal opening 1072R. Although not shown, it should be appreciated that an additional set of openings may be included on fixed sleeve 1072P (e.g., proximal of proximal openings 1072Q, distal of proximal openings 1072Q, and/or distal of distal openings 1072R) to further define a priming distance and/or dosage delivery distance.

A proximal end of fixed sleeve 1072P may include an angled interface 1071P defining a proximal opening of fixed sleeve 1072P. Angled interface 1071P may be tapered radially-inward toward the inner channel of fixed sleeve 1072P and configured to guide stem 1081 and protrusion 1085 into the inner channel. In the present example, protrusion 1085 may extend radially outward from stem 1081 in opposing lateral directions and may be compressible and/or formed of a flexible/deformable material, such that protrusion 1085 is configured to retract or deform radially inward into and/or toward stem 1081 in response to a force being applied thereto. In other embodiments, protrusion 1085 may be configured to at least partially deform fixed sleeve 1072P to facilitate movement of protrusion 1085 toward and/or between openings 1072Q, 1072R. In this instance, fixed sleeve 1072P may be formed of a flexible material operable to flex radially-outward when applying a distally-directed force onto stem 1081, thereby causing protrusion 1085 to apply a radial force onto fixed sleeve 1072P.

Still referring to FIG. 2A, fixed sleeve 1072P may be configured to receive plunger rod 1080 through the inner channel and allow stem 1081 to pass through collar 1072 to prime device 1050. Protrusion 1085 may be received within fixed sleeve 1072P in response to encountering angled surface 1071P and compressing radially inward relative to stem 1081 until plunger rod 1080 is moved distally enough so that protrusion 1085 is received by proximal openings 1072Q. As shown in FIG. 2B, protrusion 1085 may be configured to expand radially outward (decompress) when longitudinally aligned with proximal openings 1072Q to lock stem 1081 relative to flange piece 1070. In this instance, device 1050 may be in a primed position such that further translation of stem 1081 distally relative to fixed sleeve 1072P and flange piece 1070 may deliver a dose from device 1050. Alternatively, device 1050 may be preassembled with protrusion 1085 received in proximal openings 1072Q such that translation of stem 1081 distally relative to fixed sleeve 1072P may prime device 1050 until protrusion 1085 is received within distal openings 1072R.

As seen in FIG. 2C, while protrusion 1085 is positioned within proximal openings 1072Q applying a distally-directed force onto stem 1081 may cause fixed sleeve 1072P to compress (or deform) protrusion 1085 radially inward, thereby allowing stem 1081 to translate distally relative to fixed sleeve 1072P. Alternatively, protrusion 1085 may be manually compressed (or deformed) by applying a radially inward-directed force through proximal openings 1072Q. Protrusion 1085 may move distally through an inner channel of fixed sleeve 1072P and may be received by distal openings 1072R. As stem 1081 translates distally relative to collar 1072, device 1050 may transition from the primed position to a dose completion position when protrusions 1085 are received within distal openings 1072R, thus delivering the dose.

It should be appreciated that a volume of the dose delivered by device 1050 may be controlled based on the longitudinal offset distance between proximal openings 1072Q and distal openings 1072R. In some embodiments, fixed sleeve 1072P may include additional openings for receiving protrusion 1085 after priming and delivering a dose to inhibit proximal retraction of stem 1081 (e.g., pull back of plunger rod 1080) relative to flange piece 1070. For example, protrusion 1085 may be received within proximal openings 1072Q during an assembly of device 1050 at a manufacturing stage such that distal openings 1072R may define a priming position and a third set of openings (not shown) distal to distal opening 1072R may define a dosage delivery position. Alternatively, a bottom, interior surface of flange piece 1070 distal to distal opening 1072R may define the dosage delivery position of plunger rod 1080.

In some embodiments, as seen in FIGS. 2D-2G, flange piece 1070 may include a movable sleeve 1072S extending distally and proximally from collar 1072. Movable sleeve 1072S may have a circular cross-section defining an inner channel with an opening at each terminal end of movable sleeve 1072S. The inner channel of movable sleeve 1072S may extend through a longitudinal length of movable sleeve 1072S. Movable sleeve 1072S may be sized, shaped, and configured to be received through opening 1073, and the inner channel of movable sleeve 1072S may be sized to receive stem 1081. Movable sleeve 1072S may be fixed relative to collar 1072 when in an preassembled configuration and may be movable relative to collar 1072 upon engagement with plunger rod 1080.

Movable sleeve 1072S may include a plurality of openings that are sized and shaped to receive protrusion 1085. For example, movable sleeve 1072S may include a proximal opening 1072U at a proximal end of movable sleeve 1072S and a distal opening 1072T at a distal end of movable sleeve 1072S. A proximal end of movable sleeve 1072S may further include an angled interface 1071S defining a proximal opening of movable sleeve 1072S. Angled interface 1071S may be tapered radially-inward toward the inner channel of movable sleeve 1072S and configured to guide stem 1081 and protrusion 1085 into the inner channel of movable sleeve 1072S. In some embodiments, protrusion 1085 may extend radially outward from stem 1081 in opposite directions and may be compressible such that protrusion 1085 is configured to compress into and/or toward stem 1081 in response to a force being applied thereto.

Figure 2E:
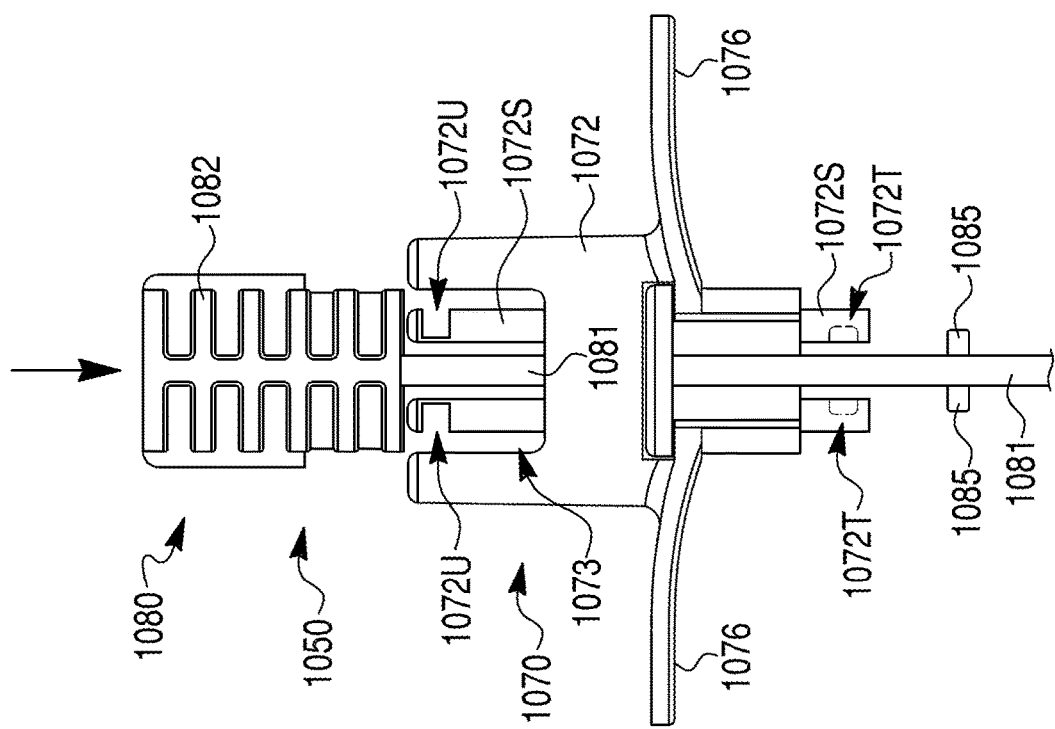
Figure 2D:
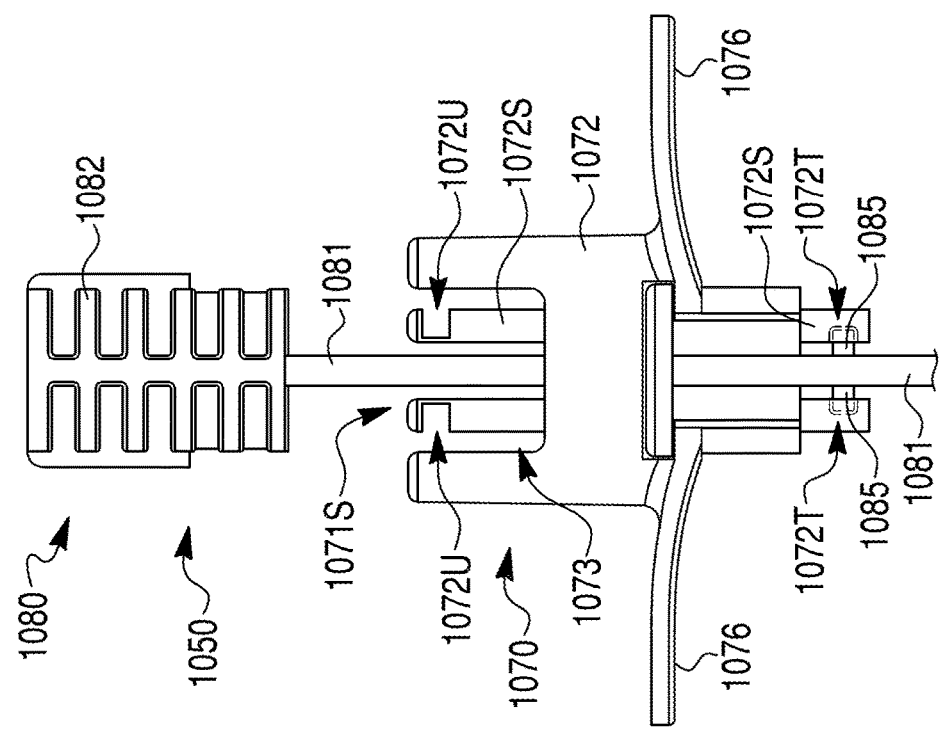

Still referring to FIG. 2D, the proximal end of movable sleeve 1072S may be positioned adjacent to a proximal end of collar 1072 and a distal end of movable sleeve 1072S may be positioned adjacent to a distal end of collar 1072 when in the preassembled position. Plunger rod 1080 may be received through the inner channel of movable sleeve 1072S with stem 1081 extending through collar 1072. Protrusion 1085 may be received within distal opening 1072T such that plunger rod 1080 may be fixed to movable sleeve 1072S. Protrusion 1085 may be configured to exit distal opening 1072T and expand laterally outward in response to plunger rod 1080 translating relative to movable sleeve 1072S.

For example, as shown in FIG. 2E, applying a distally-directed force onto actuation portion 1082 may cause protrusion 1085 to compress radially inward, thereby allowing stem 1081 to translate distally relative to movable sleeve 1072S. In this instance, protrusion 1085 may exit distal opening 1072T and expand upon translating distally from a distal end of movable sleeve 1072S. Device 1050 may transition from a preassembled state to a primed state, in response to stem 1081 translating distally relative to collar 1072, until actuation portion 1082 abuts against a proximal end of movable sleeve 1072S. In this instance, device 1050 may be in a primed state and further translation of stem 1081 relative to collar 1072 may be inhibited by the presence of movable sleeve 1072S.

Figure 2F:
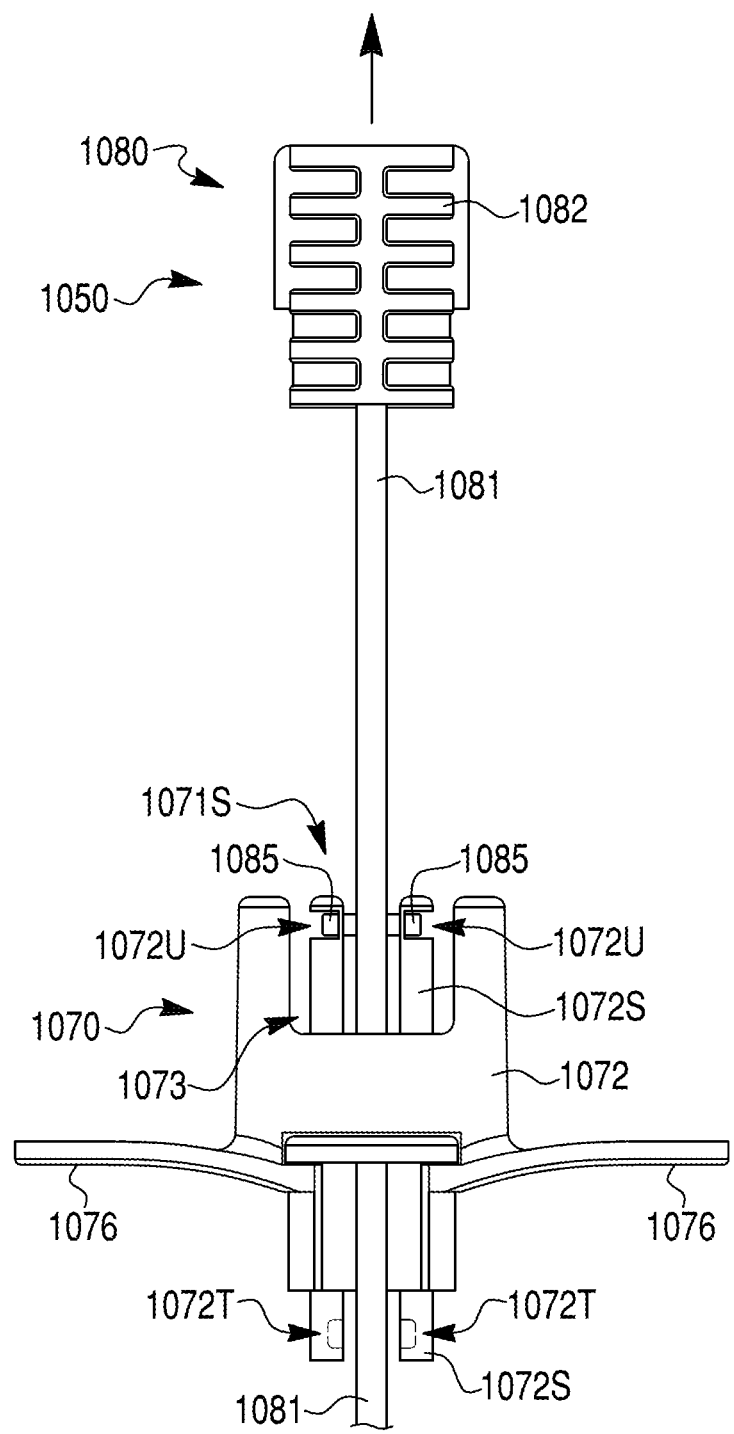

Referring now to FIG. 2F, plunger rod 1080 may couple to movable sleeve 1072S in response to proximal translation of stem 1081 relative to collar 1072 until protrusion 1085 engages proximal opening 1072U. It should be understood that protrusion 1085 may be in a compressed state when translating through an inner channel of movable sleeve 1072S and may expand into proximal opening 1072U upon longitudinal alignment therewith. With protrusion 1085 engaged to proximal opening 1072U, a distal translation of plunger rod 1080 relative to flange piece 1070 may provide a simultaneous movement of movable sleeve 1072S relative to collar 1072. It should be appreciated that a collective length of movable sleeve 1072S and plunger rod 1080 may be greater than a longitudinal length of plunger rod 1080 alone.

Figure 2G:
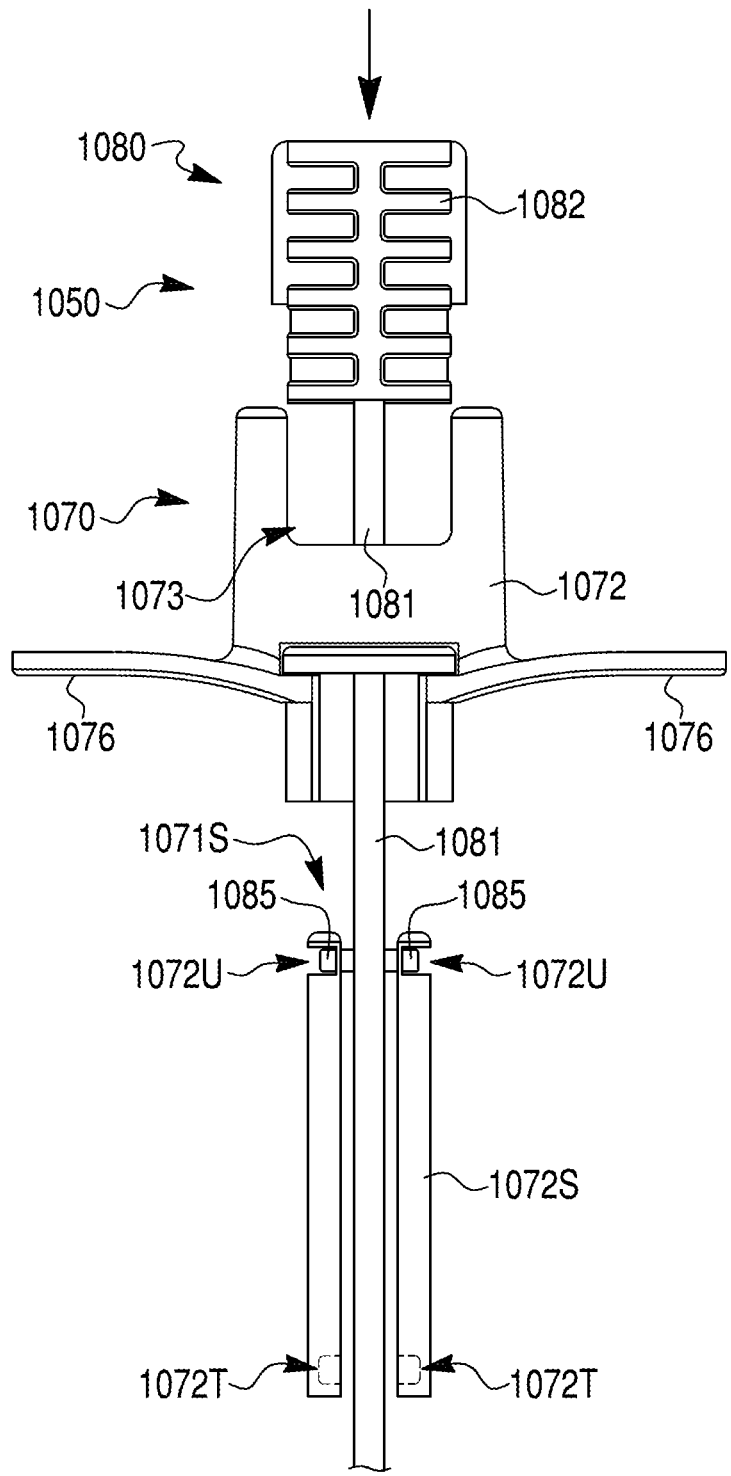

As seen in FIG. 2G, plunger rod 1080 may be configured to move movable sleeve 1072S through a channel of flange piece 1070 by a predetermined distance until actuation portion 1082 encounters a proximal end of collar 1072. Plunger rod 1080 may be configured to deliver a dose from device 1050 in response to translating movable sleeve 1072S distally relative to collar 1072. It should be appreciated that the dosage delivered by device 1050 may be controlled based on the predetermined distance between actuation portion 1082 and collar 1072 when protrusion 1085 is received within proximal opening 1072U. In some embodiments, flange piece 1070 may be configured to inhibit proximal movement of movable sleeve 1072S relative to collar 1072 when protrusion 1085 is received within proximal opening 1072U. Although not shown, flange piece 1070 may include one or more blocking components operable to restrict proximal retraction of movable sleeve 1072S from opening 1073.

In other embodiments, as seen in FIGS. 2H-2M, plunger rod 1080 may include at least one protrusion 1085W positioned on actuation portion 1082. In the example, protrusion 1085W may be positioned at or adjacent a distal end of actuation portion 1082 such that protrusion 1085W may be received within flange piece 1070 in response to translation of plunger rod 1080 into collar 1072.

As seen in FIG. 2K, flange piece 1070 may include one or more channels formed along an inner surface of collar 1072. In particular, collar 1072 may include a first (proximal) helical channel 1071W formed along an interior of collar 1072 and having a first curvature, and a second (distal) helical channel 1072W formed along the interior of collar 1072 and having a different and/or opposite curvature than the first helical channel 1071W. For example, when viewed from the proximal end of actuation portion 1082, first helical channel 1071W may be concave, while second helical channel 1072W may be convex when viewed from the same vantage point. Or, first helical channel 1071W may be convex when viewed from the proximal end of actuation portion 1082, while second helical channel 1072W is concave from the same vantage point. Further, second helical channel 1072W may be longitudinally spaced apart from first helical channel 1071W. First helical channel 1071W may be connected with second helical channel 1072W by an intermediate, third channel 1073W extending therebetween.

Third channel 1073W may extend along or substantially parallel to a longitudinal axis of collar 1072. It should be understood that a size, shape, and/or orientations of the one or more channels on collar 1072 are merely exemplary such that other suitable configurations may be included without departing from a scope of this disclosure. As described in detail below, the plurality of channels 1072 are configured to receive protrusion 1085W. In some embodiments, first helical channel 1071W and second helical channel 1072W may be threaded and configured to mesh with a corresponding component of plunger rod 1080 (e.g., protrusion 1085W). Opposite rotational movement may be required for protrusion 1085W to traverse through first helical channel 1071W and second helical channel 1072W. For example, a first rotational movement of actuation portion (e.g., clockwise) may cause protrusion 1085W to traverse first helical channel 1071W, while an opposing rotational movement (e.g., counterclockwise) may cause protrusion 1085W to traverse through second helical channel 1072W.

Referring to FIG. 2H, with plunger rod 1080 in a ready position, protrusion 1085W may be received within collar 1072 in response to a distal translation of actuation portion 1082 toward flange piece 1070. As seen in FIG. 2I, protrusion 1085W may be received within first helical channel 1071W and moved therethrough in response to a rotation of plunger rod 1080 (e.g., in a first direction) relative to flange piece 1070. It should be appreciated that plunger rod 1080 may be configured to translate axially in a distal direction relative to flange piece 1070 as plunger rod 1080 rotates within collar 1072, due to the curvature of first helical channel 1071W. For example, plunger rod 1080 may translate a first distance defined by a configuration of first helical channel 1071W until reaching a terminal end of first helical channel 1071W. The first distance may correspond to a priming step of device 1050 such that device 1050 may be at least partially primed upon protrusion 1085W moving through first helical channel 1071W.

Referring now to FIG. 2J, protrusion 1085W may be positioned at a terminal end of first helical channel 1071W and a proximal (e.g., top) end of third channel 1073W. In some embodiments, plunger rod 1080 may experience a tactile feedback formed by the terminal end of first helical channel 1071W. Plunger rod 1080 may be translated distally through third channel 1073W to complete a priming step of device 1050, as shown in FIG. 2K. It should be understood that first helical channel 1071W and third channel 1073W may collectively define a priming distance of device 1050 such that plunger rod 1080 is in a primed position when protrusion 1085W translates through third channel 1073W.

With protrusion 1085W received within second helical channel 1072W, plunger rod 1080 may be rotated in the second direction (opposite of the first direction) to translate plunger rod 1080 distally by a second distance that is defined by a configuration of second helical channel 1072W. The second distance may be less than, greater than, and/or substantially equal to the longitudinal dimension of second helical channel 1072W, depending on the particular application and need. Plunger rod 1080 may be rotated in the second direction and translated by the second distance until reaching a terminal end of second helical channel 1072W to deliver a dose from device 1050. It should be understood that the second distance may correspond to a dosage delivery step of device 1050 such that device 1050 may deliver the dose upon protrusion 1085W moving through second helical channel 1072W and arriving at a dose completion position.

In other embodiments, as seen in FIGS. 2L-2O, plunger rod 1080 may include a protrusion, a knob, and/or a thread 1085X positioned on actuation portion 1082. In the example, thread 1085X may be positioned about a circumference of actuation portion 1082 and along a distal end such that thread 1085X may be received within flange piece 1070 in response to translation of plunger rod 1080 into collar 1072.

Flange piece 1070 may further include a threaded portion 1072X disposed within opening 1073 and forming a helical path that is configured to receive thread 1085X. In the example, threaded portion 1072X may be positioned along a proximal portion of opening 1073 such that a distal portion of opening 1073 may include a non-threaded portion 1071X. As described in further detail herein, threaded portion 1072X may define a longitudinal distance corresponding to a priming step of device 1050 and non-threaded portion 1071X may define a distance corresponding to a dosage delivery step of device 1050.

For example, as seen in FIG. 2L, actuation portion 1082 may be translated distally toward flange piece 1070 until thread 1085X encounters a distal end of collar 1072. Rotation of plunger rod 1080 in a first direction (e.g., clockwise or counter clockwise) may cause thread 1085X to engage threaded portion 1072X. As shown in FIG. 2M, rotation of plunger rod 1080 may provide axial/longitudinal translation of actuation portion 1082 into collar 1072 as thread 1085X moves through the helical path of threaded portion 1072X. It should be appreciated that rotation and translation of thread 1085X through threaded portion 1072X may transition device 1050 from a ready position (FIG. 2L) to a primed position (FIG. 2N). With thread 1085X disengaged from threaded portion 1072X and positioned along non-threaded portion 1071X, device 1050 may be in the primed position. In some instances, a feedback (e.g., tactile, auditory, etc.) may be generated in response to thread 1085W exiting threaded portion 1072X and/or entering non-threaded portion 1071X.

In this instance, as shown in FIG. 2O, actuation portion 1082 may be translated distally relative to flange piece 1070 to deliver a dose from device 1050 by application of a distally-directed force against actuation portion 1082. Thread 1085X may move through the distal portion of opening 1073 when thread 1085X is positioned within non-threaded portion 1071X. A longitudinal length of non-threaded portion 1071X defined between a distal end of thread portion 1072X and a distal end of opening 1073 may control a dosage delivery of device 1050. Device 1050 may complete delivery of a dose when actuation portion 1082 engages a proximally-facing and distal surface of collar 1072 and plunger rod 1080 arrives at the dose completion position.

FIGS. 2P-2T illustrate further embodiments of a flange piece that may be configured and operable similar to flange piece 1070 shown and described above except for the differences explicitly noted herein. It should be understood that like reference numerals are used to identify like components and the flange pieces described below may be readily incorporated with one or more components of device 1050 shown and described above.

For example, referring initially to FIG. 2P, a flange piece 1070A may include one or more flanges 1076A that may be sized and configured to aid a user in holding device 1050 and/or expelling a formulated drug substance from device 1050. Flanges 1076A may be further sized and/or shaped to allow a user to hold device 1050 with a plurality of hand/grip positions, arrangements, and/or orientations. By way of illustrative example, flanges 1076A may be sized and/or shaped such that flange piece 1070A may be held similar to a writing instrument (e.g., pencil, pen, etc.) without requiring use of flanges 1076A, or sized in accordance with the example shown in FIG. 24A such that flanges 1076A may abut against one or more fingers of a user. Flange piece 1070A may include a pair of flanges 1076A extending radially outwardly from collar 1072 in opposite radial directions relative to one another. Flanges 1076A may extend transversely from collar 1072 (e.g., flanges 1076A may include an angled surface that is sloped radially-inward in a distal direction) and configured to inhibit a user's fingers from slipping off of flange piece 1070A during use of device 1050.

Flanges 1076A may be coupled to one another to form a semi-circular profile with a minimal radius relative to collar 1072. Accordingly, flanges 1076A may form a slim profile to facilitate visualization of a target treatment site at a distal end of device 1050 (not shown) when using device 1050 from a perspective proximal of finger flange 1070A. It should be understood that flange piece 1070A may include various other quantities and/or arrangements of flanges 1070A than those shown and described herein without departing from a scope of this disclosure. In other embodiments, flanges 1076 may include various other suitable sizes and/or shapes.

Flange piece 1070A may further include a distal collar 1075A extending distally from collar 1072 and configured to engage body 1060 to hold flange piece 1070A in a fixed position relative to body 1060. Distal collar 1075A may be adhered to, molded, or otherwise affixed to body 1060, or may engage body 1060 via a friction fit. In the example, distal collar 1075A includes a longitudinal length that is generally less than a longitudinal length of collar 1072. In some embodiments, distal collar 1075A may be sized sufficiently small enough to facilitate adequate exposure of body 1060 for user grasp and/or manipulation during use of device 1050. Additionally, distal collar 1075A may include a material composition that is similar to and/or different from collar 1072. For example, distal collar 1075A may be formed of a flexible material such that distal collar 1075A may be configured to flex radially-outward when receiving body 1060 into flange piece 1070A and flex radially-inward once body 1060 is fully received to facilitate a snap-fit connection (without breaking distal collar 1075A). It should be appreciated that, in other embodiments, flange piece 1070A may omit distal collar 1075A entirely.

In other embodiments, as seen in FIG. 2Q, a flange piece 1070B may include a distal collar 10756 that is substantially longer than distal collars 1075, 1075A shown and described above. For example, distal collar 1075B may be enlarged with a longitudinal length that is greater than a longitudinal length of collar 1072. In the example, distal collar 1075A may be sized sufficiently large enough to encompass a substantial length of body 1060. In this instance, an exterior surface of distal collar 10756 may provide an interface for a user to grasp and/or manipulate during use of device 1050. Additionally, distal collar 1075B may include an expanded diameter that exceeds a diameter of body 1060 to provide an enhanced surface area for grasping flange piece 10706. Stated differently, distal collar 10756 may have a widened size and/or shape to facilitate ease in gripping and/or manipulating device 1050. In the present example, distal collar 1075B may have a barrel-shape with a convex outer surface when viewed from an exterior of device flange piece 10706.

Alternatively, as seen in FIG. 2R, a flange piece 1070C may include a distal collar 1075C that is substantially similar to distal collar 1075B and includes a longitudinal length that is greater than a longitudinal length of collar 1072. In the example, an exterior surface of distal collar 1075C may be configured to provide an interface for a user to grasp and/or manipulate during use of device 1050. Distal collar 1075C may include a slim profile with a diameter that is greater than a diameter of body 1060 such that distal collar 1075C does not substantially increase a profile of body 1060. Stated differently, distal collar 1075C may have a narrowed size relative to distal collar 1075B. In some embodiments, distal collar 1075C may include a terminal lip 1077C that extends radially outward at a distal end. Terminal lip 1077C may be sized, shaped, and configured to enhance gripping and/or manipulation of distal collar 1075C. In the present example, distal collar 1075C may have a flared-shape with a concave outer surface when viewed from an exterior of device flange piece 1070C.

In other embodiments shown in FIGS. 2S-2T, a flange piece 1070D may include a collar 1072D having a proximal lip 1074D. Proximal lip 1074D may define an irregular surface configured to interface with plunger rod 1080 when actuation portion 1082 is received by collar 1072D. For example, proximal lip 1074D may include a pair of recessed surfaces 1075D positioned along opposing sides from one another along proximal lip 1074D. In other words, recessed surfaces 1075D may be separated from one another by surfaces and/or portions of proximal lip 1074D that are not recessed. In the example, recessed surfaces 1075D may be positioned adjacent to slots 1074 and may define a pathway for moving plunger rod 1080 relative to collar 1072D for priming and delivering a dose from device 1050. In some embodiments, recessed surfaces 1075D may include a spiral configuration (e.g., have a distally-directed slope) such that recessed surfaces 1075D may be tapered in a distal direction between a first ledge 1073D and a second ledge 1076D.

In some embodiments, flange piece 1070D may include visualization mechanisms, such as, for example, one or more labels or markings disposed on collar 1072D to provide instructions to a user of device 1050. For example, the one or more labels (e.g., numbering) may indicate directions in which to rotate or otherwise move plunger rod 1080 relative to flange piece 1070D to prime and deliver a dosage from device 1050. By way of example, the one or more labels may include markings that indicate a start position (e.g., "1"), a priming position (e.g., "2"), and a dosage delivery position (e.g., "3") of protrusions 1086 relative to proximal lip 1074D. The one or more labels may be adhered, printed, embossed, and/or molded onto collar 1072D.

As described in greater detail herein, flange piece 1070D may be configured to allow movement of plunger rod 1080 in a single direction when priming and delivering a dosage from device 1050. In exemplary use, plunger rod 1080 (not shown) may initially be received through flange piece 1070D and actuation portion 1082 may be positioned against collar 1072D with protrusions 1086 positioned along a first end of recessed surfaces 1075D at marking "1" and opposite of slot 1074. Protrusions 1086 may only be rotated in a single direction along recessed surface 1075D, toward marking "2," due to first ledge 1073D inhibiting protrusions 1086 from moving in an opposite direction away from marking "2".

When protrusions 1086 are received along recessed surfaces 1075D at marking "2," second ledge 1076D may further prevent protrusions 1086 from moving past slots 1074 and passing by marking "3". It should be appreciated that a configuration of proximal lip 1074D is exemplary such that flange piece 1070D may include various other sizes, shapes, and/or configurations of proximal lip 1074D and/or recessed surfaces 1075D than those shown and described herein to facilitate movement of plunger rod 1080 during use of device 1050.

In other embodiments, the components of device 1050 may include one or more color indicators in lieu of and/or in addition to the markings described above to provide instructions to a user of device 1050. For example, device 1050 may include colors, symbols (e.g., arrows), and the like indicating a direction in which to rotate or otherwise move plunger rod 1080 relative to flange piece 1070D to prime and deliver a dosage. In one embodiment, an exterior surface of plunger rod 1080 may be provided with different colors along various portions of actuation portion 1082 to indicate a respective start position (e.g., green), priming position (e.g., yellow), and dosage delivery position (e.g., red) of plunger rod 1080 relative to collar 1072D. The one or more color indicators may be printed or molded onto plunger rod 1080. In other embodiments, the various portions of plunger rod 1080 may include different textures in lieu of and/or in addition to the color indicators described above to provide instructions to a user of device 1050.

Components of device 1050 may be made of any suitable material, and each component may be made from the same or different materials as other components. It should be appreciated that, in some embodiments, one or more components of device 1050 (e.g., flange piece 1070, proximal collar 1072, plunger rod 1080, actuation portion 1082, and more) may be formed of a flexible material having sufficient flexibility to prevent breakage during flexing. In some embodiments, the one or more components of device 1050 may be rigid and have enough strength to maintain shape and provide support. In other embodiments, one or more components of device 1050 (or at least a portion of a component) may having a varying rigidity along a longitudinal length or lateral width such that the component may have a variable flexibility. In still further embodiments, the one or more components of device 1050 may have sufficient flexibility to prevent breakage during flexing while also having sufficient rigidity and strength to maintain shape and provide support. In some embodiments, such features may further provide a user feedback (e.g., tactile, audible, visual, etc.) when flexing and/or interacting with other components of device 1050. For example, each of body 1060, flange piece 1070, and plunger rod 1080 may be made of a material including a polymer, such as a plastic. In some embodiments, one or more of body 1060, flange piece 1070, and plunger rod 1080 may include multiple different materials (e.g., glass, rubber, and/or plastic). In some embodiments, for example, the cylindrical portion of body 1060 may be made of glass, Plexiglas, or any other suitable polymer (e.g., cyclic olefin polymer or cyclic olefin copolymer) or other material, and stopper 1062 may be made of, e.g., plastic, rubber, or other polymer or copolymer. By way of further example, flange piece 1070 may include a polypropylene homopolymer, an ABS (Acrylonitrile, Butadiene, and Styrene) polymer, ABS polycarbonate blend, and other suitable materials. In some embodiments, plunger rod 1080 may include an ABS polycarbonate blend. Such materials may provide greater tolerances for manufacturing (e.g., injection molding) flange piece 1070 and/or plunger rod 1080, or facilitate an increased reproducibility of said components of device 1050. As described in greater detail above, in some embodiments, one or more components of device 1050 may be formed of a flexible and/or deformable material composition providing greater tolerances for flexing or deforming said components (e.g., without breaking) when priming or delivering a dose from device 1050.

In some embodiments, a portion of body 1060 configured to contain a formulated drug substance may be made of a transparent or translucent material. In some embodiments, flange piece 1070 and plunger rod 1080 may be made of the same, similar, or different materials, such as similar or different plastics (e.g., each having a similar or different hardness). In some embodiments, parts of device 1050 may include elastic materials. For example, parts of device 1050 may include rubber or plastic configured to allow a user to better grip device 1050, or to create an airtight or otherwise sealing fit between two components of device 1050 (e.g., between body 1060 and stopper 1062). In some embodiments, some or all of plunger rod 1080 (e.g., actuation portion 1082 and/or extensions 1087, or alternately the entirety of plunger rod 1080) may be made of a material having some flexibility, e.g., to allow for bending of extensions 1087. One or more of the materials listed above (e.g., plastic, rubber, polymers, or copolymers) may have such characteristics. In some embodiments, some or all of device 1050 may be suitable for sterilization, e.g., heat or chemical sterilization.

Figure 3A:
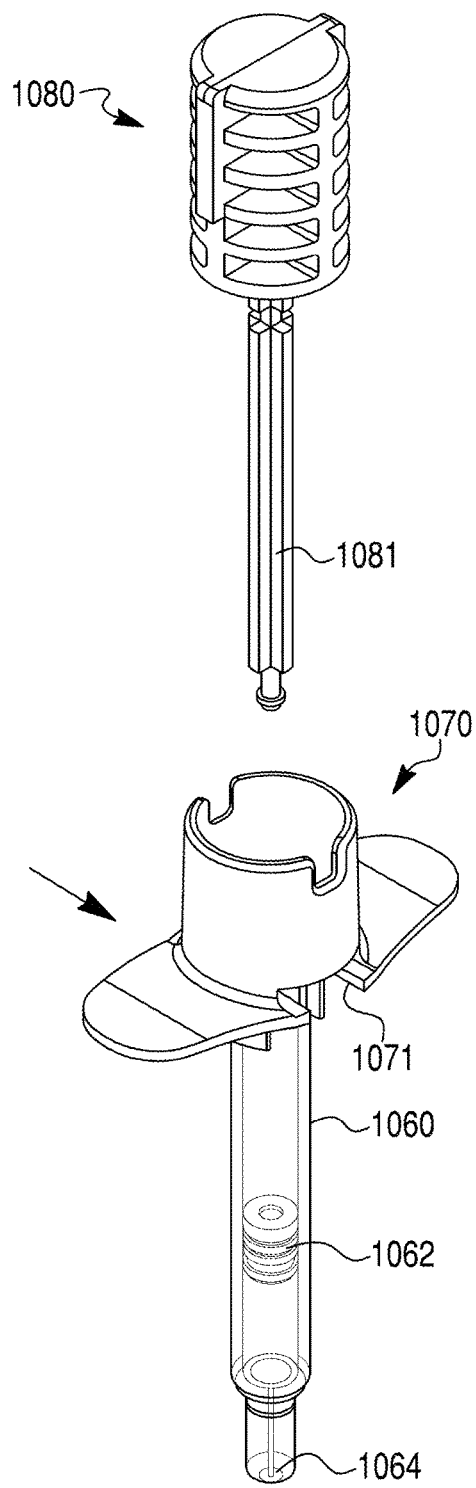
FIGS. 3A and 3B depict an exemplary method of assembling the delivery device depicted in FIGS. 1A-1E, according to aspects of the present disclosure.
Figure 3B:
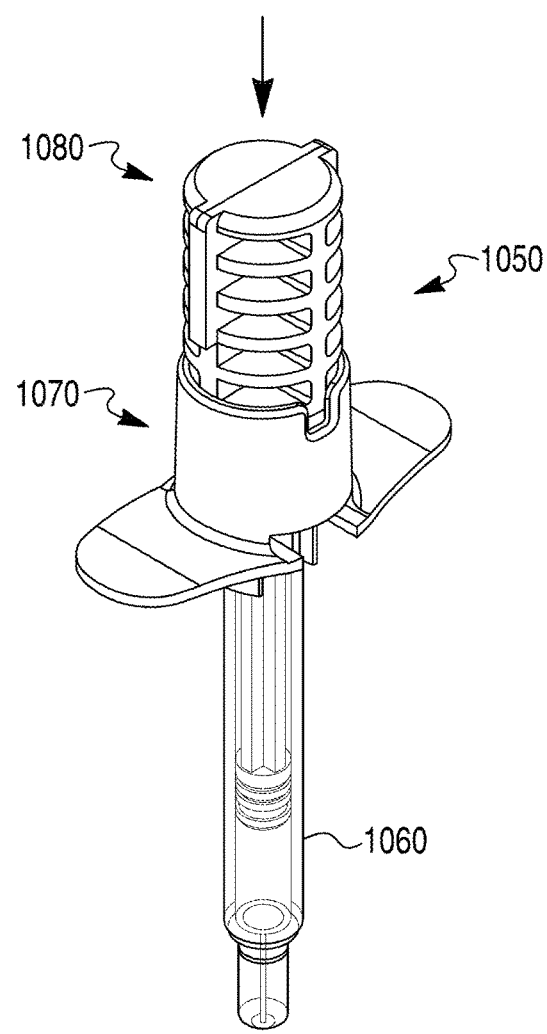
Figure 3C:
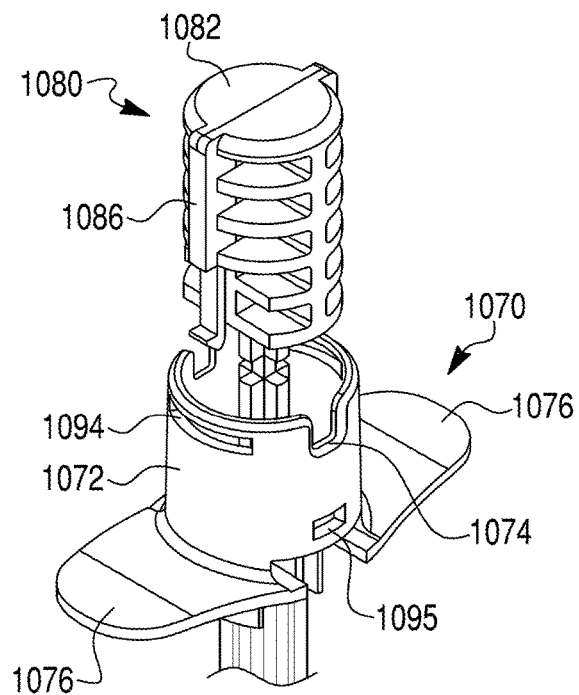
FIGS. 3C-3F depict an exemplary method of assembling an embodiment of the delivery device depicted in FIGS. 1A-1E, according to aspects of the present disclosure.
Figure 3E:
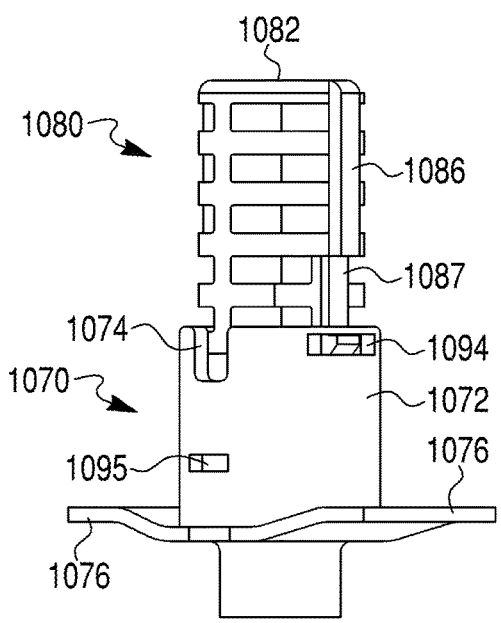
Figure 3D:
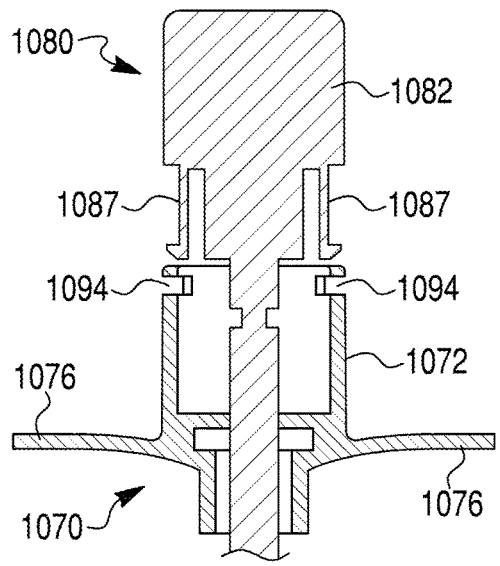
Figure 3F:
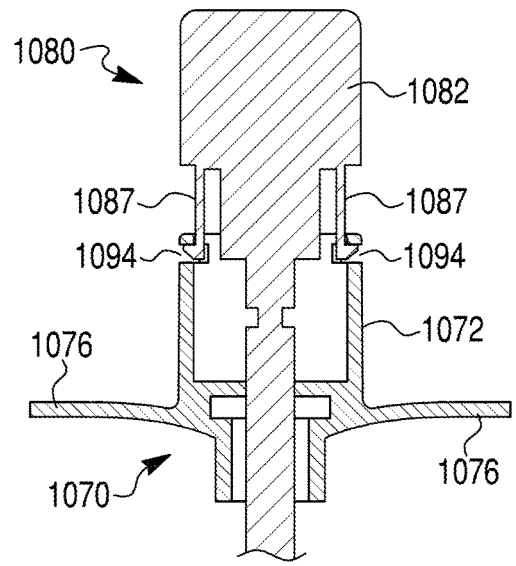

FIGS. 3A and 3B depict an exemplary method of assembling the delivery device depicted in FIGS. 1A-1E. Flange piece 1070 may be assembled to body 1060, as shown in FIG. 3A. The assembly of flange piece 1070 to body 1080 may include sliding, snapping, adhering, or otherwise affixing the two components together. As depicted in FIG. 3A, flange piece 1070 may be slid onto body 1060, e.g., such that lip 1071 of flange piece 1070 engages with body flange 1061. Plunger rod 1080 may be inserted through the assembled flange piece 1070 and body 1060, such that a distal end of plunger rod 1080 contacts stopper 1062. The assembled device 1050 may then be in a configuration suitable for packaging, sterilization, and/or use.

FIGS. 3C-3F depict an exemplary method of assembling device 1050 in which actuation portion 1082 includes extensions 1087 and collar 1072 includes side openings 1094. In such an embodiment, plunger rod 1080 may be inserted through flange piece 1070 until the hook or clip portions of extensions 1087 are received within side openings 1094, at which point the assembled device 1050 may be in a configuration suitable for packaging, sterilization, and/or use. It should be appreciated that side openings 1094 may be configured to inhibit a proximal retraction of plunger rod 1080 relative to flange piece 1070 once the hook or clip portions of extensions 1087 are received therein. Side openings 1094 may function as a first lock when device 1050 is placed into an initial assembly state to prevent disassembly of device 1050.

As described in further detail herein (see FIGS. 4G-4J), side openings 1095 may be configured to inhibit a proximal retraction of plunger rod 1080 once the hook or clip portions of extensions 1087 are received therein. Side openings 1095 may function as a second lock when device 1050 is placed in a dosage delivery state to prevent extracting patient fluid after completion of drug/medicament delivery. It should be appreciated that side openings 1094, 1095 may generate a feedback indicating a relative position of plunger rod 1080 to flange piece 1070, such as, for example, an audible feedback, a tactile feedback, and the like. In some embodiments, device 1050 may include additional and/or fewer side openings 1094, 1095 than those shown and described herein to increase and/or decrease a quantity of locks on device 1050.

In some embodiments, assembling device 1050 may include pre-filling body 1060 before combining it with flange piece 1070 and stopper 1080; for example, a predetermined amount of drug substance may be disposed in body 1060 between stopper 1062 and needle end 1064. In some embodiments, an alternate order of assembly of the components of device 1050 may be employed, depending on contemplated variations in the structures of components of device 1050. For example, in an embodiment (not shown) in which flange piece 1070 is configured to be assembled to body 1060 using a snap-fit interface, plunger rod 1080 may be first inserted through flange piece 1070, and the combined flange piece 1070 and plunger rod 1080 may be assembled to body 1060, e.g., such that flange piece 1070 snaps over a proximal body flange 1061 of body 1060 and plunger rod 1080 is inserted into body 1060.

FIGS. 4A-4F depict an exemplary method of using device 1050, according to aspects of the present disclosure. In a pre-use configuration depicted in FIG. 4A, device 1050 may hold a volume of a drug substance in between stopper 1062 and expulsion end 1064. A priming distance p may exist between protrusions 1086 and a proximal end of proximal collar 1072, and protrusions 1086 may be non-aligned with slots 1074. In a priming step depicted in FIG. 4B, plunger rod 1080 may be moved longitudinally further into body 1060. For example, a user may press actuation portion 1082 partially into proximal collar 1072 of flange piece 1070. In some embodiments, device 1050 may be held in an inverted position during this step, to ensure that air trapped in body 1060 may be expelled via expulsion end 1064, as stopper 1062 is pushed distally by plunger rod 1080. In the pre-use configuration of FIG. 4A and during the priming step shown in FIG. 4B, plunger rod 1080 may be prevented from rotating about the longitudinal axis of the syringe, due to the geometries of opening 1073 in flange piece 1070, and neck 1084 of plunger rod 1080 (as shown in the top cross-sectional view in FIG. 4B). As shown in FIG. 4C, the priming step may be stopped when protrusions 1086 of plunger rod 1080 abut a proximal end of proximal collar 1072. When the priming step is completed, neck 1084 of plunger rod 1080 may be positioned longitudinally with respect to opening 1073 of flange piece 1070, such that it may now be rotatable with respect to flange piece 1070. For example, when the priming step is completed, a narrower portion of neck 1084 may be disposed inside opening 1073 than when device was in a pre-use configuration.

As depicted in FIG. 4D, device 1050 may be in a primed configuration. In a dispensing preparation step depicted in FIG. 4E, plunger rod 1080 may be rotated about a longitudinal axis to align protrusions 1086 with slots 1074. To do so, a user may grasp and twist actuation portion 1082. In some embodiments, as has been described elsewhere, it may be possible to twist actuation portion 1082 in either direction to align protrusions 1086 and slots 1074. In other embodiments, actuation portion 1082 may be rotatable only in one direction. In some embodiments, once protrusions 1086 are aligned with slots 1074, further rotation of plunger rod 1080 relative to flange piece 1070 may be stopped by, e.g., contact between the geometries of neck 1084 and opening 1073. Thus, aligning protrusions 1086 and slots 1075 may lock device 1050 in a ready-to-dispense configuration. In some embodiments, rotation of actuation portion 1082 may align protrusions 1086 with slots 1074, and may allow plunger rod 1080 to remain longitudinally stationary relative to flange piece 1070 (e.g., no proximal or distal movement of plunger rod 1080 is caused by rotation of actuation portion 1082). As depicted in FIG. 4F, in a dispensing step, plunger rod 1080 may be moved longitudinally further into body 1060. For example, a user may press actuation portion 1082 distally into proximal collar 1072 of flange piece 1070, such that protrusions 1086 slide into slots 1074. Once protrusion 1086 abut distal ends of slots 1074, further distal movement of plunger rod 1080 is stopped. The dispensing step may ensure that a predetermined volume of a drug substance inside body 1060 is dispensed from device 1050. In some embodiments, when protrusions 1086 abut distal ends of slots 1074, stopper 1062 does not "bottom out" or abut an interior of expulsion end 1064 in body 1060. Advantageously, by ensuring that a predetermined volume of a drug substance inside body 1060 is dispensed from device 1050 before stopper 1062 can bottom out, any variations in the manufacture of expulsion end 1064 (e.g., altering the exact size or shape of expulsion end 1064) are less likely to affect the predetermined volume of drug substance that is delivered from device 1050. Indeed, in some embodiments, the predetermined volume of drug substance that is delivered from device 1050 may not be affected by typical variations in manufacturing of any component of device 1050, particularly in any component except for flange piece 1070. Advantageously, this may allow for the existence of different or larger tolerances in manufacturing variation in several components of device 1050 (e.g., variations in formation of a glass body 1060 or other glass components), without affecting the predetermined volume of drug substance to be delivered from device 1050.

Figure 4G:
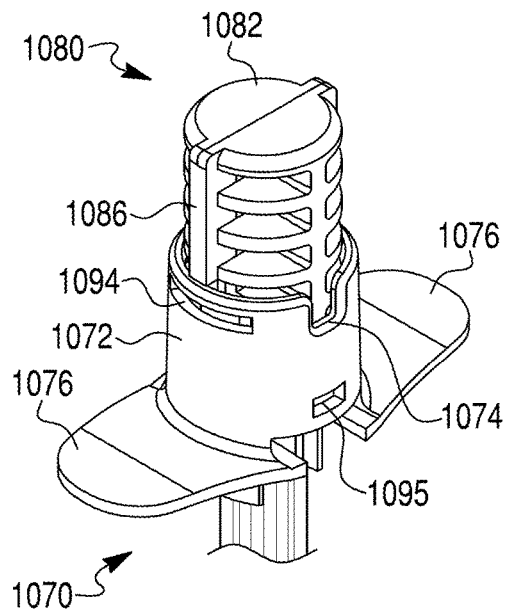
FIGS. 4G-4J depict an exemplary method of using an embodiment of the delivery device depicted in FIGS. 1A-1E, according to aspects of the present disclosure.
Figure 4I:
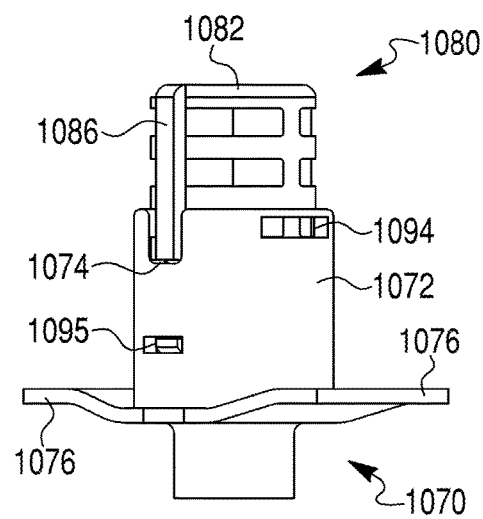
Figure 4H:
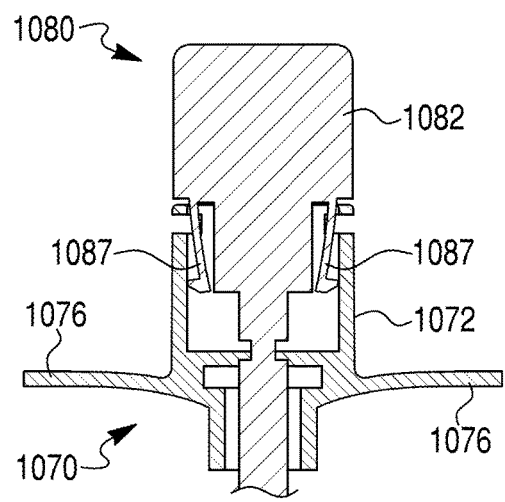
Figure 4J:
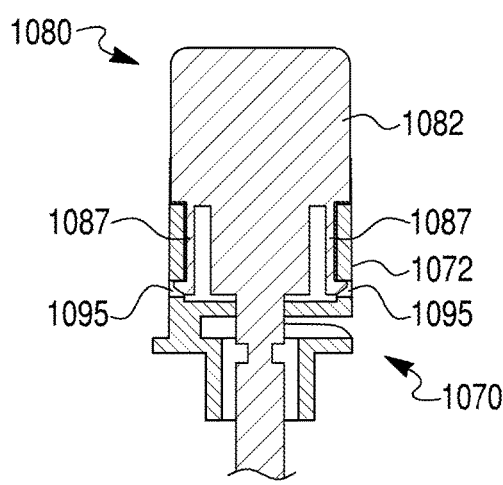

In some embodiments, after one or more steps in the use of device 1050, a user may be prevented from re-doing a step, and/or from reversing one or more steps. For example, geometries of, e.g., plunger rod neck 1084 and opening 1073 may prevent a user from pulling plunger rod 1080 proximally (e.g., out of) body 1060, from rotating plunger rod 1080 preemptively (e.g., before the priming step shown in FIG. 4C), and/or from over-rotating plunger rod 1080 during a dispensing preparation step (e.g., shown in FIG. 4E). In particular, FIGS. 4G-4J depict steps in the use of an embodiment of device 1050 having extensions 1087 on actuation portion 1082 and corresponding side openings 1094, 1095 in collar 1072 of flange piece 1070. FIGS. 4G and 4H depicts device 1050 as actuation portion 1082 is being pushed distally into collar 1072. Due to their angled distal portions, extensions 1087 are pushed inward into collar 1072. Once plunger rod 1080 has been rotated to a "delivery" position and actuation portion 1082 is further pushed distally into collar 1072 to deliver a predetermined volume of drug substance from device 1050, extensions 1087 may be received into side openings 1095 (shown in FIGS. 4I and 4J), thereafter restricting proximal movement of plunger rod 1080. Advantageously, restricting proximal movement of plunger rod 1080 may prevent inadvertent withdrawal of material into device 1050 from, e.g., a site into which a drug substance is delivered. In some embodiments, device 1050 may include either side openings 1094, or side openings 1095. In other embodiments, as shown in FIGS. 4G-4J, device 1050 may include both side openings 1094 and side openings 1095.

Figure 4K:
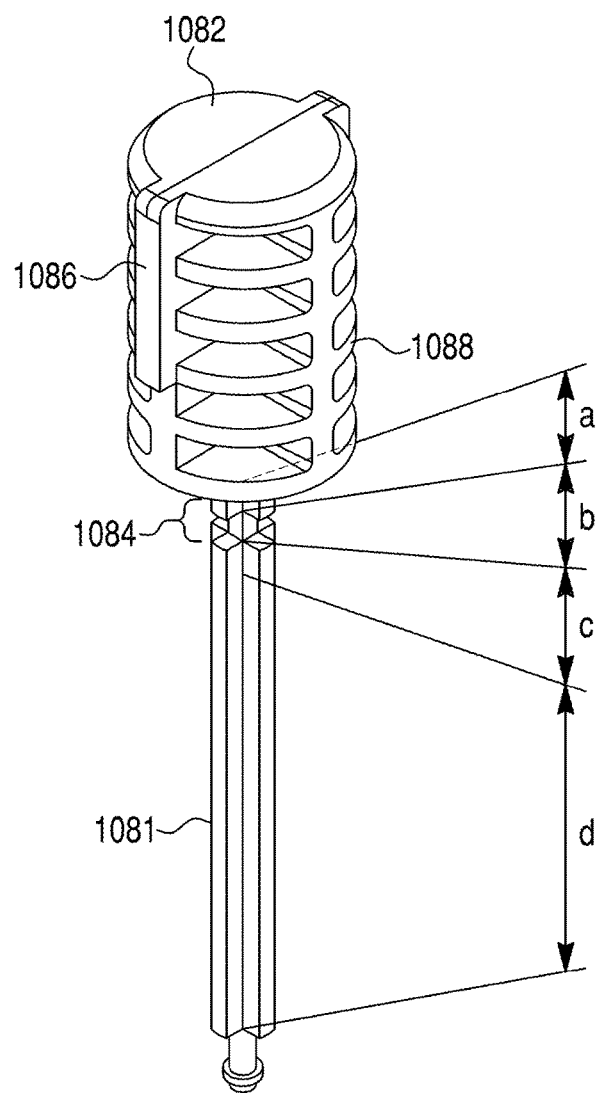
FIGS. 4K-4S depict exemplary aspects of plunger rods for use in embodiments of the delivery device depicted in FIGS. 1A-1E.
Figure 4L:
Figure 4M:
Figure 4N:
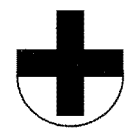
Figure 4Q:
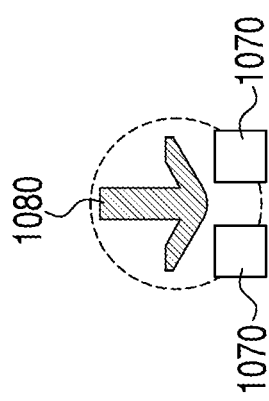
Figure 4P:
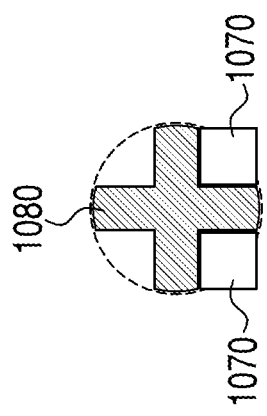
Figure 4S:
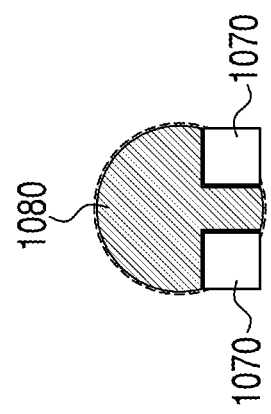
Figure 4R:
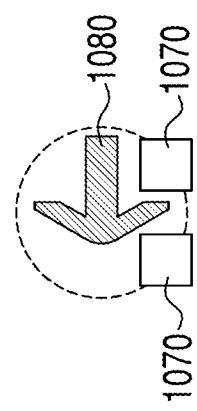
Figure 4O:
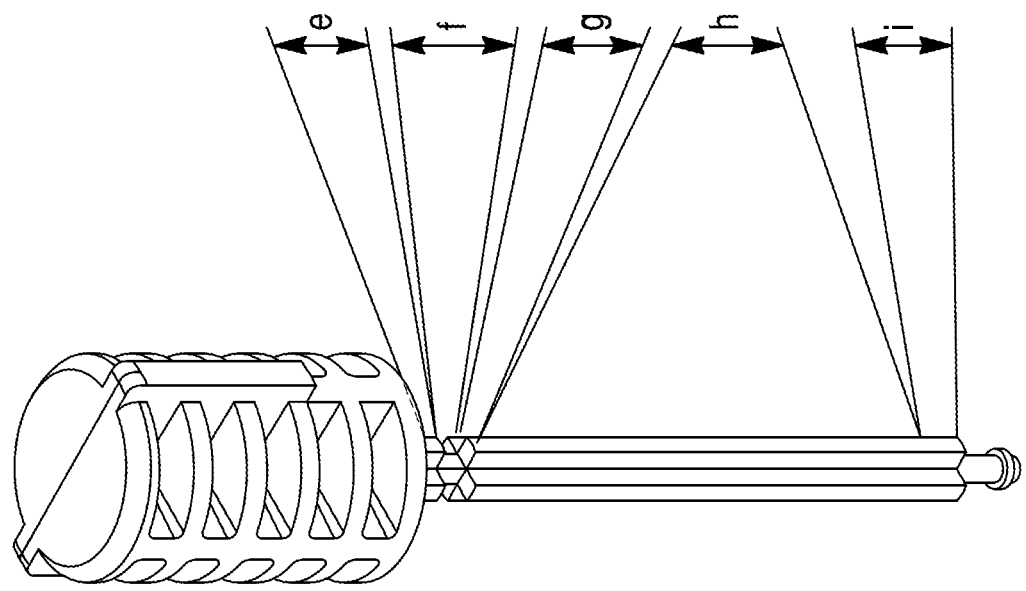

FIGS. 4K and 4O depicts in further detail exemplary aspects of a geometry of neck 1084, which may help to control movement of plunger rod 1080. For example, a proximal-most portion a of neck 1084 and stem 1081 (indicated by section d in FIG. 4K) may both have a first cross-sectional shape, as shown in FIG. 4L. This shape may allow for corresponding portions of plunger rod 1080 to move proximally/distally through an opening (e.g., opening 1073) of a blocking component (e.g., flange piece 1070), but may prevent rotation of plunger rod 1080 about a longitudinal axis. A narrow portion b of neck 1084 may have a smaller cross-sectional shape, as shown in FIG. 4M. This shape, when disposed in an opening (e.g., opening 1073) of a blocking component (e.g., flange piece 1070) may allow for unidirectional or bidirectional rotation of plunger rod 1080 about a longitudinal axis. It should be appreciated that the respective portion of neck 1084 allowing for transitional rotation of plunger rod 1080 (e.g., at narrow portion b) may have a geometry with the smallest cross-sectional shape to allow greater space for such movement, relative to the cross-sectional shapes of other portions of plunger rod 1080. A third portion c of neck 1084 may have a larger cross-sectional shape, as shown in FIG. 4N, which may correspond directly with the size and shape of an opening (e.g., opening 1073) of a blocking component (e.g., flange piece 1070). As such, proximal or distal movement of this portion of neck 1084 through opening 1073 may only be possible when plunger rod 1080 is in a specific rotational orientation relative to flange piece 1070. Moreover, plunger rod 1080 will not be rotatable while portion c of neck 1084 is disposed within opening 1073. This may ensure that, e.g., plunger rod 1080 is in a desirable position relative to flange piece 1070 (e.g., priming is complete and portion c is no longer disposed within opening 1073) before plunger rod 1080 may be rotated. Together, the various cross-sectional shapes of neck 1084 and the size and shape of opening 1073 may combine to create a specific sequence of movements of plunger rod 1080 needed to prime and deliver a drug substance from device 1050. In the example, a distal portion of opening 1073 may have the greatest cross-sectional profile relative to an intermediate and/or proximal portion of opening 1073 to accommodate the varying geometries of plunger rod 1080 therethrough (e.g., neck 1084, stem 1081, etc.).

In a further embodiment depicted in FIG. 4O, a proximal-most portion e of neck 1084 and a majority portion h of stem 1081 may both have a first cross-sectional shape, as shown in FIG. 4P. This shape may allow for corresponding portions of plunger rod 1080 to move proximally/distally through an opening (e.g., opening 1073) of a blocking component (e.g., flange piece 1070), but may prevent rotation of plunger rod 1080 about a longitudinal axis. A narrow portion f of neck 1084 may have a smaller winged (or arrow-shaped) cross-sectional shape, as shown in FIG. 4Q (in a pre-rotation configuration relative to flange piece 1070) and FIG. 4R (in a post-rotation configuration relative to flange piece 1070). This "winged" shape, when disposed in an opening (e.g., opening 1073) of a blocking component (e.g., flange piece 1070) may allow for unidirectional or bidirectional rotation of plunger rod 1080 about a longitudinal axis, and may restrict or resist "backwards" rotation of plunger rod 1080 in the opposite direction after rotation has been completed (as described further with respect to FIGS. 4T-4X). Portions g and l of plunger rod 1080 may have a larger cross-sectional shape, as shown in FIG. 4S, which may correspond directly with the size and shape of an opening (e.g., opening 1073) of a blocking component (e.g., flange piece 1070). As such, proximal or distal movement of these portions of plunger rod 1080 through opening 1073 may only be possible when plunger rod 1080 is in a specific rotational orientation relative to flange piece 1070. Moreover, plunger rod 1080 will not be rotatable while portions g or l of plunger rod 1080 are disposed within opening 1073. This may ensure that, e.g., plunger rod 1080 is in a desirable position relative to flange piece 1070 at certain steps during assembly and use of device 1050, allowing for precise assembly and use of device 1050. Additionally, the "larger" cross sectional area of portions g and l may assist in preventing plunger rod "back-out", as they will not be able to move proximally through opening 1073 unless in a particular rotational position relative to flange piece 1070. For example, after rotation of plunger rod 1080 from a "primed" position to a "delivery" position, portion g of plunger rod 1080 may not be able to move through opening 1073, thus preventing plunger rod "back-out" at that stage of use of device 1050. Together, the various cross-sectional shapes of plunger rod 1080 and the size and shape of opening 1073 may combine to create a specific sequence of movements of plunger rod 1080 needed to assemble, prime, and deliver a drug substance from device 1050.

Figure 4T:
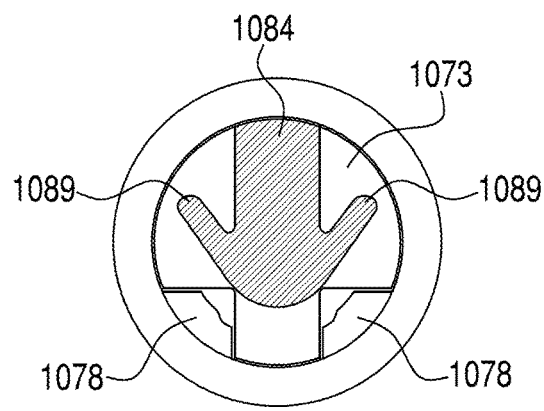
FIGS. 4T-4X depict views of an exemplary neck portion of a plunger rod and opening of a flange piece in embodiments of the delivery device depicted in FIGS. 1A-1E.
Figure 4U:
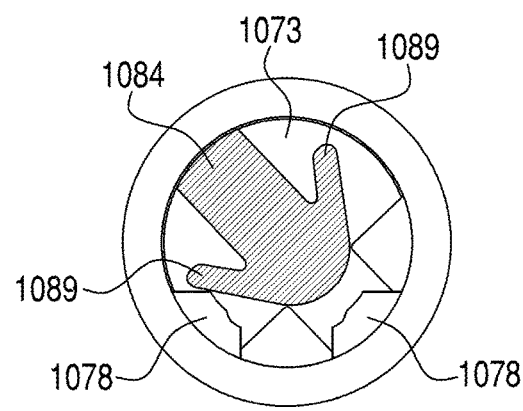
Figure 4V:
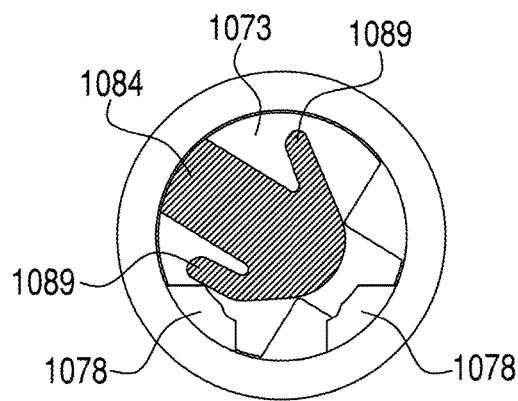
Figure 4W:
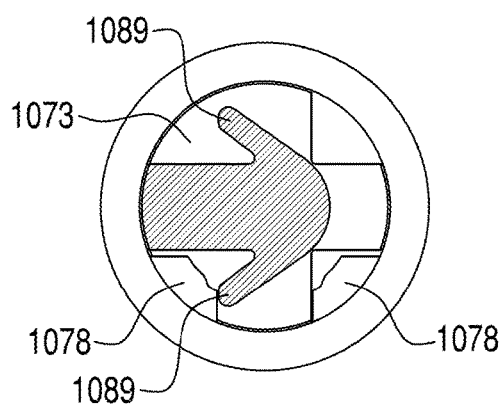
Figure 4X:
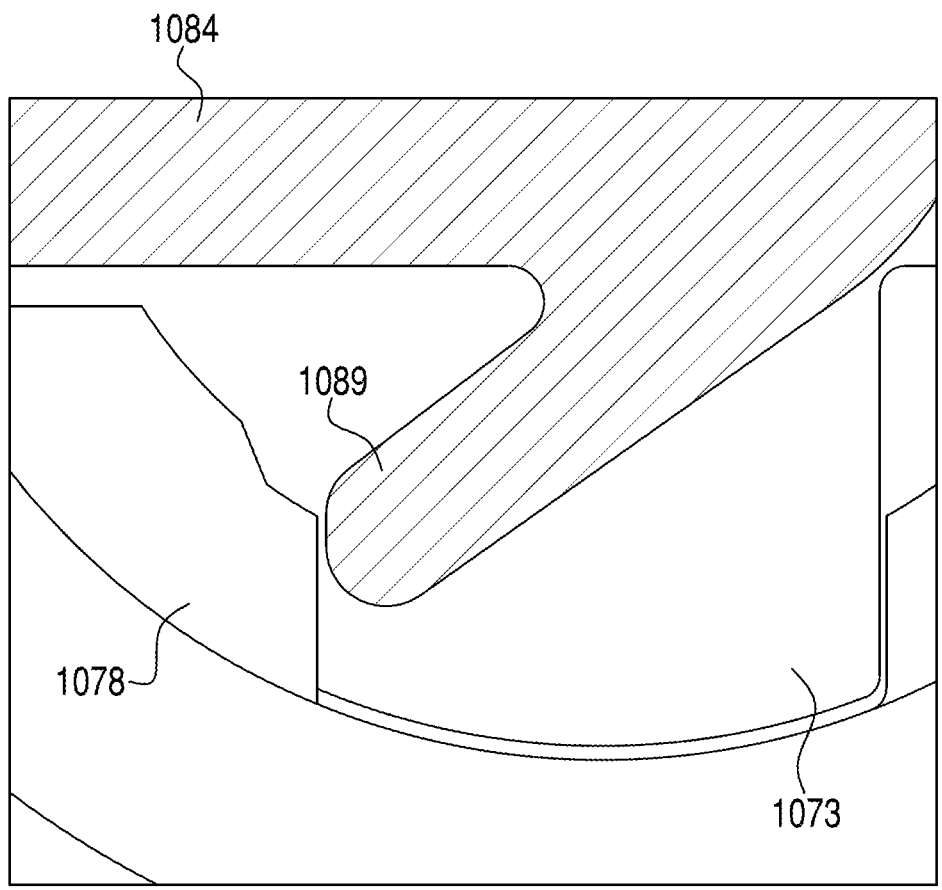

FIGS. 4T-4X depict in further detail specific interactions between a wing-shaped part of neck 1084 and opening 1073 in flange piece 1070. Flange piece 1070 may include detents 1078 either adjacent to or within opening 1073, which may interface with wings 1089 on neck 1084. FIG. 4T depicts a cross-sectional view of neck 1084 inside opening 1073 in a pre-rotation configuration (e.g., after device 1050 has been primed but before plunger rod 1080 has been rotated to a "delivery" configuration relative to flange piece 1070). FIG. 4U depicts that, as plunger rod 1080 is rotated about a longitudinal axis, one of wings 1089 may contact one of detents 1078 (depending on the direction of rotation). As rotation continues, one of detents 1078 may cause one of wings 1089 to be compressed towards the remainder of neck 1084. When rotation is complete, the one of wings 1089 has passed the one of detents 1078 and has expanded. This expansion of a wing 1089 past detent 1078 may cause an auditory "click" feedback and/or a tactile feedback to indicate that rotation is complete, and may thereafter prevent "backwards" rotation of plunger rod 1080 relative to flange piece 1070. Wings 1089 and detents 1078 may be configured to interact in a similar fashion regardless of whether plunger rod 1080 is rotated in a clockwise or counterclockwise direction, thereby allowing for bidirectional rotation of plunger rod 1080 to move plunger rod 1080 from a "primed" position to a "delivery" position. As shown in further detail in FIG. 4X, each wing 1089 may have a rounded shape to allow for ease of rotation in one direction, and the expansion of a wing 1089 past a detent 1078 may place the wing 1089 in a position relative to detent 1078 that greatly resists or otherwise prohibits rotation in the opposite direction. Detent 1078 may have any suitable contour configured to assist unidirectional movement of a wing 1089 past detent 1078.

Advantageously, the various configurations of plunger rod 1080 described herein may allow for modeling, molding, and/or manufacturing one piece (e.g., plunger rod 1080) or two pieces (e.g., plunger rod 1080 and flange piece 1070) in order to achieve several goals—e.g., control desired plunger rod movement and assembly, reduce user error, prevent plunger rod back-out, and minimize a number of disparate parts needing to be manufactured and handled in order to assemble device 1050.

In some embodiments, as seen in FIGS. 4Y-4Z, device 1050 may include a pair of plunger rods in one kit, interchangeable with a single actuation portion 1082, or coupled to separate actuation portions 1082. For example, referring initially to FIG. 4Y, device 1050 may include a first plunger rod 1080A that is substantially similar to plunger rod 1080 shown and described above except for the differences explicitly noted herein. First plunger rod 1080A may include a stem 1081A having a longitudinal length A defined between a distal end of actuation portion 1082 and a tip 1083A. As described in detail below, longitudinal length A may define a priming distance for moving plunger rod 1080A relative to flange piece 1070 for priming device 1050. Tip 1083A may have a flat and/or planar interface that may be configured to inhibit engagement of stopper 1062 when first plunger rod 1080A is received within body 1060.

Referring now to FIG. 4Z, device 1050 may further include a second plunger rod 1080B that is substantially similar to plunger rod 1080. Second plunger rod 1080B may include a stem 1081B extending distally from actuation portion 1082 and having a longitudinal length B defined between a distal end of actuation portion 1082 and a tip 1083B. Tip 1083B is substantially similar to tip 1083A described above. Longitudinal length B of stem 1083B is relatively greater than longitudinal length A of stem 1081A and may define a dosage delivery distance for moving plunger rod 1080A relative to flange piece 1070 to deliver a dose from device 1050.

First plunger rod 1080A may be configured to prime device 1050 in response to translating stem 1081A through collar 1072 and into body 1060 (see FIGS. 1A-1B). In this instance, tip 1083A may contact and push stopper 1062 distally by the priming distance. It should be understood that the priming distance of device 1050 may be controlled based on a size of longitudinal length A of first plunger rod 1080A. Upon priming device 1050, first plunger rod 1080A may be removed from body 1060 and flange piece 1070 without retracting stopper 1062 due to a flattened-interface of tip 1083A. Accordingly, stopper 1062 may remain at a fixed position relative to body 1060 upon retraction of first plunger rod 1080A.

Second plunger rod 1080B may be configured to deliver a dose from device 1050 in response to translating stem 1081B through collar 1072 and into body 1060 (see FIGS. 1A-1B), after the priming step described above using stem 1081A. In this instance, tip 1083B may contact and push stopper 1062 distally by the dosage delivery distance. It should be understood that the dosage delivery distance of device 1050 may be controlled based on a size of longitudinal length B of second plunger rod 1080B. The dosage delivery distance may be substantially equal to the difference in length between stem 1081B and stem 1081A.

FIGS. 5A-5C depict another exemplary delivery device 1200 according to additional embodiments of the present disclosure. Device 1200 includes a body 1220, and a flange piece 1240 with a proximal collar 1242, in which an inner collar 1260 may be disposed. Together, proximal collar 1242 and inner collar 1260 may form a blocking component for device 1200. A plunger rod 1280 may pass through inner collar 1260 and flange piece 1240, into body 1060. Plunger rod 1280 may share a longitudinal axis with a central axis of proximal collar 1242 and inner collar 1260, and may have an actuation portion 1282 sized and configured to fit (e.g., nest or otherwise fit) inside inner collar 1260.

Device 1200 may be, for example, an injection device, such as a syringe, for dispensing a predetermined volume of a formulated drug substance. Generally, device 1200 may share size, capacity, material, preparation, assembly, manufacturing, operation, or use characteristics with device 1050, or with other delivery devices disclosed herein. As with device 1050, device 1200 may be configured for ease of use and may include one or more features that aid a user by providing tactile, auditory, or visual feedback (e.g., using any of the features described elsewhere herein).

Body 1220 may have any or all of the same characteristics as, e.g., body 1060 of device 1050, or as any syringe body known in the art. For example, in some embodiments, body 1220 may be pre-fillable or pre-filled (e.g., fillable or filled with a drug substance prior to completed assembly, packaging, sterilization and/or shipment of device 1200 to users). In some embodiments, a stopper 1222 may be configured to be inserted into body 1220 and may be configured to hold a predetermined volume of a formulated drug substance inside body 1200, between stopper 1222 and an expulsion end 1224.

Flange piece 1240 may be of any suitable size and/or shape to close, partially close, cover, or partially cover an end of body 1220 opposite expulsion end 1224, and/or to support and hold plunger rod 1280 in place inside body

1220. In some embodiments, flange piece 1240 may share some characteristics with flange piece 1070 of device 1050. For example, flange piece 1240 may include a distal collar 1244 configured to engage with body 1220 and hold flange piece 1240 in place in relation to body 1220. For example, distal collar 1244 may include a lip 1245 that may slide over a body flange 1226, to hold flange piece 1240 in place. In alternative embodiments, lip 1245 of distal collar 1244 may be made of a flexible or semi-flexible material, so that it may snap in place over body flange 1226. In further embodiments, distal collar 1244 or another portion of flange piece 1240 may be adhered to, molded to, or otherwise affixed to, body 1220, or may engage with body 1220 via a friction fit.

In some embodiments, flange piece 1240 may include one or more flanges 1246, which may be sized and configured to aid a user in holding device 1200 and/or expelling a formulated drug substance from device 1200. In some embodiments, as depicted in FIGS. 1A-1E, flange piece 1240 may include two flanges 1246 opposite to one another and extending perpendicularly from a longitudinal dimension of device 1200. In some embodiments, flange piece 1240 may include other arrangements of a flange or flanges, such as four flanges, or one circumferential flange extending radially outward from a central longitudinal axis of device 1200. In some embodiments, flange piece 1240 may extend radially outward from a central longitudinal axis of device 1200 farther than a circumference of body 1220. In such embodiments, flange piece 1240 may support device 1200 if device 1200 is placed on a surface, may prevent device 1200 from rolling on a flat surface, and/or may allow device 1200 to be picked up more easily.

In some embodiments, flange piece 1240 and inner collar 1260 may be sized and configured to serve as a blocking component in device 1200, e.g., by limiting and/or directing rotational and longitudinal movement of plunger rod 1280. Proximal collar 1242 of flange piece 1240 may be sized and configured to accept part of inner collar 1260, while blocking protrusions 1262 from moving distally until inner collar 1260 is rotated to a particular position. In turn, inner collar 1260 may be sized and configured to receive part or all of an actuation portion 1282 of plunger rod 1280. As shown in FIGS. 5A-5C, proximal collar 1242, inner collar 1260, and actuation portion 1282 may all have generally cylindrical shapes; in alternate embodiments, each of proximal collar 1242, inner collar 1260, and actuation portion 1282 may have any suitable size or shape that allows for actuation portion 1282 to fit (e.g., nest) within inner collar 1260, and inner collar 1260 to fit within proximal collar 1242.

Plunger rod 1280 and inner collar 1260 may be in general rotatable about a shared central longitudinal axis (e.g., in one direction or in both directions). Moreover, both plunger rod 1280 and inner collar 1260 may be movable along the central longitudinal axis, e.g., in a distal direction to prime device 1200 and/or deliver a volume of drug substance from distal end 1224 of body 1220. Actuation portion 1282 of plunger rod 1280 may include a distal geometry which, when actuation portion 1282 is moved distally into inner collar 1260, interfaces with inner collar 1260 to prevent proximal movement (e.g., back-out) of plunger rod 1280 from inner collar 1260. For example, actuation portion 1282 may include a wedge-shaped distal portion that, when it passes a distal portion of inner collar 1260, expands distally from inner collar 1260 so that actuation portion 1282 can no longer move freely in relation to inner collar 1260.

Flange piece 1240 may include cavities, such as slots 1248, into which protrusions 1262 of inner collar 1260 may slide when inner collar 1260 is rotated to a particular position. As with slots 1074 of device 1050, slots 1248 may have a depth dimension parallel to a longitudinal axis of device 1200, and the depth of slots 1248 may correspond to a distance plunger rod 1280 must move distally in order to push stopper 1222 towards expulsion end 1224, and dispense a predetermined volume of formulated drug substance from body 1220 through expulsion end 1224.

In some embodiments, device 1200 may have additional features. For example, in some embodiments, a neck of plunger rod 1280 may have a geometry complementary to an opening of flange piece 1240 that restricts the extent and direction that plunger rod 1280 may rotate or move longitudinally, similar to neck 1084 and opening 1073 of device 1050. For example, rotation and/or longitudinal movement of plunger rod 1280 may be restricted based on priming, preparing, and/or drug delivery steps during use of device 1200. As another example, plunger rod 1280 may be prevented from being pulled or backed out of body 1220 at any point during preparation or use of device 1200.

In a contemplated method of use of device 1200, device 1200 may be filled with a predetermined volume of drug substance. The predetermined volume of drug substance may be greater than a volume of drug substance suitable for delivery to a patient. In some embodiments, device 1200 (e.g., body 1220) may contain both a predetermined volume of drug substance and an air bubble (not shown) that should be removed prior to delivery of the drug substance to a patient. In some embodiments, device 1200 may be a pre-filled syringe. In order to prime device 1200 (e.g., removing an air bubble if any and ensuring that a suitable volume of the drug substance will be delivered to a patient), a user may push actuation portion 1282 of plunger rod 1280 into inner collar 1260. A geometry of actuation portion 1282 may interact with inner collar 1260 (e.g., a distal wedge or clip of actuation portion 1282 may expand on a distal side of inner collar 1260) to secure actuation portion 1282 in and/or to inner collar 1260 and to prevent back-out of plunger rod 1280. At this point, device 1200 may be in a "primed" state. Subsequently, inner collar 1260 may be rotated about a longitudinal axis, until protrusions 1262 become longitudinally aligned with slots 1248. At this point, device 1200 may be in a "delivery" state. To deliver a predetermined volume of drug substance from device 1200, inner collar 1260, together with actuation portion 1282 and plunger rod 1280, may then be moved distally until protrusions 1262 abut a distal end of slots 1248. The distance traveled by plunger rod 1280 in this step may push stopper 1222 distally by a distance required to dispense the predetermined volume of drug substance from expulsion end 1224 of device 1200.

Referring now to FIGS. 6A-6E, views of a delivery device 1300 and component parts are depicted. Delivery device 1300 includes a blocking component comprising a distal flange piece 1340 and a proximal flange piece 1360, a plunger rod 1380, and a body 1320. Distal flange piece 1340 and proximal flange piece 1360 each include flanges (1346 and 1366, respectively). The flanges 1366 of proximal flange piece 1360 optionally may include a texture 1365. Distal flange piece 1340 includes a channel 1341 which may allow for distal flange piece 1340 and body 1320 to be slidably assembled. Proximal flange piece 1360 includes a clip 1364 which may allow for proximal flange piece 1360 and distal flange piece 1340 to be movably affixed to one another, such that they may still be rotatable relative to one another about a longitudinal axis of delivery device 1300 (see, e.g., FIGS. 6D and 6E). Proximal flange piece 1360 includes clips 1362 bordering a central opening 1368 through which plunger rod 1380 may pass. Plunger rod 1380 includes an actuation portion 1382, which optionally may include a texture 1381. Plunger rod 1380 further includes a distal neck shape 1384, a proximal neck shape 1387, and a proximal stop 1386 having a cavity 1385, all of which are configured to interface with distal flange piece 1340 and proximal flange piece 1360 in a plurality of configurations to allow for controlled priming and delivery of a predetermined volume of a drug substance using delivery device 1300. Plunger rod 1380 further includes a distal tip 1383 at a distal end of a stem 1389, where tip 1383 is configured to interface with stopper 1322. Tip 1383 may have any suitable size, shape, and mode of attaching to, affixing to, or pushing stopper 1322 as has been described with respect to, e.g., tip 1083 of plunger rod 1080. As with stem 1081, stem 1389 may have any size and configuration suitable to fit inside body 1320. In some embodiments, step 1389 may be sized and configured to provide sufficient size (e.g., thickness), stability and/or rigidity to reduce a likelihood of undesirable bending, wobbling, or breaking.

Body 1320 (depicted in FIGS. 6D and 6E) may have any or all of the same characteristics as, e.g., body 1060 of device 1050, or as any syringe body known in the art. For example, in some embodiments, body 1320 may be pre-fillable or pre-filled. A stopper 1322 may be configured to be inserted into body 1320 and may be configured to hold a predetermined volume of a formulated drug substance inside body 1320, between stopper 1322 and an expulsion end 1324.

Delivery device 1300 may be, for example, an injection device, such as a syringe, for dispensing a predetermined volume of a formulated drug substance. Generally, delivery device 1300 may share size, capacity, material, preparation, assembly, or manufacturing characteristics with device 1050, device 1200, or with other delivery devices disclosed herein. As with devices 1050 and 1200, delivery device 1300 may be configured for ease of use and may include one or more features that aid a user by providing tactile, auditory, or visual feedback (e.g., textures 1365, 1381, other textures, labels, colors, or tactile or auditory feedback, or using any of the other features described elsewhere herein). As with devices 1050 and 1200, such features are optional, and one or more such features may be combined to improve ease of use.

Proximal flange piece 1360 and distal flange piece 1340 may be of any suitable size and/or shape to serve as a blocking component in delivery device 1300, to close, partially close, cover, or partially cover an end of body 1320 opposite expulsion end 1324, and/or to support and hold plunger rod 1380 in place inside body 1320. In some embodiments, proximal flange piece 1360 and distal flange piece 1340 may each include one or more flanges, which may be sized and configured to aid a user in holding device 1300 and/or expelling a formulated drug substance from expulsion end 1324. In some embodiments, as depicted in FIGS. 6A-6E, flange pieces 1360, 1340 may each include two flanges 1366, 1346 respectively, where each pair of flanges is opposite to one another and extending perpendicularly from a longitudinal dimension of device 1300. In general, other arrangements of a flange or flanges, such as one flange on each of flange pieces 1360, 1340, are possible. Each of flange pieces 1340, 1360 may extend radially outward from a central longitudinal axis of device 1300 farther than a circumference of body 1320, to, e.g., support device 1300 if device 1300 is placed on a surface, prevent device 1300 from rolling on a flat surface, and/or allow device 1300 to be picked up more easily.

Flange pieces 1360 and 1340 may, in combination, form a central opening having a changeable size and/or shape depending on a relative position of proximal flange piece 1360 and distal flange piece 1340. For example, in the configuration depicted in FIG. 6D, proximal flange piece 1360 and distal flange piece 1340 may combine to form an opening sized and configured to allow for distal passage of distal neck portion 1384 of plunger rod 1380, but to block passage of proximal neck portion 1387. In the second configuration depicted in FIG. 6E (e.g., where flanges 1346 and 1366 are in alignment), the central opening formed by flange pieces 1360 and 1340 may be sized and configured to allow for distal passage of proximal neck portion 1387. Proximal stop 1386 may be of a size and shape that is too large to pass through the central opening formed by flange pieces 1360 and 1340 in any combination. In some embodiments, distal flange 1340 may be assembled with body 1320 and plunger rod 1380 such that distal flange 1340 is not movable relative to body 1320 and not rotatable relative to plunger rod 1380. Proximal flange 1360 may, in contrast, be assembled to distal flange 1340 (and body 1320) such that it is rotatable about a longitudinal axis in relation to distal flange 1340, body 1320, and plunger rod 1380, which may pass through central opening 1368. Specifically, proximal flange 1360 may be rotatable relative to distal flange 1340 from a first configuration in which flanges 1346, 1366 are offset from one another (see FIG. 6D), to a second configuration in which flanges 1346, 1366 overlay one another (see FIG. 6E). One of ordinary skill in the art will understand that in alternate embodiments, distal flange 1340 may be rotatable in relation to other parts of device 1300, while proximal flange 1360 may not be rotatable. In yet further embodiments, both proximal flange 1360 and distal flange 1340 may be assembled with body 1320 and plunger rod 1380 such that they are both rotatable relative to other components of device 1300.

Clips 1362 of proximal flange piece 1360 may overhang and be biased towards opening 1368. In a pre-use configuration (depicted in FIG. 6D), clips 1362 may be compressed by plunger rod 1380. They may be positioned on proximal flange piece 1360 such that, upon distal movement of plunger rod 1380 such that distal neck portion 1384 passes through opening 1368, they expand inward to abut the sides of distal neck portion 1384. Once clips 1362 expand in this manner, they may block proximal movement of plunger rod 1380, e.g., to prevent plunger rod back-out (see, e.g., FIG. 7C). A cavity 1385 may be positioned on proximal stop 1386 for each clip 1362, such that when plunger rod 1380 is moved distally into body 1320 to a fullest desired extent, each clip 1362 may fit into a cavity 1385.

Figure 7D:
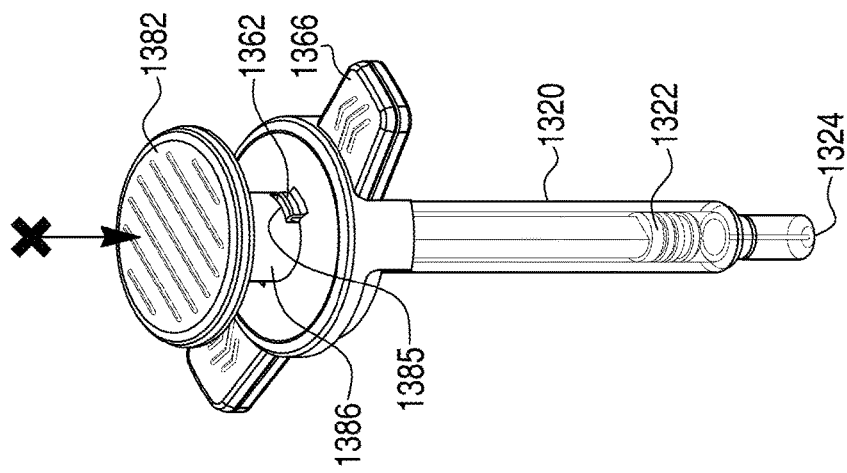
Figure 7E:
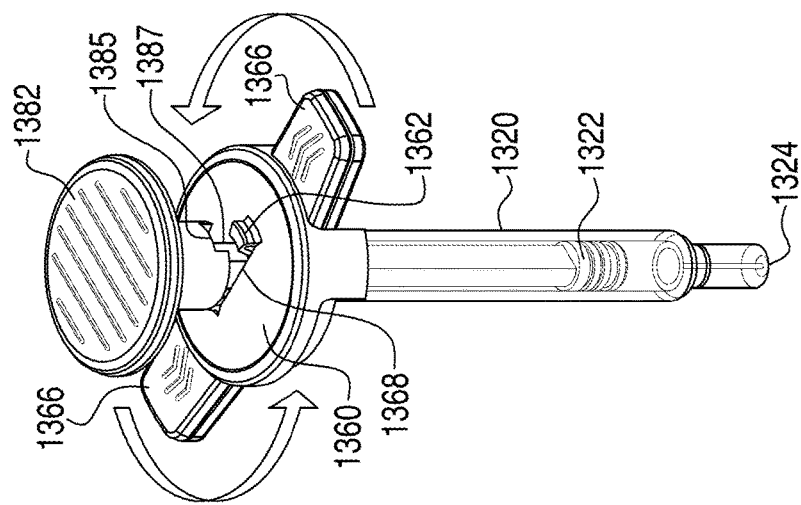

FIGS. 7A-7F depict an exemplary method of using device 1300, according to aspects of the present disclosure. In a pre-use configuration depicted in FIG. 7A, device 1300 may hold a volume of a drug substance in between stopper 1322 and expulsion end 1324. Flange pieces 1340 and 1360 may be in a pre-use configuration, in which flanges 1346, 1366 are offset from one another. Plunger rod 1380, which may abut or be assembled to stopper 1322, may be partially inserted into body 1320 through flange pieces 1340, 1360. Proximal flange piece 1360 may be prevented from rotating about the longitudinal axis of the syringe, due to the geometries of plunger rod 1380 and flange piece 1360. In a priming step depicted in FIG. 7B, plunger rod 1380 may be moved longitudinally further into body 1320, until distal movement is blocked by the abutment of proximal neck portion 1385 against a surface of proximal flange piece 1360. For example, a user may press actuation portion 1382 towards proximal flange piece 1360. In some embodiments, device 1300 may be held in an inverted position during this step, to ensure that air trapped in body 1320 may be expelled via expulsion end 1324, as stopper 1322 is pushed distally by plunger rod 1380. In the "primed" configuration, distal neck portion 1384 may be disposed in opening 1368 of proximal flange piece 1360. Moreover, as depicted in FIG. 7C, once the priming step is stopped, clips 1362 may be released from their compressed configuration such that they may expand inwards and abut a side of distal neck portion 1384. As distal neck portion 1384 may be comparatively narrower than the part of plunger rod 1380 previously disposed in opening 1368, the expansion of clips 1362 may prevent proximal movement (e.g., back-out) of plunger rod 1380.

Figure 7F:
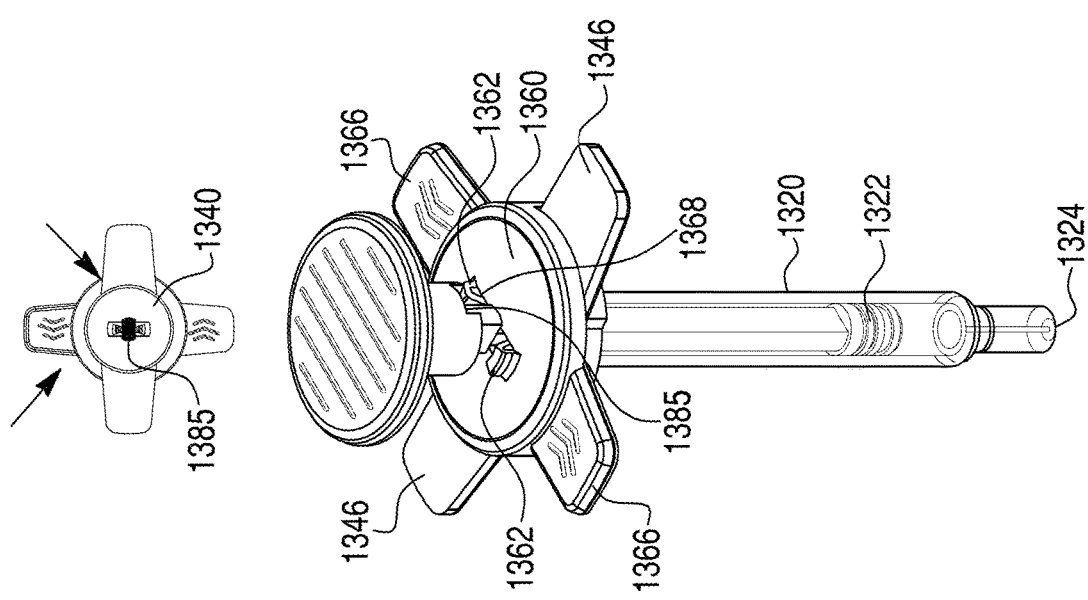

As depicted in FIG. 7D, device 1300 may be in a primed configuration. In a dispensing preparation step depicted in FIG. 7E, proximal flange piece 1360 may be rotated about a longitudinal axis to align flanges 1366 and flanges 1346, and to change (e.g., enlarge) a shape of the central opening formed by the combined openings of proximal flange piece 1360 and distal flange piece 1340. To do so, a user may grasp and twist proximal flange piece 1360. In some embodiments, it may be possible to twist proximal flange piece in either direction to align flanges 1366 and flanges 1346. In other embodiments, proximal flange piece 1360 may be rotatable only in one direction. In some embodiments, once flanges 1366 and flanges 1346 are aligned (as shown in, e.g., FIG. 7E), further rotation of plunger rod 1080 relative to flange piece 1070 may be stopped by, e.g., clip 1362 abutting against flange 1346. Thus, device 1300 may be locked in a ready-to-dispense configuration. As depicted in FIG. 7F, in a dispensing step, plunger rod 1380 may be moved longitudinally further into body 1320. For example, a user may press actuation portion 1382 distally, until each of clips 1362 enter a cavity 1385 in a proximal stop 1386, and/or until proximal stop 1386 abuts a proximal surface of proximal flange piece 1360. The dispensing step may ensure that a predetermined volume of a drug substance inside body 1320 is dispensed from device 1300.

In some embodiments, after each successive step in the use of device 1300, a user may be prevented from re-doing a step, and/or from reversing one or more steps. For example, geometries of, e.g., plunger rod 1380 and the combined openings of proximal flange piece 1360 and distal flange piece 1340 may prevent a user from pulling plunger rod 1380 proximally (e.g., out of) body 1320, from rotating plunger rod 1380, from rotating proximal flange piece 1360 preemptively (e.g., before completion of the priming step shown in FIGS. 7B and 7C), and/or from over-rotating flange piece 1360 during a dispensing preparation step (e.g., shown in FIG. 7E).

FIGS. 8A-8G depict a further exemplary delivery device 1400 and component parts Delivery device 1400 includes a plunger rod 1480, a blocking component 1460, a flange piece 1440, and a body 1420. Plunger rod 1480 includes an actuation portion 1482 and a protrusion 1484. Blocking component 1460 may be a rotatable alignment component that is configured to partially or fully surround plunger rod 1480, and includes three connected channels 1462, 1464, 1468 sized and configured to allow for passage of protrusion 1484. Flange piece 1440 includes a proximal collar 1442 having a channel 1447 into which tabs 1461 of blocking component 1460 may slidably fit, a distal collar 1444 including a channel 1445 into which a flange 1421 of body 1420 may fit (e.g., may be slidably assembled), and flanges 1446.

Body 1420 (depicted in FIGS. 8D and 8E) may have any or all of the same characteristics as, e.g., body 1060 of device 1050, or as any syringe body known in the art. For example, in some embodiments, body 1420 may be pre-fillable or pre-filled. A stopper 1422 may be configured to be inserted into body 1420 and may be configured to hold a predetermined volume of a formulated drug substance inside body 1420, between stopper 1422 and an expulsion end 1424.

Delivery device 1400 may be, for example, an injection device, such as a syringe, for dispensing a predetermined volume of a formulated drug substance. Generally, delivery device 1400 may share size, capacity, material, preparation, assembly, or manufacturing characteristics with device 1050, device 1200, device 1300, or with other delivery devices disclosed herein. As with other devices disclosed herein, delivery device 1400 may be configured for ease of use and may include one or more features that aid a user by providing tactile, auditory, or visual feedback, using any of the features described elsewhere herein.

Blocking component 1460 may be of any suitable size and/or shape to assist in controlling proximal and distal movement of plunger 1480 in device 1400.

Flange piece 1440 may be of any suitable size and shape to close, partially close, cover, or partially cover an end of body 1420 opposite expulsion end 1424, and/or to support and hold blocking component 1460 and plunger rod 1480 in relation to body 1420. For example, proximal collar 1442 and channel 1447 may be sized and configured to hold blocking component 1460, and distal collar 1444 and channel 1445 may be sized and configured to hold a flange 1421 of body 1420, such that blocking component 1460 is held stationary in relation to body 1420. Further, blocking component 1460 may be sized and configured to plunger rod 1480 inside body 1420, and to limit movement of plunger rod 1480 with respect to body 1420. Flange piece 1440 may include one or more flanges 1446, which may be sized and configured to aid a user in holding device 1400 and/or expelling a formulated drug substance from expulsion end 1424. In some embodiments, as depicted in FIGS. 8A-8E, flange piece 1440 may include two flanges 1446, opposite to one another. In general, other arrangements of a flange or flanges, such as one flange or three flanges, are possible. Flange piece 1440 may extend radially outward from a central longitudinal axis of device 1400 farther than a circumference of body 1420, to, e.g., support device 1400 if device 1400 is placed on a surface, prevent device 1400 from rolling on a flat surface, and/or allow device 1400 to be picked up more easily.

Channels 1462, 1464, 1468 in blocking component 1460 together form a path through which protrusion 1484 may travel, to allow for controlled movement of plunger rod 1480. A first channel 1462 may allow for sufficient distal movement of plunger rod 1480 to prime device 1400. A second channel 1464 may allow for movement of the plunger rod between a "primed" state and a "delivery" state. Channel 1464 may have a path requiring rotation of plunger rod 1480 about a longitudinal axis of device 1400 (as opposed to distal movement of plunger rod 1480), such that the likelihood of plunger rod 1480 being accidentally or unintentionally moved to a "delivery" state may be reduced. Channel 1464 may provide a path of any suitable length (corresponding to any suitable angle of rotation of plunger rod 1480) to ensure adequate separation between the "primed" state and the "delivery" state. A third channel 1468 may allow for sufficient distal movement of plunger rod 1480 to dispense a predetermined volume of drug substance from device 1400.

Figure 8E:
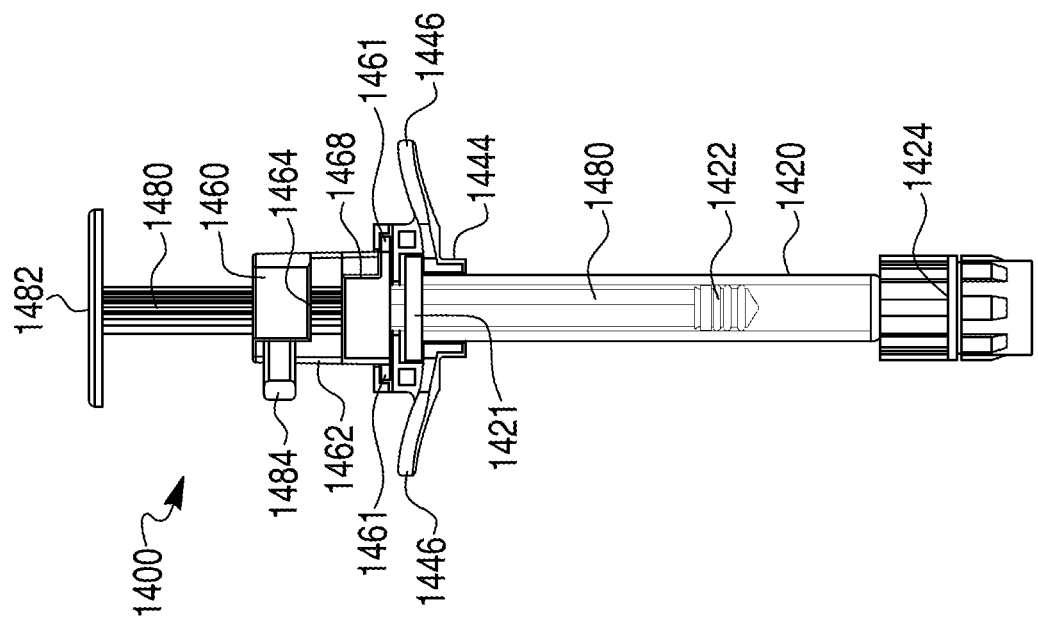
Figure 8D:
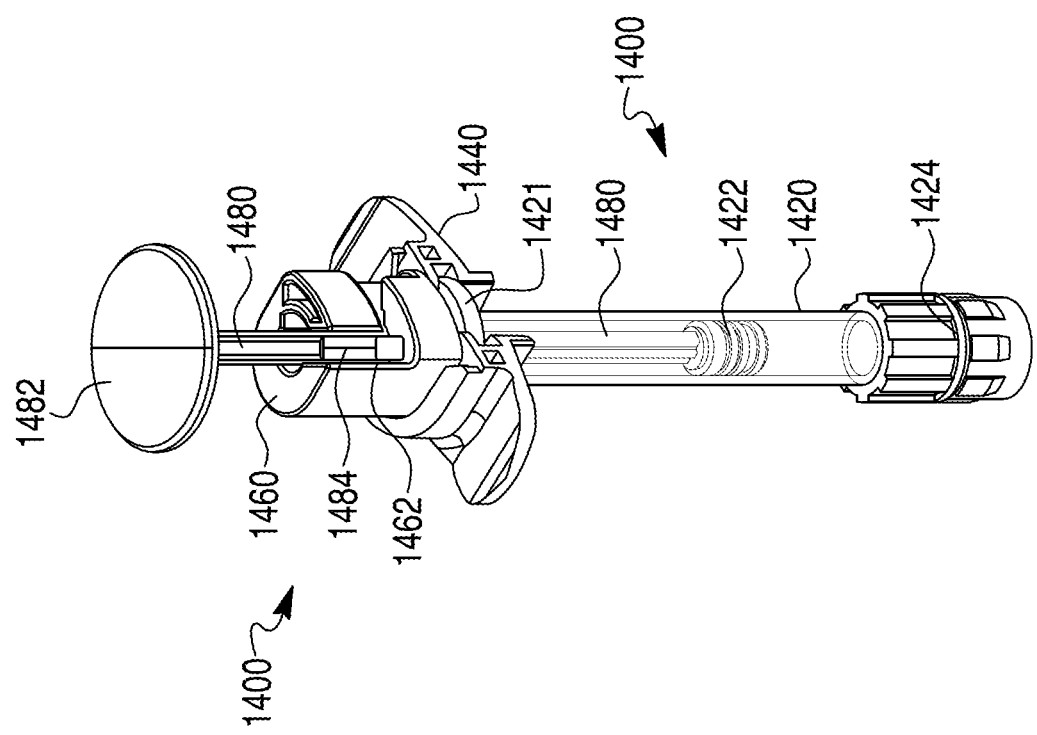
Figure 8F:
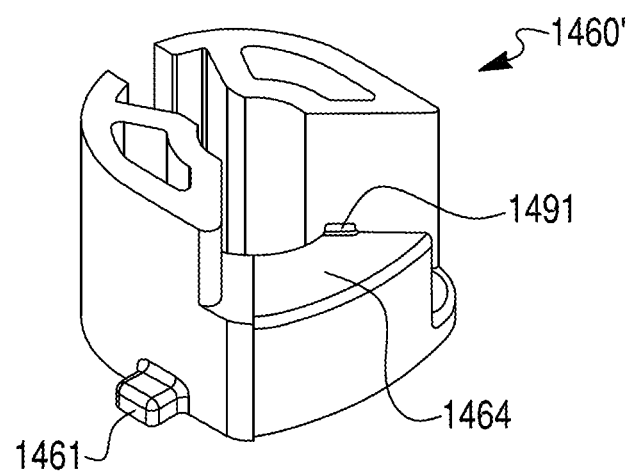
FIGS. 8F and 8G depict a blocking component of the delivery device depicted in FIGS. 8A-8E according to embodiments of the present disclosure.
Figure 8G:
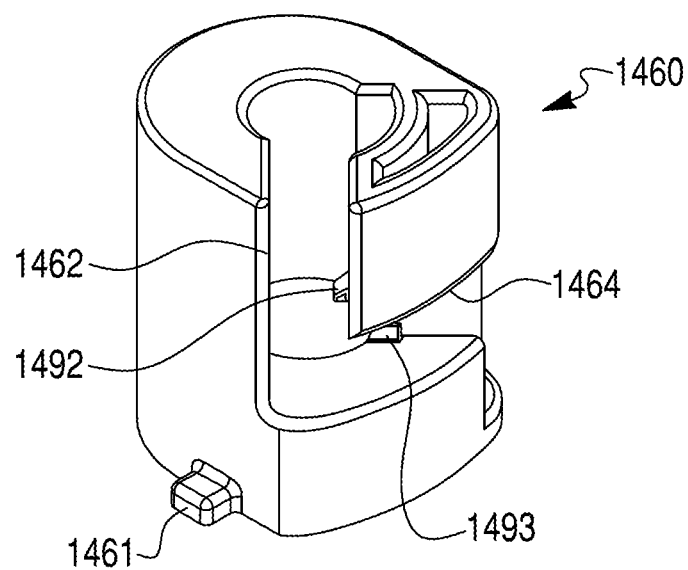
Figure 9B:
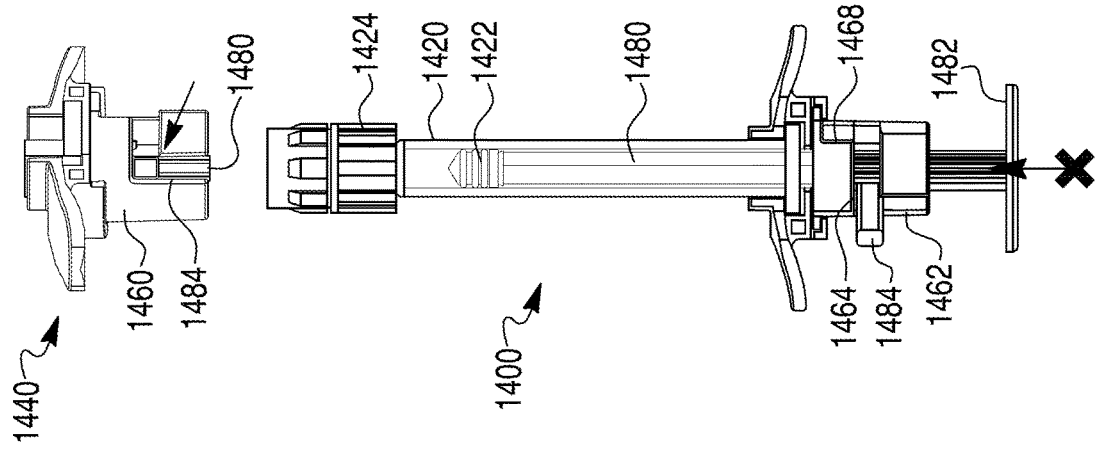
Figure 9A:
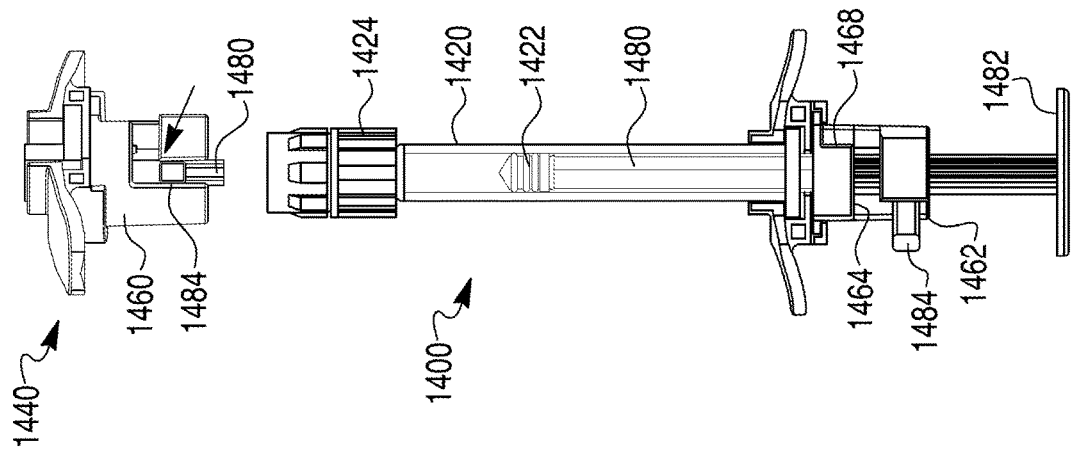

One or more of each channel 1462, 1464, 1468 may include one or more detents, as shown in FIGS. 8F and 8G. For example, a cross sectional view of blocking component 1460 in FIG. 8F shows an interior of channel 1464 having a small detent 1491 disposed on one side. FIG. 8G depicts two larger detents 1492, 1493 in channels 1462, 1464, respectively. Each detent may provide resistance to the movement of protrusion 1484 through channels 1462, 1464, and/or 1468 to provide auditory feedback and/or to prevent unintended movement of protrusion 1484. In some embodiments, detents 1491, 1492, 1493 may be angled on one side, to allow for passage of protrusions 1484 in one direction, but not in the other direction. Detents such as those shown in FIGS. 8F and 8G may be suitable for inclusion in any device disclosed herein, as well as in device 1400.

FIGS. 9A-9E depict an exemplary method of using device 1400, according to aspects of the present disclosure. In a pre-use configuration depicted in FIG. 9A, device 1400 may hold a volume of a drug substance in between stopper 1422 and expulsion end 1424. Plunger rod 1480 may be partially inserted into body 1420 such that protrusion 1484 of plunger rod 1480 is disposed in a proximal end portion of channel 1462. In a priming step depicted in FIG. 9B, plunger rod 1480 may be moved longitudinally further into body 1420, until distal movement is blocked by the abutment of protrusion 1484 against a distal end of channel 1462. For example, a user may press actuation portion 1482 distally through blocking component 1460. In some embodiments, device 1400 may be held in an inverted position during this step, to ensure that air trapped in body 1420 may be expelled, as stopper 1422 is pushed distally by plunger rod 1480. In the "primed" configuration, depicted in FIG. 9C, protrusion 1484 of plunger rod 1480 may be disposed at a first end of channel 1464.

In a dispensing preparation step depicted in FIG. 9D, plunger rod 1480 may be rotated about a longitudinal axis such that protrusion 1484 is moved from a first end of channel 1464 to a second end of channel 1464. For example, a user may grasp and twist actuation portion 1482 of plunger rod 1480. Device 1400 may then be in a ready-to-dispense configuration, wherein protrusion 1484 is disposed at a proximal end of channel 1468. As depicted in FIG. 9E, in a dispensing step, plunger rod 1480 may be moved longitudinally further into body 1420. For example, a user may press actuation portion 1482 distally, until protrusion 1484 abuts a distal end of channel 1468. The dispensing step may ensure that a predetermined volume of a drug substance inside body 1420 is dispensed from device 1400.

In some embodiments, after each successive step in the use of device 1050, a user may be prevented from re-doing a step, and/or from reversing one or more steps. For example, geometries of, e.g., plunger rod 1480, protrusion 1484, and/or channels 1462, 1464, 1468 may prevent a user from pulling plunger rod 1480 proximally (e.g., out of) body 1420.

Figure 10A:
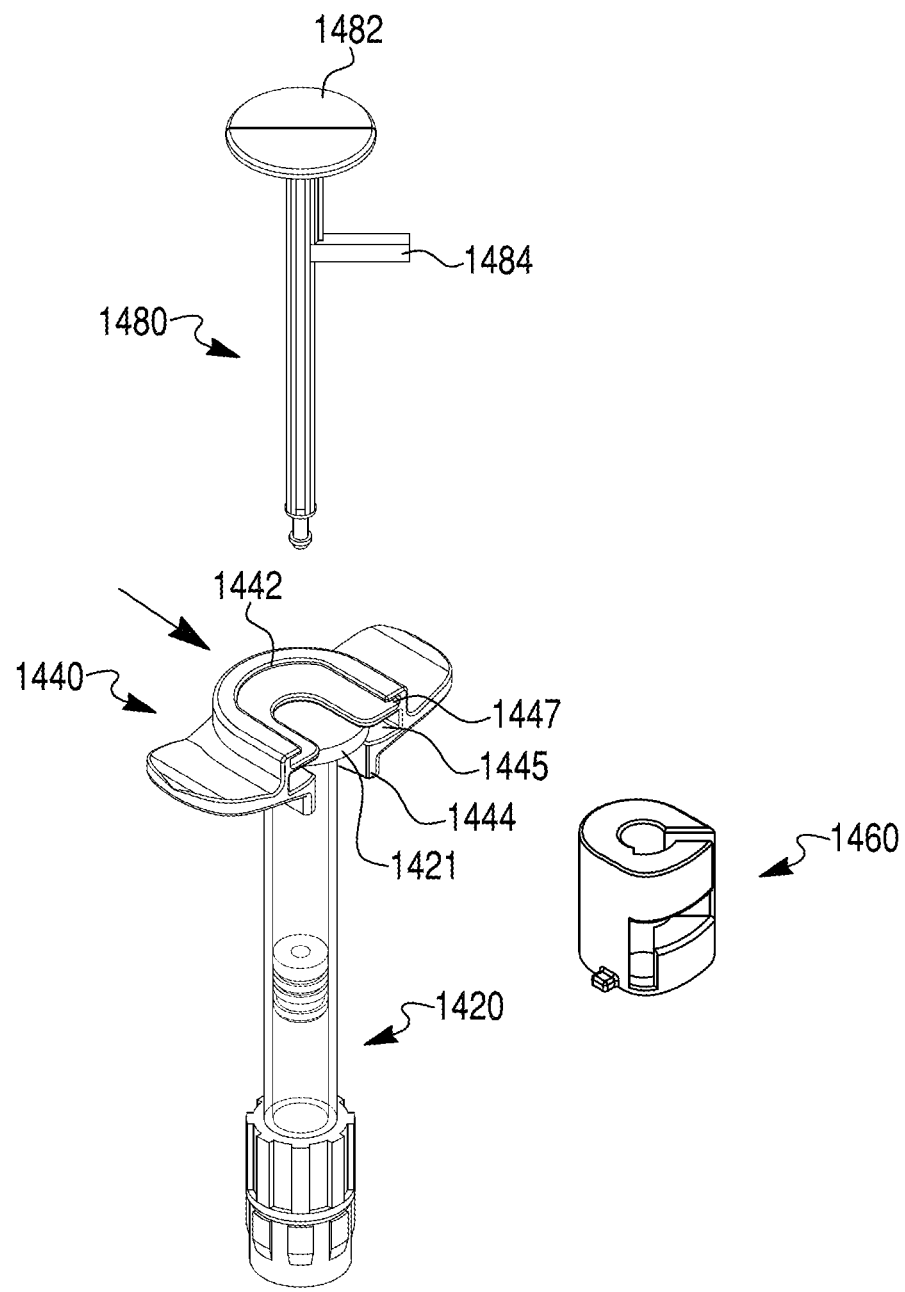
FIGS. 10A-10C depict an exemplary method of assembling the delivery device depicted in FIGS. 8A-8E, according to aspects of the present disclosure.
Figure 10B:
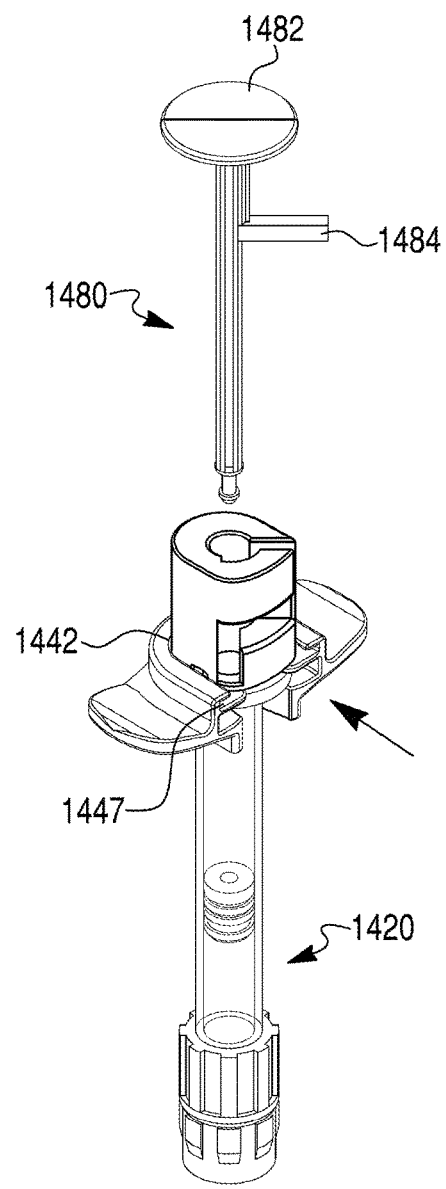
Figure 10C:
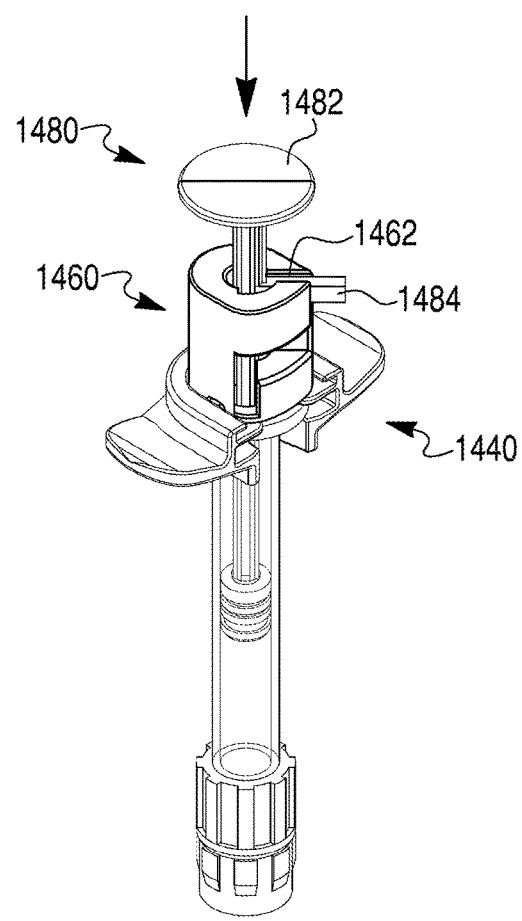

FIGS. 10A-10C depict an exemplary method of assembly of device 1400. As depicted in FIG. 10A, flange piece 1440 may be slidably assembled to body 1420 such that flange 1421 fits into channel 1445 and collar 1444 partially surrounds body 1420. As depicted in FIG. 10B, blocking component 1460 may be slidably assembled to flange piece 1440, such that tabs 1461 rest within channels 1447 and blocking component 1460 abuts proximal collar 1442. As depicted in FIG. 10C, plunger rod 1480 may then be inserted into the combined blocking component 1460, flange piece 1440, and body 1420, such that protrusion 1484 is disposed within channel 1462 of body 1460.

Figure 10E:
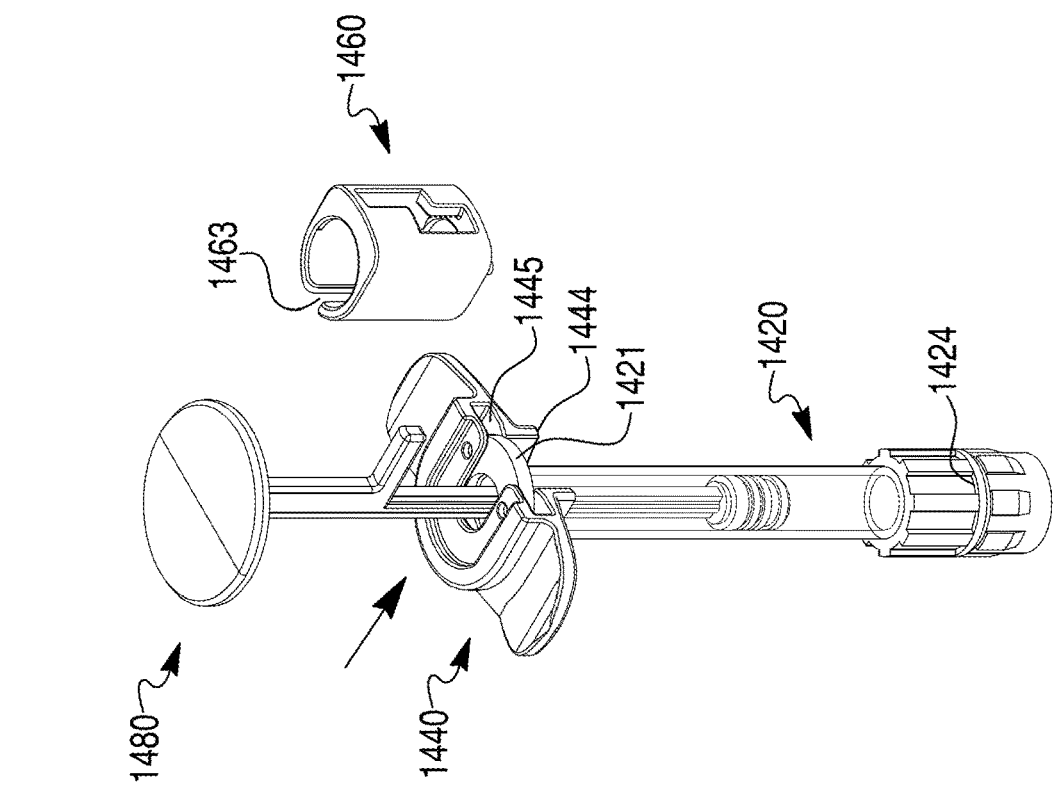
FIGS. 10D-10G depict another exemplary method of assembling a variation of the delivery device depicted in FIGS. 8A-8E, according to aspects of the present disclosure.
Figure 10D:
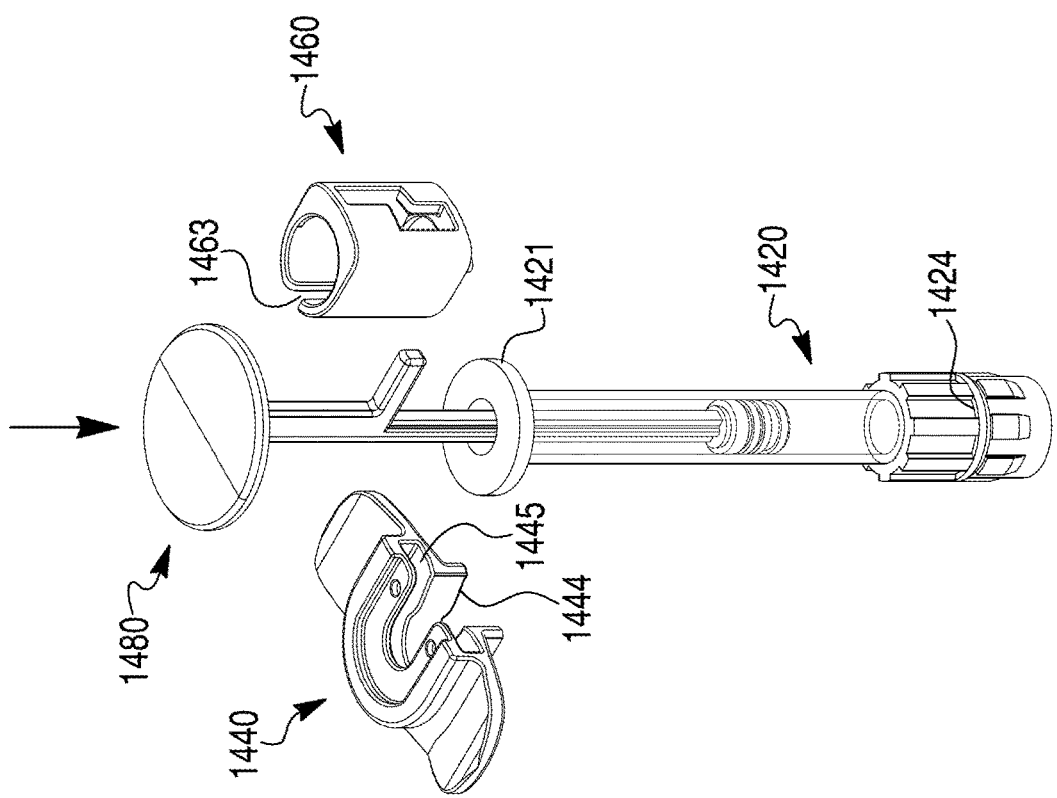
Figure 10G:
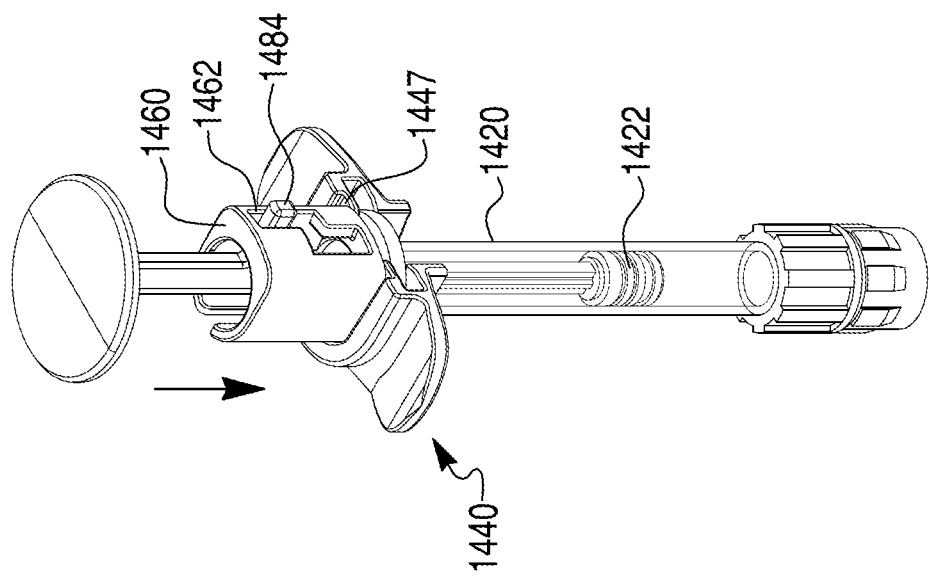
Figure 10F:
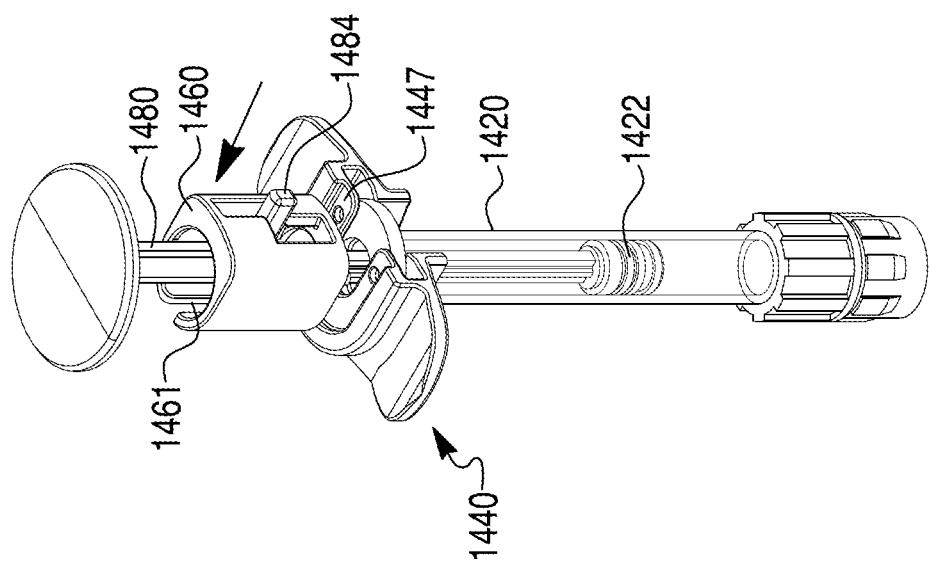
Figure 11E:
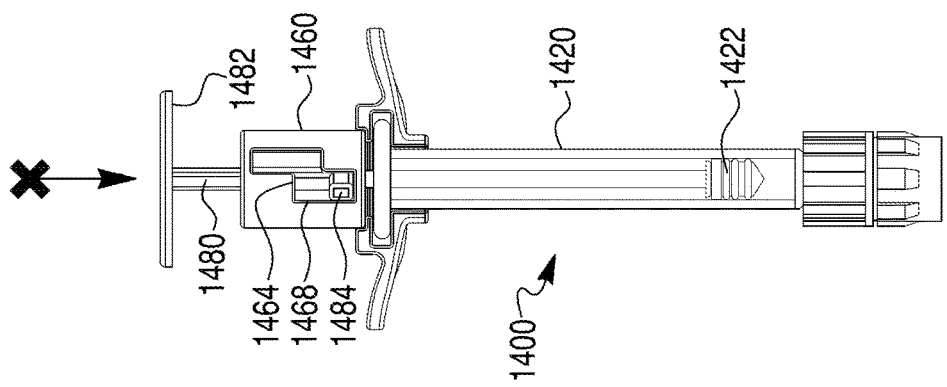
Figure 11D:
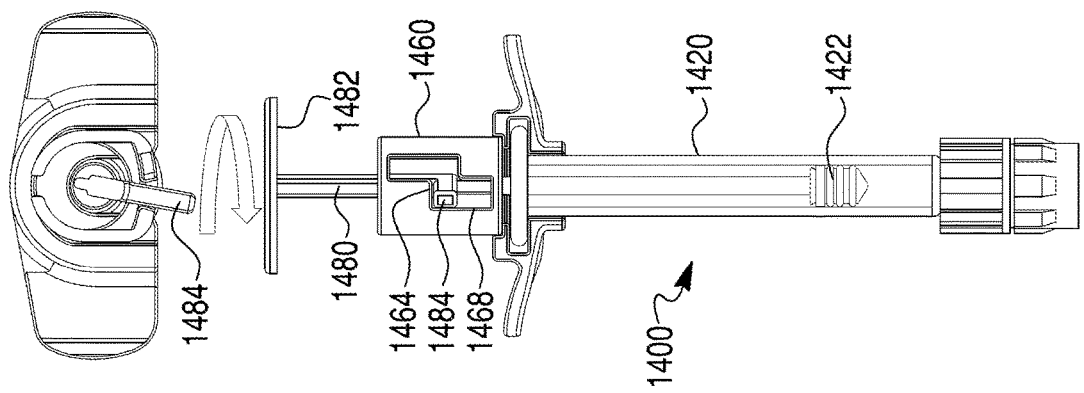
Figure 12A:
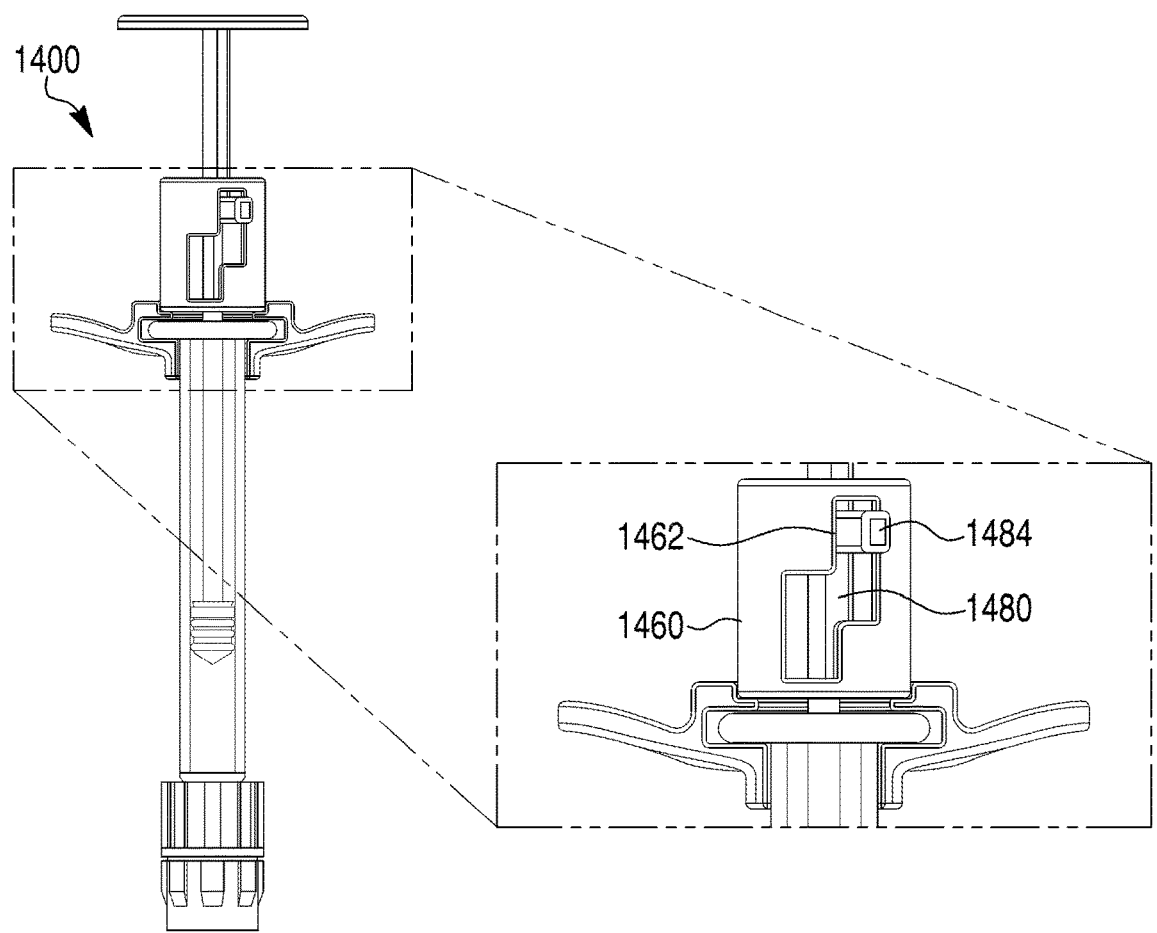
FIGS. 12A-12D depict a close-up view of aspects of the exemplary method depicted in FIGS. 11A-11E.
Figure 12B:
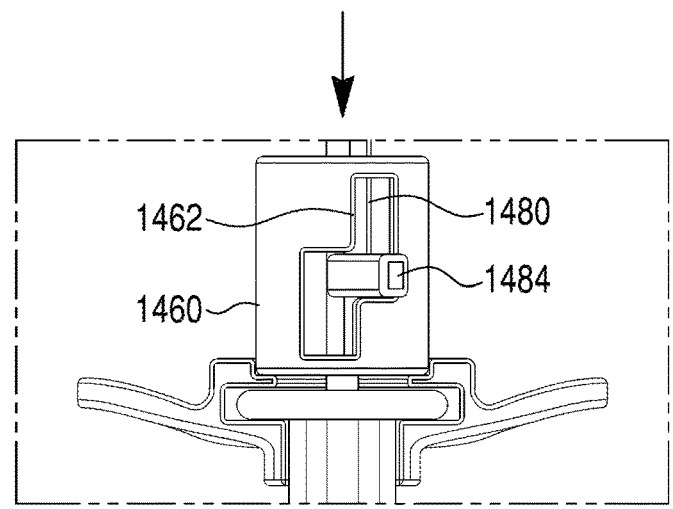
Figure 12C:
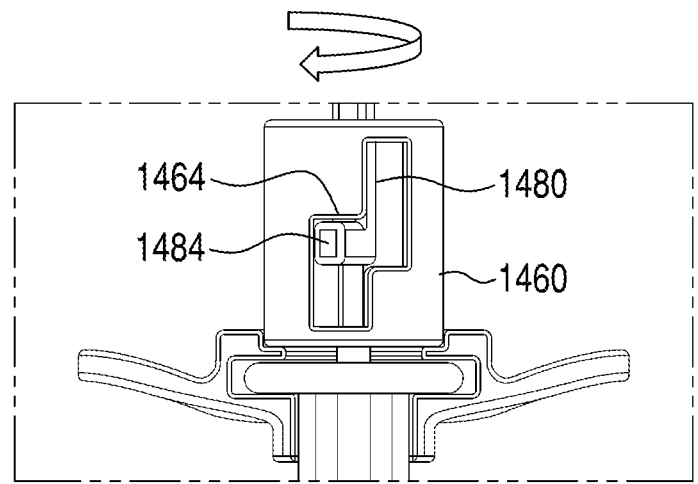
Figure 12D:
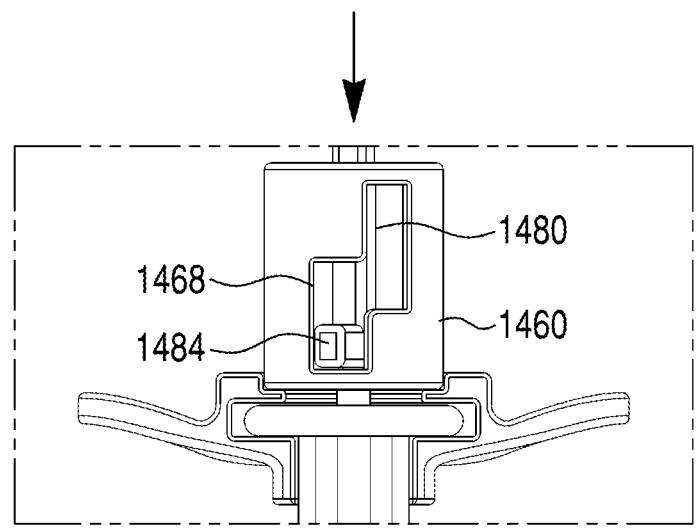

FIGS. 10D-10G, 11A-11E, and 12A-12D depict a variation on a configuration and method of use of device 1400, and to avoid redundancy will not be described in great detail. FIGS. 10D-10G depict an alternate method of assembly of device 1400, where blocking component 1460 includes an opening 1463 through which plunger rod 1480 may fit. In this embodiment, the channels within blocking component 1460 (e.g., channels 1462, 1468) may be closed on a proximal and distal end, to prevent back-out or over-insertion of plunger rod 1480 relative to body 1420. As depicted in FIG. 10E, plunger rod 1480 may be partially inserted into body 1420, and flange piece 1440 may be slidably assembled to body 1420 such that flange 1421 fits into channel 1445 and collar 1444 partially surrounds body 1420. As depicted in FIG. 10F, blocking component 1460 may be assembled to plunger rod 1480, such that protrusion 1484 is disposed within one of the channels in blocking component 1460. As depicted in FIG. 10G, blocking component 1460 may then be assembled to flange piece 1440 such that it is disposed in channel 1447. Blocking component may be affixed to flange piece 1440 in any suitable manner (e.g., using clips, adhesive, a friction fit, a dovetail connection, etc.). FIGS. 12A-12D depict a close-up view of protrusion 1484 moving through the channels of blocking component 1460, per the method of use shown in FIGS. 11A-11E.

Figure 13B:
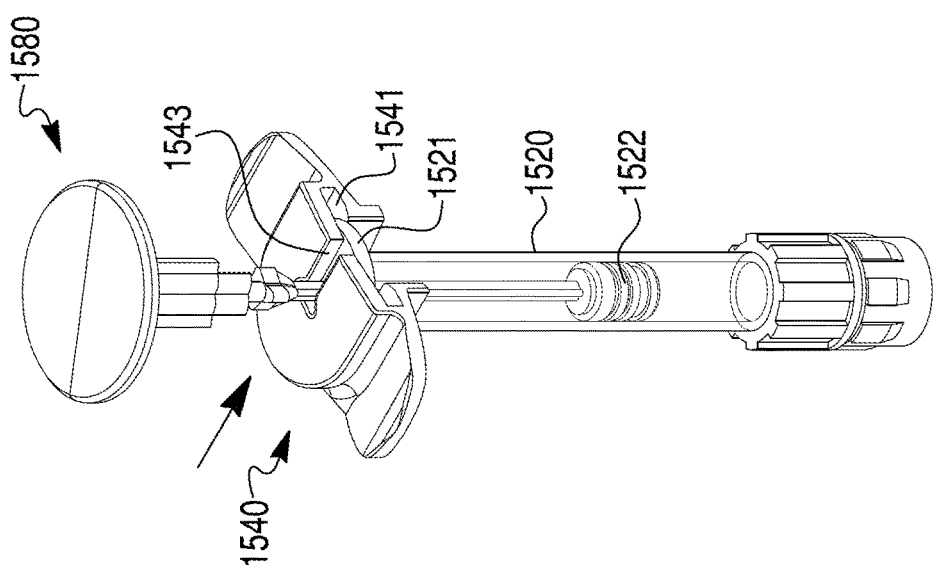
FIGS. 13A and 13B depict a further exemplary delivery device and method of assembling said delivery device, according to additional embodiments of the present disclosure.
Figure 13A:
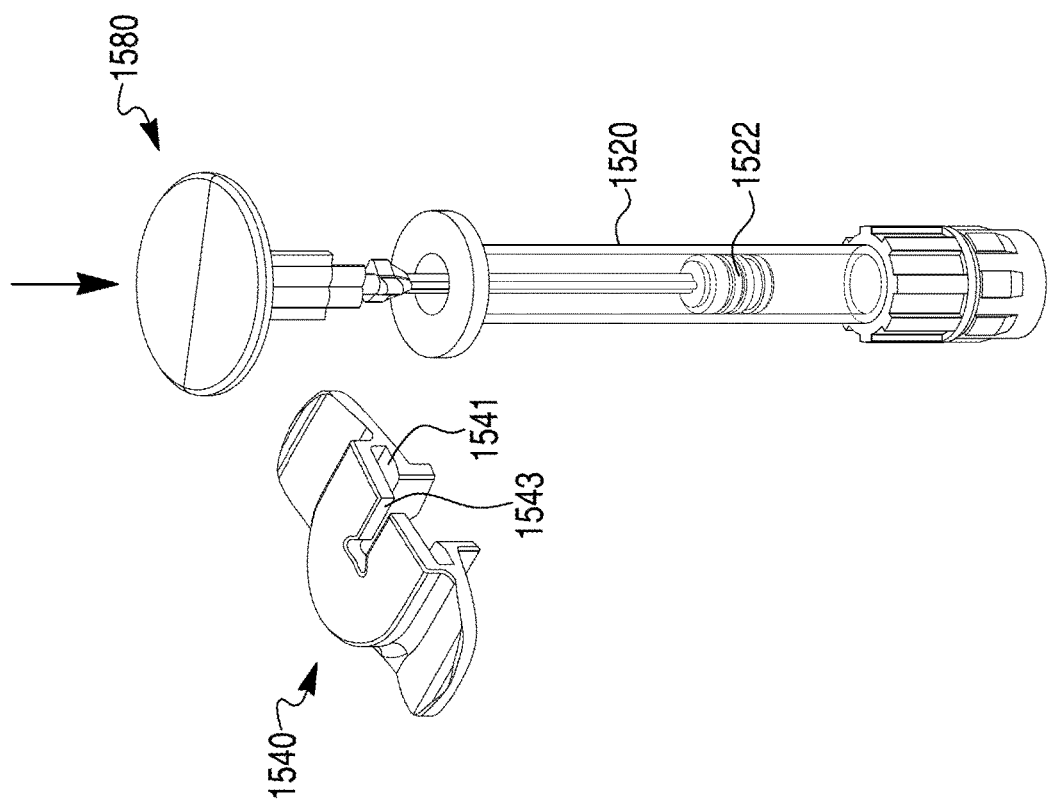

FIGS. 13A and 13B depict a further exemplary delivery device 1500, and a method of assembling said delivery device, according to additional embodiments of the present disclosure. Device 1500 includes a plunger rod 1580, a blocking component in the form of flange piece 1540, and a body 1520. To assemble device 1500, plunger rod may be inserted into body 1520 (e.g., as shown in FIG. 13A), such that it abuts or attaches to a stopper 1522 in body 1520, and flange piece 1540 may be slidably assembled to 1521, e.g., by sliding a channel 1541 on to a flange 1521 of body 1520 (e.g., as shown in FIG. 13B). An opening 1543 may allow for flange piece 1540 to be assembled to body 1520 around plunger rod 1580. It is contemplated that, depending on the size, shape, and structure of each component of device 1500, alternate methods of assembly are possible.

Delivery device 1500 may be, for example, an injection device, such as a syringe, for dispensing a predetermined volume of a formulated drug substance. Generally, delivery device 1500 may share size, capacity, material, preparation, assembly, or manufacturing characteristics with device 1050, device 1200, device 1300, or with other delivery devices disclosed herein. As with other devices disclosed herein, delivery device 1500 may be configured for ease of use and may include one or more features that aid a user by providing tactile, auditory, or visual feedback, using any of the features described elsewhere herein.

Figures 14A, 14B, 14C:
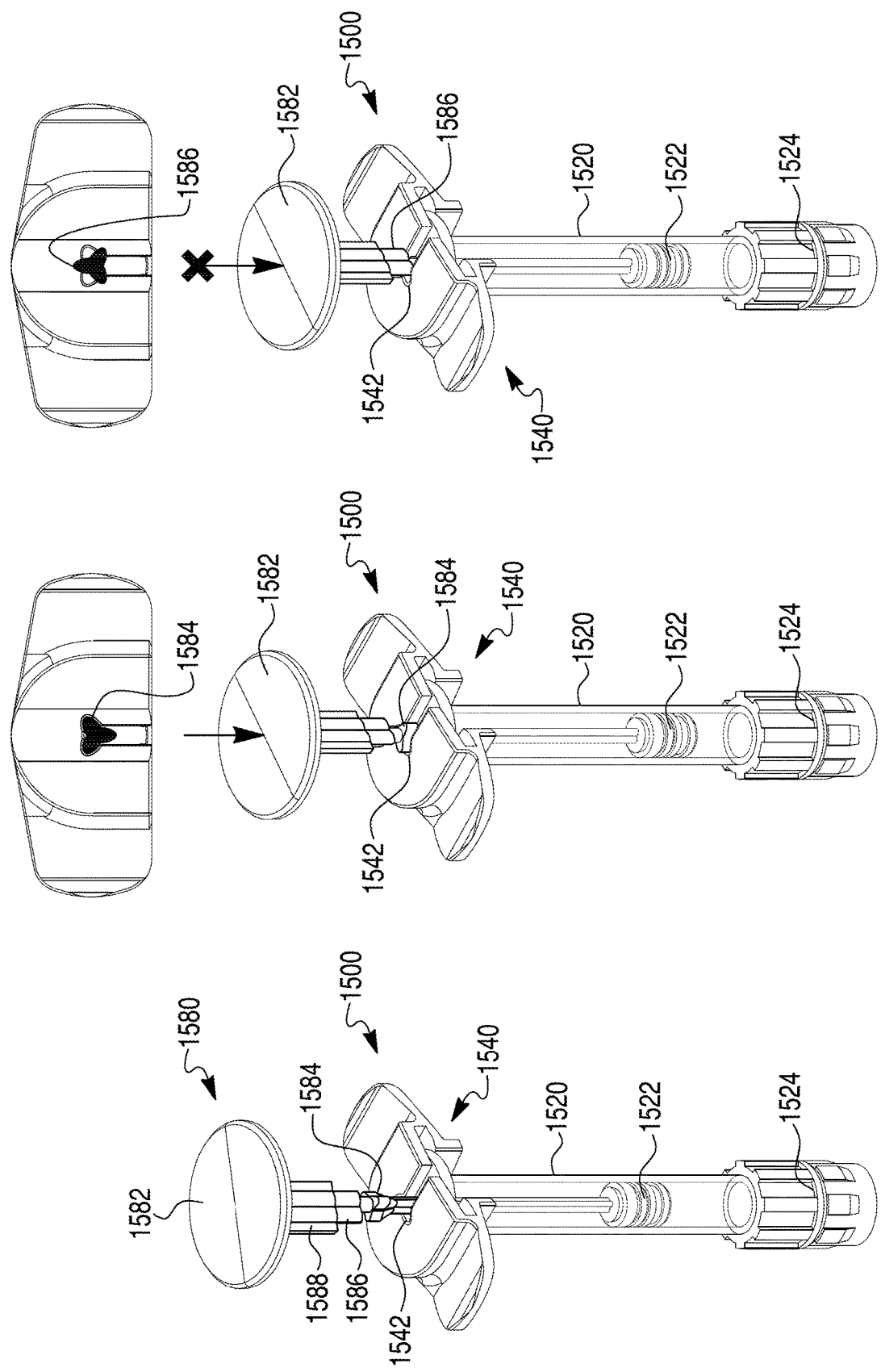

FIG. 14A-14F depict a further view of device 1500 and a method of using device 1500. As shown in FIG. 14A, plunger rod 1580 may include an actuation portion 1582, a proximal stop 1588, a proximal neck portion 1586, and a distal neck portion 1584. Body 1520 may have any or all of the same characteristics as, e.g., body 1060 of device 1050, or as any syringe body known in the art. For example, in some embodiments, body 1520 may be pre-fillable or pre-filled. Stopper 1522 may be configured to be inserted into body 1520 and may be configured to hold a predetermined volume of a formulated drug substance inside body 1520, between stopper 1522 and an expulsion end 1524.

Flange piece 1540 may be of any suitable size and shape to partially close, cover, or partially cover an end of body 1520 opposite expulsion end 1524, and/or to support and hold plunger rod 1580 in body 1520. An opening 1542 may have a size and shape configured to allow passage of plunger rod 1580 in two different configurations. Distal neck portion 1584 and proximal neck portion 1586 may have similar shapes, but may be rotationally offset from one another (e.g., such that once distal neck portion 1584 passes through opening 1542, plunger rod 1580 must be rotated about a longitudinal axis to allow proximal neck portion 1587 to pass. Distal neck portion 1584 may include, e.g., a tapered distal side, which may assist in orienting plunger rod 1580 such that distal neck portion 1584 may pass through opening 1542. This may increase the ease of, e.g., a priming step.

FIG. 14A depicts a pre-use configuration of device 1500. In such a configuration, device 1500 may hold a volume of a drug substance in between stopper 1522 and expulsion end 1524. Plunger rod 1580 may be partially inserted into body 1520 such that distal neck portion 1584 is positioned proximally from flange piece 1540. In a priming step depicted in FIG. 14B, plunger rod 1580 may be moved longitudinally further into body 1520, until distal movement is blocked by the abutment of proximal neck portion 1586 against opening 1542 (as shown in FIG. 14C). For example, a user may press actuation portion 1582 until distal neck portion passes through opening 1542. In some embodiments, device 1500 may be held in an inverted position during this step, to ensure that air trapped in body 1520 may be expelled, as stopper 1522 is pushed distally by plunger rod 1580. In the "primed" state, depicted in FIG. 14D, proximal neck portion 1586 may be disposed against a surface of flange piece 1540.

In a dispensing preparation step depicted in FIG. 14D, plunger rod 1580 may be rotated about a longitudinal axis such that the shape of proximal neck portion 1586 aligns with opening 1542. For example, a user may grasp and twist actuation portion 1582 of plunger rod 1580. Device 1500 may then be in a ready-to-dispense configuration. As depicted in FIG. 14E, in a dispensing step, plunger rod 1580 may be moved longitudinally further into body 1520. For example, a user may press actuation portion 1582 distally, until proximal stop 1588 abuts a surface of flange piece 1540. The dispensing step may ensure that a predetermined volume of a drug substance inside body 1520 is dispensed from device 1500.

In some embodiments, after each successive step in the use of device 1500, a user may be prevented from re-doing a step, and/or from reversing one or more steps. For example, geometries of, e.g., plunger rod 1580, distal neck portion 1584, proximal neck portion 1586, and opening 1542 may interface with one another to prevent a user from pulling plunger rod 1580 proximally (e.g., out of) body 1520.

Additional variations on blocking components, dosage control components, and the like will now be described. FIGS. 15A-23C depict exemplary plunger rod dials according to further embodiments of the present disclosure. For example, FIG. 15A depicts a plunger rod 1600 having an actuation portion 1610. Actuation portion 1610 may have a shape generally corresponding to a flange piece 1640. Plunger rod 1600 may be rotatable with respect to flange piece 1640 and/or a body of the device. A device may be in a configuration suitable for delivery of a desired amount of a drug substance when, e.g., a shape of plunger rod 1610 is generally aligned with shape of 1640 (as shown in, e.g., the top view of FIG. 15A). As another example, FIG. 15B depicts an actuation portion 1610' with a ridged side, to allow for ease of rotation of plunger rod 1600' with respect to flange piece 1640 and/or a remainder of the syringe. FIG. 16A depicts an actuation portion 1610'' with a ribbed side, again to allow for ease of rotation of plunger rod 1600. FIG. 16B depicts an exemplary combination of actuation portion 1610'' with device 1500. One of ordinary skill in the art will understand that any of the actuation portions or other features described herein may be combined with devices described herein.

Figure 18B:
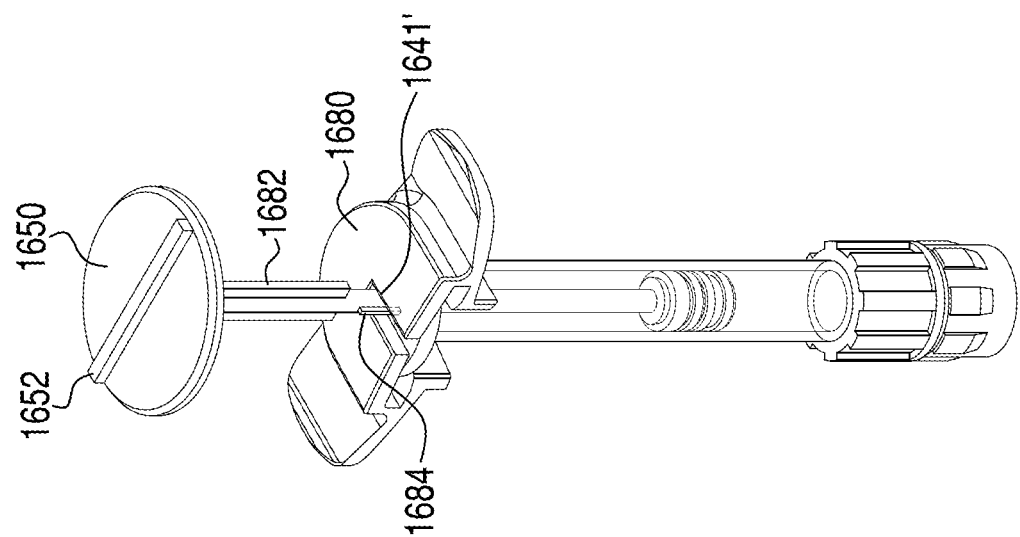
FIGS. 18A and 18B depict a further exemplary plunger rod and dial according to additional embodiments of the present disclosure.
Figure 18A:
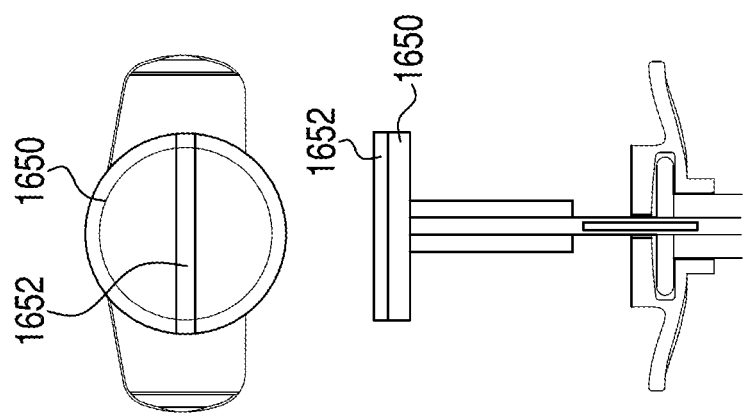
Figure 17:
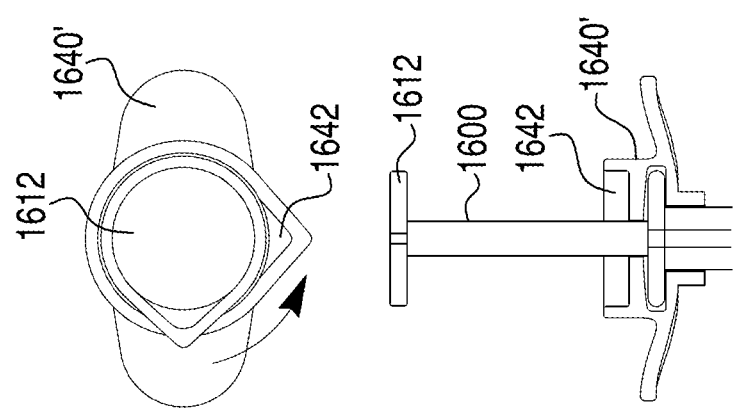
FIG. 17 depicts an exemplary plunger rod and dial according to further embodiments of the present disclosure.

FIG. 17 depicts an exemplary plunger rod and dial according to further embodiments of the present disclosure. An actuation portion 1612 may be sized and configured to fit into a collar 1642 of a flange piece 1640' in only a particular configuration. A depth of collar 1642 may correspond to, e.g., a distance that plunger rod 1600 must travel to dispense a predetermined volume of a drug substance from a drug delivery device. In one embodiment, actuation portion 1612 may be moved distally until it abuts collar 1642, and then may be rotated until its shape corresponds with the shape of collar 1642 so that it may be pushed into collar 1642 in a dispensing step. FIGS. 18A and 18B depict a further exemplary plunger rod and dial, which combine exemplary features that allow for precision dose delivery. The plunger rod may include, e.g., protrusions 1684 and 1682, which may each fit through an opening 1641' in a flange piece 1680 in a particular configuration. Each of protrusions 1682 and 1684 may correspond to a distance required to deliver a desired volume of a drug substance from a device and/or prime the device. Actuation portion 1650 may include a raised portion 1652, which may aid a user in twisting the plunger rod in relation to flange piece 1680.

Figure 19A:
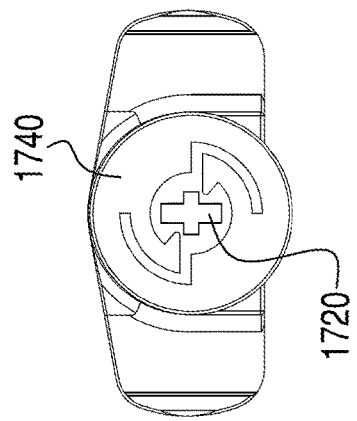
FIGS. 19A and 19B depict an exemplary rotation lock mechanism according to additional embodiments of the present disclosure.
Figure 19B:
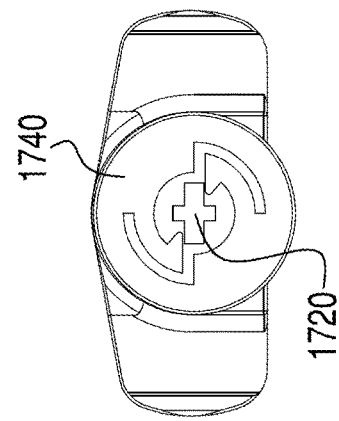

FIGS. 19A and 19B depict a top view of a flange piece 1740 and a plunger rod 1720. Flange piece 1740 and plunger rod 1720 may have a cross-sectional shape allowing for limited rotation of plunger rod 1720 relative to flange piece 1740 in a single direction. For example, flange piece 1740 may have inner protrusions that may interact with an irregular cross-sectional shape of plunger rod 1720 to resist a first portion of plunger rod 1720 as it rotates past the inner protrusions, and to stop a second portion of plunger rod 1720 when it abuts the inner protrusions.

Figure 20:
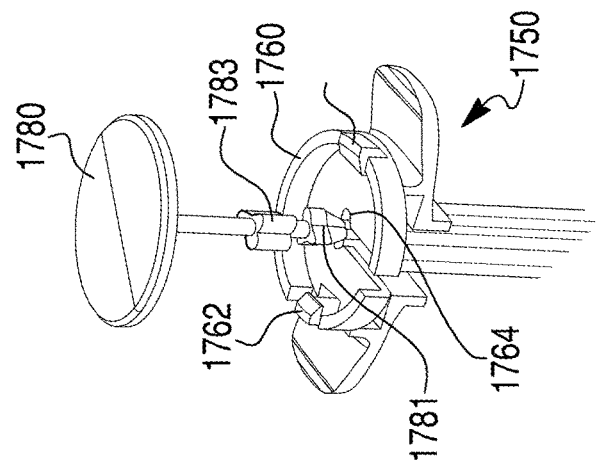
FIG. 20 depicts an exemplary plunger rod snap feature according to additional embodiments of the present disclosure.

FIG. 20 depicts an exemplary flange piece 1750 with a well 1760 having clips 1762. A plunger rod actuation portion 1780 may be pushed distally into well 1760 until clips 1762 overlay actuation portion 1780, to hold actuation portion 1780 in place and, e.g., prevent back-out of the plunger rod. The plunger rod includes a distal protrusion 1781 and a proximal protrusion 1783, each of which is sized to fit through an opening 1764 when the plunger rod is rotated to a particular position. Distal protrusion 1781 includes a tapered distal side, which may assist in orienting the plunger rod into the position required to advance the plunger rod distally such that distal protrusion 1781 passes through opening 1764. This may increase the ease of, e.g., a priming step. In some embodiments, a height of well 1760 and/or actuation portion 1780 may correspond to a height that a plunger rod must travel to dispense a predetermined volume of a drug substance. Thus, a device may be primed when actuation portion 1780 abuts a proximal side of well 1760, and may deliver a predetermined volume of a drug substance as actuation portion 1780 travels distally into well 1760.

Figure 21:
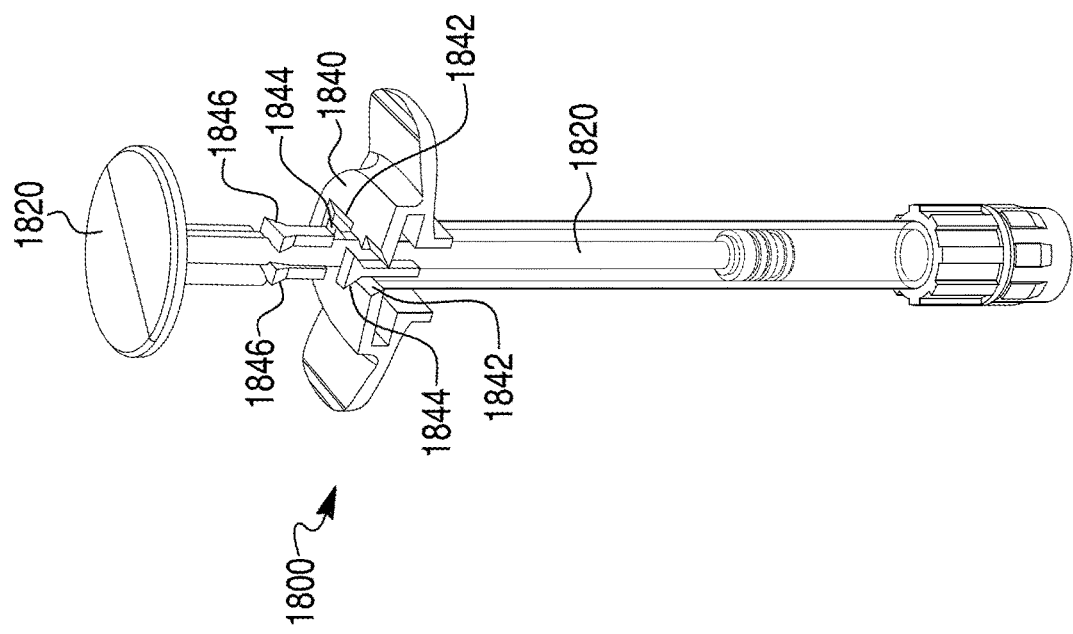
FIG. 21 depicts an exemplary plunger rod with a bump feature according to additional embodiments of the present disclosure.

FIG. 21 depicts an exemplary device 1800 with a plunger rod 1820 and a complementary flange piece 1840. Plunger rod 1820 may include, e.g., protrusions 1844, 1846 having an angled or wedge shape, corresponding to a shape of one or more openings 1842 in flange piece 1840. The wedge or angled shapes of protrusions 1844, 1846 and openings 1842 may suffice to resist distal movement of plunger rod 1820 when a protrusion 1844 or 1846 abuts a side of opening 1842, but may be able to move past one another given enough force. The resistance provided by the abutment of protrusions 1844, 1846 against the sides of openings 1842 may suffice to indicate to a user that a particular step in the use of device 1800 is completed. A user may then apply enough force to move plunger rod 1820 past the resistance and continue to a next step (e.g., from a completed priming step to a delivery-ready step).

Figure 22:
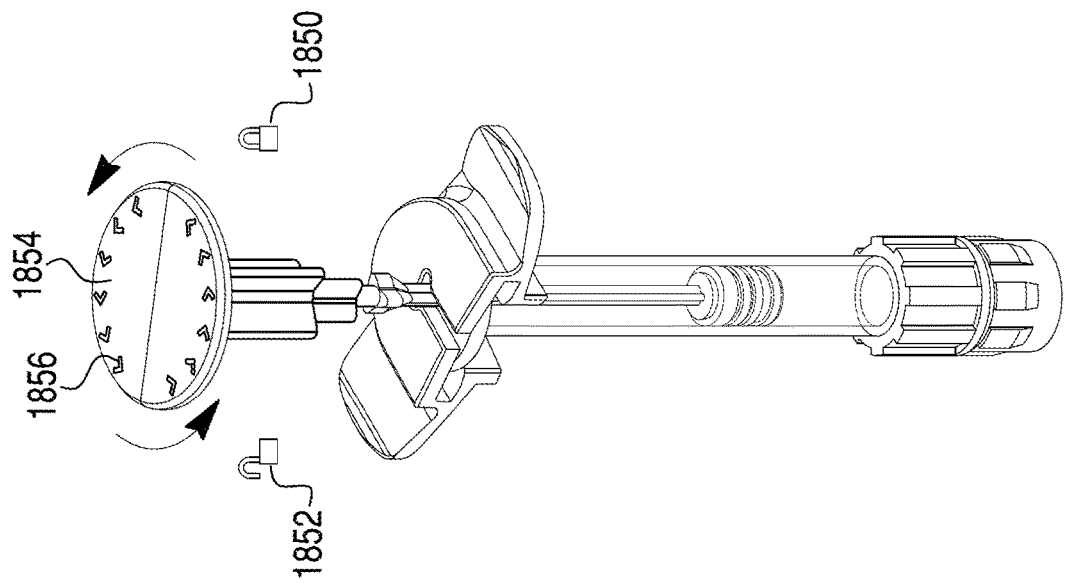
FIG. 22 depicts exemplary visual feedback features according to some embodiments of the present disclosure.

As has been described elsewhere, any of the devices disclosed herein may be combined with labels, auditory feedback, and/or tactical feedback in the form of symbols (e.g., in FIG. 22 depicted as lock and unlock symbols 1850, 1852, chevrons 1856 on actuation portion 1854). Rotation of a plunger rod also may be accompanied by a "clicking" sound.

Figure 23C:
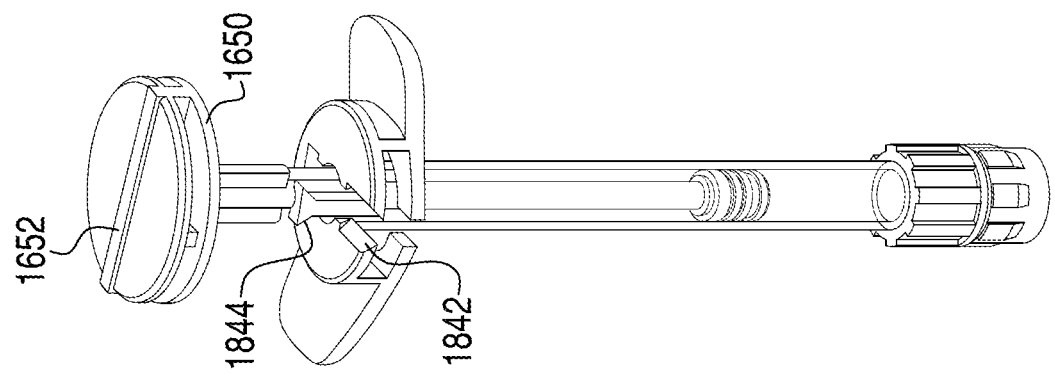
FIGS. 23A-23C depict a further exemplary delivery device according to aspects of the present disclosure.
Figure 23B:
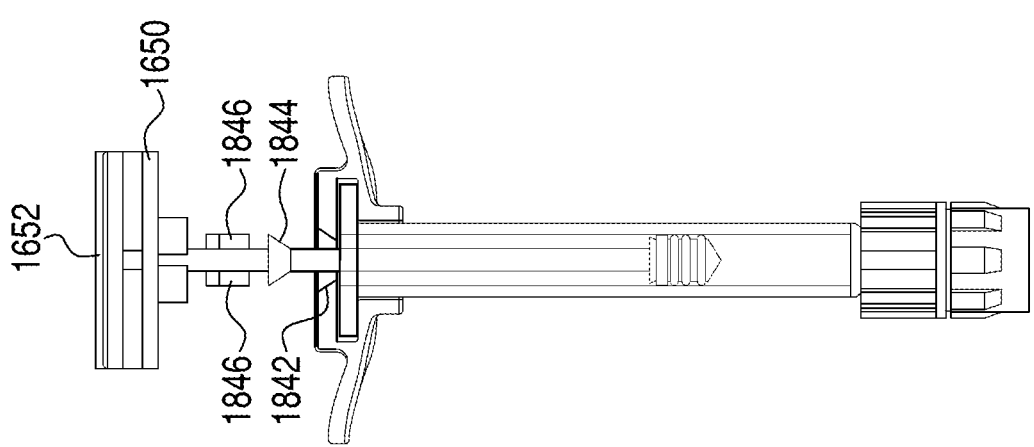
Figure 23A:
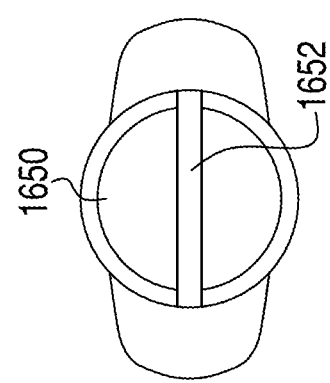

FIGS. 23A-23C depict a further exemplary combination of components in a delivery device. For example, a plunger rod actuation portion 1650 may include, e.g., ribbed sides and a raised portion 1652, to assist in twisting the actuation portion. A device with these characteristics may include, e.g., openings 1842 and corresponding angled protrusions 1844, 1846 (described with respect to FIG. 21).

Figure 24A:
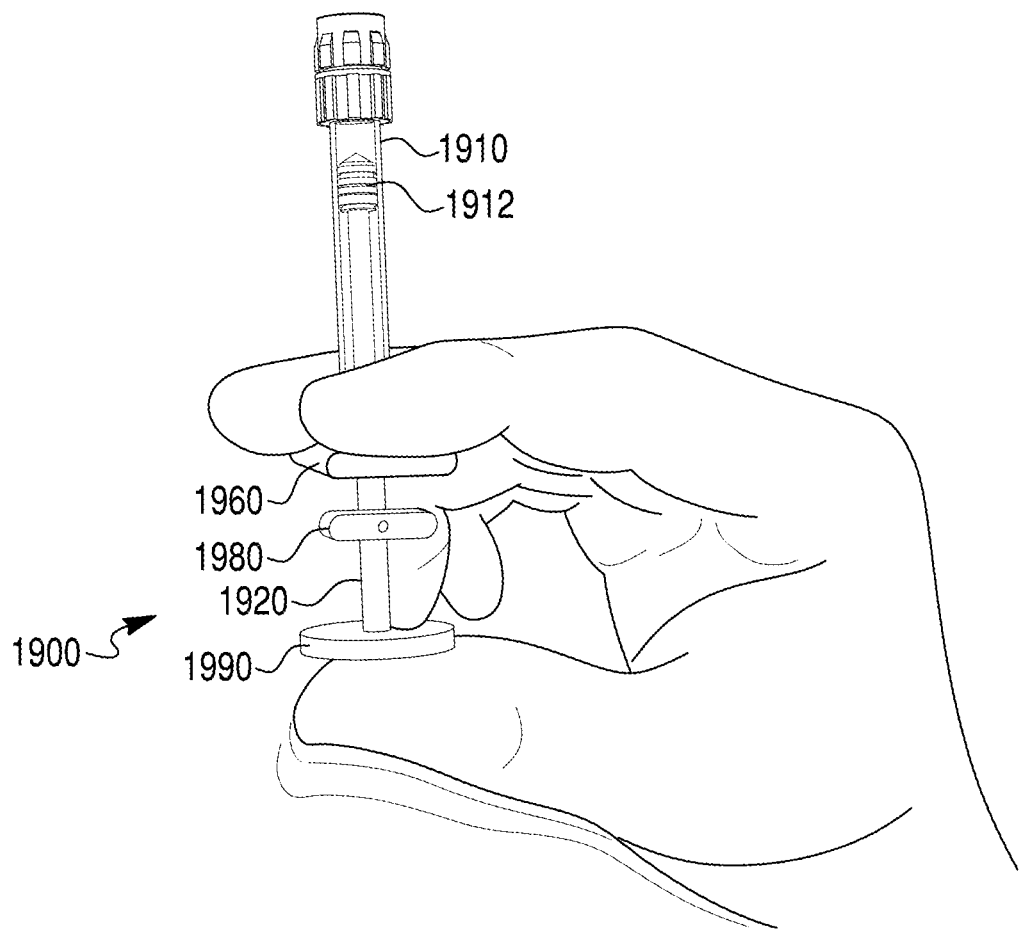

FIGS. 24A-24E depict a further exemplary delivery device 1900 and a method of using device 1900. Device 1900 may include an actuation portion 1940 and a blocking component 1980 depicted on a plunger rod 1920. Plunger rod 1240 may abut a stopper 1912 in a body 1910. Blocking component 1980 may be rotatable relative to plunger rod 1920. In a pre-use configuration depicted in FIG. 24B, blocking component 1980 may be in a first position with respect to plunger rod 1920 and flange piece 1960. In a priming step depicted in FIG. 24C, plunger rod 1920 may be moved longitudinally further into body 1910, until distal movement is blocked by the abutment of blocking component 1980 against a recess 1962 in flange piece 1960. For example, a user may press actuation portion 1940 distally towards flange piece 1960. In a dispensing preparation step depicted in FIG. 24D, blocking component 1980 may be rotated such that a shorter dimension of blocking component 1980 faces flange piece 1960. Recess 1962 may be curved to allow for ease of rotation of blocking component 1980. A distance between blocking component 1980 and flange piece 1960 after blocking component 1980 is rotated may correspond to a distance that plunger rod 1920 may move to dispense a predetermined volume of a drug substance from device 1900. As depicted in FIG. 24E, in a dispensing step, plunger rod 1920 may be moved longitudinally further into body 1910, until the rotated blocking component 1980 abuts flange piece 1960 in a second position. For example, a user may press actuation portion 1940 distally, until protrusion blocking component abuts flange piece 1960. The dispensing step may ensure that a predetermined volume of a drug substance inside body 1910 is dispensed from device 1900.

Figure 25C:
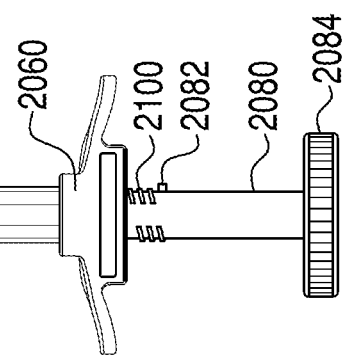
Figure 25D:
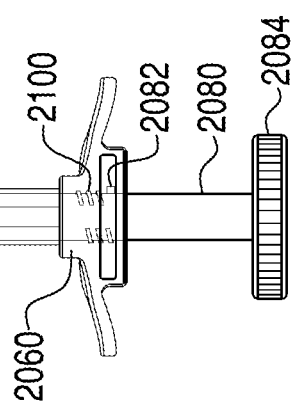
Figure 25E:
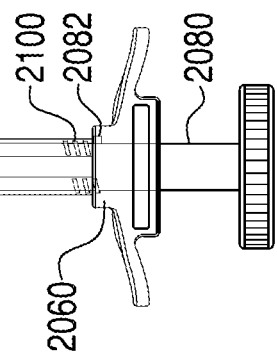

FIGS. 25A-25E depict a further exemplary delivery device 2000, and a method of using delivery device 2000. A plunger rod 2080 of device 2000 may include threads 2100, corresponding to inner threads (not pictured) in a flange piece 2062. As depicted in FIG. 25A, plunger rod 2080 may be rotatable relative to other portions of device 2000. Plunger rod 2080 may also include a protrusion 2082 located proximally from threads 2100 (see, e.g., FIG. 25B), which may correspond to an opening 2062 in a flange piece 2062, such that plunger rod 2080 must be in a particular configuration and position to allow protrusion 2082 to pass into and/or through flange piece 2060. In a pre-use configuration depicted in FIG. 25C, threads 2100 and protrusion 2082 may be positioned proximally to flange piece 2060. In a priming step, plunger rod 2080 may be rotated with respect to the inner threads of flange piece 2060 until threads 2100 pass through flange piece 2060 and/or protrusion 2082 prevents further rotation or distal movement of plunger rod 2080. In a dispensing preparation step, protrusion 2082 may be moved towards opening 2062. In a dispensing step, protrusion 2082 may be moved through opening 2062 to further advance plunger rod 2080, and to dispense a predetermined volume of a drug substance inside the body of device 2000.

Figure 26E:
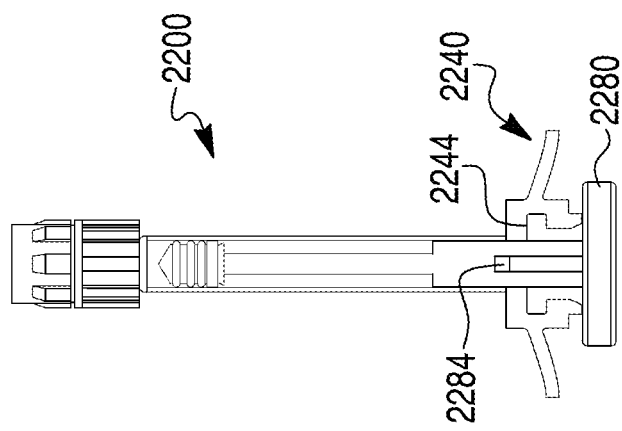
Figure 26D:
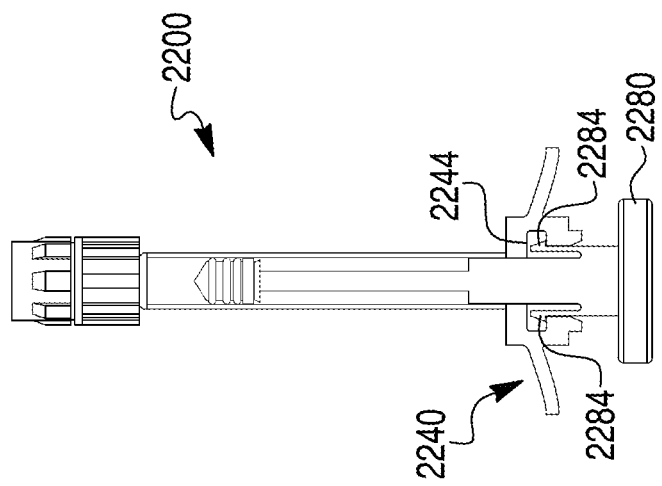
Figure 26C:
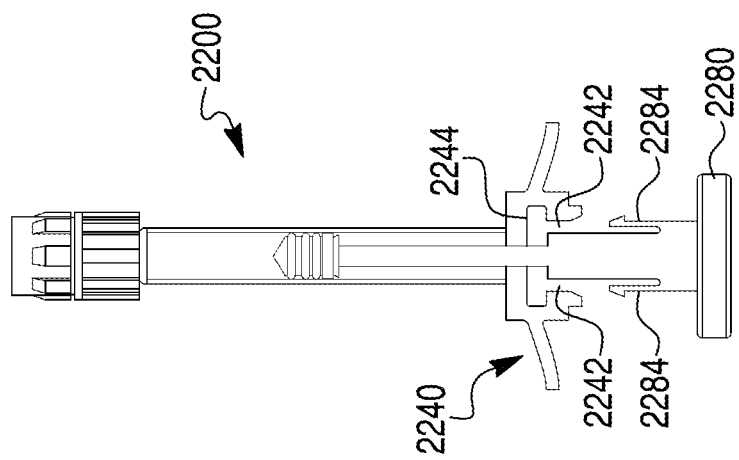

FIGS. 26A-26E depict a delivery device 2200 having further variations on dosage control components. For example, device 2200 includes a plunger rod 2280 with one or more clips 2284, each of which may be configured to slide distally into a channel 2242 of a flange piece 2240 and, once having slid distally, to resist sliding proximally out of channel 2242 (e.g., to prevent or resist back-out of plunger rod 2280). Flange piece 2240 may further have a second channel 2244 and a third channel 2246, through which each of clips 2284 may slide in delivery preparation and dosage delivery steps, as has been previously described. Alternately, as shown in FIG. 26B, channel 2242' may have an open proximal end through which a protrusion 2284' may move, allowing for proximal and/or distal movement of a plunger rod 2280 relative to flange piece 2240'. As depicted in FIG. 26C, in a pre-use configuration, clips 2284 may be disposed proximally to channels 2242 of flange piece 2240. In a priming step, plunger rod 2280 may be moved distally into a body of device 2200, until clips 2284 move into channels 2242 and abut a distal end of channels 2242. In a dispensing preparation step, plunger rod 2280 may be rotated relative to flange piece 2240. In a dispensing step, plunger rod 2280 may be moved further distally into a body of device 2200 to dispense a predetermined volume of the drug substance from device 2200.

Figure 26G:
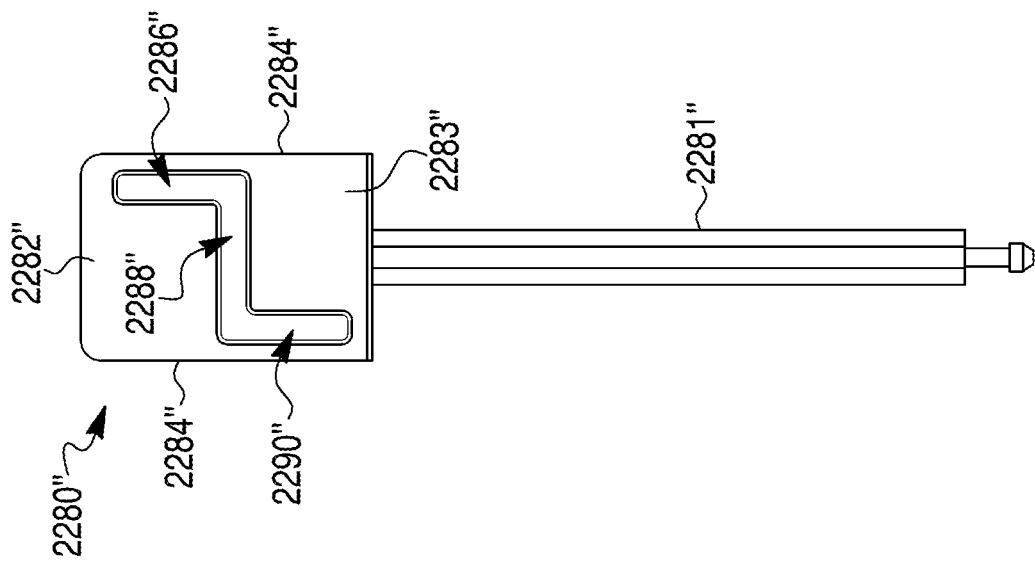
Figure 26F:
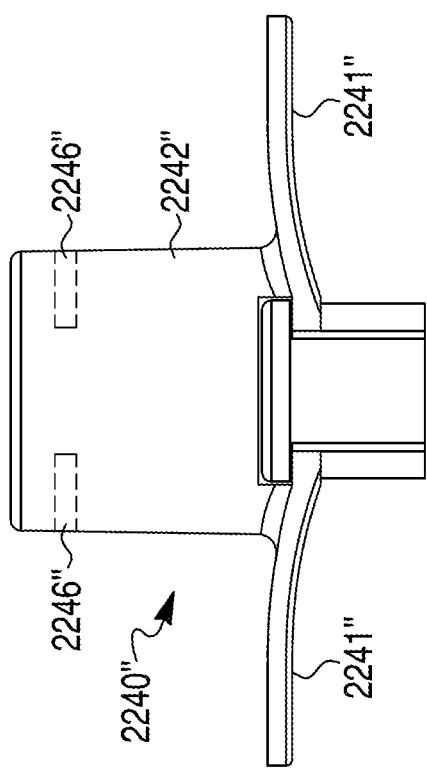

In other embodiments, as shown in FIGS. 26F-26G, a flange piece 2240" may include one or more projections 2246" disposed within a collar 2242". In the present example, collar 2242" may include a pair of projections 2246" extending radially inward from an interior surface of collar 2242" and in opposite directions relative to another. For example, projections 2246" may be disposed approximately 180 degrees away from one another. It should be appreciated that flange piece 2240" may include additional and/or fewer projections 2246" than those shown and described herein without departing from a scope of this disclosure. Flange piece 2240" may be configured to engage a plunger rod 2080" in response to plunger rod 2280" receiving projections 2246".

As seen in FIG. 26G, a plunger rod 2280" may include an actuation member 2284" defined by a proximal end 2282" and a distal end 2283". Plunger rod 2280" may include a series of channels along opposing sides of actuation member 2284", such as, for example, a first channel 2286", a second channel 2288", and a third channel 2290" positioned between proximal end 2282" and distal end 2283". First channel 2286" is offset from third channel 2290" and connected to third channel 2290" by second channel 2288" positioned therebetween. As described in detail below, first channel 2286" may define a longitudinal and axial priming path of plunger rod 2280", second channel 2288" may define a circumferential path of plunger rod 2280", and third channel 2290" may define a longitudinal and axial dose completion path. It should be appreciated that an opposing surface and/or side of actuation member 2284" (not shown) includes a substantially similar series of interconnected first channel 2286", second channel 2288", and third channel 2290" as seen in FIG. 26G. In the present example, first channel 2286" and third channel 2290" may be aligned parallel relative to one another.

First channels 2286", second channels 2288", and third channels 2290" may be sized, shaped, and configured to receive at least one of the pair of projections 2246". With plunger rod 2280" coupled to flange piece 2240", projections 2246" may protrude and slide through first channels 2286", second channels 2288", and third channels 2290" to prime and deliver a dosage from device 2200 (FIG. 26A) as described in detail above. In some embodiments, first channels 2286" may have an open end at proximal end 2282" through which projections 2246" may be received in. In some embodiments, first channels 2286" may have a closed proximal end and projections 2246" may be at least partially flexible and/or deformable such that projections 2246" may be configured to flex radially-outward when being received at the proximal end of first channels 2286". In other embodiments, first channels 2286" may have a sloped, chamfered, and/or tapered end to facilitate guiding projections 2246" toward second channels 2288". In this instance, the sloped end may inhibit retraction (e.g., proximal movement) of plunger rod 2280" relative to flange piece 2240". A longitudinal length of first channels 2286" may define an axial priming path (e.g., an amount or extent priming) that is configured to facilitate proximal and/or distal movement of plunger rod 2280" relative to flange piece 2240". For example, projections 2246" may be disposed at a proximal end of first channels 2286" and proximally of second channels 2288" when device 2200 is in an assembly state. In a priming step, plunger rod 2280" may move distally relative to flange piece 2240" until projections 2246" are positioned within second channels 2288" and at a distal end of first channels 2286". Second channels 2288" may define a circumferential path of plunger rod 2280".

In a dispensing preparation step, plunger rod 2280" may be rotated relative to flange piece 2240" to translate projections 2246" laterally through the circumferential path of second channels 2288" and toward a dose completion path defined by third channels 2290". In some embodiments, plunger rod 2280" and/or flange piece 2240" may be configured to generate a user feedback (e.g., tactile, audible, visual, etc.) when device 1050 is in the dispensing preparation step. In a dispensing step, plunger rod 2280" may move distally into a body of device 2200 to dispense a controlled volume of substance by translating projections 2246" through third channels 2290". A longitudinal length of third channels 2290" may define a dosage delivery path (e.g., a dosage amount). It should be appreciated that the axial priming path (length of first channels 2286") may vary relative to the dosage delivery path (length of third channels 2290"). In other embodiments, plunger rod 2280" may include additional and/or fewer channels along actuation member 2284" (e.g., corresponding to a quantity of projections 2246" on flange piece 2240"), or have various other relative channel configurations, than those shown and described herein.

Figure 27C:
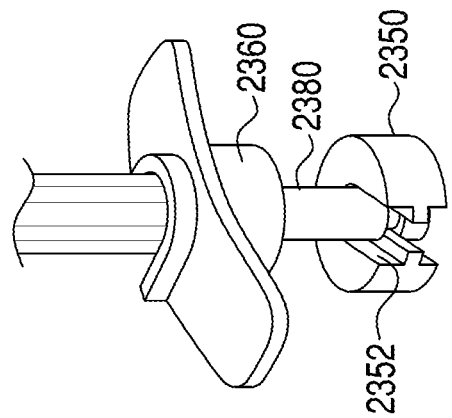
Figure 27B:
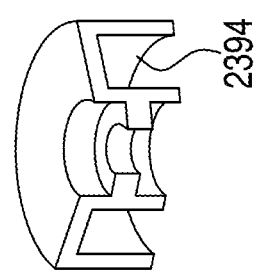
Figure 27A:
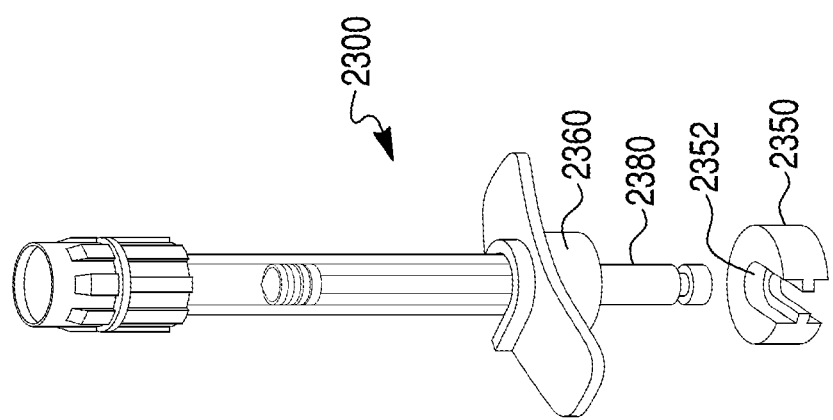

FIGS. 27A-27H depict an exemplary delivery device 2300 and method of using delivery device 2300. An actuation portion 2350 may also serve as a blocking component of device 2300. Actuation portion 2350 may be slidably coupled to plunger rod 2380 in two configurations, via a channel 2352. As depicted in FIG. 27B, one side of actuation portion 2350 may include a channel 2354. A depth of channel 2354 may correspond to a distance that a plunger rod may move to dispense a predetermined volume of a drug substance once device 2300 has been primed. As depicted in FIG. 27C and FIG. 27D, in a pre-use configuration, actuation portion 2350 may be assembled onto plunger rod 2380 such that a flat side of actuation portion 2350 faces a collar 2360 of device 2300. In a priming step, actuation portion 2350 may be used to move plunger rod 2380 distally until the flat side 2356 of actuation portion 2350 abuts a proximal side of collar 2360. To prepare for a dosage delivery step, actuation portion 2350 may be removed from plunger rod 2380, and may be rotated or flipped and reassembled with plunger rod 2380 such that channel 2354 faces collar 2360, as depicted in FIGS. 27F and 27G. In a dosage delivery step, actuation portion 2350 may be used to push plunger rod 2380 further distally, until a proximal end of collar 2360 abuts an inner end of channel 2354. This movement of plunger rod 2380 may be sufficient to dispense a predetermined dose of a drug substance from device 2300.

FIGS. 28A-28C depict an exemplary delivery device 2400 and method of using delivery device 2400. Delivery device 2400 may include substantially similar features as those shown and described above such that like reference numerals are used to identify like components. As shown in FIG. 28A, delivery device 2400 may include a removable clip 2402 coupled to body 1060 at a position distal to flange piece 1070. Removable clip 2402 may be an obstruction and/or blocking component configured to inhibit movement of flange piece 1070 relative to body 1060. Removable clip 2402 is selectively removable such that removable clip 2402 may be configured to disengage body 1060 in response to manual actuation of removable clip 2402.

By way of illustrative example, removable clip 2402 may have a body that wraps about an exterior of body 1060 and is configured to selectively deform (e.g., break, tear, etc.) upon application of a force thereto to decouple removable clip 2402 from body 1060. In other examples, removable clip 2402 may have a flexible body that is configured to bend in response to a radially-outward force being applied thereto, thereby disengaging removable clip 2402 from body 1060. By way of further example, removable clip 2402 may have a body that is configured to selectively transition between a closed configuration encapsulating a circumference of body 1060 therein and an open configuration permitting removal of body 1060 from the body of removable clip 2402. Removable clip 2402 may include various other suitable sizes, shapes, and/or configurations than those shown and described herein without departing from a scope of the present disclosure.

Delivery device 2400 may include a radial wall 1063 extending laterally outward from an exterior of body 1060, thereby forming an obstruction along body 1060. As seen in FIG. 28A, radial wall 1063 may be configured to inhibit distal translation of removable clip 2402 along body 1060. In some embodiments, radial wall 1063 may be an add-component attached to body 1060, while in other embodiments, radial wall 1063 may be integrally formed onto body 1060. Referring now to FIG. 28B, flange piece 1070 and plunger rod 1080 may be configured to translate distally along body 1060 to prime delivery device 2400 upon removal of removable clip 2402 from body 1060. In this instance, plunger rod 1080 may remain stationary relative to flange piece 1070, as the combined assembly of flange piece 1070 and plunger rod 1080 moves relative to body 1060. In other embodiments, plunger rod 1080 may remain stationary as flange piece 1070 translates distally along body 1060 to prime delivery device 2400. For example, at least a portion of flange piece 1070 may extend into body 1060 (e.g., and behind stopper 1062) when priming device 2400. In this instance, plunger rod 1080 may be translated separately to deliver a dosage from delivery device 2400.

With flange piece 1070 translated from a proximal position (FIG. 28A) to a distal position (FIG. 28B), delivery device 2400 may be in a primed position. It should be appreciated that body 1060 may be configured to limit movement by flange piece 1070 to a defined distance based on a location of radial wall 1063, which may correspond to a priming distance of delivery device 2400. Accordingly, a priming distance of delivery device 2400 may be controlled by adjusting a range of movement of flange piece 1070 along body 1060.

As seen in FIG. 28C, plunger rod 1080 may be translated distally relative to body 1060 in response to applying a distally-directed force onto actuation portion 1082. In this instance, stem 1081 may move relative to flange piece 1070, thereby causing stopper 1062 to move within body 1060 to deliver a dose. It should be appreciated that an extent that plunger rod 1080 translates relative to flange piece 1070 may define a dosage delivery distance of delivery device 2400. The dosage delivery distance may be controlled based on a gap formed between collar 1072 and actuation portion 1082.

In other embodiments, as seen in FIGS. 28D-28F, delivery device 2400 may further include a locking component, such as, for example, a removable rod 2404 coupled to flange piece 1070. Referring specifically to FIG. 28D, removable rod 2404 may be received through a proximal end of collar 1072, such as, for example, through one or more lateral apertures (not shown) formed through collar 1072. Removable rod 2404 may be configured to inhibit movement of plunger rod 1080 relative to flange piece 1070, such as, for example, preventing receipt of actuation portion 1082 into collar 1072. Removable rod 2404 may be selectively removable and configured to disengage collar 1072 upon manual actuation of removable rod 2404. It should be appreciated that delivery device 2400 may include various other locking components in addition to and/or in lieu of removable od 2404, such as, for example, a pin, a tab, a bar, and the like.

For example, referring now to FIG. 28E, flange piece 1070 and plunger rod 1080 (e.g., stem 1081 and actuation portion 1082) may be configured to translate distally along body 1060 to prime delivery device 2400 in response to removal of removable clip 2402 from body 1060. Plunger rod 1080 may remain stationary relative to flange piece 1070 as the assembly of flange piece 1070 and plunger rod 1080 moves relative to body 1060. With flange piece 1070 translated from a proximal position (FIG. 28D) to a distal position (FIG. 28E), delivery device 2400 may be in a primed position. It should be appreciated that body 1060 may be configured to limit movement by flange piece 1070 to a defined distance based on a location of radial wall 1063 along body 1060, which may correspond to a priming distance of delivery device 2400.

As seen in FIG. 28F, removable rod 2404 may be disengaged from collar 1072 such that plunger rod 1080 is no longer inhibited from moving distally relative to flange piece 1070. Actuation portion 1082 may be translated into collar 1072 to move stem 1081 and stopper 1062 within body 1060 to deliver a dose. An extent that plunger rod 1080 translates relative to flange piece 1070 may define a dosage delivery distance of delivery device 2400.

In other embodiments, as seen in FIGS. 28G-28I, removable clip 2402 may be omitted entirely such that delivery device 2400 may include a single obstruction and/or blocking component, i.e., rod 2404. In this instance, flange piece 1070 may be fixed relative to body 1060. With actuation portion 1082 positioned proximally of rod 2404, delivery device 2400 may be primed in response to plunger rod 1080 translating distally toward flange piece 1070 until encountering rod 2402. It should be appreciated that flange piece 1070 and/or rod 2404 may be configured to inhibit distal translation of plunger rod 1080 relative thereto absent an application of a distally-directed force thereto. In other examples, delivery device 2400 may include a blocking component positioned between actuation portion 1082 and rod 2404 (e.g., removable clip 2404) to inhibit distal movement of plunger rod 1080.

Accordingly, a priming distance of delivery device 2400 may be defined by a distance between the distal end of actuation portion 1082 and rod 2404 when delivery device 2400 is in an assembled, pre-primed state (FIG. 28G). With actuation portion 1082 engaged against rod 2402, as seen in FIG. 28H, delivery device 2400 may be in a primed state. Rod 2402 may be removed from collar 1072 to thereby allow further translation of plunger rod 1080 distally relative to flange piece 1070. As shown in FIG. 28I, a dose may be delivered from delivery device 2400 in response to collar 1072 receiving actuation portion 1082. It should be appreciated that a longitudinal offset of a distal end of actuation portion 1082 and an inner surface of collar 1072 may be determinative to a dosage delivery distance. Accordingly, an extent (e.g., the dosage delivery distance) that plunger rod 1080 translates relative to flange piece 1070 may define a volume of dosage delivered by delivery device 2400.

Figure 28L:
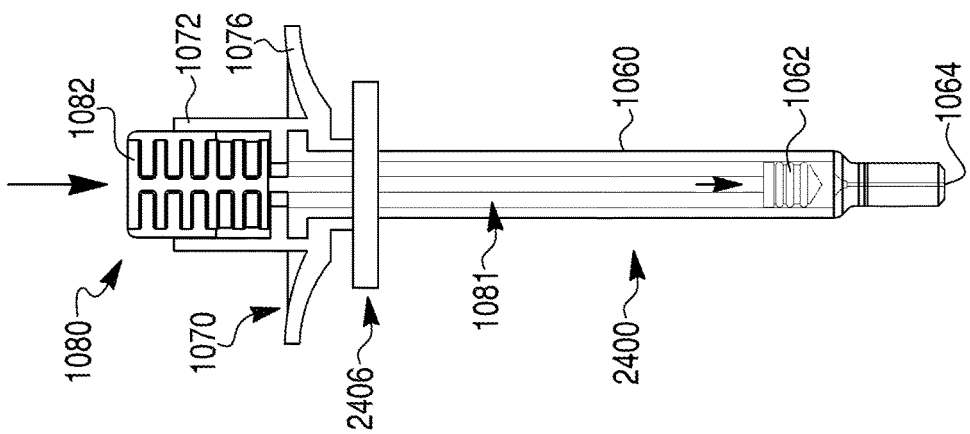
FIGS. 28A-28Z depict further exemplary delivery devices and methods of using said delivery devices, according to aspects of the present disclosure.
Figure 28K:
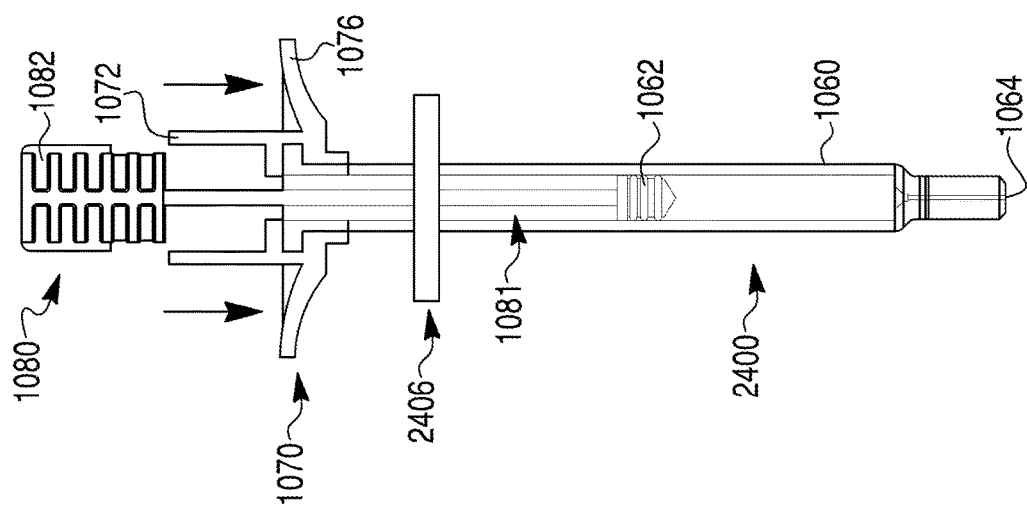
Figure 28J:
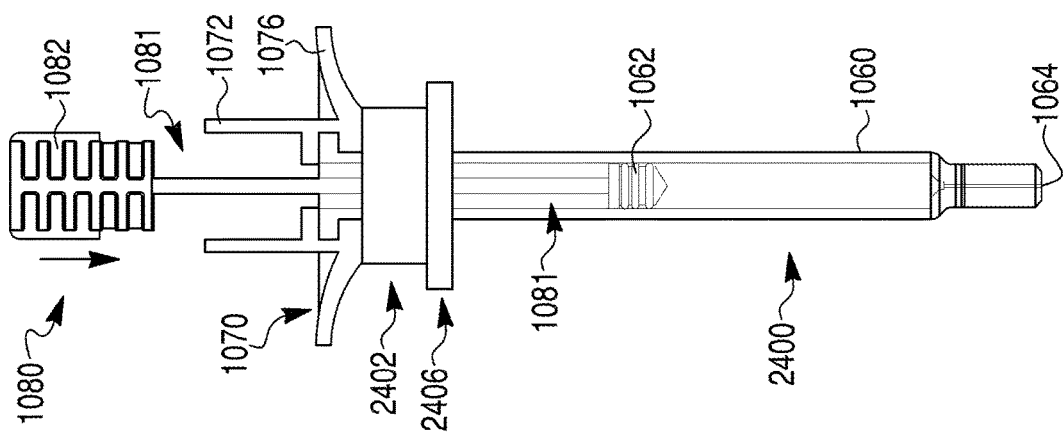

In further embodiments, as shown in FIGS. 28J-28L, delivery device 2400 may include a fixed clip 2406 attached to body 1060 at a location relatively distal of removable clip 2402. Fixed clip 2406 may be an obstruction and/or blocking component positioned in contact with removable clip 2402 such that fixed clip 2406 may be configured to inhibit movement of removable clip 2402 along body 1060. With flange piece 1070 positioned proximally of removable clip 2402, fixed clip 2406 may be further configured to inhibit movement of flange piece 1070 when removable clip 2402 is positioned therebetween.

Referring now to FIG. 28K, flange piece 1070 may be configured to translate distally along body 1060 to prime delivery device 2400 upon removing removable clip 2402 from body 1060. In this instance, plunger rod 1080 may remain stationary relative to flange piece 1070 as the assembly of plunger rod 1080 and flange piece 1070 moves toward fixed clip 2406. With flange piece 1070 translated from a proximal position (FIG. 28J) to a distal position (FIG. 28K) engaged against fixed clip 2406, delivery device 2400 may be in a primed position. It should be appreciated that body 1060 may be configured to limit movement by flange piece 1070 to a defined distance, which may correspond to a priming distance of delivery device 2400.

As seen in FIG. 28L, plunger rod 1080 may be translated distally relative to body 1060 in response to applying a distally-directed force onto actuation portion 1082. Stem 1081 may move relative to flange piece 1070, causing stopper 1062 to move within body 1060 to deliver a dose. It should be appreciated that an extent that plunger rod 1080 translates relative to flange piece 1070 may define a dosage delivery distance of delivery device 2400. The dosage delivery distance may be controlled based on a position of fixed clip 2406 along body 1060.

In further embodiments, delivery device 2400 may include a sleeve 2408 extending distally from flange piece 1070, as shown in FIG. 28M. Sleeve 2408 may be attached to a distal end of flange piece 1070 and/or be integral with flange piece 1070, thereby forming a unitary structure.

Sleeve 2408 may be disposed within body 1060 and include a distal end 2410. Sleeve 2408 may define a lumen that is sized and shaped to receive stem 1081 when plunger rod 1080 is coupled to flange piece 1070. As described in further detail herein, sleeve 2408 may be configured to move within a lumen of body 1060 in response to flange piece 1070 translating along an exterior of body 1060.

Sleeve 2408 may further include a locking component, such as, for example, a second protrusion 2412 formed along an interior surface of sleeve 2408 such that second protrusion 2412 extends at least partially into the lumen defined by sleeve 2408. In the embodiment, second protrusion 2412 is positioned relatively proximal of distal end 2410. In other embodiments, sleeve 2408 may include various other suitable locking components in lieu of second protrusion 2412, such as, for example, an opening sized, shaped, and configured to receive protrusion 1085.

Referring specifically to FIG. 28M, protrusion 1085 may extend radially outward from stem 1081 and positioned proximally relative to second protrusion 2412 when plunger rod 1080 is received through flange piece 1070 and sleeve 2408. To prime delivery device 2400, plunger rod 1080 may be translated distally relative to flange piece 1070 and sleeve 2408 until protrusion 1085 contacts second protrusion 2412. It should be appreciated that an extent that plunger rod 1080 translates relative to sleeve 2408 may define a priming distance of delivery device 2400. The priming distance may be controlled based on a position of protrusion 1085 and second protrusion 2412 relative to one another.

With protrusion 1085 engaged against second protrusion 2412 and a distal end of actuation portion 1082 received against an inner surface of collar 1072, plunger rod 1080 may be coupled to sleeve 2408 and delivery device 2400 may be in a primed state, as shown in FIG. 28N. Actuation portion 1082 may be fully received within collar 1072 and stem 1081 may be locked onto sleeve 2408. Accordingly, further translation of plunger rod 1080 may provide translation of flange piece 1070 and sleeve 2408 relative to body 1060. For example, as seen in FIG. 28O, plunger rod 1080 and flange piece 1070 may be translated distally relative to body 1060 in response to applying a distally-directed force onto actuation portion 1082. Stem 1081 may move relative to body 1060, causing stopper 1062 to move within body 1060 to deliver a dose.

Distal end 2410 may translate toward expulsion end 1064 as plunger rod 1080 and flange piece 1070 move distally until encountering fixed clip 2406. It should be appreciated that an extent that plunger rod 1080 and flange piece 1070 translate may define a dosage delivery distance of delivery device 2400. The dosage delivery distance may be controlled based on a position of fixed clip 2406 along body 1060.

In other embodiments, as seen in FIGS. 28P-28Q, delivery device 2400 may include an obstruction and/or blocking component in the form of a pull tab 2420. Pull tab 2420 may include a body 2422 having a circular-cross section defining a center opening 2424. Body 2422 may be formed of various flexible materials, including, for example, plastic, rubber, and the like. As described in further detail herein, pull tab 2420 may be frangible and/or deformable in response to an application of force onto body 2422. Pull tab 2420 may further include a graspable feature 2426 extending outwardly from body 2422 and configured to facilitate manual actuation of pull tab 2420. As seen in FIG. 28P, graspable feature 2426 may be integrally formed with body 2422 such that applying a radially-outward force (e.g., a pulling force) onto graspable feature 2426 may cause body 2422 to deform (e.g., tear, break, etc.), as shown in FIG. 28Q.

Referring now to FIG. 28R, pull tab 2420 may be secured to flange piece 1070 along a proximal end of collar 1072. Pull tab 2420 may be disposed over collar 1072 such that flange piece 1070 is separated from actuation portion 1082 by pull tab 2420 positioned therebetween. Stem 1081 may be received through center opening 2424 and into collar 1072 when body 2422 is attached to collar 1072. Pull tab 2420 may be configured to inhibit translation of actuation portion 1082 into collar 1072. A thickness and/or width of body 2422 may be sized such that a diameter of center opening 2424 is smaller than a diameter of actuation portion 1082 to block actuation portion 1082 from passing through pull tab 2420.

Figure 28T:
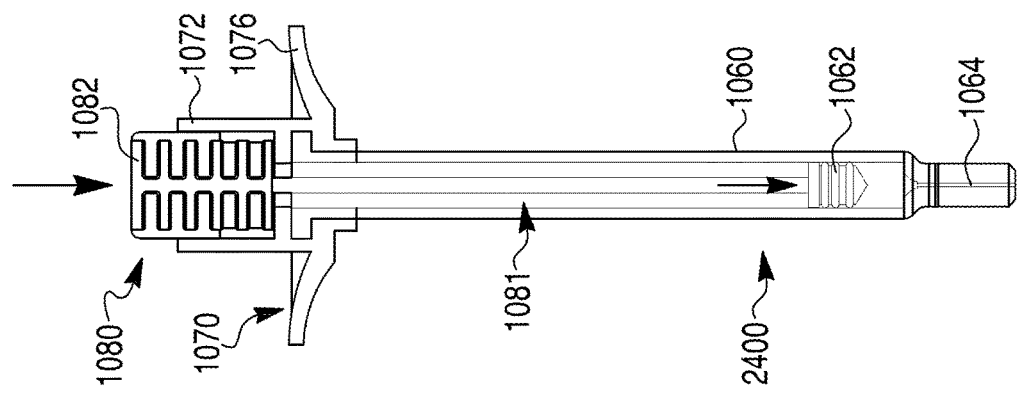
Figure 28S:
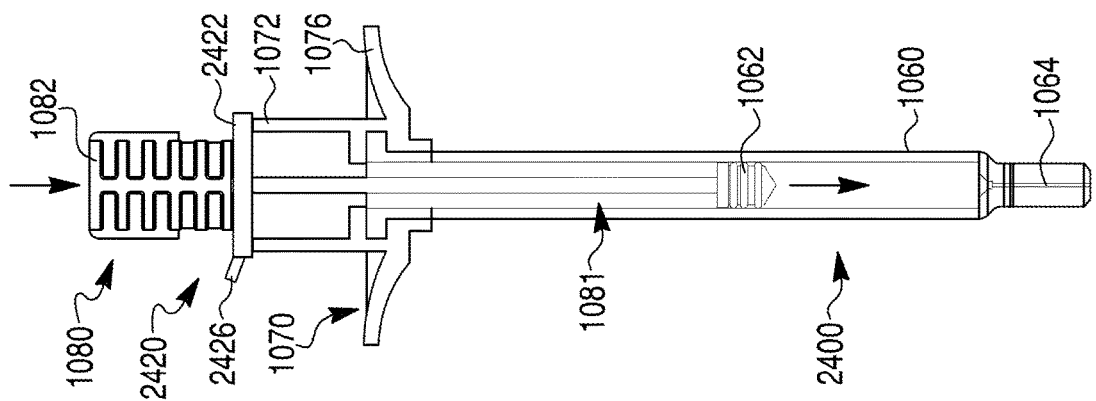

Delivery device 2400 may be primed in response to translating plunger rod 1080 distally relative to flange piece 1070 until encountering body 2422, as seen in FIG. 28S. It should be appreciated that an extent plunger rod 1080 translates relative to flange piece 1070 may correspond to a priming distance of delivery device 2400. The priming distance may be controlled based on a thickness of body 2422, thereby varying a relative distance between actuation portion 1082 and collar 1072. With actuation portion 1082 engaged against body 2422, graspable feature 2426 may be actuated to remove (e.g., break, tear, pull, etc.) pull tab 2420 from collar 1072. In this instance, body 2422 may be deformed (see FIG. 28Q) and disengaged from flange piece 1070, thereby permitting further translation of plunger rod 1080 distally relative to flange piece 1070.

As seen in FIG. 28T, actuation portion 1082 may be received within collar 1072 in response to applying a distally-directed force onto actuation portion 1082. Stem 1081 may move relative to body 1060, causing stopper 1062 to move within body 1060 to deliver a dose. It should be appreciated that an extent that plunger rod 1080 translates relative to collar 1072 may correspond to a dosage delivery distance of delivery device 2400. The dosage delivery distance may be controlled based on a thickness of pull tab 2420, thereby varying a relative distance between actuation portion 1082 and a distal (e.g., bottom) end of collar 1072.

In further embodiments, as shown in FIGS. 28U-28X, delivery device 2400 may include a removable cap 2430 coupled to plunger rod 1080. Removable cap 2430 may include a body 2432 defining a cavity 2434 that is sized and shaped to receive at least a portion of plunger rod 1080 therein (e.g., actuation portion 1082). Removable cap 2430 may include an opening along a bottom (e.g., distal) wall of body 2342 for receiving stem 1081. In some embodiments, removable cap 2430 may be attached to actuation portion 1082, while in other embodiments body 2342 may be directly coupled to stem 1081. Removable cap 2340 may be an obstruction and/or blocking component configured to increase a cross-sectional profile of actuation portion 1082 to inhibit movement of plunger rod 1080 relative to flange piece 1070, and more specifically to prevent translation of actuation portion 1082 into collar 1072.

Referring now to FIG. 28V, plunger rod 1080 may be configured to translate distally relative to flange piece 1070 to prime delivery device 2400 until a bottom wall of body 2432 encounters a proximal end of collar 1072. Removable cap 2430 may inhibit actuation portion 1082 from being received within collar 1072 due to at least a portion of body 2342 being disposed between actuation portion 1082 and collar 1072. With plunger rod 1080 translated from a proximal position (FIG. 28U) to a distal position (FIG. 28V) with body 2432 engaged against collar 1072, delivery device 2400 may be in a primed position. It should be appreciated that an extent that plunger rod 1080 translates relative to flange piece 1070 may correspond to a priming distance of delivery device 2400. The priming distance may be controlled based on a size of removable cap 2430 and/or a position of removable cap 2430 relative to plunger rod 1080. For example, in other embodiments, a bottom wall of body 2432 may be secured to a proximal portion of stem 1081 positioned relatively distal of actuation portion 1082. In this instance, a priming distance of delivery device 2400 may be reduced relative to that shown and described herein as body 2432 may be positioned in closer proximity to collar 1072. Accordingly, plunger rod 1080 may be required to move a smaller distance for removable cap 2430 to encounter collar 1072.

As seen in FIG. 28X, removable cap 2430 may be detached from plunger rod 1080 such that actuation portion 1082 may be exposed from body 2432. Plunger rod 1080 may be translated distally relative to body 1060 and received within collar 1072 in response to applying a distally-directed force onto actuation portion 1082. Stem 1081 may move relative to flange piece 1070, causing stopper 1062 to move within body 1060 to deliver a dose. It should be appreciated that an extent that plunger rod 1080 translates relative to flange piece 1070 may correspond to a dosage delivery distance of delivery device 2400. The dosage delivery distance may be controlled based on an attachment of removable cap 2430 relative to actuation portion 1082 and/or stem 1081 as described above. Further, a depth of collar 1072 may be determinative of the dosage delivery distance such that a size of collar 1072 may be adjusted accordingly to form various suitable dosage delivery distances.

For example, attaching removable cap 2430 such that a distal wall of removable cap 2430 is positioned flush against a distal end of actuation portion 1082 may increase a relative priming distance of delivery device 2400 by providing a longer separation between removable cap 2430 and collar 1072. Accordingly, the attachment position of removable cap 2430 may correspond to a smaller dosage delivery distance upon translating actuation portion 1082 into collar 1072 after removal of removable cap 2420. Alternatively, attaching removable cap 2430 such that the distal wall of removable cap 2430 is positioned distally from the distal end of actuation portion 1082 may decrease a relative priming distance, thereby providing a greater dosage delivery distance as actuation portion 1082 may require further longitudinal translation to be fully received within collar 1072. It should be appreciated that a size and/or shape of removable cap 2430 may vary to accommodate the various attachment positions described above.

In some embodiments, as shown in FIGS. 28W-28Z, delivery device 2400 may include one or more tabs 2440 secured to plunger rod 1080, such as, for example, along actuation portion 1082, stem 1081, and/or various other portions of plunger rod 1080. In the example, delivery device 2400 includes a pair of tabs 2440 extending radially outward from a distal end of actuation portion 1082. Tabs 2440 may be an obstruction and/or blocking component configured to increase a cross-sectional profile of actuation portion 1082 to inhibit movement of plunger rod 1080 relative to flange piece 1070, and more specifically to inhibit translation of actuation portion 1082 into collar 1072. In some embodiments, tabs 2440 may be selectively removable from actuation portion 1082 upon an application of force thereto. In other embodiments, tabs 2440 may be compressible and configured to be pushed into actuation portion 1082 in response to an application of force thereto. In either instance, tabs 2440 may be configured to transition actuation portion 1082 from an expanded profile (FIGS. 28W-28Y) to a compressed profile (FIG. 28Z).

Referring now to FIG. 28Y, plunger rod 1080 may be configured to translate distally relative to flange piece 1070 to prime delivery device 2400 until tabs 2440 encounter a proximal end of collar 1072. Tabs 2440 may inhibit collar 1072 receiving actuation portion 1082 therein. With plunger rod 1080 translated from a proximal position (FIG. 28W) to a distal position (FIG. 28Y) with tabs 2440 engaged against collar 1072, delivery device 2400 may be in a primed position. It should be appreciated that an extent that plunger rod 1080 translates relative to flange piece 1070 may correspond to a priming distance of delivery device 2400.

The priming distance may be controlled based on a size (e.g., thickness, width, height, etc.) of tabs 2440 and/or a position of tabs 2440 relative to plunger rod 1080. For example, in other embodiments, the pair of tabs 2440 may be secured to an intermediate and/or proximal portion of actuation portion 1082, or alternatively along stem 1081. In this instance, a priming distance of delivery device 2400 may be increased and/or decreased, respectively, relative to that shown and described herein.

As seen in FIG. 28Z, tabs 2440 may be compressed into actuation portion 1082 by collar 1072 applying an inward, pushing force thereto (or alternatively decoupled from actuation portion 1082 by applying an outward, pulling force, a rotating snapping force, or the like) such that actuation portion 1082 may form a smaller cross-sectional profile. Plunger rod 1080 may be translated distally relative to body 1060 and received within collar 1072 in response to applying a distally-directed force onto actuation portion 1082. Stem 1081 may move relative to flange piece 1070, causing stopper 1062 to move within body 1060 to deliver a dose. It should be appreciated that an extent that plunger rod 1080 translates relative to flange piece 1070 may correspond to a dosage delivery distance of delivery device 2400. As described above, the dosage delivery distance may be controlled based on a position of tabs 2440 relative to actuation portion 1082, a size (e.g., longitudinal depth) of collar 1072, and the like. For example, a relative position of tabs 2440 that increases a priming distance of delivery device 2400 may correspond to a smaller dosage delivery distance, and a position of tabs 2440 that corresponds to a reduced priming distance may provide a greater dosage delivery distance. In other examples, plunger rod 1080 may include a second set of tabs (not shown) along actuation portion 1082 which may define a dosage delivery distance based on a relative position of the tabs relative to tabs 2440.

FIGS. 29A-29C depict an exemplary delivery device 2500 and method of using delivery device 2500. Delivery device 2500 may include substantially similar features as those shown and described above such that like reference numerals are used to identify like components. As shown in FIG. 29A, delivery device 2500 may include a plunger rod 2580 comprising a first actuation portion 2502, a second actuation portion 2504, and a cam lever 2510. First actuation portion 2502 may be coupled to second actuation portion 2504 by one or more arms 2506. In the example, a pair of arms 2506 may be fixed to first actuation portion 2502 along a first end of arms 2506, and arms 2506 may be further coupled to second actuation portion 2504 at a second end of arms 2506 that is opposite of the first end. Second actuation portion 2504 may be a rotatable element including a proximal end 2505 and an opposing distal end having a joint

2508. The pair of arms 2506 may be coupled to the distal end of second actuation portion 2504 at joint 2508.

It should be understood that, when in a ready position as seen in FIG. 29A, second actuation portion 2504 may be oriented such that joint 2508 is positioned proximate to first actuation portion 2502 relative to proximal end 2505. A proximal end 1088 of stem 1081 may be positioned adjacent to joint 2508 at a distal end of second actuation portion 2504. For example, proximal end 1088 may be in contact with and/or abut against the distal end of second actuation portion 2504. In some embodiments, stem 1081 may extend through a center of first actuation portion 2502 and/or be positioned alongside first actuation portion 2502. Second actuation portion 2504 may be configured to move relative to first actuation portion 2502 and about joint 2508. Cam lever 2510 may be coupled to second actuation portion 2504 at joint 2508 and configured to move (e.g., rotate, pivot, translate, etc.) second actuation portion 2504 relative to first actuation portion 2502. Accordingly, it should be appreciated that second actuation portion 2504 may be configured to move stem 1081 relative to body 1060 in response to cam lever 2510 moving second actuation portion 2504 relative to first actuation portion 2502.

For example, referring to FIG. 29A, cam lever 2510 may be actuated by rotating cam lever 2510 about joint 2508, thereby causing second actuation portion 2504 to rotate about joint 2508. Proximal end 2505 may be moved toward first actuation portion 2502 in response to second actuation portion 2504 rotating about joint 2508. In this instance, proximal end 2505 may be moved toward first actuation portion 2502. With proximal end 2505 moved from a proximal position (FIG. 29A) to a distal position (FIG. 29B), proximal end 1088 may be pushed distally, thereby translating stem 1081 relative to body 1060 to prime delivery device 2500. Stated differently, rotation of cam lever 2510 and/or second actuation portion 2504 relative to first actuation portion 2502 may prime delivery device 2500 by forcing stem 1081 distally.

It should be appreciated that a travel length of proximal end 2505 toward first actuation portion 2502 may correspond to a priming distance of delivery device 2500. In other words, a priming distance of delivery device 2500 may be controlled by a longitudinal length of second actuation portion 2504 between proximal end 2505 and joint 2508. In some embodiments, first actuation portion 2502, arms 2506, and/or cam lever 2510 may be to inhibit further rotation of second actuation portion 2504 after plunger rod 2580 is moved from the ready position (FIG. 29A) to the primed position (FIG. 29B).

As seen in FIG. 29C, plunger rod 2580 may be translated distally relative to body 1060 in response to applying a distally-directed force onto first actuation portion 2502 and second actuation portion 2504. In this instance, cam lever 2510 may be depressed (e.g., pushed and/or pulled) distally to move first actuation portion 2502 and second actuation portion 2504 toward flange piece 1070 until encountering a proximal end of collar 1072. Stem 1081 may move relative to collar 1072 thereby causing stopper 1062 to move within body 1060 to deliver a dose. It should be appreciated that an extent of translation of plunger rod 2580 relative to flange piece 1070 may correspond to a dosage delivery distance of delivery device 2500. The dosage delivery distance may be controlled based on a gap formed between collar 1072 and cam lever 2510.

Figure 31:
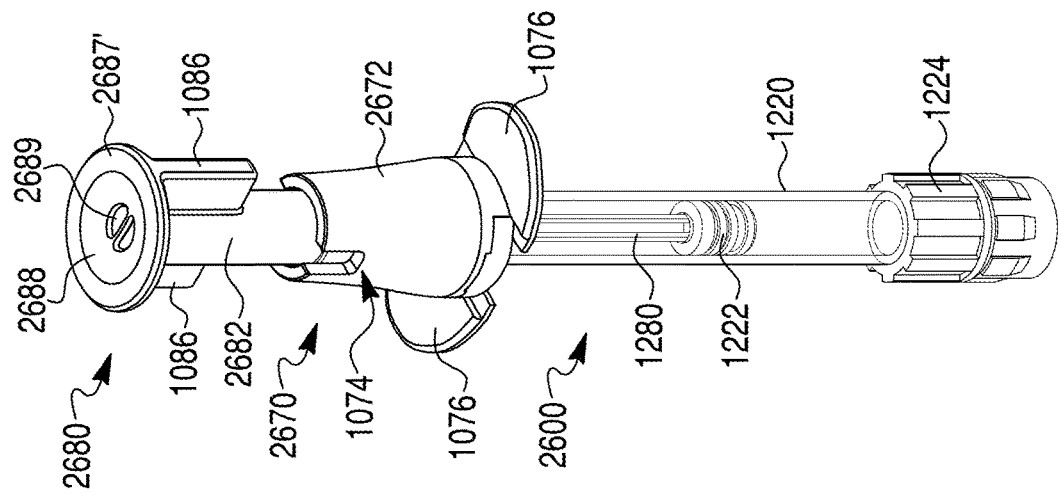
FIGS. 30-31 depict a further exemplary delivery device and method of using said delivery device, according to aspects of the present disclosure.
Figure 30:
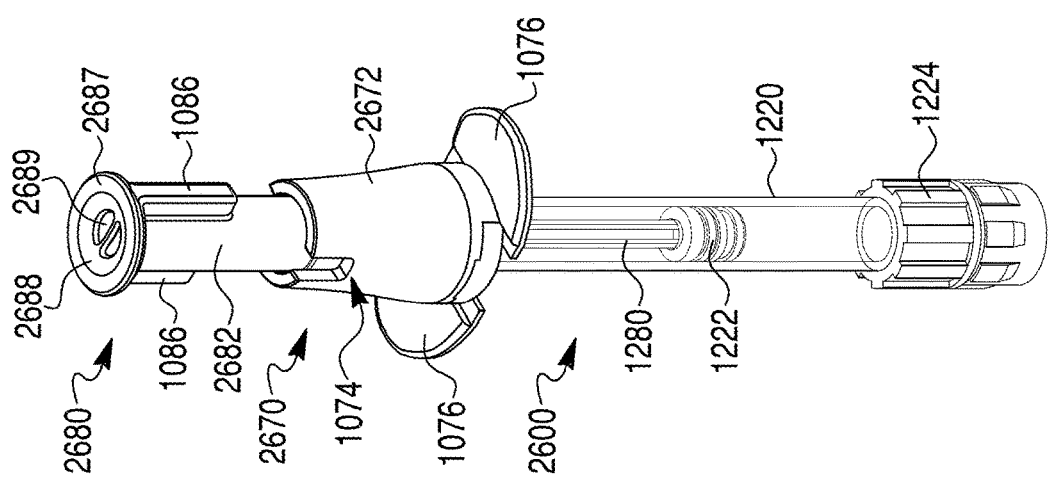

FIGS. 30-31 depict an exemplary delivery device 2600 that may include substantially similar features as those shown and described above such that like reference numerals are used to identify like components. Delivery device 2600 may include a flange piece 2670, a plunger rod 2680, and body 1220. Flange piece 2670 may include a tapered collar 2672 having a varying size and/or shape between a distal end and a proximal end. In the example, tapered collar 2672 may have a greater cross-sectional profile (e.g., diameter) along a distal end adjacent to flanges 1076 than at a proximal end adjacent to slots 1074. Tapered collar 2672 may be configured to minimize an overall profile and/or weight of delivery device 2600 by minimizing a configuration of flange piece 2670. In some embodiments, flanges 1076 may have a reduced length to facilitate enhanced control and maneuverability of flange piece 2670.

Plunger rod 2680 may include an actuation portion 2682 having a cross-sectional profile (e.g., diameter) that is relatively smaller than tapered collar 2672 to facilitate receipt of actuation portion 2682 therethrough. Accordingly, actuation portion 2682 may be similarly configured to minimize an overall profile and/or weight of delivery device 2600 by minimizing a configuration of actuation portion 2682. Further, plunger rod 2680 may omit inclusion of a textured and/or ribbed surface along actuation portion 2682 to simplify an exterior appearance of plunger rod 2680.

Referring specifically to FIG. 30, actuation portion 2682 may further include a proximal end having an outer ring 2687, an inner surface 2688, and one or more openings 2689 formed through inner surface 2688. In the example, inner surface 2688 may be disposed within outer ring 2687 and may have an angled profile that is sloped radially-inward toward the one or more openings 2689. Inner surface 2688 may be configured to define an interface for actuating plunger rod 2680 (e.g., applying a distally-directed force onto actuation portion 2682 by a finger of a user). Although plunger rod 2680 is shown as including a pair of openings 2689, it should be appreciated that in other embodiments additional and/or fewer openings 2689 may be included on inner surface 2688.

In some embodiments, as seen in FIG. 31, plunger rod 2680 may include an outer ring 2687' having a width that defines an outer surface disposed about inner surface 2688. For example, an outer surface of outer ring 2687' may be angled inwardly toward inner surface 2688 and openings 2689 and/or be transverse relative to inner surface 2688. In the present example, outer ring 2687' defines a planar outer surface that is substantially perpendicular to a longitudinal length of actuation portion 2682. The enhanced width of outer ring 2687' may provide additional surface area for a user of device 1050 to contact when actuating plunger rod 2680. It should be appreciated that a width of outer ring 2687' may be greater and/or less than that shown and described herein without departing from a scope of this disclosure.

Figure 33:
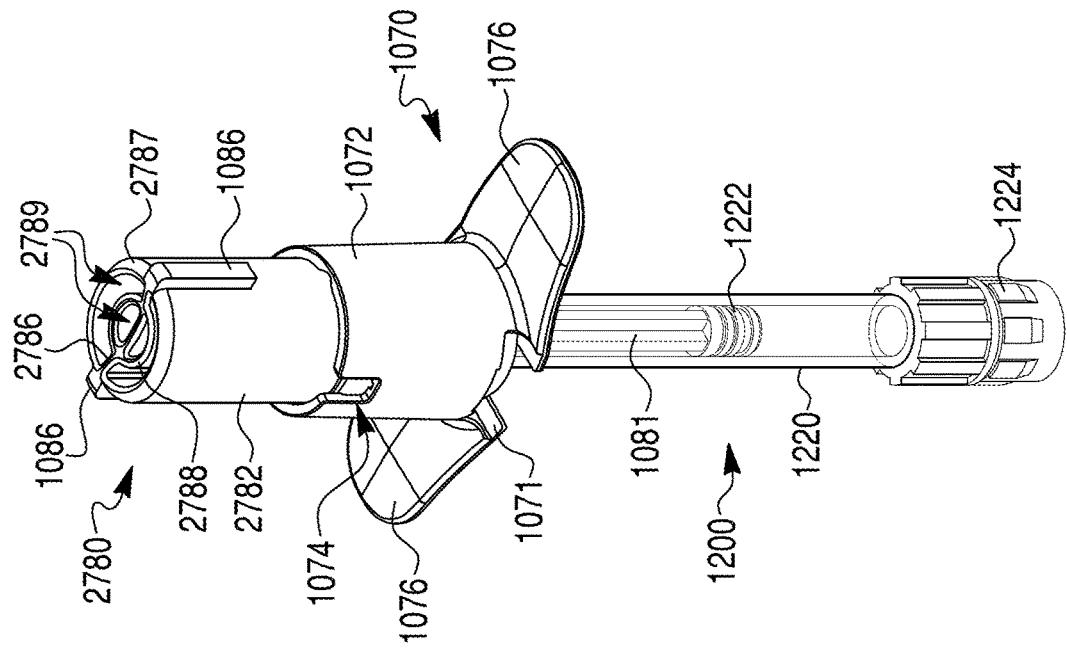
FIGS. 32-33 depict a further exemplary delivery device and method of using said delivery device, according to aspects of the present disclosure.
Figure 32:
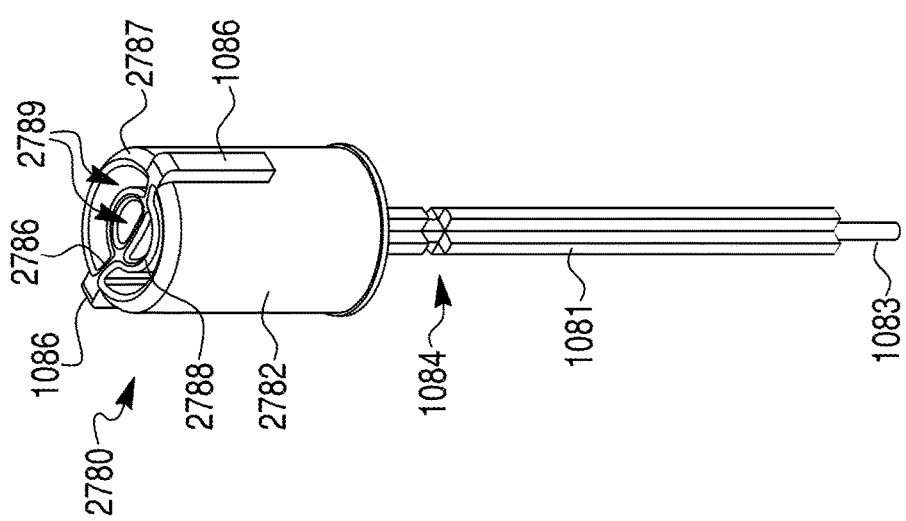

FIGS. 32-33 depict an exemplary plunger rod 2780 that may include substantially similar features as plunger rod 1080 shown and described above such that like reference numerals are used to identify like components. Plunger rod 2780 may include an actuation portion 2782 having a proximal end defined by an outer ring 2787, an inner ring 2788, and one or more openings 2789. In the example, inner ring 2788 may be disposed within outer ring 2787 and may define at least one opening 2789. Outer ring 2787 may further define at least one opening 2789 positioned radially outward of inner ring 2788. One or more of openings 2789 may minimize an overall weight of plunger rod 2780, enhance a molding manufacturing ability of plunger rod 2780 by providing nominal wall thicknesses for actuation portion 2782, and more. Additionally, actuation portion 2782 may include a lateral ledge 2786 extending across a width of the distal end and aligned with protrusions 1086. Lateral edge 2786 may bifurcate the one or more openings 2789 defined by outer ring 2787 and inner ring 2788. Lateral edge 2786 may be collinear with protrusions 1086 to provide visual alignment and/or identification of protrusions 1086 to a user of plunger rod 2780.

As seen in FIG. 33, with plunger rod 2780 received within flange piece 1070 and body 1220, lateral edge 2786 may be configured to enhance an identification of movement by plunger rod 2780 relative to flange piece 1070 from a perspective proximal of device 1200. For example, lateral ledge 2786 may facilitate identifying a relative position of protrusions 1086 to slots 1074 from a perspective proximal to actuation portion 2782 during use of device 1200. In some embodiments, plunger rod 2780 may omit a textured and/or ribbed surface along actuation portion 2782 to simplify an exterior appearance of plunger rod 2780.

Figure 34:
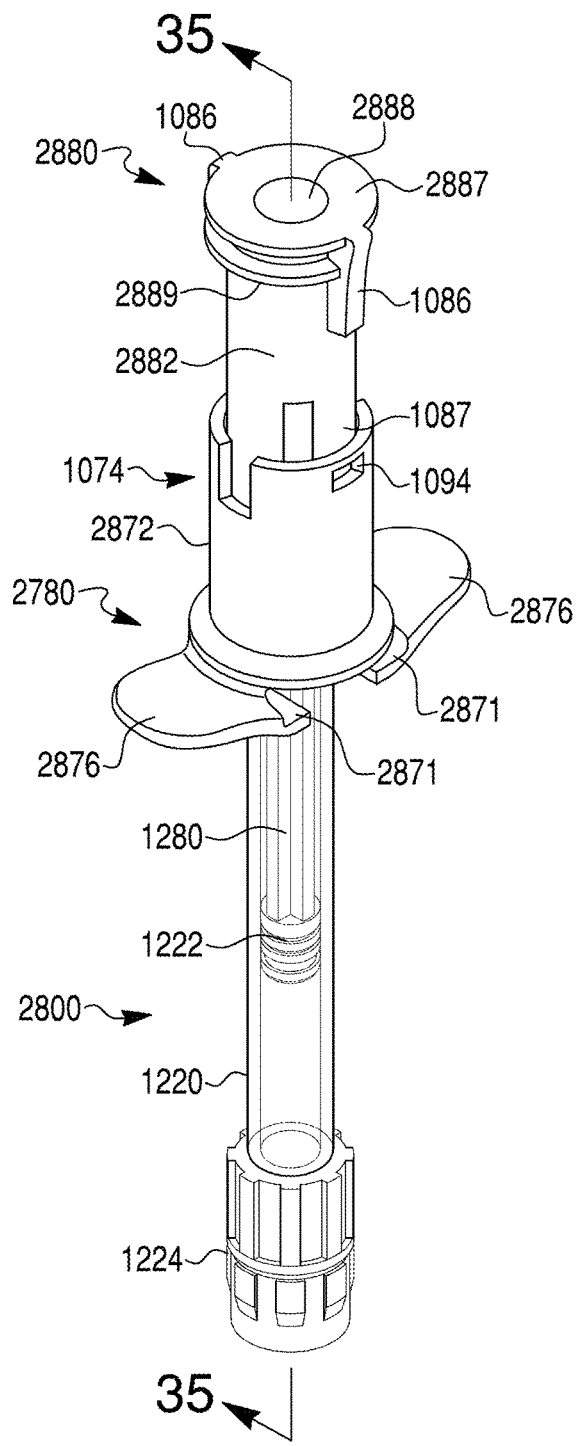
FIGS. 34-40C depict a further exemplary delivery device and method of using said delivery device, according to aspects of the present disclosure.
Figure 35:
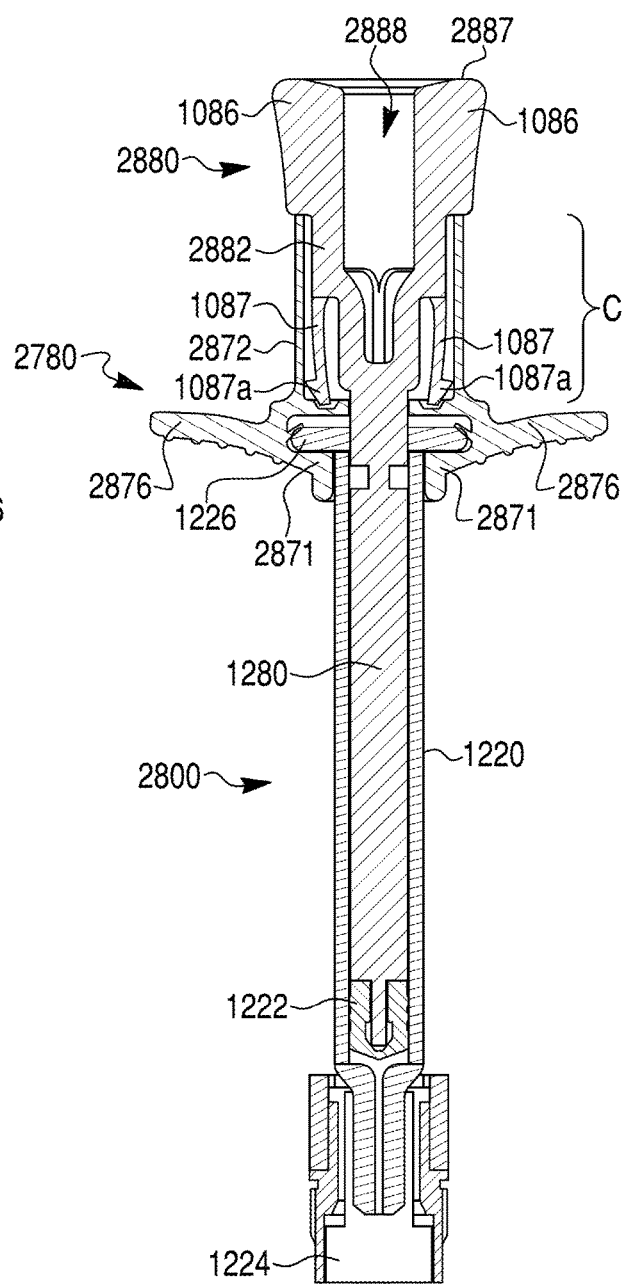

FIG. 34 depicts another exemplary delivery device 2800 in accordance with an example of this disclosure. Delivery device 2800 may include substantially similar features as delivery device 1050 and delivery device 1200 shown and described above such that like reference numerals are used to identify like components. Delivery device 2800 may include a flange piece 2870, a plunger rod 2880, and body 1220. Flange piece 2870 may have a collar 2872 and a pair of flanges 2876 extending laterally outward from collar 2872. Collar 2872 may have a narrowed profile, such as, for example, relative to collar 1072. Additionally, flanges 2876 may have a shortened length relative to flanges 1076. Accordingly, flange piece 2870 of the present example may generally have a narrowed profile. Flange piece 2870 may further include a lip 2871 that may slide under or otherwise receive body flange 1226 (FIG. 35). Lip 2871 may be configured to hold flange piece 2870 in place by slidably coupling flange piece 2870 to body 1220. As described in further detail below, lip 2871 may be made of a flexible or semi-flexible material capable of forming a snap-fit connection with body flange 1226.

Plunger rod 2880 may include an actuation portion 2882 having one or more protrusions 1086 along a proximal end and one or more extensions 1087 along a distal end. Actuation portion 2882 may have a diameter that is generally smaller than actuation portion 1082 shown and described above. Accordingly, it should be appreciated that plunger rod 2880 and flange piece 2870 may collectively form a narrowed profile relative to an assembly of plunger rod 1080 and flange piece 1070. By providing a reduced profile, delivery device 2800 may be configured to provide a user enhanced control and maneuverability of plunger rod 2880 and flange piece 2870 during use of delivery device 2800.

In the embodiment, protrusions 1086 may have a curvature configured to enhance a grip, comfort, and/or ergonomics of plunger rod 2880 for a user of delivery device 2800. A curvature of protrusions 1086 may have a concave exterior configuration that taper inwardly along a distal portion of protrusions. A proximal end of actuation portion 2882 may further include a first ring 2887, an opening 2888, and a second ring 2889 positioned distally relative to first ring 2887. First ring 2887 may define a proximal interface of actuation portion 2882 and opening 2888 may be positioned at a center of first ring 2887. The proximal interface defined by first ring 2887 may be angled toward opening 2888 such that a proximal end of actuation portion 2882 may be sloped radially inward. In some embodiments, first ring 2887 may be sized, shaped, and configured to facilitate actuation of plunger rod 2880 by defining a finger pad for receiving a finger of a user. Opening 2888 may be configured to maintain a nominal wall thickness of actuation portion 2882 to facilitate molding of plunger rod 2880 during a manufacturing process of delivery device 2800. Openings 2888 may further minimize an overall weight of plunger rod 2880.

Still referring to FIG. 34, second ring 2889 may extend radially outward from an exterior surface of actuation portion 2882 and is positioned adjacent to first ring 2887. Second ring 2889 may be configured to form a graspable feature along actuation portion 2882 to enhance control of plunger rod 2880, such as, for example, when rotating plunger rod 2880. First ring 2887 may have a greater diameter than actuation portion 2882 such that the finger pad formed by first ring 2887 may have a greater cross-sectional profile than actuation portion 2882. In some embodiments, second ring 2889 may include a diameter greater than actuation portion 2882 and substantially similar to first ring 2887. Plunger rod 2880 may omit inclusion of a textured and/or ribbed surface along actuation portion 2882 to simplify an appearance of plunger rod 2880.

As seen in FIG. 35, actuation portion 2882 may be sized to have a predetermined length C between a distal end of protrusion 1086 and hook or clip shaped part 1087a of extensions 1087. In some embodiments, predetermined length C may be sized in accordance with a type and/or size of a syringe cap used with delivery device 2800 (e.g., Ompi Alba ITC, Ompi Alba OVS, Gerresheimer TELC, silicone-free syringes, etc.). For example, predetermined length C may be decreased and/or increased according to a lower and/or higher fill volume requirement, respectively, determined based on the syringe cap. Further, predetermined length C may be sized to provide a complete stroke of plunger rod 2880 into flange piece 2870 to ensure a complete dosage is delivered by delivery device 2800. The predetermined length C may be further adjusted to provide one of a plurality of suitable dosage delivery distances for delivery device 2800. Flange piece 2870 may include additional features and/or components configured to allow for a complete stroke of plunger rod 2880.

Figure 36:
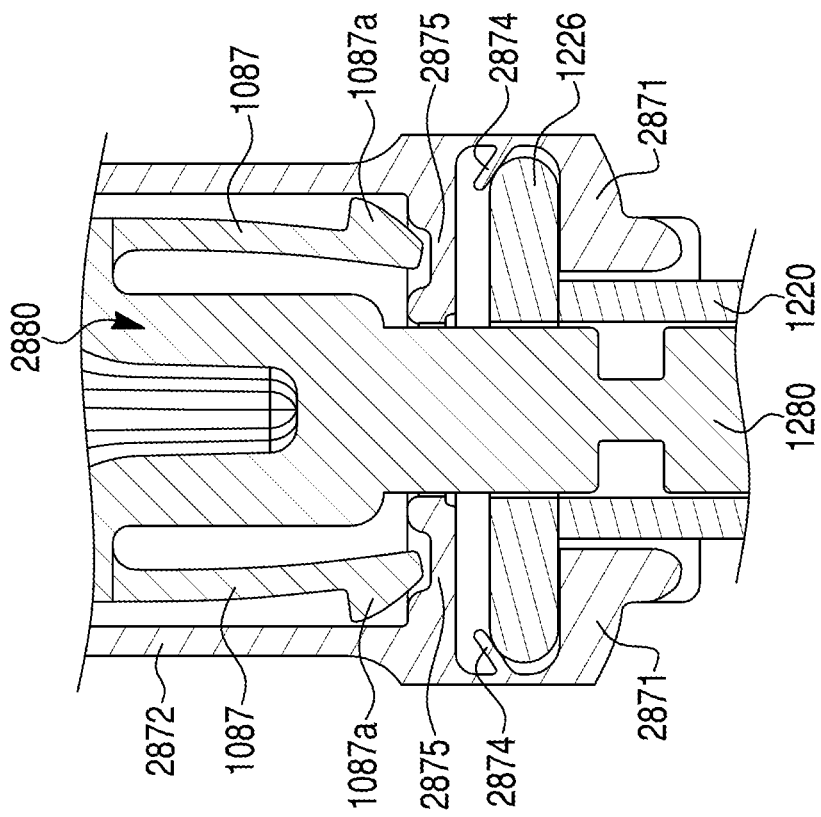

For example, referring now to FIG. 36, flange piece 2870 may include one or more indents 2875 formed along a proximally-facing and distally-located (bottom) surface of collar 2872. Indent 2875 may be sized and/or shaped to form a recessed surface into the bottom surface of collar 2872. Indent 2875 may be configured to facilitate receipt of plunger rod 2880 into flange piece 2870 to allow for a complete stroke. Stated differently, indent 2875 may provide an increased space and/or clearance within collar 2872 to receive one or more components of plunger rod 2880, such as, for example, hook or clip shaped part 1087a of extensions 1087.

In the present example, delivery device 2800 may be configured to deliver a complete dose upon the pair of protrusions 1086 contacting a distal end (the bottom) of slots 1074. The pair of extensions 1087 may be positioned adjacent to (but not in contact with) a bottom surface of collar 2872 when protrusions 1086 contact the distal end of slots 1074. That is, in some embodiments, extensions 1087 may positioned proximal to the bottom surface of collar 2872 such that extensions 1087 do not contact the bottom surface when plunger rod 2880 has bottomed out and/or when a complete dose has been delivered from delivery device 2800. By forming a depression along the bottom surface of collar 2872, indent 2875 may allow actuation portion 2882 to translate distally relative to collar 2872 to complete a full stroke of plunger rod 2880 without extensions 1087 engaging or contacting the bottom surface of collar 2872. In some embodiments, extensions 1087 may bend inwardly toward indent 2875 upon hook or clip shaped parts 1087a encountering the bottom surface of collar 2872, thereby guiding hook or clip shaped parts 1087a into indent 2875. It should be appreciated that an increased space formed by indent 2875 may ensure extensions 1087 are not prevented from contacting the bottom surface of collar 2872 to complete the full stroke of plunger rod 2880 and/or to deliver a complete dose.

Still referring to FIG. 36, flange piece 2870 may further include one or more ribs 2874 configured to engage body flange 1226 when body 1220 is coupled to flange piece 2870. The one or more ribs 2874 may be positioned adjacent to lip 2871, such as, for example, distally of the bottom surface of collar 2872 and proximally of lip 2871. In some embodiments, ribs 2874 may extend radially inward from an inner sidewall of flange piece 2870, while in other embodiments ribs 2874 may extend outwardly from an inner top wall of flange piece 2870. In the present example, ribs 2874 may extend radially inward at an angle relative to the inner sidewall of flange piece 2870. It should be appreciated that ribs 2874 may be positioned and/or extend from various other suitable locations, and at various other suitable angles, within flange piece 2870 for engaging body flange 1226.

In the embodiment, ribs 2876 may be formed of a flexible and/or semi-flexible material (e.g., plastic, rubber, etc.) and configured to interact with body flange 1226 upon receipt of body 1220 within flange piece 2870. By way of illustrative example, ribs 2874 may be configured to flex and/or bend proximally toward a bottom surface of collar 2872 in response to lip 2871 receiving body flange 1226. Ribs 2874 may be operable to secure body flange 1226 to flange piece 2870 by applying a distally-directed force thereto. Accordingly, ribs 2874 may secure a position (e.g., longitudinal, rotational, etc.) of body 1220 relative to flange piece 2870 by engaging a top/proximal surface of body flange 1226 as lip 2871 engages a bottom surface of body flange 1226. In other embodiments, additional and/or fewer ribs 2874 may be included for inhibiting movement of body flange 1226 and/or body 1220 relative to flange piece 2870.

Figure 37:
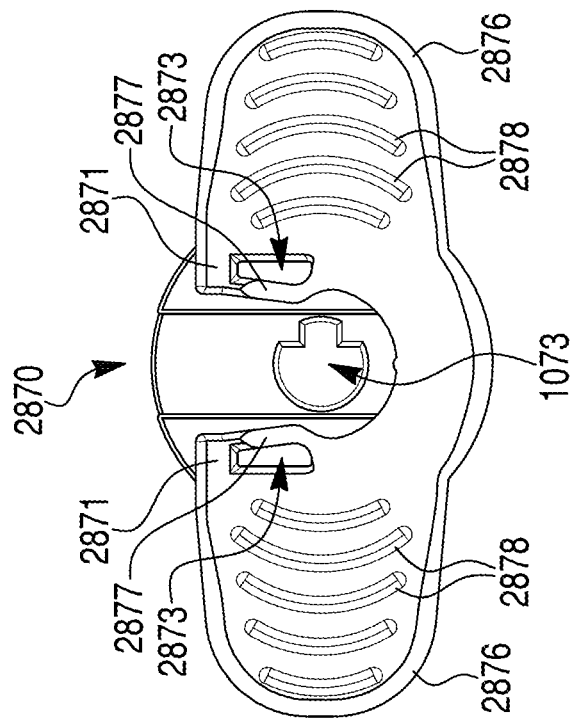

Referring now to FIG. 37, flange piece 2870 may include a textured and/or patterned interface 2878 along a bottom, distally-facing surface of flanges 2876. Textured interface 2878 may include one or more protrusions, depressions, and/or various other features forming at least one of a plurality of patterns to enhance a grip, control, and/or ergonomics of flange piece 2870. In the example, textured interface 2878 includes a plurality of semi-circular protrusions of varying sizes. As shown in FIG. 37, each interface 2878 may be concave when viewed from a radial center of flange 2876. However, in alternate embodiments, one or more interface 2878 may be convex when viewed from the radial center of flange 2876. As described in further detail below, textured interface 2878 may include various other designs, features, and/or patterns along the bottom surface (see FIGS. 41A-41D) of flanges 2876. Flange piece 2870 may further include a pair of movable tabs 2877 positioned adjacent to lip 2871 and along opposing sides of opening 1073. Movable tabs 2877 may be formed of a flexible and/or semi-flexible material and may be configured to move relative to collar 2872 and/or flanges 2876 in response to a force being applied thereto (e.g., by body 1220).

Each movable tab 2877 may define an opening 2873 disposed between movable tab 2877 and flange 2876. Accordingly, movable tabs 2877 may be separated from flanges 2876 by opening 2873 formed therebetween. Openings 2873 may provide a gap and/or clearance space to accommodate lateral movement of movable tabs 2877 upon receiving a radially-outward directed force. For example, movable tabs 2877 may be deflected radially outward toward flanges 2876 in response to flange piece 2870 receiving body 1220 through opening 1073, thereby changing a size and/or shape of openings 2873. In this instance, movable tabs 2877 may bend outwardly away from opening 1073 until body flange 1226 is received by lip 2871. Movable tabs 2877 may be configured to bend inwardly toward body 1220 to return to an original configuration upon lip 2871 fully receiving body flange 1226 therein. In some embodiments, movable tabs 2877 may bend toward body 1220 to a substantially originally configuration such that movable tabs 2877 may remain at least partially compressed against body 1220 to inhibit movement of body 1220 relative to flange piece 2870 to allow pressure to be continually applied onto body 1220 to prevent slippage.

Still referring to FIG. 37, movable tabs 2877 may be configured to apply a radially-inward directed force onto body 1220 (e.g., with a radially-inward directed material bias), thereby forming a snap-fit connection between flange piece 2870 and body 1220. Additionally, movable tabs 2877 may maintain body 1220 in a stabilized and fixed position relative to flange piece 2870, thereby coupling flange piece 2870 to body 1220. It should be appreciated that openings 2873 may be included between movable tabs 2877 and flanges 2876 to decrease a required force to couple body 1200 to flange piece 2870. For example, openings 2873 may be operable to reduce a force necessary to snap body 1200 into flange piece 2870 by a minimum force ranging from about 15 Newton to about 25 Newton, compared to a design omitting openings 2873.

FIGS. 38A-40C show an illustrative method of using delivery device 2800. As seen in FIG. 38A, delivery device 2800 may be preassembled with a distal portion of actuation portion 2882 received within collar 2872 and extensions 1087 received within and coupled to openings 1094. With extensions 1087 coupled to collar 2872 via openings 1094, it should be appreciated that flange piece 2870 may inhibit proximal retraction of actuation portion 2882. Accordingly, disassembly of plunger rod 2880 from flange piece 2870 may be prevented. In this instance, delivery device 2800 may be primed by distally translating plunger rod 2880 into flange piece 2870.

As seen in FIG. 38B, actuation portion 2882 may be translated distally relative to flange piece 2870 until protrusions 1086 encounter a proximal end of collar 2872. Plunger rod 2880 may complete a priming process of delivery device 2800 upon protrusions engaging and/or abutting collar 2872. It should be appreciated that an extent that plunger rod 2880 translates distally relative to flange piece 2870 may correspond to a priming distance of delivery device 2800. The priming distance may be controlled based on a longitudinal length of protrusions 1086 and/or extensions 1087, thereby varying a relative distance between the proximal end of collar 2872 and a distal end of protrusions 1086.

Figure 38D:
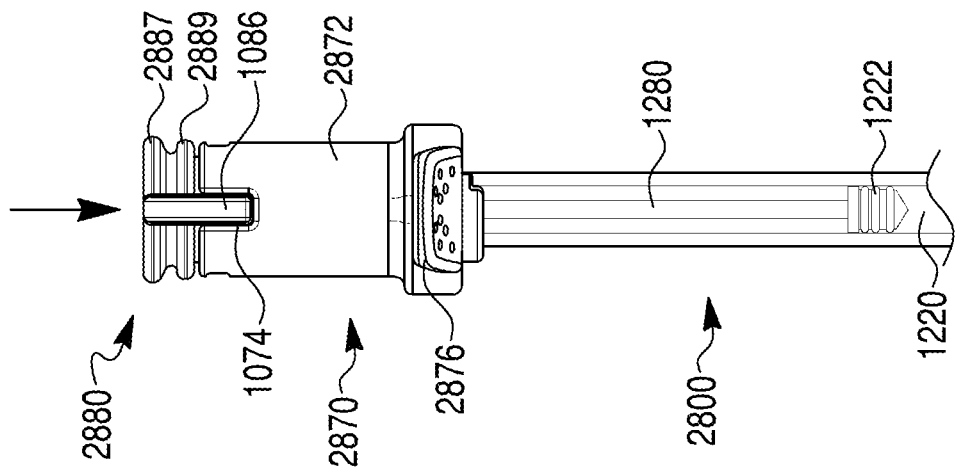
Figure 38C:
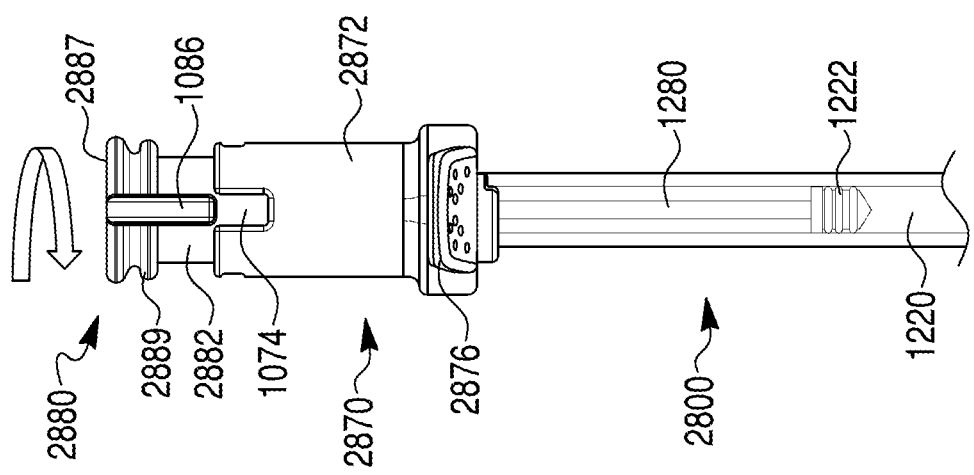
Figure 39A:
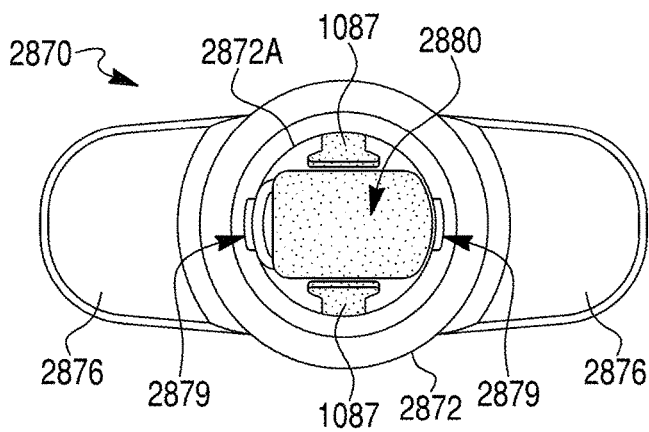
Figure 39D:
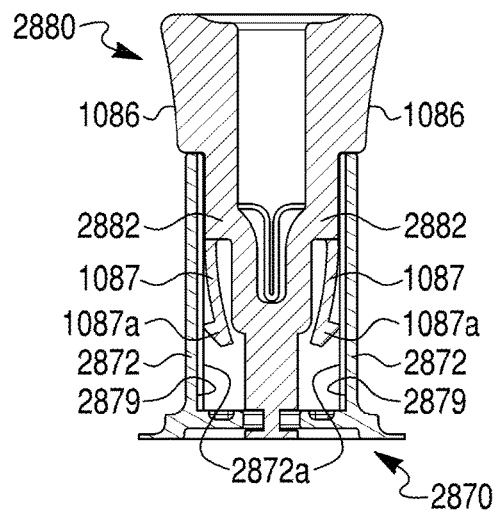
Figure 39B:
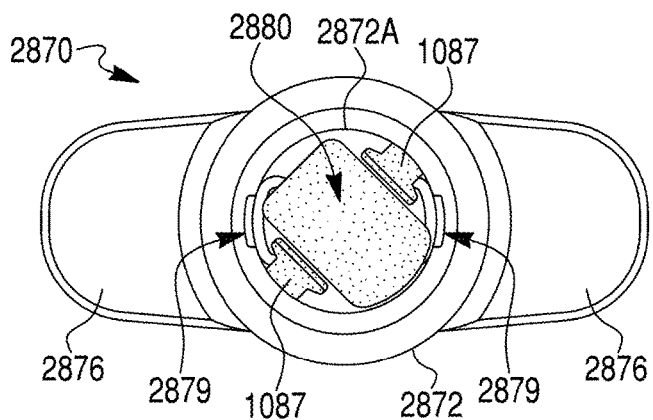

As shown in FIG. 38C, flange piece 2870 may be rotated relative to plunger rod 2880, or vice versa, to move protrusions 1086 relative to collar 2872 until arriving into radial and longitudinal alignment with slots 1074. Referring to FIGS. 39A-39B, extensions 1087 may contact an interior surface 2872A of collar 2872 as plunger rod 2880 rotates relative to flange piece 2870. As seen in FIG. 39D, with hook or clip shaped part 1087a engaged against interior surface 2872A, extensions 1087 may be deflected radially-inward by collar 2872 until plunger rod 2880 is rotated to align extensions 1087 with internal grooves 2879 of flange piece

Figure 39C:
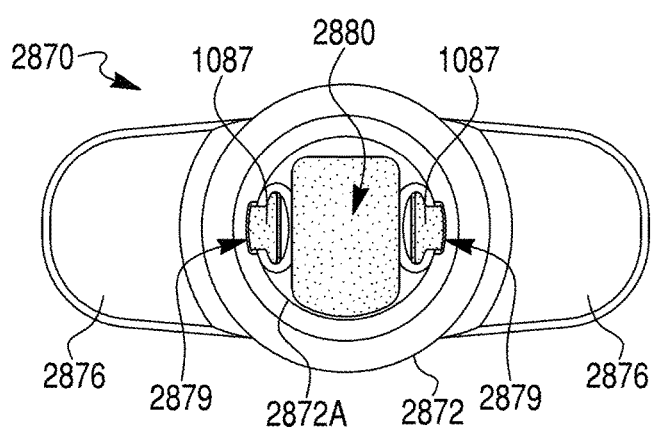
Figure 39E:
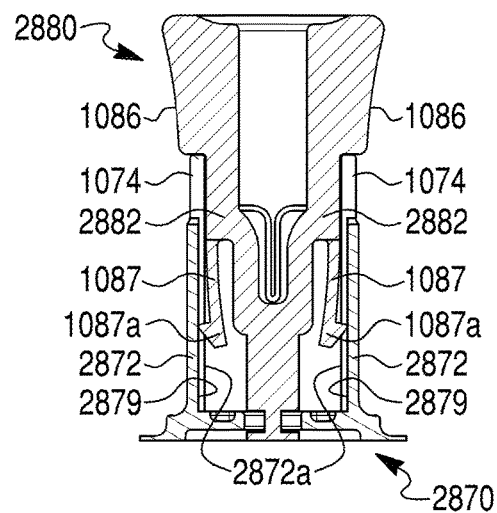

2870. Internal grooves 2879 may define recesses formed along interior surface 2872A. As seen in FIG. 39C and FIG. 39E, internal grooves 2879 may be sized and shaped to receive extensions 1087 therein. It should be appreciated that collar 2872 may have a greater diameter at internal grooves 2879 than along interior surface 2872A such that extensions 1087 are configured to expand radially-outward from a compressed configuration (FIGS. 39A-39B and FIG. 39D) to an expanded configuration (FIG. 39C and FIG. 39E) when extensions 1087 are moved into radial alignment with internal grooves 2879.

Stated differently, extensions 1087 may be transitioned to a relaxed state when received within internal grooves 2879 due to the additional space provided by internal grooves 2879, as seen in FIG. 39E. In some instances, a feedback (e.g., tactile, auditory, etc.) may be generated in response to extensions 1087 being received within internal grooves 2879. Delivery device 2800 may be positioned in a dosage delivery state such that further actuation of plunger rod 2880 may provide a dose delivery. In some embodiments, flange piece 2870 may be operable to generate a user feedback (e.g., tactile, audible, etc.) upon rotating plunger rod 2880 relative to flange piece 2870 to prime delivery device 2800.

Figure 40A:
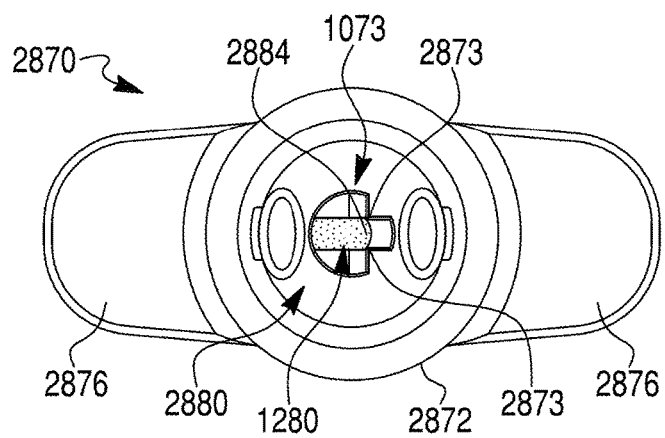
Figure 40B:
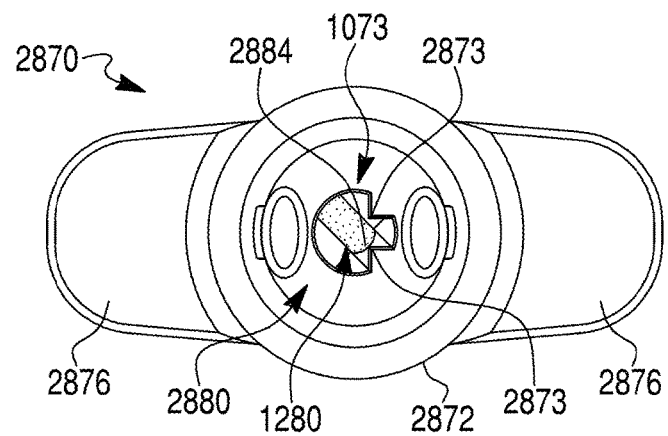
Figure 40C:
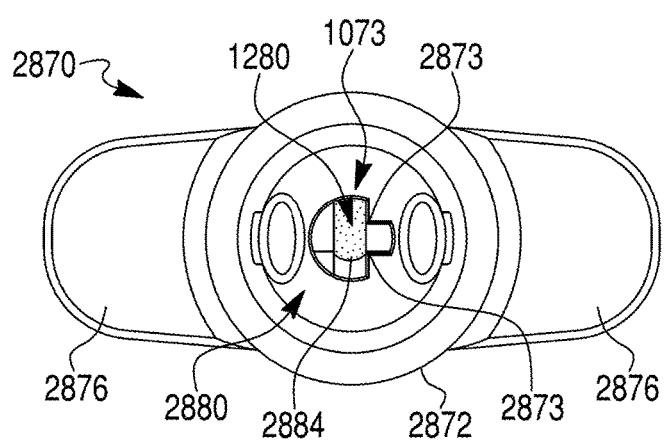

As described in detail above and as seen in FIGS. 40A-40C, opening 1073 may have a semi-circular shape with one or more edges 2873 extending into opening 1073. With plunger rod 2880 coupled to flange piece 2870, stem 1280 may be received through opening 1073. Stem 1280 may include a rounded sidewall 2884 that is configured to interact with the one or more edges 2873 as plunger rod 2880 rotates relative to collar 2872. For example, rounded sidewall 2884 may define a semi-circular end along stem 1280 that may contact edges 2873 when plunger rod 2880 is moved from the primed position (FIG. 38B) to the dosage delivery position (FIG. 38C). As described in detail above (FIGS. 4K-4X), it should be appreciated that stem 1280 may have various suitable shapes and/or configurations for facilitating movement (e.g., rotation) of plunger rod 2880 relative to flange piece 2870.

Referring now to FIG. 38D, with protrusions 1086 aligned with slots 1074, actuation portion 2880 may be translated distally relative to collar 2872 to complete a full stroke of plunger rod 2880 in response to applying a distally-directed force onto actuation portion 2882. In this instance, stem 1280 may move relative to flange piece 2870, thereby causing stopper 1222 to move within body 1220 to deliver a dosage. In this instance, protrusions 1086 may be received within slots 1074 and second ring 2889 may be positioned proximate to a proximal end of collar 2872. In other words, in some embodiments, second ring 2889 does not contact the proximal end of collar 2872. Further, as described in greater detail above, indents 2875 may receive extensions 1087 (FIG. 36) therein when completing a full stroke of plunger rod 2880. It should be appreciated that an extent that plunger rod 2880 translates relative to flange piece 2870 may define a dosage delivery distance of delivery device 2800. The dosage delivery distance may be controlled based on a longitudinal length of protrusions 1086 relative to actuation portion 2882 and/or a depth of slots 1074 relative to collar 2872.

As seen in FIGS. 41A-41D, delivery device 2800 may include various other flange pieces 2870 having at least one of a plurality of textured interfaces on flanges 2876. As merely an illustrative example, as seen in FIG. 41A, an alternative exemplary flange piece 2870A may include a textured interface 2878A on flanges 2876 comprising a plurality of circular protrusions and/or depressions arranged in an annular array relative to one another. As seen in FIG. 41B, another exemplary flange piece 2870B may include a textured interface 2878B comprising an ornamental design, such as a snowflake, on each flange 2876. FIG. 41C shows an exemplary flange piece 2870C including a textured interface 2878C on flanges 2876 comprising a plurality of circular protrusions and/or depressions arranged in an irregular pattern relative to one another.

By way of further example, referring now to FIG. 41D, a flange piece 2870D may include a textured interface 2878D comprising a plurality of diamond-shaped protrusions and/or apertures positioned in a grid-like arrangement along flanges 2876. It should be understood that the various textured interfaces shown and described herein may be configured to enhance a grip, control, aesthetic, and/or ergonomics of the flange piece. It should further be appreciated that the textured interfaces shown and described herein are merely illustrative such that various other suitable patterns, textures, and/or features may be included on the flange pieces without departing from a scope of this disclosure.

Components of the devices described herein may be designed and/or suited for manufacture in one or more ways. In some embodiments, for example, components of the devices described herein (e.g., device 1050, device 1200, device 1300, device 1400, device 2400, device 2500, device 2600, device 2800, etc.) may be suitable for manufacture via, e.g., injection molding, 3-dimensional printing, or machining. In one embodiment, for example, components of device 1050 may be particularly suited for manufacture via injection molding. For example, in some existing devices, molding is not suitable for high volume production, resulting in the use of 3-dimensional printing. In some embodiments, while manufacturing tolerances may be tighter with molding techniques than with 3-dimensional printing techniques, devices formed by 3-dimensional printing do not have the same level of precision as devices formed by molding. Precision may be particularly important for devices of the present disclosure, for example, those devices used for vitreous injections at volumes of 100 μL or less.

Accordingly, it should be appreciated that devices of the present disclosure described herein may be designed to store predefined volumes of therapeutic agent that may be suitable for vitreous (IVT) injections, such as, for example, 100 μL or less. In some embodiments, the devices described herein may be designed for injection of certain volumes of vitreous based on an intended use of the device in a particular procedure. For example, devices of the present disclosure may be configured to store a volume of vitreous of about 65 μL to about 75 μL for high dose aflibercept procedures; about 95 μL to about 105 μL for Mini Trap procedures; and/or about 5 μL to about 15 μL for Retinopathy of Prematurity (ROP).

Devices of the present disclosure may be further configured to store relatively greater volumes of vitreous for injection based on a degree of myopia, such as about 3 milliliters, 4 milliliters, and greater. Additionally, the devices described herein may be designed for injection of larger volumes of vitreous based on an intended procedure, such as, about 3 ml to about 6 ml of silicone or gas for tamponade post vitrectomy. It should be appreciated that the devices of the present disclosure may be designed to inject various other volumes of vitreous relative to other procedures, such as, Diabetic Eye Disease, post-injection noninfectious Endophthalmitis, Neovascular (Wet) Age-related Macular Degeneration (AMD), Macular Edema following Retinal Vein Occlusion (RVO), Diabetic Macular Edema (DME), and Diabetic Retinopathy (DR).

Devices of the present disclosure are operable to provide accurate measurements in delivering large volumes of vitreous with high precision by minimizing instances of user error in improperly setting a dose line. As described in detail above, the various designs and configurations of the one or more components of the devices described herein (e.g., a plunger rod, a flange piece, etc.) may provide dosage precision by controlling a priming distance and a dosage delivery distance of the device, thereby removing user determination in setting the device at each respective configuration.

Features enumerated above have been described within the context of particular embodiments. However, as one of ordinary skill in the art would understand, features and aspects of each embodiment may be combined, added to other embodiments, subtracted from an embodiment, etc. in any manner suitable to assist with controlled preparation and/or delivery of a drug.

Aspects of the embodiments disclosed herein are described with respect to priming drug delivery devices and removing excess air bubbles from within drug delivery devices, and some embodiments disclosed herein are described as being particular types of drug delivery devices (e.g., pre-filled syringes). Aspects of the present disclosure may also be employed and/or found in other types of drug delivery devices (e.g., fillable syringes, pipettes, and the like). For example, devices having features according to the present disclosure may provide more precise means for transferring a volume of a drug substance or other fluid from one container to another, such as from a vial to a syringe. The precision in fluid transfer afforded by embodiments disclosed herein may reduce or minimize unwanted overfilling and/or decrease wastage of a drug substance.

While a number of embodiments are presented herein, multiple variations on such embodiments, and combinations of elements from one or more embodiments, are possible and are contemplated to be within the scope of the present disclosure. Moreover, those skilled in the art will appreciate that the conception upon which this disclosure is based may readily be used as a basis for designing other devices, methods, and systems for carrying out the several purposes of the present disclosure.

What is claimed is:

1. A drug delivery device, comprising:
   a body;
   a plunger rod including a proximal end portion and a distal end portion disposed partially inside the body, wherein the proximal end portion has a diameter greater than a diameter of the distal end portion;
   a protrusion extending from an outer surface of the proximal end portion of the plunger rod; and
   a blocking component coupled to a proximal end portion of the body, wherein the blocking component is a flange piece that includes a channel with an open distal end and a slot with a closed distal end,
   wherein, when the protrusion is in a first position relative to the blocking component, the protrusion is misaligned with the slot and the blocking component restricts distal movement of the plunger rod through the open distal end to a first stopping point, and when the protrusion is in a second position relative to the blocking component, the protrusion is aligned with the slot and the blocking component restricts distal movement of the plunger rod through the open distal end to a second stopping point when the protrusion abuts against the closed distal end.

2. The drug delivery device of claim 1, further comprising:
   a stopper disposed in the body, wherein distal movement of the plunger rod distally moves the stopper; and
   a drug substance disposed in the body in between the stopper and a distal end of the body,
   wherein distal movement of the plunger rod to the first stopping point primes the drug delivery device, and distal movement of the plunger rod to the second stopping point dispenses a predetermined volume of the drug substance from a distal end of the device.

3. The drug delivery device of claim 1, wherein moving the protrusion from the first position to the second position includes twisting the plunger rod relative to the blocking component, such that the protrusion is positioned external to the blocking component when in the second position.

4. The drug delivery device of claim 1,
   wherein the slot is positioned on a proximal side of the blocking component, the slot is sized and configured to receive a distal end of the protrusion, such that a proximal end of the protrusion is positioned external to the slot when the distal end is received within the slot,
   wherein when the protrusion is in the second position relative to the blocking component, the distal end of the protrusion is positioned proximally from the slot and disengaged from the proximal side of the blocking component, such that distal movement of the plunger rod moves the distal end of the protrusion into the slot.

5. The drug delivery device of claim 4, wherein the slot is a first slot and the protrusion is a first protrusion, and further comprising:
   a second slot in a proximal side of the blocking component, the second slot sized and configured to receive a second protrusion extending from the outer surface of the proximal end portion of the plunger rod,
   wherein the first and second slots are located on opposite sides of a central longitudinal axis of the drug delivery device.

6. The drug delivery device of claim 4, wherein, when the protrusion is in the first position relative to the blocking component, the proximal side engages the distal end of the protrusion and restricts distal movement of the plunger rod to the first stopping point; and when the protrusion is in the second position relative to the blocking component, the distal end of the protrusion aligns with the slot and is disengaged from the proximal side.

7. The drug delivery device of claim 6, wherein the plunger rod further includes a pair of extensions protruding distally from an actuation portion of the proximal end portion, and the blocking component includes a pair of openings; and
   wherein a portion of each extension is configured to be received by one of the pair of openings, prior to the plunger rod moving to the first stopping point, to restrict proximal movement of the plunger rod relative to the blocking component.

8. The drug delivery device of claim 7, wherein the blocking component includes one or more indents formed along a bottom wall of the blocking component; and
   wherein a portion of each extension is configured to be received by the one or more indents upon distal movement of the plunger rod relative to the blocking component to allow distal movement of the plunger rod to the second stopping point.

9. The drug delivery device of claim 7, wherein the blocking component includes a pair of internal grooves formed along a sidewall of the blocking component; and wherein a portion of each extension is configured to be received by at least one of the pair of internal grooves upon rotation of the plunger rod relative to the blocking component to expand the extensions radially-outward from a compressed state to a relaxed state.

10. The drug delivery device of claim 1, wherein the blocking component is slidably coupled to the body and includes a cavity and a pair of ribs that extend into the cavity, wherein the body includes a top flange and the pair of ribs are configured to engage the top flange received in the cavity; and wherein the pair of internal ribs are configured to apply a distally-directed force onto the top flange.

11. The drug delivery device of claim 1, wherein the blocking component is slidably coupled to the body and includes a pair of moveable tabs that are configured to engage the body; and wherein the pair of moveable tabs are laterally deflectable upon receiving the body in the blocking component and are configured to apply a radially-inward directed force onto the body.

12. A drug delivery device, comprising:
a body;
a plunger rod having a distal end contacting a stopper inside the body, and a proximal end including an actuation portion with a thumb pad;
a plurality of protrusions extending from the thumb pad and along the actuation portion; and
a blocking component disposed on the body, the blocking component including a proximal collar having a proximal-facing surface, a channel with an open distal end, and a plurality of slots extending past the proximally-facing surface, each of the plurality of slots including a closed distal end;
wherein, when the protrusions and the slots are in a first configuration relative to one another, the plunger rod is moveable relative to the blocking component until the proximally-facing surface abuts against the plurality of protrusions and the blocking component restricts distal movement of the plunger rod through the open distal end to a first stopping point, wherein, in the first configuration, the plurality of protrusions are mis-aligned with the plurality of slots; and
wherein, when the protrusions and the slots are in a second configuration, the proximally-facing surface is separated from the plurality of protrusions and the plunger rod is moveable relative to the blocking component until the blocking component restricts distal movement of the plunger rod through the open distal end to a second stopping point, wherein, in the second configuration, the slots are aligned with the protrusions and configured to receive the protrusions until each of the protrusions abuts against the closed distal end of the slots.

13. The drug delivery device of claim 12, wherein the protrusions and the slots are moveable from the first stopping point to the second stopping point by rotation of the actuation portion about a longitudinal axis in relation to the blocking component, and translation of the plunger rod relative to the blocking component;

wherein when the protrusions and the slots are at the second stopping point, the protrusions and the slots are not rotatable.

14. The drug delivery device of claim 12, wherein a longitudinal difference between the first stopping point and the second stopping point is equivalent to a distance that the stopper must travel to expel a predetermined volume of a drug product from a distal end of the body, the distance defined by a depth of the slots from the proximally-facing surface of the blocking component, and wherein the plunger rod is prevented from moving from the second stopping point to the first stopping point.

15. The drug delivery device of claim 12, wherein the drug delivery device is changeable:
(a) from a pre-use state to a primed state, by longitudinally moving the plunger rod until the plunger rod reaches the first stopping point;
(b) from the primed state to a delivery state by rotating the plunger rod in relation to the blocking component until the protrusions and the blocking component are in the second configuration; and
(c) from the delivery state to a used state by longitudinally moving the plunger rod until the plunger reaches the second stopping point, and
wherein the drug delivery device is not changeable from the used state to the delivery state, from the delivery state to the primed state, or from the primed state to the pre-use state.

16. The drug delivery device of claim 15, wherein the plunger rod includes a neck disposed distally from the actuation portion, wherein the neck interfaces with an opening in the blocking component to prevent proximal movement of the plunger rod.

17. The drug delivery device of claim 16, wherein the neck further interfaces with the opening in the blocking component to prevent movement of the drug delivery device from the delivery state to the primed state.

18. The drug delivery device of claim 12, wherein when the plunger rod is at the second stopping point, the stopper does not contact a distal end of the body.

19. A drug delivery device, comprising:
a body;
a plunger rod extending along a longitudinal axis, including:
a distal portion contacting a stopper inside the body;
a proximal end including a generally cylindrical actuation portion and a thumb pad disposed outside of the body, the thumb pad positioned proximal to the generally cylindrical actuation portion; and
two protrusions extending from opposite sides of the actuation portion in a symmetrical configuration, wherein distally-facing surfaces of the two protrusions are located at a same longitudinal position along the longitudinal axis; and
a blocking component coupled to the body, the blocking component including:
a collar having a channel with an open proximal end configured to accept a distal part of the actuation portion, and an open distal end configured to accept the distal portion of the plunger rod; and
two slots in the collar having closed distal ends, wherein each slot is configured to accept a distal portion of one of the two protrusions;
wherein the plunger rod is longitudinally moveable and rotatable about a longitudinal axis relative to the blocking component, and
wherein, when the drug delivery device is in a pre-use state, the protrusions and the slots are not longitudinally aligned such that the plunger rod is moveable relative to the open distal end until the distally-facing surfaces abut against the collar, and when the drug delivery device is in a delivery state, the protrusions and the slots are longitudinally aligned such that the plunger rod is moveable relative to the open distal end until the distally-facing surfaces abut against the closed distal ends.

20. The drug delivery device of claim 19, wherein the plunger rod further includes:
   two extensions protruding distally from the actuation portion; and
   a plurality of openings in the collar of the blocking component,
   wherein a portion of each extension is configured to be received by one of the plurality of openings upon distal movement of the plunger rod relative to the blocking component.

* * * * *